US012486260B2

(12) United States Patent
Dorsch et al.

(10) Patent No.: US 12,486,260 B2
(45) Date of Patent: Dec. 2, 2025

(54) INDAZOLYL-ISOXAZOLE DERIVATIVES FOR THE TREATMENT OF DISEASES SUCH AS CANCER

(71) Applicant: Merck Patent GmbH, Darmstadt (DE)

(72) Inventors: Dieter Dorsch, Ober-Ramstadt (DE); Andreas Blum, Bensheim (DE)

(73) Assignee: Merck Patent GmbH, Darmstadt (DE)

( * ) Notice: Subject to any disclaimer, the term of this patent is extended or adjusted under 35 U.S.C. 154(b) by 1070 days.

(21) Appl. No.: 17/429,938

(22) PCT Filed: Feb. 10, 2020

(86) PCT No.: PCT/EP2020/053241

§ 371 (c)(1),
(2) Date: Aug. 10, 2021

(87) PCT Pub. No.: WO2020/165062

PCT Pub. Date: Aug. 20, 2020

(65) Prior Publication Data

US 2022/0127254 A1 Apr. 28, 2022

(30) Foreign Application Priority Data

Feb. 11, 2019 (EP) .................................... 19156318

(51) Int. Cl.

| | |
|---|---|
| ***C07D 413/14*** | (2006.01) |
| ***A61P 35/00*** | (2006.01) |
| ***C07D 231/56*** | (2006.01) |
| ***C07D 401/14*** | (2006.01) |
| ***C07D 403/14*** | (2006.01) |
| ***C07D 413/04*** | (2006.01) |
| ***C07D 417/14*** | (2006.01) |
| ***C07D 471/04*** | (2006.01) |
| ***C07D 487/10*** | (2006.01) |
| ***C07D 491/048*** | (2006.01) |
| ***C07D 491/08*** | (2006.01) |
| ***C07D 491/107*** | (2006.01) |
| ***C07D 495/04*** | (2006.01) |
| ***C07D 495/08*** | (2006.01) |
| ***C07D 495/10*** | (2006.01) |
| ***C07D 498/10*** | (2006.01) |

(52) U.S. Cl.

CPC ............ *C07D 413/14* (2013.01); *A61P 35/00* (2018.01); *C07D 231/56* (2013.01); *C07D 401/14* (2013.01); *C07D 403/14* (2013.01); *C07D 413/04* (2013.01); *C07D 417/14* (2013.01); *C07D 471/04* (2013.01); *C07D 487/10* (2013.01); *C07D 491/048* (2013.01); *C07D 491/08* (2013.01); *C07D 491/107* (2013.01); *C07D 495/04* (2013.01); *C07D 495/08* (2013.01); *C07D 495/10* (2013.01); *C07D 498/10* (2013.01)

(58) Field of Classification Search

CPC .. C07D 413/14; C07D 231/56; C07D 401/14; C07D 403/14; C07D 413/04; C07D 417/14; C07D 471/04; C07D 487/10; C07D 491/048; C07D 491/08; C07D 491/107; C07D 495/04; C07D 495/08; C07D 495/10; C07D 498/10; A61P 35/00

See application file for complete search history.

(56) References Cited

U.S. PATENT DOCUMENTS

| | | | |
|---|---|---|---|
| 2005/0090529 | A1 | 4/2005 | McAlpine et al. |
| 2005/0137201 | A1 | 6/2005 | Aronov et al. |
| 2013/0095193 | A1 | 4/2013 | Charrier et al. |

FOREIGN PATENT DOCUMENTS

| | | |
|---|---|---|
| CN | 103429585 | 12/2013 |
| CN | 108473485 | 8/2018 |
| EP | 3088400 | 11/2016 |
| JP | 2007504252 | 3/2007 |
| JP | 2014510151 | 4/2014 |
| JP | 2017-526342 | 9/2017 |
| RU | 2 418 800 | 5/2011 |
| RU | 2012 111 695 | 10/2013 |
| WO | 2005/028475 | 3/2005 |
| WO | 2008/011110 | 1/2008 |
| WO | 2011/017561 | 2/2011 |
| WO | 2011/042368 | 4/2011 |
| WO | 2012/138938 | 10/2012 |
| WO | 2017/121444 | 7/2017 |

(Continued)

OTHER PUBLICATIONS

CAS Registry No. 1446255-71-5, which entered STN on Jul. 25, 2013 (Year: 2013).*

(Continued)

*Primary Examiner* — Joseph K McKane
*Assistant Examiner* — Quincy McKoy
(74) *Attorney, Agent, or Firm* — Grüneberg and Myers PLLC

(57) ABSTRACT

Compounds of the formula I

I

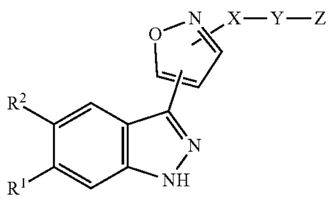

are provided. These compounds can inhibit c-Kit kinase and can be employed for the treatment of cancer.

11 Claims, No Drawings

(56) References Cited

FOREIGN PATENT DOCUMENTS

| | | |
|---|---|---|
| WO | 2019/051199 | 3/2019 |
| WO | 2012/084704 | 6/2020 |

OTHER PUBLICATIONS

International Search Report issued for PCT/EP2020/053241 on Apr. 28, 2020.
Written Opinion issued for PCT/EP2020/053241 on Apr. 28, 2020.
I. L. Knunânz, "Chemical Encyclopedia [in Russian]", section Solvates, hydrates, Soviet Encyclopedia, 1983, pp. 130-131, with English translation.
Klaus Kümmerer, "Pharmaceuticals in the Environment", Annu. Rev. Environ. Resources, vol. 35, 2010, abstract of pp. 57-75.
M. D. Maškovskij, "Medicaments [in Russian]", Manual for doctors, 15th edition, 2005, pp. 10-11, with English translation.
Russian Office Action dated Jul. 7, 2023, in Russian Patent Application No. 2021 126 014, with English translation, 22 pages.
V. G. Belikov, "Pharmaceutical Chemistry [in Russian]", Textbook, Fourth edition, 2007, pp. 27-29, with English translation.
V. V. Alekseev, "Optical Isomerism and Pharmacological Activity of Drugs [in Russian]", Soros educational Journal, Military Medical Academy, 1998, pp. 49-55, with English translation.
Durnov et al., "Pediatric Oncology", Educational Literature for Students of Medicine, Second Edition, Revised and Supplemented, 2002, 4 pages with English translation.
Dyson et al., "Chemistry of Synthetic Drugs", MYR, 1964, 18 pages with English translation.
Office Action received for Egyptian Patent Application No. 2021071164, mailed on May 7, 2024, 14 pages with English translation.
Smit et al., "Organic Synthesis: The Science Behind the Art", Moscow: MIR, 2001, 3 pages with English translation.
Allan B. Foster, "Deuterium Isotope Effects in the Metabolism of Drugs and Xenobiotics: Implications for Drug Design", XP009086953, Drug Metabolism Team, Advances in Drug Research, vol. 14, 1985, pp. 1-40.
An et al., "Design, synthesis and insight into the structure-activity relationship of 1,3-disubstituted indazoles as novel HIF-1 inhibitors", Bioorangic & Medicinal Chemistry Letters, vol. 21, 2011, pp. 6297-6300.
Ashman et al., "Therapeutic targeting of c-KIT in cancer", Expert Opinion on Investigation Drugs, vol. 22, No. 1, 2013, pp. 103-115.
Barder et al., "Catalyst for Suzuki-Miyaura Coupling Processes: Scope and Studies of the Effect of Ligand Structure", J. Am. Chem. Soc., vol. 127, No. 13, 2005, pp. 4685-4696.
Chen et al., "A Missense Mutation in KIT Kinase Domain 1 Correlates with Imatinib Resistance in Gstrointestinal Stromal Tumors", Cancer Research, vol. 64, Sep. 1, 2004, pp. 5913-5919.
Gillette et al., "Theory for the Observed Isotope Effects on the Formation of Multiple Products by Different Kinetic Mechanisms of Cythochrome P450 Enzymes", Biochemistry, vol. 33, No. 10, 1994, pp. 2927-2937.
Hanzlik et al., "Active Site Dynamics of Toulene Hydroylation by Cytochrome P-450[1]" Journal of Organic Chemistry, vol. 55, No. 13, 1990, pp. 3992-3997.
Hirota et al., "Gain-of-Function Mutation of Platelet-Derived Growth Factor Receptor α Gene in Gastrointestinal Stromal Tumors", Gastroenterolgy, vol. 125, Sep. 2003, pp. 660-667.
Jarman et al., "The deuterium isotope effect for the α-hydroxylation of tamoxifen by rat liver microsomes accounts for the reduced genotoxicity of [D-$_5$-ethyl]tamoxifen", Carcinogenesis, vol. 16, No. 4, 1995, pp. 638-688.
Kotha et al., "Recent applications of the Suzuki-Miyaura cross-coupling reaction in organic synthesis", Tetrahedron, vol. 58, 2002, pp. 9633-9695.
Reider et al., "*Synthesis of* (*R*)-*Serine-2-d and Its Conversion to the Broad Spectrum Antibiotic Fludalanine*", Journal of Organic Chemistry, vol. 52, No. 15, 1987, pp. 3326-3334.
Roberts et al., "*Resistance to c-KIT kinase inhibitors conferred by V654A mutation*", Molecular Cancer Therapeutics, vol. 6, No. 3, Mar. 2007, pp. 1159-1166.
Vivona et al., "*Lead Tetraacetate Oxidation of Phenylhydrazones of 3-Benzoylazoles. Synthesis of Azoacetates and Their Conversion into Indazoles*", Institute of Organic Chemistry, Journal of Heterocyclic Chem., vol. 22, No. 29, Jan.-Feb. 1985, pp. 29-32.
Chinese Office Action and Search Report dated Oct. 18, 2023, in Chinese Patent Application No. 202080013792.X, with English translation of the Office Action and Search Report, 5 pages.
STN Registry database, RN:1446255-71-5, ACS, Jul. 25, 2013, 3 pages.

* cited by examiner

INDAZOLYL-ISOXAZOLE DERIVATIVES FOR THE TREATMENT OF DISEASES SUCH AS CANCER

CROSS-REFERENCE TO RELATED APPLICATIONS

This application is a National Stage entry under § 371 of International Application No. PCT/EP2020/053241, filed on Feb. 10, 2020, and which claims the benefit of European Application No. 19156318.8, filed on Feb. 11, 2019. The content of each of these applications is hereby incorporated by reference in its entirety.

BACKGROUND OF THE INVENTION

Field of the Invention

The invention had the object of finding novel compounds having valuable properties, in particular those which can be used for the preparation of medicaments.

The present invention relates to indazolyl-isoxazole derivatives which inhibit c-KIT kinase across a wide range of c-KIT mutations and secondary mutations (V654A secondary resistance mutation in Exon 13) that may arise in GIST (gastrointestinal stromal tumor) patients.

The compounds of this invention are therefore useful in treating diseases such as cancer.

The present invention also provides methods for preparing these compounds, pharmaceutical compositions comprising these compounds, the compounds for use for the treatment of diseases and methods of treating diseases utilizing pharmaceutical compositions comprising these compounds.

Description of Related Art

Mutated forms of the receptor tyrosine kinase c-KIT are drivers in several cancers and are attractive targets for therapy. While benefits have been obtained from use of inhibitors of KIT kinase activity such as imatinib, especially in GIST, primary resistance occurs with certain oncogenic mutations. Furthermore, resistance frequently develops due to secondary mutations (L. K. Ashman & R. Griffith (2013) Expert Opinion on Investigational Drugs, 22:1, 103-115).

L. L. Chen et al. describe "A Missense Mutation in KIT kinase domain 1 correlates with imatinib resistance in gastrointestinal stromal tumors" in Cancer res. 2004; 64:5913-5919.

K. G. Roberts et al. describe "Resistance to c-KIT kinase inhibitors conferred by V654A mutation" in Mol. Cancer Ther. 2007; 6:1159-1166.

Gastrointestinal stromal tumors (GISTs) are the most common mesenchymal tumors of the gastrointestinal (GI) tract.

GISTs are defined as c-KIT (CD117, stem cell factor receptor)-positive mesenchymal spindle cell or epitheloid neoplasms.

GISTs have commonly primary activating mutations of the KIT gene (90%) leading to ligand-independent activation of the receptor tyrosine kinase c-KIT rendering the tumor dependent on oncogenic KIT activity.

Imatinib treatment of GISTs with primary mutation has an initial response rate of ~70% but acquired resistance develops in 40-50% of cases with an average of two years. The secondary mutation V654A in exon13 is the most frequent resistance mutation post Imatinib.

There is a high unmet medical need for development of a safe and specific inhibitor against KIT V654A resistance mutation.

SUMMARY OF THE INVENTION

It has been found that the compounds according to the invention and salts thereof have very valuable pharmacological properties while being well tolerated.

The present invention specifically relates to compounds of the formula I which inhibit c-KIT kinase, preferably the mutant V654A of c-KIT kinase.

Moreover, compounds of the formula I inhibit PDGFRα (V651D). The gain-of-function mutations of PDGFRα appear to play an important role in development of GISTs without KIT mutations (S. Hirota et al., Gastroenterology 2003; 125:660-667).

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed is assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

PRIOR ART

WO 2012/084704 discloses indazolyl triazole derivatives of the following formula as inhibitors of the kinase IRAK:

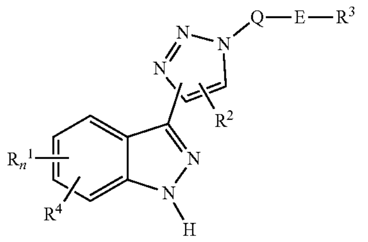

Isoxazole compounds presently claimed show higher activity in comparison to the corresponding triazole derivatives (table 2).

In Hongchan An et al (Bioorganic and Medicinal Chemistry Letters 21 (2011) 6297-6300, indazolyl-isoxazoles are described as HIF-1 inhibitors:

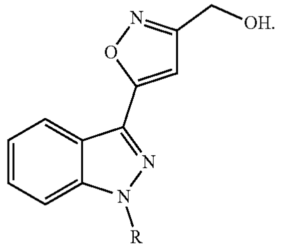

R = $CH_3$, $CH_2Ph$

In Nicolò Vivona et al, Journal of Heterocyclic Chemistry 22 (1985) 29-32, the following indazolyl-isoxazole is described:

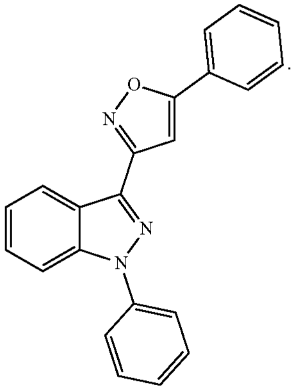 [SMILES: c1ccc(-c2cc(-c3nn(-c4ccccc4)c4ccccc34)no2)cc1]

DETAILED DESCRIPTION OF THE INVENTION

The invention relates to compounds of the formula I

I

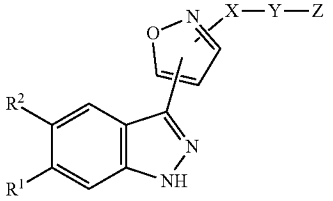

in which $R^1$ denotes Hal, $CF_3$, OA, $Het^1$, $COOR^3$ or $CON(R^3)_2$, $R^2$ denotes H, Hal or CN, $R^3$ denotes H or A, X denotes phenylene, pyridin-diyl, 1,3-thiazol-diyl or pyrazol-diyl, each of which is unsubstituted or mono-, di- or trisubstituted by Hal and/or A, Y is absent or denotes CO, $O[C(R^3)_2]_n$, $NR^3CO$, $CONR^3$, $CONR^3[C(R^3)_2]_n$, $CONHCH_2C(CH_3)_2$, $SO_2$, $SO_2N(R^3)$, —N═ or S(═O, ═$NR^3$), Z denotes H, A, Hal, OA, $[C(R^3)_2]_nHet^2$ or N═S(═O)$A_2$, A denotes unbranched or branched alkyl with 1-10 C-atoms, wherein one or two non-adjacent CH- and/or $CH_2$-groups may be replaced by O-atoms and wherein 1-7 H-atoms may be replaced by $R^5$, or denotes $(CH_2)_nCyc$, Cyc denotes cyclic alkyl having 3-7 C atoms, $R^5$ denotes F, Cl, OH, $SO_2A$ or $N(R^3)_2$, $Het^1$ denotes pyrazolyl which may be mono- or disubstituted by A, $Het^2$ denotes a 4- to 7-membered monocyclic aromatic, unsaturated or saturated heterocycle having 1 to 4 N, O and/or S atoms, which may be unsubstituted or mono-, di- or trisubstituted by A, Hal, CN, $OR^3$, $[C(R^3)_2]_nN(R^3)_2$, $[C(R^3)_2]_nSO_2A$, $[C(R^3)_2]_nNR^3SO_2A$, $Het^3$, ═$NR^3$ and/or ═O, or denotes a 7- to 10-membered bicyclic aromatic, unsaturated or saturated heterocycle having 1 to 4 N, O and/or S atoms, which may be unsubstituted or mono-, di- or trisubstituted by A, Hal, CN, $OR^3$, $[C(R^3)_2]_nN(R^3)_2$, $[C(R^3)_2]_nSO_2A$, $[C(R^3)_2]_nNR^3SO_2A$, $Het^3$, ═$NR^3$ and/or ═O, $Het^3$ denotes a 4- to 7-membered monocyclic aromatic, unsaturated or saturated heterocycle having 1 to 4 N, O and/or S atoms, which may be unsubstituted or mono- or disubstituted by A, Hal, $OR^3$, oxetanyl and/or ═O, or denotes a 7- to 10-membered bicyclic aromatic, unsaturated or saturated heterocycle having 1 to 4 N, O and/or S atoms, which may be unsubstituted or mono- or disubstituted by A, Hal, $OR^3$, oxetanyl and/or ═O, Hal denotes F, Cl, Br or I, n denotes 0, 1, 2 or 3, and pharmaceutically acceptable salts, tautomers and stereoisomers thereof, including mixtures thereof in all ratios.

The invention also relates to the optically active forms (stereoisomers), the enantiomers, the racemates, the diastereomers and the hydrates and solvates of these compounds.

Moreover, the invention relates to pharmaceutically acceptable derivatives of compounds of formula I.

The term solvates of the compounds is taken to mean adductions of inert solvent molecules onto the compounds which form owing to their mutual attractive force. Solvates are, for example, mono- or dihydrates or alkoxides.

It is understood, that the invention also relates to the solvates of the salts. The term pharmaceutically acceptable derivatives is taken to mean, for example, the salts of the compounds according to the invention and also so-called prodrug compounds.

As used herein and unless otherwise indicated, the term "prodrug" means a derivative of a compound of formula I that can hydrolyze, oxidize, or otherwise react under biological conditions (in vitro or in vivo) to provide an active compound, particularly a compound of formula I. Examples of prodrugs include, but are not limited to, derivatives and metabolites of a compound of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

The invention relates to the compounds of the formula I and salts thereof and to a process for the preparation of compounds of the formula I and pharmaceutically acceptable salts, solvates, tautomers and stereoisomers thereof, characterised in that a) for the preparation of compounds of the formula I, in which X denotes phenylene, Y denotes CO, Z denotes $[C(R^3)_2]_n Het^2$ and n denotes 0, a compound of the formula II

II

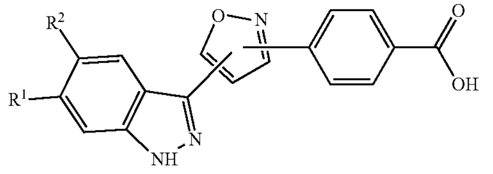

in which $R^1$ and $R^2$ have the meanings indicated in formula I, is reacted with a compound of formula III $Het^2$ III in which $Het^2$ has the meaning indicated in formula I, or b) for the preparation of compounds of the formula I, in which $R^1$ denotes $Het^1$, a compound of the formula IV

IV

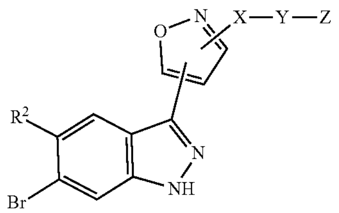

in which $R^2$, X, Y and Z have the meanings indicated in formula I, is reacted with a compound of formula V

V

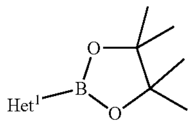

in which $Het^1$ has the meanings indicated in formula I, or c) for the preparation of compounds of the formula Ia, Ia

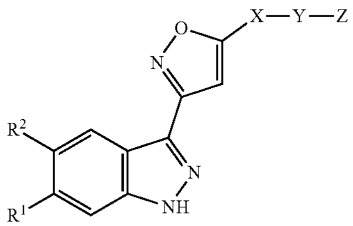

in which $R^1$, $R^2$, X, Y and Z the meanings indicated in formula I, a compound of the formula VI

VI

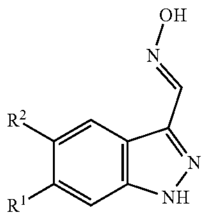

in which $R^1$ and $R^2$ have the meanings indicated in formula I, is reacted with a compound of formula VII

VII

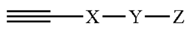

in which

X, Y and Z have the meanings indicated in formula I, or d) for the preparation of compounds of the formula Ib, Ib

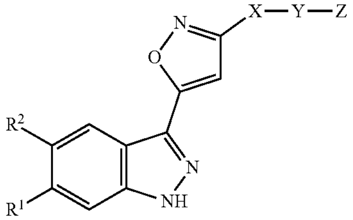

in which $R^1$, $R^2$, X, Y and Z have the meanings indicated in formula I, a compound of the formula VIII

VIII

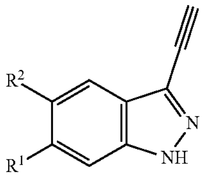

in which $R^1$ and $R^2$ have the meanings indicated in formula I, is reacted with a compound of formula IX

HO—N═CH—X—Y—Z IX in which

X, Y and Z have the meanings indicated in formula I, and/or a base or acid of the formula I is converted into one of its salts.

For all radicals which occur more than once, such as, for example, $R^3$, their meanings are independent of one another.

Above and below, the radicals $R^1$, $R^2$, X, Y and Z have the meanings indicated for the formula I, unless explicitly stated otherwise.

Preferably preferred are compounds of the formula Ia,

Ia

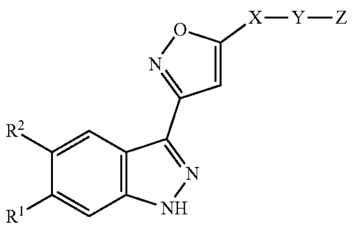

In which $R^1$, $R^2$, X, Y and Z have the meanings indicated in formula I,

Moreover, preferably preferred are compounds of the formula Ib

Ib

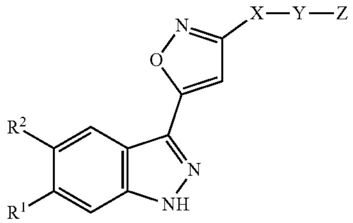

in which $R^1$, $R^2$, X, Y and Z have the meanings indicated in formula I,

A denotes alkyl, this is unbranched (linear) or branched, and has 1, 2, 3, 4, 5, 6, 7, 8, 9 or 10 C atoms. A preferably denotes methyl, ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cyc preferably denotes cyclopropyl, cyclobutyl, cyclopentyl or cyclohexyl. Moreover, A denotes preferably $CH_2OCH_3$, $CH_2CH_2OH$ or $CH_2CH_2OCH_3$.

$R^1$ preferably denotes Hal, $CF_3$, $OCH_3$, $OCH_2CH_2OCH_3$, $OCH_2CH_2OH$, 1-methyl-1H-pyrazol-4-yl, $COOCH_3$, $CONH_2$, $CONHCH_3$ or $CONHCH_2CH_2OCH_3$, $R^2$ preferably denotes H, Hal or CN.

$R^3$ denotes H or A, preferably H or $CH_3$.

X preferably denotes 1,4-phenylene, 1,3-phenylene, 2-fluoro-1,4-phenylene, 2-methyl-1,4-phenylene, pyridine-3,6-diyl, 1,3-thiazol-3,5-diyl, 1,3-thiazol-2,4-diyl, 1,3-thiazol-2,5-diyl or pyrazol-1,4-diyl, each of which is unsubstituted or mono-, di- or trisubstituted by Hal and/or A.

Y preferably denotes CO, $SO_2$, NHCO, $NCH_3$, CONH $(CH_2)_n$, $CONHCH_2C(CH_3)_2$, $CON(CH_3)(CH_2)_n$, O, $OCH_2$, $OCH_2CH_2$, S(═O)(═NH), —N═, $SO_2N(CH_3)$ or is absent.

Z preferably denotes H, Hal, OA, $Het^2$, A, N═S(═O)$A_2$.

Bicyclic compounds also include spiro compounds.

Irrespective of further substitutions, $Het^2$ denotes, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzo-thiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, pyrrolopyridinyl, purinyl, further preferably 1,3-benzodioxol-5-yl, 1,4-benzodioxan-6-yl, 2,1,3-benzothiadiazol-4- or -5-yl, 2,1,3-benzoxadiazol-5-yl, azabicyclo[3.2.1]-octyl or dibenzo-furanyl.

The heterocyclic radicals may also be partially or fully hydrogenated. Irrespective of further substitutions, $Het^2$ can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-,-2-,-3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Irrespective of further substitutions, $Het^3$ denotes, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzo-thiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, pyrrolopyridinyl, purinyl, further preferably 1,3-benzodioxol-5-yl, 1,4-benzodioxan-6-yl, 2,1,3-benzothiadiazol-4- or -5-yl, 2,1,3-benzoxadiazol-5-yl, azabicyclo[3.2.1]-octyl or dibenzo-furanyl.

The heterocyclic radicals may also be partially or fully hydrogenated. Irrespective of further substitutions, $Het^3$ can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-,-2-,-3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

$Het^2$ preferably denotes pyrrolidinyl, piperazinyl, piperidinyl, triazolyl, azetidinyl, morpholinyl, thiomorpholinyl, 2-oxa-6-azaspiro[3.3]heptane-6-yl, 6-oxa-2-azaspiro[3.4]octane-2-yl, 1-oxa-6-azaspiro[3.3]heptane-6-yl, 2,6-diazaspiro[3.3]heptane-2-yl, octahydropyrrolo[3,4-b]pyrrolyl, octahydropyrrolo[3,2-b]pyrrolyl, 1,4-diazepanyl, pyridinyl, 1H-pyridinyl, 2H-pyridazinyl, 2,3-dihydropyridazinyl, octahydro-1H-pyrrolo[3.2-b]pyridinyl, 3-thia-6-azabicyclo[3.1.1]heptanyl, 6-oxa-1-azaspiro[3.3]heptane-1-yl, 1H-pyrazolyl, thiazolidinyl, 2-oxa-7-azaspiro[3.5]nonane-7-yl, 1,4-oxazepanyl, 2-thia-6-azaspiro[3.3]heptane-6-yl, 2,8-dioxa-5-azaspiro[3.5]nonane-5-yl, 1H-1,3-benzodiazol-2-yl (benzimidazole-2-yl), 2-oxa-7-azaspiro[4.4]nonane-7-yl, 2-oxa-6-azaspiro[3.4]octane-6-yl, 8-oxa-2-azaspiro[4.5]decane-2-yl, 2,6-diazaspiro[3.4]octane-6-yl, 6-oxa-3-azabicyclo[3.1.1]heptane-3-yl, 2-oxa-5-azabicyclo[2.2.1]heptane-5-yl, 7-oxa-2-azaspiro[3.5]nonane-2-yl, 6-oxa-1-azaspiro[3.3]heptane-1-yl, 2,7-diazaspiro[3.5]nonane-7-yl, 3-oxa-6-azabicyclo[3.1.1]heptane-6-yl, 1H,2H,3H-pyrrolo[3,4-c]pyridine-2-yl (1,3-dihydropyrrolo[3,4-c]pyridine-2-yl), 2,7-diazaspiro[3.5]nonane-2-yl, hexahydro-1H-furo[3,4-c]pyrrole-5-yl, octahydropyrrolo[2,3-c]pyrrole-5-yl, 5H,6H,7H-pyrrolo[3,4-d]pyrimidine-6-yl, 1H, 4H, 5H,6H-pyrrolo[3,4-c]pyrazole-5-yl, octahydropyrano[3,4-c]pyrrole-2-yl, octahydrofuro[3,4-c]pyridine-5-yl, octahydropyrrolo[3,4-c]pyrrole-2-yl, hexahydro-1H-2lambda6-thieno[3,4-c]pyrrole-5-yl, tetrahydrofuro[3,4-c]pyrrole-5-yl, each of which may be unsubstituted or mono-, di- or trisubstituted by A, Hal, CN, $OR^3$, $[C(R^3)_2]_nN(R^3)_2$, $[C(R^3)_2]_nSO_2A$, $[C(R^3)_2]_nNR^3SO_2A$, $Het^3$, $=NR^3$ and/or $=O$.

$Het^3$ preferably denotes morpholinyl, 1H-pyrazolyl, 1lambda6-thiomorpholinyl, imidazolyl, azetidinyl, piperazinyl, piperidinyl, pyridinyl, oxetanyl, 1,2,4-oxadiazolyl, pyrimidinyl, oxolanyl, pyrrolidinyl, 2-oxa-6-azaspiro[3.3]heptane-6-yl, oxan-4-yl, 1,2,3-triazolyl, 1,2,4-triazolyl, each of which may be unsubstituted or mono- or disubstituted by A, Hal, $OR^3$, oxetanyl and/or $=O$.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to If, which conform to the formula I and in which the radicals not designated in greater detail have the meaning indicated for the formula I, but in which in Ia $R^1$ denotes Hal, $CF_3$, $OCH_3$, $OCH_2CH_2OCH_3$, $OCH_2CH_2OH$, 1-methyl-1H-pyrazol-4-yl, $COOCH_3$, $CONH_2$, $CONHCH_3$ or $CONHCH_2CH_2OCH_3$, in Ib $R^3$ denotes H or $CH_3$;

in Ic X denotes 1,4-phenylene, 1,3-phenylene, 2-fluoro-1,4-phenylene, 2-methyl-1,4-phenylene, pyridine-3,6-diyl, 1,3-thiazol-3,5-diyl, 1,3-thiazol-2,4-diyl, 1,3-thiazol-2,5-diyl or pyrazol-1,4-diyl, each of which is unsubstituted or mono-, di- or trisubstituted by Hal and/or A;

in Id Y denotes is absent or denotes CO, $SO_2$, NHCO, $NCH_3$, $CONH(CH_2)_n$, $CONHCH_2C(CH_3)_2$, $CON(CH_3)(CH_2)_n$, O, $OCH_2$, $OCH_2CH_2$, S(=O)(=NH), —N= or $SO_2N(CH_3)$;

in Ie $Het^2$ denotes pyrrolidinyl, piperazinyl, piperidinyl, triazolyl, azetidinyl, morpholinyl, thiomorpholinyl, 2-oxa-6-azaspiro[3.3]heptane-6-yl, 6-oxa-2-azaspiro[3.4]octane-2-yl, 1-oxa-6-azaspiro[3.3]heptane-6-yl, 2,6-diazaspiro[3.3]heptane-2-yl, octahydropyrrolo[3,4-b]pyrrolyl, octahydropyrrolo[3,2-b]pyrrolyl, 1,4-diazepanyl, pyridinyl, 1H-pyridinyl, 2H-pyridazinyl, 2,3-dihydropyridazinyl, octahydro-1H-pyrrolo[3.2-b]pyridinyl, 3-thia-6-azabicyclo[3.1.1]heptanyl, 6-oxa-1-azaspiro[3.3]heptane-1-yl, 1H-pyrazolyl, thiazolidinyl, 2-oxa-7-azaspiro[3.5]nonane-7-yl, 1,4-oxazepanyl, 2-thia-6-azaspiro[3.3]heptane-6-yl, 2,8-dioxa-5-azaspiro[3.5]nonane-5-yl, 1H-1,3-benzodiazol-2-yl (benzimidazole-2-yl), 2-oxa-7-azaspiro[4.4]nonane-7-yl, 2-oxa-6-azaspiro[3.4]octane-6-yl, 8-oxa-2-azaspiro[4.5]decane-2-yl, 2,6-diazaspiro[3.4]octane-6-yl, 6-oxa-3-azabicyclo[3.1.1]heptane-3-yl, 2-oxa-5-azabicyclo[2.2.1]heptane-5-yl, 7-oxa-2-azaspiro[3.5]nonane-2-yl, 6-oxa-1-azaspiro[3.3]heptane-1-yl, 2,7-diazaspiro[3.5]nonane-7-yl, 3-oxa-6-azabicyclo[3.1.1]heptane-6-yl, 1H,2H,3H-pyrrolo[3,4-c]pyridine-2-yl (1,3-dihydropyrrolo[3,4-c]pyridine-2-yl), 2,7-diazaspiro[3.5]nonane-2-yl, hexahydro-1H-furo[3,4-c]pyrrole-5-yl, octahydropyrrolo[2,3-c]pyrrole-5-yl, 5H,6H,7H-pyrrolo[3,4-d]pyrimidine-6-yl, 1H, 4H, 5H,6H-pyrrolo[3,4-c]pyrazole-5-yl, octahydropyrano[3,4-c]pyrrole-2-yl, octahydrofuro[3,4-c]pyridine-5-yl, octahydropyrrolo[3,4-c]pyrrole-2-yl, hexahydro-1H-2lambda6-thieno[3,4-c]pyrrole-5-yl, tetrahydrofuro[3,4-c]pyrrole-5-yl, each of which may be unsubstituted or mono-, di- or trisubstituted by A, Hal, CN, $OR^3$, $[C(R^3)_2]_nN(R^3)_2$, $[C(R^3)_2]_nSO_2A$, $[C(R^3)_2]_nNR^3SO_2A$, $Het^3$, $=NR^3$ and/or =O;

in If $Het^3$ denotes morpholinyl, 1H-pyrazolyl, 1lambda6-thiomorpholinyl, imidazolyl, azetidinyl, piperazinyl, piperidinyl, pyridinyl, oxetanyl, 1,2,4-oxadiazolyl, pyrimidinyl, oxolanyl, pyrrolidinyl, 2-oxa-6-azaspiro[3.3]heptane-6-yl, oxan-4-yl, 1,2,3-triazolyl, 1,2,4-triazolyl, each of which may be unsubstituted or mono- or disubstituted by A, Hal, $OR^3$, oxetanyl and/or =O;

and pharmaceutically acceptable salts, tautomers and stereoisomers thereof, including mixtures thereof in all ratios.

Preferred are compounds of the formula Ib

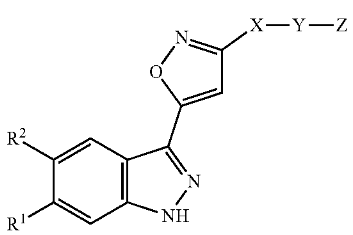

Ib in which $R^1$ denotes Hal, $CF_3$, $OCH_3$, $OCH_2CH_2OCH_3$, $OCH_2CH_2OH$, 1-methyl-1H-pyrazol-4-yl, $COOCH_3$, $CONH_2$, $CONHCH_3$ or $CONHCH_2CH_2OCH_3$, $R^2$ denotes H, Hal or CN, $R^3$ denotes H or $CH_3$, X denotes 1,4-phenylene, 1,3-phenylene, 2-fluoro-1,4-phenylene, 2-methyl-1,4-phenylene, pyridine-3,6-diyl, 1,3-thiazol-3,5-diyl, 1,3-thiazol-2,4-diyl, 1,3-thiazol-2,5-diyl or pyrazol-1,4-diyl, each of which is unsubstituted or mono-, di- or trisubstituted by Hal and/or A, Y is absent or denotes CO, $SO_2$, NHCO, $NCH_3$, $CONH(CH_2)_n$, $CONHCH_2C(CH_3)_2$, $CON(CH_3)(CH_2)_n$, O, $OCH_2$, $OCH_2CH_2$, S(=O)(=NH), —N= or $SO_2N(CH_3)$, Z denotes H, A, Hal, OA, $[C(R^3)_2]_nHet^2$ or N=S(=O)$A_2$, A denotes unbranched or branched alkyl with 1-10 C-atoms, wherein one or two non-adjacent CH- and/or $CH_2$-groups may be replaced by O-atoms and wherein 1-7 H-atoms may be replaced by $R^5$, or denotes $(CH_2)_nCyc$, Cyc denotes cyclic alkyl having 3-7 C atoms, $R^5$ denotes F, C, OH, $SO_2A$ or $N(R^3)_2$, $Het^1$ denotes pyrazolyl which may be mono- or disubstituted by A, $Het^2$ denotes pyrrolidinyl, piperazinyl, piperidinyl, triazolyl, azetidinyl, morpholinyl, thiomorpholinyl, 2-oxa-6-azaspiro[3.3]heptane-6-yl, 6-oxa-2-azaspiro[3.4]octane-2-yl, 1-oxa-6-azaspiro[3.3]heptane-6-yl, 2,6-diazaspiro[3.3]heptane-2-yl, octahydropyrrolo[3,4-b]pyrrolyl, octahydropyrrolo[3,2-b]pyrrolyl, 1,4-diazepanyl, pyridinyl, 1H-pyridinyl, 2H-pyridazinyl, 2,3-dihydropyridazinyl, octahydro-1H-pyrrolo[3.2-b]pyridinyl, 3-thia-6-azabicyclo[3.1.1]heptanyl, 6-oxa-1-azaspiro[3.3]heptane-1-yl, 1H-pyrazolyl, thiazolidinyl, 2-oxa-7-azaspiro[3.5]nonane-7-yl, 1,4-oxazepanyl, 2-thia-6-azaspiro[3.3]heptane-6-yl, 2,8-dioxa-5-azaspiro[3.5]nonane-5-yl, 1H-1,3-benzodiazol-2-yl, 2-oxa-7-azaspiro[4.4]nonane-7-yl, 2-oxa-6-azaspiro[3.4]octane-6-yl, 8-oxa-2-azaspiro[4.5]decane-2-yl, 2,6-diazaspiro[3.4]octane-6-yl, 6-oxa-3-azabicyclo[3.1.1]heptane-3-yl, 2-oxa-5-azabicyclo[2.2.1]heptane-5-yl, 7-oxa-2-azaspiro[3.5]nonane-2-yl, 6-oxa-1-azaspiro[3.3]heptane-1-yl, 2,7-diazaspiro[3.5]nonane-7-yl, 3-oxa-6-azabicyclo[3.1.1]heptane-6-yl, 1H,2H,3H-pyrrolo[3,4-c]pyridine-2-yl, 2,7-diazaspiro[3.5]nonane-2-yl, hexahydro-1H-furo[3,4-c]pyrrole-5-yl, octahydropyrrolo[2,3-c]pyrrole-5-yl, 5H,6H,7H-pyrrolo[3,4-d]pyrimidine-6-yl, 1H, 4H, 5H,6H-pyrrolo[3,4-c]pyrazole-5-yl, octahydropyrano[3,4-c]pyrrole-2-yl, octahydrofuro[3,4-c]pyridine-5-yl, octahydropyrrolo[3,4-c]pyrrole-2-yl, hexahydro-1H-2lambda6-thieno[3,4-c]pyrrole-5-yl or tetrahydrofuro[3,4-c]pyrrole-5-yl, each of which may be unsubstituted or mono-, di- or trisubstituted by A, Hal, CN, $OR^3$, $[C(R^3)_2]_nN(R^3)_2$, $[C(R^3)_2]_nSO_2A$, $[C(R^3)_2]_nNR^3SO_2A$, $Het^3$, $=NR^3$ and/or $=O$, $Het^3$ denotes morpholinyl, 1H-pyrazolyl, 1lambda6-thiomorpholinyl, imidazolyl, azetidinyl, piperazinyl, piperidinyl, pyridinyl, oxetanyl, 1,2,4-oxadiazolyl, pyrimidinyl, oxolanyl, pyrrolidinyl, 2-oxa-6-azaspiro[3.3] heptane-6-yl, oxan-4-yl, 1,2,3-triazolyl or 1,2,4-triazolyl, each of which may be unsubstituted or mono- or disubstituted by A, Hal, $OR^3$, oxetanyl and/or $=O$, Hal denotes F, Cl, Br or I, n denotes 0, 1, 2 or 3, and pharmaceutically acceptable salts, tautomers and stereoisomers thereof, including mixtures thereof in all ratios.

Moreover, the invention relates to intermediates selected from the group 2-bromo-5-fluoro-4-(2-methoxyethoxy)benzaldehyde

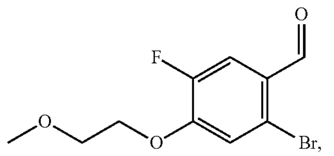

N'-[(1E)-[2-bromo-5-fluoro-4-(2-methoxyethoxy)phenyl] methylidene]-4-methylbenzene-1-sulfonohydrazide

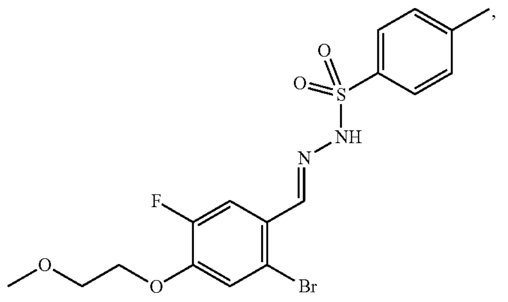

5-fluoro-6-(2-methoxyethoxy)-1-(4-methylbenzenesulfonyl)-1H-indazole

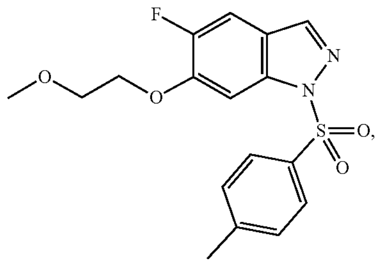 [SMILES: COCCOc1cc2c(cnn2S(=O)(=O)c2ccc(C)cc2)cc1F]

5-fluoro-6-(2-methoxyethoxy)-1H-indazole

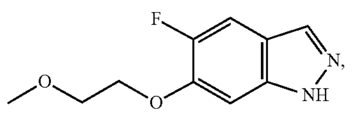

5-fluoro-3-iodo-6-(2-methoxyethoxy)-1H-indazole

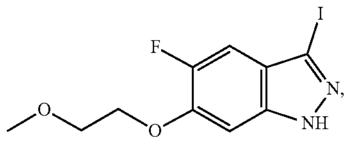 [SMILES: COCCOc1cc2[nH]nc(I)c2cc1F]

tert-butyl 5-fluoro-3-iodo-6-(2-methoxyethoxy)-1H-indazole-1-carboxylate

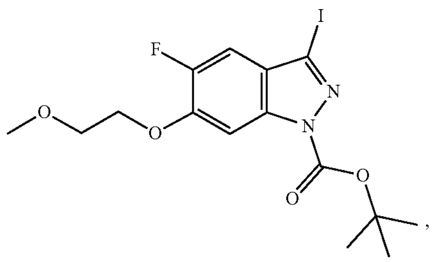 [SMILES: COCCOc1cc2c(cc1F)c(I)nn2C(=O)OC(C)(C)C]

tert-butyl 5-fluoro-6-(2-methoxyethoxy)-3-[2-(trimethylsilyl)ethynyl]-1H-indazole-1-carboxylate

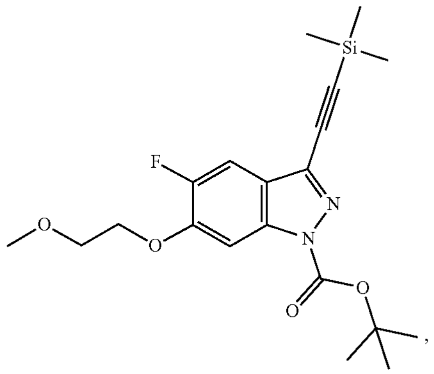 [SMILES: COCCOc1cc2c(cc1F)c(C#C[Si](C)(C)C)nn2C(=O)OC(C)(C)C]

3-ethynyl-5-fluoro-6-(2-methoxyethoxy)-1H-indazole

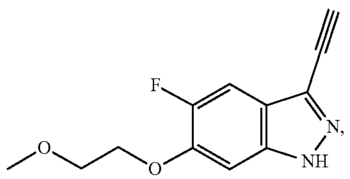 [SMILES: C#Cc1n[nH]c2cc(OCCOC)c(F)cc12]

tert-butyl 3-ethynyl-5-fluoro-6-(2-methoxyethoxy)-1H-indazole-1-carboxylate

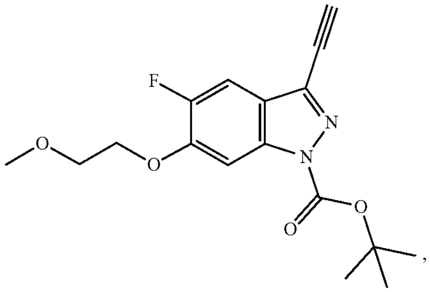 [SMILES: C#Cc1nn(C(=O)OC(C)(C)C)c2cc(OCCOC)c(F)cc12]

tert-butyl 5-fluoro-3-{3-[4-(methoxycarbonyl)phenyl]-1,2-oxazol-5-yl}-6-(2-methoxyethoxy)-1H-indazole-1-carboxylate

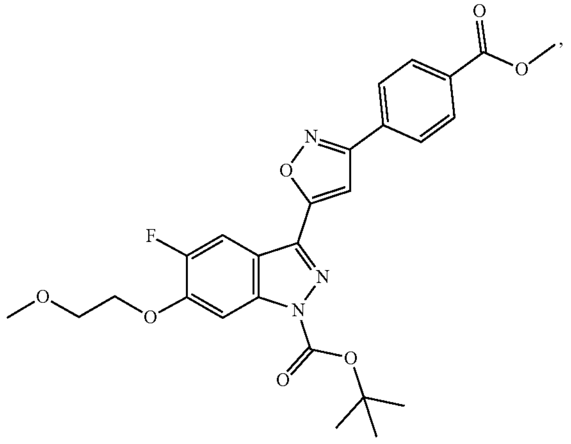

methyl 4-{5-[5-fluoro-6-(2-methoxyethoxy)-1H-indazol-3-yl]-1,2-oxazol-3-yl}benzoate

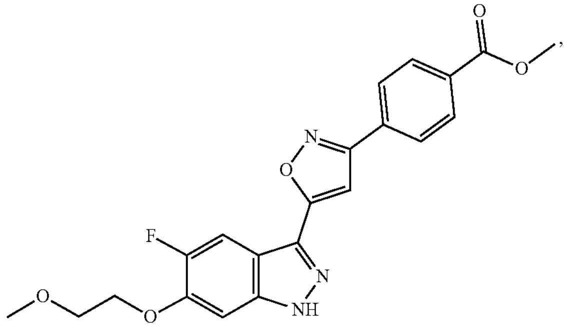

4-{5-[5-fluoro-6-(2-methoxyethoxy)-1H-indazol-3-yl]-1,2-oxazol-3-yl}benzoic acid

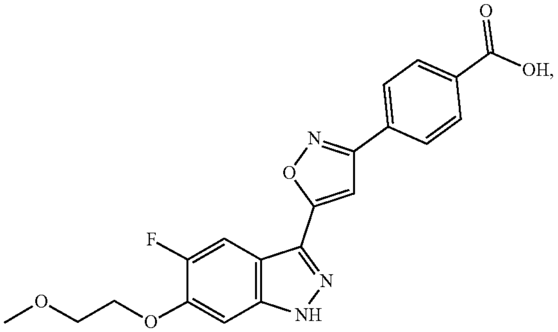 [SMILES: COCCOc1cc2[nH]nc(-c3cc(-c4ccc(C(=O)O)cc4)no3)c2cc1F]

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

Compounds of the formula I in which

X denotes phenylene,

Y denotes CO,

Z denotes $[C(R^3)_2]_n Het^2$ and n denotes 0, can preferably be obtained by reacting a compound of the formula II with a compound of the formula III.

The starting compounds of the formula II and III are generally known. If they are novel, however, they can be prepared by methods known per se.

The reaction is generally carried out in the presence of compounds such as N-(3-dimethyl-aminopropyl)-N'-ethyl-carbodiimide hydrochloride and 1-hydroxybenzotriazole.

The reaction is generally carried out in the presence of an acid-binding agent, preferably an organic base, such as DIPEA, triethylamine, dimethyl-aniline, pyridine, quinoline or 4-methylmorpholine.

The addition of an alkali or alkaline earth metal hydroxide, carbonate or bicarbonate or another salt of a weak acid of the alkali or alkaline earth metals, preferably of potassium, sodium, calcium or caesium, may also be favourable.

Depending on the conditions used, the reaction time is between a few minutes and 14 days, the reaction temperature is between about −30° and 140°, normally between −10° and 100°, in particular between about 30° and about 90°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon di-sulfide; carboxylic acids, such as formic acid or acetic acid; nitro compounds, such as nitromethane or nitrobenzene; esters, such as ethyl acetate, or mixtures of the said solvents.

Particular preference is given to acetonitrile, dichloromethane and/or DMF.

Compounds of the formula I in which $R^1$ denotes $Het^1$, can preferably be obtained by reacting a compound of the formula IV with a compound of the formula V.

The starting compounds of the formula IV and V are generally known. If they are novel, however, they can be prepared by methods known per se.

Alternatively, compounds of formula Va $Het^1$-$B(OH)_2$ Va may be used instead of compounds of formula V.

This coupling is generally carried out at elevated temperature using a palladium catalyst, a base and an inert solvent. An overview of catalysts and reaction conditions can be found in the literature [see, for instance, S. Kotha et al., Tetrahedron 2002, 58, 9633-9695; T. E. Barder et al., J. Am. Chem. Soc. 2005, 127, 4685-4696]. The preferred catalyst in this reaction is tetrakis(triphenylphosphine)-palladium(0) or $PdCl_2(PPh_3)_2$. The preferred base is sodium carbonate employed as an aqueous solution. The reaction is carried out in organic solvents that are inert under the reaction conditions, such as 1,4-dioxane, acetonitrile, N,N-dimethylformamide (DMF) or dimethylsulfoxide (DMSO), or in water or in mixtures of these solvents. Preferably, the reaction is carried out in a mixture of 1,4-dioxane and water or acetonitrile and water. The reaction is generally performed at temperatures between +100° C. and +250° C., preferably at +110° C. to +150° C. Heating is preferably effected by singlemode microwave device. The reactions are usually run under an inert gas atmosphere, preferably under argon.

Compounds of the formula Ia

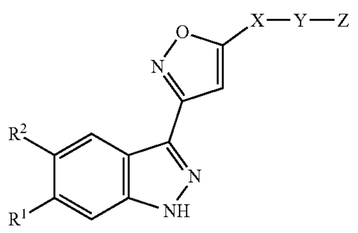

Ia in which $R^1$, $R^2$, X, Y and Z have the meanings indicated in formula I, can preferably be obtained by reacting a compound of the formula VI with a compound of the formula VII.

The starting compounds of the formula VI and VII are generally known. If they are novel, however, they can be prepared by methods known per se.

Compounds of the formula Ib

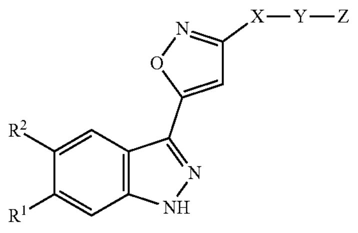

Ib in which $R^1$, $R^2$, X, Y and Z have the meanings indicated in formula I, can preferably be obtained by reacting a compound of the formula VIII with a compound of the formula IX.

The starting compounds of the formula VIII and IX are generally known. If they are novel, however, they can be prepared by methods known per se.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methyl-glutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, formate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese (III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion ex-changer resins, for example arginine, betaine, caffeine, chloroprocaine, choline, N,N'-dibenzylethylenediamine (benzathine), dicyclohexylamine, diethanolamine, diethylamine, 2-diethylamino-ethanol, 2-dimethylamino-ethanol, ethanolamine, ethylenediamine, N-ethylmorpholine, N-ethyl-piperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$)alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Isotopes

There is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other isotopes of other atoms is intended to be part of the present invention. An isotope-labelled compound of the formula I can be used in a number of beneficial ways. For example, an isotope-labelled compound of the formula I into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula I has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of the formula I can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a compound of the formula I that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t½), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is deter-mined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The invention furthermore relates to medicaments comprising at least one compound of the formula I and/or pharmaceutically acceptable salts, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like.

The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an ab-sorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and pharmaceutically salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, tautomers and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxy-ethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihy-droxypyrans, polycyanoacrylates and crosslinked or amphipathic block co-polymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

A combined treatment of this type can be achieved with the aid of simultaneous, consecutive or separate dispensing of the individual components of the treatment. Combination products of this type employ the compounds according to the invention.

The invention furthermore relates to medicaments comprising at least one compound of the formula I and/or pharmaceutically acceptable salts, tautomers and stereoisomers thereof, including mixtures thereof in all ratios, and at least one further medicament active ingredient.

The invention also relates to a set (kit) consisting of separate packs of (a) an effective amount of a compound of the formula I and/or pharmaceutically acceptable salts, tautomers and stereoisomers thereof, including mixtures thereof in all ratios,
and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically acceptable salts, tautomers and stereoisomers thereof, including mixtures thereof in all ratios, and an effective amount of a further medicament active ingredient in dissolved or lyophilised form.

“Treating” as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term “effective amount” in connection with a compound of formula I can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer or metabolic conditions.

In one embodiment an effective amount of a compound of formula I is an amount that inhibits c-KIT kinase in a cell, such as, for example, in vitro or in vivo. In some embodiments, the effective amount of the compound of formula I inhibits c-Kit in a cell by 10%, 20%, 30%, 40%, 50%, 60%, 70%, 80%, 90% or 99%, compared to the activity of c-KIT kinase in an untreated cell. The effective amount of the compound of formula I, for example in a pharmaceutical composition, may be at a level that will exercise the desired effect; for example, about 0.005 mg/kg of a subject’s body weight to about 10 mg/kg of a subject’s body weight in unit dosage for both oral and parenteral administration.

USE

The present compounds are suitable as pharmaceutical active ingredients for mammals, especially for humans, in the treatment of cancer, such as gastrointestinal stromal tumor.

The present invention encompasses the use of the compounds of the formula I and/or pharmaceutically acceptable salts, tautomers and stereoisomers thereof for the preparation of a medicament for the treatment or prevention of cancer, preferably for the treatment of gastrointestinal stromal tumor.

Preferably, the present invention relates to a method for treating a disease, wherein the disease is a cancer, preferably a gastrointestinal stromal tumor.

Particularly preferable, the present invention relates to a method wherein the disease is a cancer, wherein administration is simultaneous, sequential or in alternation with administration of at least one other active drug agent.

The disclosed compounds of the formula I can be administered in combination with other known therapeutic agents, including anticancer agents. As used here, the term “anticancer agent” relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating Agents
: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds
: such as carboplatin, cisplatin, eptaplatin, miriplatine hydrate, oxaliplatin, lobaplatin, nedaplatin, picoplatin, satraplatin;
: lobaplatin, nedaplatin, picoplatin, satraplatin;

DNA Altering Agents
: such as amrubicin, bisantrene, decitabine, mitoxantrone, procarbazine, trabectedin, clofarabine;
: amsacrine, brostallicin, pixantrone, laromustine[1,3];

Topoisomerase Inhibitors
: such as etoposide, irinotecan, razoxane, sobuzoxane, teniposide, topotecan; amonafide, belotecan, elliptinium acetate, voreloxin;

Microtubule Modifiers such as cabazitaxel, docetaxel, eribulin, ixabepilone, paclitaxel, vinblastine, vincristine, vinorelbine, vindesine, vinflunine;

fosbretabulin, tesetaxel;

Antimetabolites such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur;

doxifluridine, elacytarabine, raltitrexed, sapacitabine, tegafur[2,3], trimetrexate;

Anticancer Antibiotics such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin;

aclarubicin, peplomycin, pirarubicin;

Hormones/Antagonists such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol;

acolbifene, danazol, deslorelin, epitiostanol, orteronel, enzalutamide[1,3];

Aromatase Inhibitors such as aminoglutethimide, anastrozole, exemestane, fadrozole, letrozole, testolactone;

formestane;

Small Molecule Kinase Inhibitors such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib;

afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers such as methoxsalen[3];

porfimer sodium, talaporfin, temoporfin;

Antibodies such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3];

catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];

Cytokines such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates such as denileukin diftitox, ibritumomab tiuxetan, iobenguane I123, prednimustine, trastuzumab emtansine, estramustine, gemtuzumab, ozogamicin, aflibercept;

cintredekin besudotox, edotreotide, inotuzumab ozogamicin, naptumomab estafenatox, oportuzumab monatox, technetium (99mTc) arcitumomab[1,3], vintafolide[1,3];

Vaccines such as sipuleucel[3]; vitespen[3], emepepimut-S[3], oncoVAX[4], rindopepimut[3], troVax[4], MGN-16014, MGN-17034;

Miscellaneous alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat;

celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-17034;

[1] Prop. INN (Proposed International Nonproprietary Name)

[2] Rec. INN (Recommended International Nonproprietary Names)

[3] USAN (United States Adopted Name)

[4] no INN.

The following abbreviations refer respectively to the definitions below:

aq (aqueous), h (hour), g (gram), l (liter), mg (milligram), MHz (Megahertz), min. (minute), mm (millimeter), mmol (millimole), mM (millimolar), m.p. (melting point), eq (equivalent), ml (milliliter), μl (microliter), ACN (acetonitrile), AcOH (acetic acid), $CDCl_3$ (deuterated chloroform), $CD_3OD$ (deuterated methanol), $CH_3CN$ (acetonitrile), c-hex (cyclohexane), DCC (dicyclohexyl carbodiimide), DCM (dichloromethane), DIC (diisopropyl carbodiimide), DIPEA (diisopropylethyl-amine), DMF (dimethylformamide), DMSO (dimethylsulfoxide), DMSO-$d_6$ (deuterated dimethylsulfoxide), EDC (1-(3-dimethyl-amino-propyl)-3-ethylcarbodiimide), ESI (Electro-spray ionization), EtOAc (ethyl acetate), $Et_2O$ (diethyl ether), EtOH (ethanol), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), $K_2CO_3$ (potassium carbonate), LC (Liquid Chromatography), MeOH (methanol), $MgSO_4$ (magnesium sulfate), MS (mass spectrometry), MTBE (Methyl tert-butyl ether), $NaHCO_3$ (sodium bicarbonate), $NaBH_4$ (sodium borohydride), NMM (N-methyl morpholine), NMR (Nuclear Magnetic Resonance), PyBOP (benzotriazole-1-yl-oxy-tris-pyrrolidino-phosphonium hexafluorophosphate), RT (room temperature), Rt (retention time), SPE (solid phase extraction), TBTU (2-(1-H-benzotriazole-1-yl)-1,1,3,3-tetramethyl-uromium tetrafluoro borate), TEA (triethylamine), TFA (trifluoroacetic acid), THF (tetrahydrofuran), TLC (Thin Layer Chromatography), UPLC (Ultra Performance Liquid Chromatography), UV (Ultraviolet).

Above and below, all temperatures are indicated in ° C. $^1H$ NMR was recorded on Bruker DPX-300, DRX-400, AVII-400 or on a 500 MHz spectrometer, using residual signal of deuterated solvent as internal reference. Chemical shifts (δ) are reported in ppm relative to the residual solvent signal (δ=2.49 ppm for $^1H$ NMR in DMSO-$d_6$). $^1H$ NMR data are reported as follows: chemical shift (multiplicity, coupling constants, and number of hydrogens). Multiplicity is abbreviated as follows: s (singlet), d (doublet), t (triplet), q (quartet), m (multiplet), br (broad), bs (broad singlet), p (pentet).

HPLC/MS Conditions A:

HPLC/MS: Agilent 1200/6100
eluent A: water+0.05% formic acid
eluent B: acetonitrile+0.04% formic acid
column: Chromolith HR RP-18e; 50-4.6 mm
flow rate: 3.3 ml/min
gradient: 0%→100% B: 0.0→2.0 min 100% B: 2.0→2.5 min
UV detection: 220 nm
MS detection: 65-800 amu positive HPLC/MS Conditions B:

HPLC/MS: Agilent 1200/6100
eluent A: water+0.05% formic acid
eluent B: acetonitrile+0.04% formic acid
column: Kinetex XB-C18; 2.6 μm; 50-4.6 mm
flow rate: 2.5 ml/min
gradient: 0%→100% B: 0.0→1.4 min 100% B: 1.4→2.0 min
UV detection: 220 nm
MS detection: 65-800 amu positive UPLC/MS Conditions:

UPLC/MS: Waters Acquity/SQD
eluent A: water+0.05% formic acid
eluent B: acetonitrile+0.04% formic acid
column: Kinetex XB-C18; 1.7 μm; 50-2.1 mm
flow rate: 0.9 ml/min
gradient: 2%→100% B: 0.0→1.0 min 100% B: 1.0→1.3 min
UV detection: 220 nm/254 nm/MaxPlot/TotalPlot
MS detection: 61-800 amu positive Assays c-Kit(V654A) Assay:

c-Kit(V654A) (N-terminal GST-tagged, recombinant human c-Kit, amino acids 544-end containing the V654A mutation) is incubated with 8 mM MOPS pH 7.0, 0.2 mM EDTA, 250 μM GGMEDIYEFMGGKKK, 10 mM MgAcetate and [gamma-33P-ATP] (specific activity approx. 500 cpm/pmol, concentration 200 μM). The reaction is initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

Assay Principle for Cellular Testing of cKIT Mutant Inhibitors

The GIST430/654 cell line expressing mutated constitutively active cKIT receptor tyrosine kinase (Δ560-576 and V654A) was employed for assessing cellular potency of compounds. Cellular activity of mutant cKIT was determined by the degree of cKIT autophosphorylation at tyrosine 307 using a Luminex-based bead assay. GIST430/654 cells were plated with 25,000 cells per well of a 96-well plate in 100 μl medium (85% IMDM/15% FCS supplemented with 100 nM Imatinib). At the following day compounds were added in a serial dilution for 45 min. Then, cells were lysed with 90 μl lysis buffer (20 mM Hepes pH 7.5, 200 mM NaCl, 1.5 mM MgCl2×6H2O, 0.4 mM EDTA, 1% Triton-X-100, 1% Phosphatase-Inhibitor II, 20 mM β-Glycerolphosphat, 0.1% Protease-Inhibitor Cocktail III, 0.01% Benzonase) und lysates were cleared by centrifugation through a 96-well filter plate (0.65 μm). Samples were incubated with Luminex-beads which were coupled with an anti-total cKIT antibody overnight at 4° C. under gentle agitation. For detection of phospho-Y307-cKIT a phospho-specific antibody and a species-specific PE-labelled secondary antibody were added. The amount of phospho-Y307-cKIT was determined in a Luminex 200 instrument measuring 100 events per well within 60 seconds.

Counts from samples treated with compounds were calculated as percent of control from solvent treated (0.3% DMSO) samples. Dose-response curves were fitted and $IC_{50}$ values were determined using Genedata Screener software.

Pharmacological Data

TABLE 1

Inhibition ($IC_{50}$) of c-KIT (V654A) and GIST 430/654 of compounds of the formula I

| Compound No. | c-KIT (V654A) $IC_{50}$ [M] | GIST 430/654 $IC_{50}$ [M] | Compound No. | c-KIT (V654A) [M] | GIST 430/654 $IC_{50}$ [M] |
|---|---|---|---|---|---|
| "A1" | 1.5E−08 | 3.5E−07 | "A81" | 6E−09 | 2.1E−07 |
| "A2" | 4.8E−09 | 2.5E−07 | "A82" | 9.8E−09 | 4.2E−07 |
| "A3" | 1.4E−09 | 3.8E−08 | "A83" | 7.6E−08 | |
| "A4" | 1.3E−08 | 3.3E−07 | "A84" | 3.5E−08 | 1.8E−06 |
| "A5" | 5.5E−10 | 2E−08 | "A85" | 6.3E−10 | 1.3E−07 |
| "A6" | 4.1E−09 | 1.5E−07 | "A86" | 6.9E−08 | |
| "A7" | 7.5E−10 | 4E−08 | "A87" | 3.8E−08 | 5.9E−07 |
| "A8" | 2E−08 | 2.8E−07 | "A88" | 2.3E−09 | 1.7E−07 |
| "A9" | 8.8E−09 | 1.3E−07 | "A89" | 5.7E−10 | 3.2E−07 |
| "A10" | 1.6E−09 | 1.8E−07 | "A90" | 4.7E−10 | 1.2E−07 |
| "A11" | 2.4E−09 | 1.7E−07 | "A91" | 7.2E−09 | 2.9E−07 |
| "A12" | 9.1E−10 | 1.6E−07 | "A92" | 5.5E−08 | 3.6E−07 |
| "A13" | 1.1E−08 | 3E−07 | "A93" | 5.3E−08 | 3.9E−07 |
| "A14" | 8.8E−09 | 5.1E−07 | "A94" | 5.8E−10 | 1E−07 |
| "A15" | 5.8E−09 | 2.4E−07 | "A95" | 9.1E−10 | 3.7E−08 |
| "A16" | 4.8E−09 | 9.4E−08 | "A96" | 2.1E−08 | 7.4E−07 |
| "A17" | 5.3E−09 | 1.3E−07 | "A97" | 9.7E−10 | 4.1E−08 |
| "A18" | 8.2E−09 | 1.6E−07 | "A98" | 1.5E−08 | 8.6E−07 |
| "A19" | 8.2E−09 | | "A99" | 6.9E−09 | 6.7E−07 |
| "A20" | 1.7E−09 | 4.8E−08 | "A100" | 5.7E−09 | 3.4E−07 |
| "A21" | 1.2E−08 | 5.7E−07 | "A101" | 9.4E−10 | 1.6E−07 |
| "A22" | 3.2E−08 | 2.2E−06 | "A102" | 1.3E−09 | 1.6E−07 |
| "A23" | 1E−08 | | "A103" | 9.6E−10 | 1.4E−07 |
| "A24" | 8.8e−08 | | "A104" | 7.9E−10 | 5.8E−08 |
| "A25" | 3E−08 | 5.7E−06 | "A105" | 1.2E−09 | 1.4E−07 |
| "A26" | 2.1E−09 | 4.5E−08 | "A106" | 7E−10 | 7.7E−08 |
| "A27" | 1.2E−09 | 5.7E−08 | "A107" | 5.6E−09 | 5.3E−08 |
| "A28" | 2E−09 | 3.9E−08 | "A108" | 8.1E−10 | 5.6E−08 |
| "A29" | 9.5E−10 | 3.9E−07 | "A109" | 9.1E−09 | 4.3E−07 |
| "A30" | 7.3E−10 | 5.6E−08 | "A110" | 7.6E−10 | 5E−08 |
| "A31" | 1.1E−09 | 3.5E−08 | "A111" | 1.2E−09 | 6.2E−08 |
| "A32" | 9.1E−10 | 3.9E−08 | "A112" | 1.3E−09 | 3.2E−08 |
| "A33" | 1.3E−09 | 6.1E−08 | "A113" | 2.6E−09 | 8.2E−08 |
| "A34" | 8.3E−10 | 1.2E−07 | "A114" | 9.1E−10 | 5.6E−08 |
| "A35" | 6.3E−09 | 1.7E−07 | "A115" | 8.3E−10 | 4.5E−08 |
| "A36" | 1.2E−09 | 1.2E−07 | "A116" | 4.1E−09 | 1.2E−07 |
| "A37" | 2E−09 | 7.9E−08 | "A117" | 3.6E−09 | 1E−07 |
| "A38" | 3.5E−08 | 4.4E−06 | "A118" | 7.1E−09 | 6.4E−07 |
| "A39" | 1.7E−09 | 1.5E−07 | "A119" | 1.2E−08 | 3.4E−07 |
| "A40" | 2.7E−09 | 1.4E−07 | "A120" | 6.4E−10 | 2.4E−08 |
| "A41" | 3.1E−09 | 1.2E−07 | "A121" | 6E−10 | 4.2E−08 |
| "A42" | 7.3E−10 | 1.7E−07 | "A122" | 5.4E−08 | |
| "A43" | 2.2E−09 | 1.2E−07 | "A123" | 3.9E−10 | 3.8E−08 |
| "A44" | 1.1E−09 | 4.1E−08 | "A124" | 3.5E−10 | 8.5E−08 |
| "A45" | 1.2E−09 | 5.9E−08 | "A125" | 1.9E−09 | 2.3E−07 |
| "A46" | 9.6E−10 | 5.8E−08 | "A126" | 1.7E−09 | 2E−07 |
| "A47" | 2.4E−09 | 7.7E−08 | "A127" | 3.7E−10 | 2.4E−08 |
| "A48" | 1.3E−08 | | "A128" | 7.9E−10 | 1E−07 |
| "A49" | 1.9E−09 | 5E−07 | "A129" | 1.7E−09 | 8E−08 |
| "A50" | 1.4E−08 | 7.3E−07 | "A130" | 2.7E−08 | |
| "A51" | 8.8E−10 | 5.7E−08 | "A131" | 3E−09 | 6.5E−08 |
| "A52" | 8.2E−10 | 5.5E−08 | "A132" | 1.6E−09 | 9.3E−08 |
| "A53" | 1.4E−09 | 1.5E−08 | "A133" | 1E−09 | 1.3E−07 |
| "A54" | 7.3E−10 | 1.3E−07 | "A134" | 1.5E−09 | 1.5E−07 |
| "A55" | 7.3E−10 | 6.5E−08 | "A135" | 4.9E−09 | 3.4E−07 |
| "A56" | 1.6E−09 | 1.7E−07 | "A136" | 5.9E−09 | 1.4E−07 |
| "A57" | 1.9E−09 | 1.8E−07 | "A137" | 7.6E−09 | 1.8E−07 |
| "A58" | 7.8E−10 | 5.2E−08 | "A138" | 6.4E−09 | 1.6E−07 |
| "A59" | 5.1E−10 | 3.3E−08 | "A139" | 1.2E−09 | 6.8E−08 |
| "A60" | 4.4E−10 | 2.8E−08 | "A140" | 1.6E−09 | 4.6E−08 |
| "A61" | 5.5E−09 | 1.1E−07 | "A141" | 7.7E−09 | 2.2E−07 |
| "A62" | 5.6E−09 | 4.5E−07 | "A142" | 6E−09 | 7.5E−08 |
| "A63" | 5.7E−09 | 2.9E−07 | "A143" | 1.8E−08 | 8.6E−07 |
| "A64" | 5.3E−10 | 3.2E−08 | "A144" | 3.2E−09 | 1.9E−06 |
| "A65" | 8.9E−10 | 1.6E−07 | "A145" | 4.8E−09 | 1.1E−06 |
| "A66" | 6.5E−10 | 5.2E−08 | "A146" | 2.9E−09 | 9E−08 |

TABLE 1-continued

Inhibition ($IC_{50}$) of c-KIT (V654A) and GIST 430/654 of compounds of the formula I

| Compound No. | c-KIT (V654A) $IC_{50}$ [M] | GIST 430/654 $IC_{50}$ [M] | Compound No. | c-KIT (V654A) [M] | GIST 430/654 $IC_{50}$ [M] |
|---|---|---|---|---|---|
| "A67" | 8.8E−10 | 9.4E−08 | "A147" | 2.2E−09 | 6.7E−08 |
| "A68" | 1.6E−08 | 8.7E−07 | "A148" | 1.8E−09 | 7E−08 |
| "A69" | 2E−08 | 1.9E−07 | "A149" | 6.9E−10 | 4.6E−08 |
| "A70" | 2.1E−09 | 8.1E−08 | "A150" | 1.7E−09 | 1.1E−07 |
| "A71" | 4.3E−09 | 9E−08 | "A151" | 7.1E−10 | 2.4E−07 |
| "A72" | 2.6E−09 | 3.2E−07 | "A152" | 8.8E−10 | 6.4E−08 |
| "A73" | 4E−09 | 4.3E−07 | "A153" | 8.3E−10 | 4.6E−08 |
| "A74" | 1.3E−09 | 5.2E−08 | "A154" | 8.9E−10 | 1.1E−07 |
| "A75" | 1.4E−09 | 5.9E−08 | "A155" | 1.6E−09 | 6E−08 |
| "A76" | 2E−09 | 7.9E−08 | "A156" | 5.2E−09 | 3.5E−07 |
| "A77" | 1E−09 | 4.7E−08 | "A157" | 4.4E−10 | 2.3E−08 |
| "A78" | 7.6E−10 | 1.6E−07 | "A158" | 4.6E−10 | 3.2E−08 |
| "A79" | 1.1E−09 | 1.7E−07 | "A159" | 2.9E−10 | 2.1E−08 |
| "A80" | 9.9E−10 | 4.6E−07 | "A160" | 2.5E−09 | 1.7E−07 |
| "A161" | 4.5E−10 | 4E−08 | "A171" | 1.4E−09 | 6.3E−08 |
| "A162" | 6.5E−10 | 4.4E−08 | "A172" | 8.9E−10 | 5.4E−08 |
| "A163" | 5.4E−10 | 3.8E−08 | "A173" | 1.1E−09 | 3E−08 |
| "A164" | 1.5E−09 | 1.3E−07 | "A174" | 1.3E−09 | 3.5E−08 |
| "A165" | 5.3E−10 | 2.7E−08 | "A175" | 8.6E−10 | 4.3E−08 |
| "A166" | 9.6E−10 | 8.7E−08 | "A176" | 2.6E−09 | 3.2E−07 |
| "A167" | 4E−10 | 7.4E−08 | "A177" | 1E−09 | 6.5E−08 |
| "A168" | 3.3E−09 | 4.9E−08 | "A178" | 1.1E−09 | 6.2E−08 |
| "A169" | 1.2E−09 | 4.4E−08 | "A179" | 5.9E−10 | 8.5E−08 |
| "A170" | 2.6E−09 | 1.2E−07 | "A180" | 2E−09 | 6.6E−08 |
| "A181" | 1E−09 | 4E−08 | "A191" | 1.8E−09 | 5.8E−08 |
| "A182" | 9.4E−10 | 3.8E−08 | "A192" | 4.5E−10 | 1.4E−08 |
| "A183" | 5.5E−10 | 1.8E−08 | "A193" | 2.5E−09 | 7.3E−08 |
| "A184" | 1.1E−09 | 1.2E−07 | "A194" | 7.8E−10 | 4.4E−08 |
| "A185" | 1.1E−09 | 6E−08 | "A195" | 1.4E−08 | 7.1E−07 |

TABLE 1-continued

Inhibition ($IC_{50}$) of c-KIT (V654A) and GIST 430/654 of compounds of the formula I

| Compound No. | c-KIT (V654A) $IC_{50}$ [M] | GIST 430/654 $IC_{50}$ [M] | Compound No. | c-KIT (V654A) [M] | GIST 430/654 $IC_{50}$ [M] |
|---|---|---|---|---|---|
| "A186" | 1.1E−09 | 4.8E−08 | "A196" | 3.8E−09 | 4.8E−08 |
| "A187" | 1.4E−09 | 2.9E−07 | "A197" | 1.9E−09 | 8.7E−08 |
| "A188" | 6.1E−10 | 3.4E−08 | "A198" | 9.2E−10 | 7.3E−08 |
| "A189" | 1.9E−09 | 4.8E−08 | "A199" | 7.6E−10 | 2.8E−08 |
| "A190" | 1.6E−09 | 5.5E−08 | "A200" | 1.3E−09 | 1.9E−08 |
| "A201" | 2E−09 | 3.1E−08 | "A211" | 1.3E−09 | 3.9E−08 |
| "A202" | 1.1E−09 | 1.9E−08 | "A212" | 5.9E−10 | 4.1E−08 |
| "A203" | 1.4E−09 | 5.6E−07 | "A213" | 4.9E−10 | 4.8E−08 |
| "A204" | 8.8E−10 | 6.1E−08 | "A214" | 4.4E−10 | 3.7E−08 |
| "A205" | 2.3E−08 | 1.3E−07 | "A215" | 7.6E−10 | 3.5E−08 |
| "A206" | 6.7E−10 | 7.9E−08 | "A216" | 1.1E−09 | 2.7E−08 |
| "A207" | 1E−09 | 7.3E−08 | "A217" | 3.2E−10 | 4.3E−08 |
| "A208" | 7.4E−10 | 7.5E−08 | "A218" | 6.2E−10 | 4.7E−08 |
| "A209" | 8.6E−10 | 1.2E−07 | "A219" | 8E−09 | 2.8E−07 |
| "A210" | 8E−10 | 3E−08 | "A220" | 2.2E−09 | 1.6E−07 |
| "A221" | 5.4E−10 | 1.2E−07 | "A231" | 6.1E−10 | 5.2E−08 |
| "A222" | 5.2E−10 | 1.1E−07 | "A232" | 0.9E−10 | 1.0E−07 |
| "A223" | 1.1E−09 | 3.8E−07 | "A233" | 1.0E−09 | 7.6E−08 |
| "A224" | 1.1E−09 | 2.5E−07 | "A234" | 9E−10 | 1.7E−07 |
| "A225" | 3.1E−09 | 3.4E−07 | | | |
| "A226" | 2E−09 | 1.5E−07 | | | |
| "A227" | 3E−09 | 1.7E−07 | | | |
| "A228" | 5.7E−07 | 4.7E−07 | | | |
| "A229" | 4.7E−08 | 1.1E−06 | | | |
| "A230" | 4E−10 | 1.1E−07 | | | |

Explanation: 1,4E-06 means $1.4\times10^{-6}$

The compounds shown in Table 1 are particularly preferred compounds according to the invention.

TABLE 2

Inhibition ($IC_{50}$) of c-KIT (V654A) and GIST 430/654 of some representative compounds of the formula I in comparison to the corresponding triazole derivatives

| isoxazole derivatives presently claimed | | | | triazole derivatives | | |
|---|---|---|---|---|---|---|
| Nr. | structure | c-Kit (V654A) $IC_{50}$ [M] | GIST 430/654 $IC_{50}$ [M] | structure | c-Kit (V654A) $IC_{50}$ [M] | GIST 430/654 $IC_{50}$ [M] |
| "A115" | 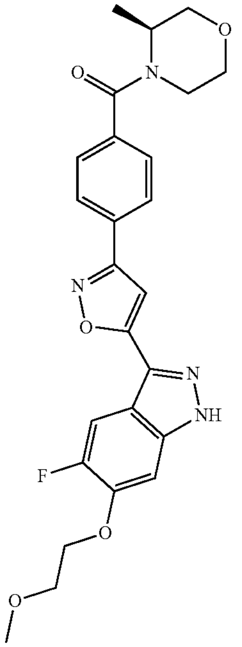 [SMILES: COCCOc1cc2[nH]nc(-c3cc(-c4ccc(C(=O)N5CCOC[C@@H]5C)cc4)no3)c2cc1F] | 8.3E−10 | 4.5E−08 | 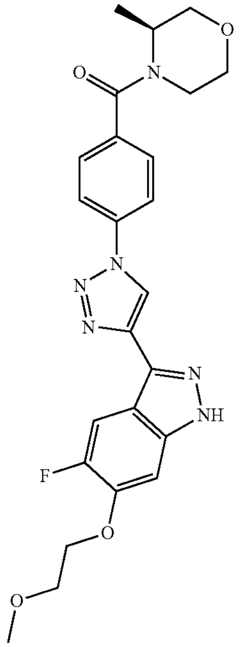 [SMILES: COCCOc1cc2[nH]nc(-c3cn(-c4ccc(C(=O)N5CCOC[C@@H]5C)cc4)nn3)c2cc1F] | 6.9E−09 | 2.3E−07 |

TABLE 2-continued
Inhibition ($IC_{50}$) of c-KIT (V654A) and GIST 430/654 of some representative compounds of the formula I in comparison to the corresponding triazole derivatives
| | isoxazole derivatives presently claimed | | | triazole derivatives | | |
|---|---|---|---|---|---|---|
| Nr. | structure | c-Kit (V654A) $IC_{50}$ [M] | GIST 430/654 $IC_{50}$ [M] | structure | c-Kit (V654A) $IC_{50}$ [M] | GIST 430/654 $IC_{50}$ [M] |
| "A5" | 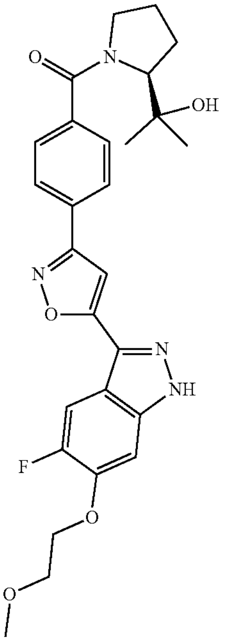 [SMILES: COCCOc1cc2[nH]nc(-c3cc(-c4ccc(C(=O)N5CCC[C@H]5C(C)(C)O)cc4)no3)c2cc1F] | 5.5E−10 | 2E−08 | 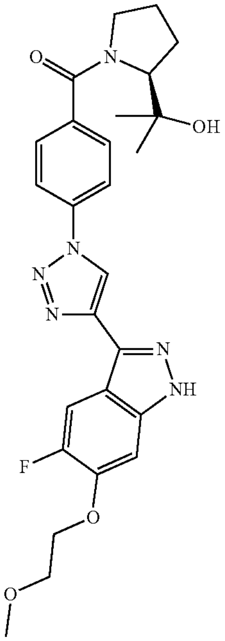 [SMILES: COCCOc1cc2[nH]nc(-c3cn(-c4ccc(C(=O)N5CCC[C@H]5C(C)(C)O)cc4)nn3)c2cc1F] | 2.5E−09 | 7.9E−08 |
| "A36" | 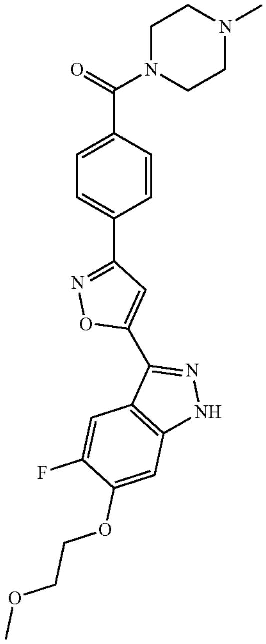 | 1.2E−09 | 1.2E−07 | 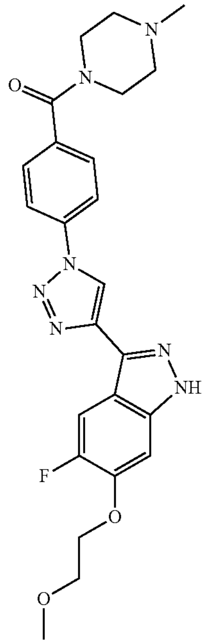 [SMILES: COCCOc1cc2[nH]nc(-c3cn(-c4ccc(C(=O)N5CCN(C)CC5)cc4)nn3)c2cc1F] | 1.5E−08 | 8.4E−07 |

TABLE 2-continued
| Inhibition ($IC_{50}$) of c-KIT (V654A) and GIST 430/654 of some representative compounds of the formula I in comparison to the corresponding triazole derivatives | | | | | | |
|---|---|---|---|---|---|---|
| | isoxazole derivatives presently claimed | | | triazole derivatives | | |
| Nr. | structure | c-Kit (V654A) $IC_{50}$ [M] | GIST 430/654 $IC_{50}$ [M] | structure | c-Kit (V654A) $IC_{50}$ [M] | GIST 430/654 $IC_{50}$ [M] |
| "A104" | 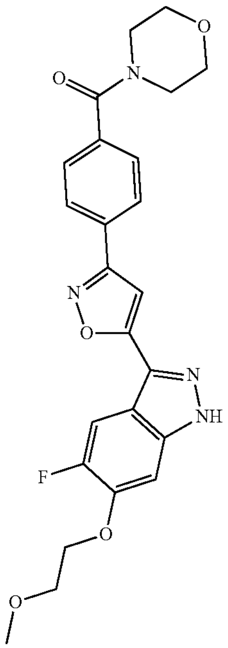 [SMILES: COCCOc1cc2[nH]nc(-c3cc(-c4ccc(C(=O)N5CCOCC5)cc4)no3)c2cc1F] | 7.9E−10 | 5.8E−08 | 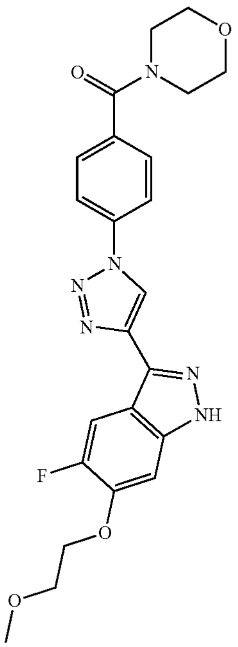 [SMILES: COCCOc1cc2[nH]nc(-c3cn(-c4ccc(C(=O)N5CCOCC5)cc4)nn3)c2cc1F] | 2.4E−08 | 4.9E−07 |
| "A114" | 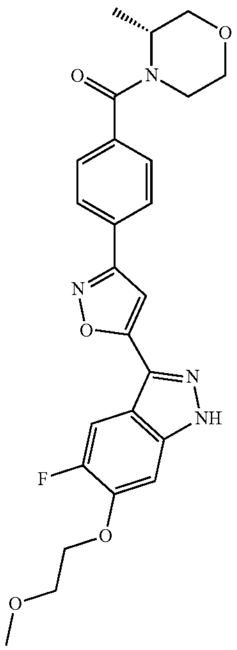 [SMILES: COCCOc1cc2[nH]nc(-c3cc(-c4ccc(C(=O)N5CCOC[C@H]5C)cc4)no3)c2cc1F] | 9.1E−10 | 5.6E−08 | 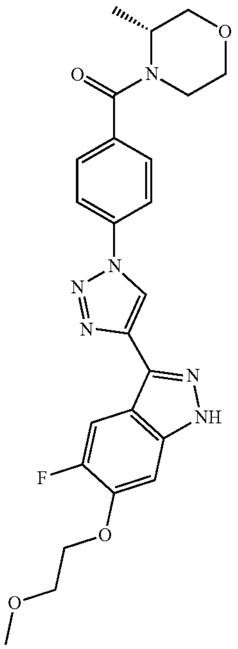 [SMILES: COCCOc1cc2[nH]nc(-c3cn(-c4ccc(C(=O)N5CCOC[C@H]5C)cc4)nn3)c2cc1F] | 4.3E−09 | 2.3E−07 |

TABLE 2-continued
Inhibition ($IC_{50}$) of c-KIT (V654A) and GIST 430/654 of some representative compounds of the formula I in comparison to the corresponding triazole derivatives
| | isoxazole derivatives presently claimed | | | triazole derivatives | | |
|---|---|---|---|---|---|---|
| Nr. | structure | c-Kit (V654A) $IC_{50}$ [M] | GIST 430/654 $IC_{50}$ [M] | structure | c-Kit (V654A) $IC_{50}$ [M] | GIST 430/654 $IC_{50}$ [M] |
| "A20" | 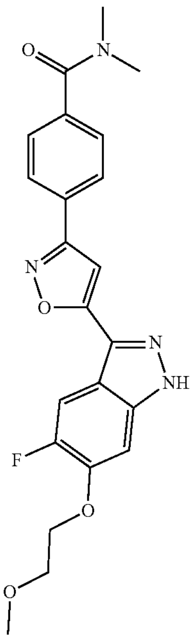 [SMILES: COCCOc1cc2[nH]nc(-c3cc(-c4ccc(C(=O)N(C)C)cc4)no3)c2cc1F] | 1.7E−09 | 4.8E−08 | 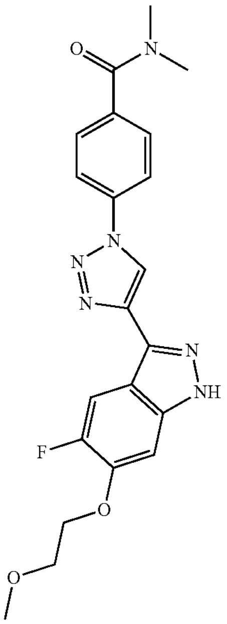 [SMILES: COCCOc1cc2[nH]nc(-c3cn(-c4ccc(C(=O)N(C)C)cc4)nn3)c2cc1F] | 1.1E−08 | 1.4E−06 |
| "A3" | 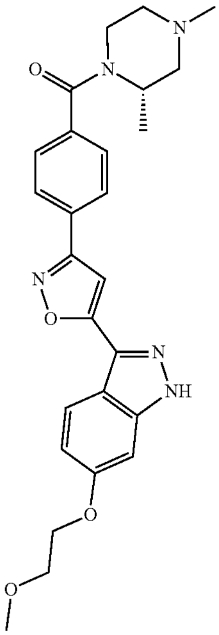 | 1.4E−09 | 3.8E−08 | 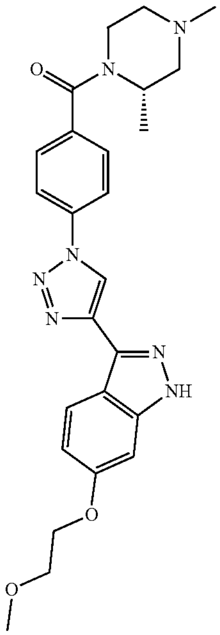 | 6.1E−09 | 3.2E−07 |

TABLE 2-continued
Inhibition ($IC_{50}$) of c-KIT (V654A) and GIST 430/654 of some representative compounds of the formula I in comparison to the corresponding triazole derivatives
| | isoxazole derivatives presently claimed | | | triazole derivatives | | |
|---|---|---|---|---|---|---|
| Nr. | structure | c-Kit (V654A) $IC_{50}$ [M] | GIST 430/654 $IC_{50}$ [M] | structure | c-Kit (V654A) $IC_{50}$ [M] | GIST 430/654 $IC_{50}$ [M] |
| "A230" | 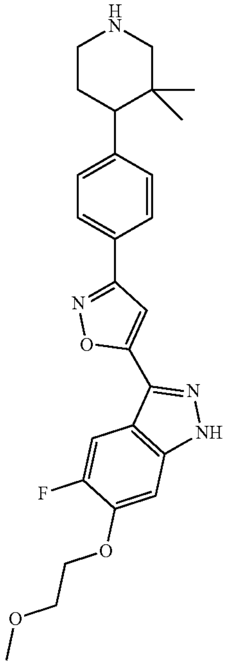 [SMILES: COCCOc1cc2[nH]nc(-c3cc(-c4ccc(C5CCNCC5(C)C)cc4)no3)c2cc1F] | 4E−10 | 1.1E−07 | 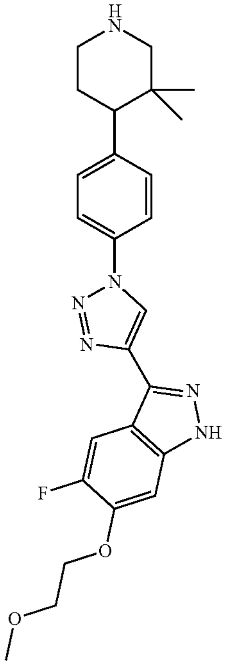 [SMILES: COCCOc1cc2[nH]nc(-c3cn(-c4ccc(C5CCNCC5(C)C)cc4)nn3)c2cc1F] | 2.1E−08 | 1.2E−07 |
| "A37" | 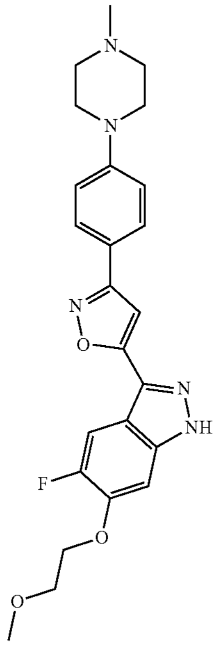 [SMILES: COCCOc1cc2[nH]nc(-c3cc(-c4ccc(N5CCN(C)CC5)cc4)no3)c2cc1F] | 2E−09 | 7.9E−08 | 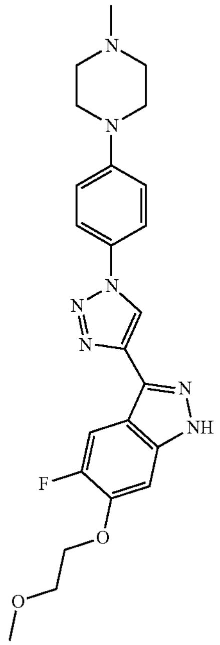 [SMILES: COCCOc1cc2[nH]nc(-c3cn(-c4ccc(N5CCN(C)CC5)cc4)nn3)c2cc1F] | 1.5E−08 | 1.0E−06 |

TABLE 2-continued
Inhibition ($IC_{50}$) of c-KIT (V654A) and GIST 430/654 of some representative compounds of the formula I in comparison to the corresponding triazole derivatives
| | isoxazole derivatives presently claimed | | | triazole derivatives | | |
|---|---|---|---|---|---|---|
| Nr. | structure | c-Kit (V654A) $IC_{50}$ [M] | GIST 430/654 $IC_{50}$ [M] | structure | c-Kit (V654A) $IC_{50}$ [M] | GIST 430/654 $IC_{50}$ [M] |
| "A28" | 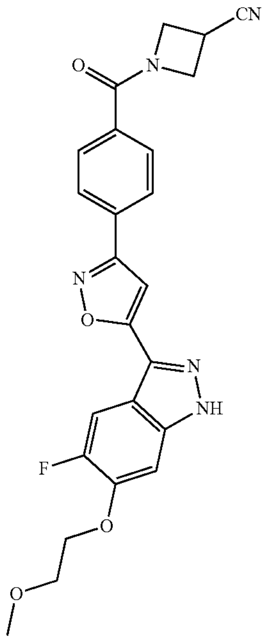 [SMILES: COCCOc1cc2[nH]nc(-c3cc(-c4ccc(C(=O)N5CC(C#N)C5)cc4)no3)c2cc1F] | 2E−09 | 3.9E−08 | 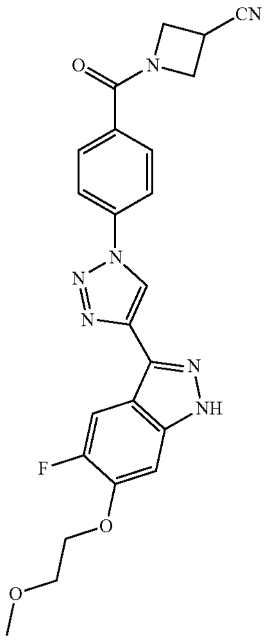 [SMILES: COCCOc1cc2[nH]nc(-c3cn(-c4ccc(C(=O)N5CC(C#N)C5)cc4)nn3)c2cc1F] | 1.3E−08 | 2.2E−06 |
| "A26" | 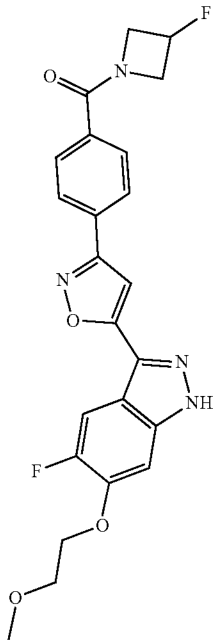 [SMILES: COCCOc1cc2[nH]nc(-c3cc(-c4ccc(C(=O)N5CC(F)C5)cc4)no3)c2cc1F] | 2.1E−09 | 4.5E−08 | 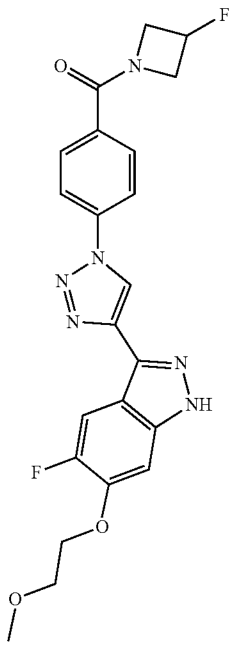 [SMILES: COCCOc1cc2[nH]nc(-c3cn(-c4ccc(C(=O)N5CC(F)C5)cc4)nn3)c2cc1F] | 1.1E−08 | 5.8E−07 |

TABLE 2-continued
| Inhibition ($IC_{50}$) of c-KIT (V654A) and GIST 430/654 of some representative compounds of the formula I in comparison to the corresponding triazole derivatives | | | | | | |
|---|---|---|---|---|---|---|
| isoxazole derivatives presently claimed | | | | triazole derivatives | | |
| Nr. | structure | c-Kit (V654A) $IC_{50}$ [M] | GIST 430/654 $IC_{50}$ [M] | structure | c-Kit (V654A) $IC_{50}$ [M] | GIST 430/654 $IC_{50}$ [M] |
| "A51" | 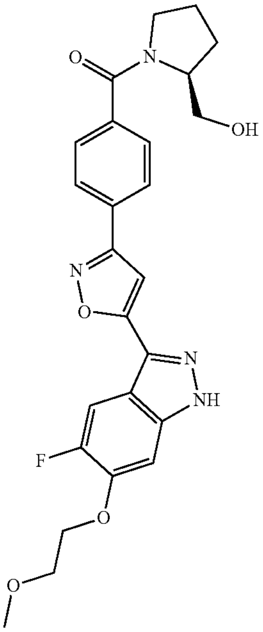 [SMILES: COCCOc1cc2[nH]nc(-c3cc(-c4ccc(C(=O)N5CCC[C@H]5CO)cc4)no3)c2cc1F] | 8.8E−10 | 5.7E−08 | 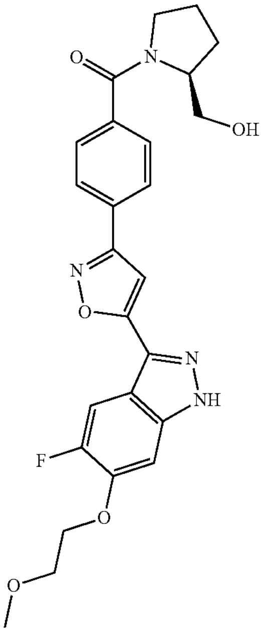 [SMILES: COCCOc1cc2[nH]nc(-c3cc(-c4ccc(C(=O)N5CCC[C@H]5CO)cc4)no3)c2cc1F] | 8.5E−09 | 9.1E−07 |
| "A53" | 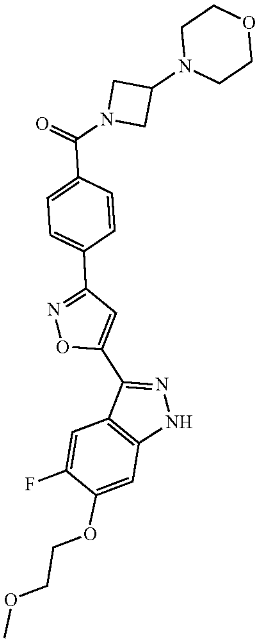 [SMILES: COCCOc1cc2[nH]nc(-c3cc(-c4ccc(C(=O)N5CC(N6CCOCC6)C5)cc4)no3)c2cc1F] | 1.4E−09 | 1.5E−08 | 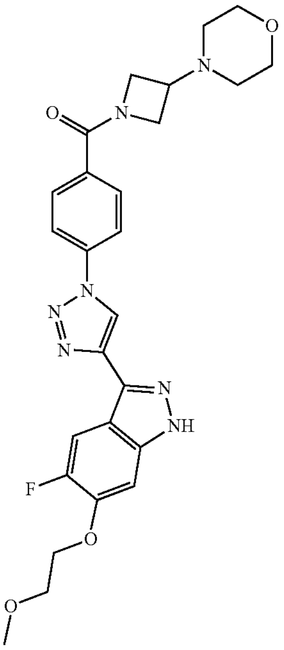 [SMILES: COCCOc1cc2[nH]nc(-c3cn(-c4ccc(C(=O)N5CC(N6CCOCC6)C5)cc4)nn3)c2cc1F] | 1.1E−09 | 6.1E−07 |

TABLE 2-continued
| Inhibition ($IC_{50}$) of c-KIT (V654A) and GIST 430/654 of some representative compounds of the formula I in comparison to the corresponding triazole derivatives | | | | | | |
| --- | --- | --- | --- | --- | --- | --- |
| isoxazole derivatives presently claimed | | | | triazole derivatives | | |
| Nr. | structure | c-Kit (V654A) $IC_{50}$ [M] | GIST 430/654 $IC_{50}$ [M] | structure | c-Kit (V654A) $IC_{50}$ [M] | GIST 430/654 $IC_{50}$ [M] |
| "A58" | 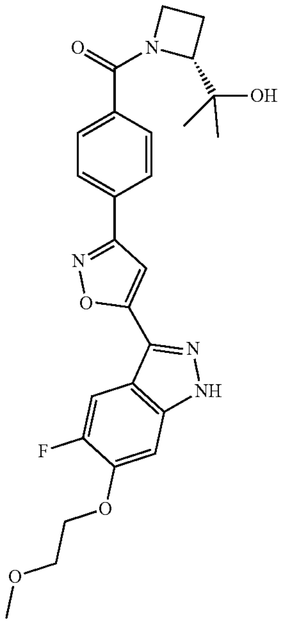 [SMILES: COCCOc1cc2[nH]nc(-c3cc(-c4ccc(C(=O)N5CC[C@@H]5C(C)(C)O)cc4)no3)c2cc1F] | 7.8E−10 | 5.2E−08 | 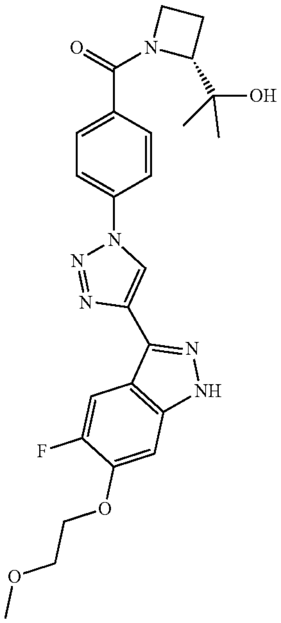 [SMILES: COCCOc1cc2[nH]nc(-c3cn(-c4ccc(C(=O)N5CC[C@@H]5C(C)(C)O)cc4)nn3)c2cc1F] | 5.1E−09 | 2.2E−07 |
| "A59" | 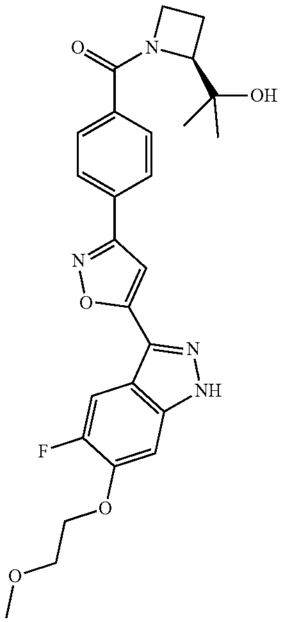 [SMILES: COCCOc1cc2[nH]nc(-c3cc(-c4ccc(C(=O)N5CC[C@H]5C(C)(C)O)cc4)no3)c2cc1F] | 5.1E−10 | 3.3E−08 | 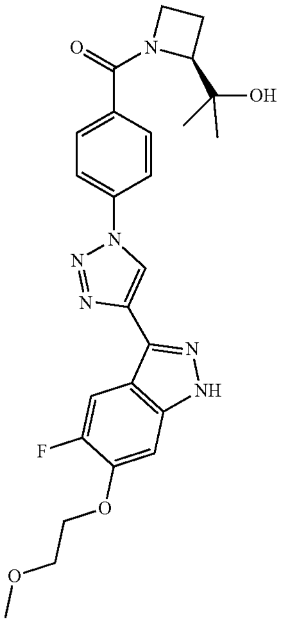 [SMILES: COCCOc1cc2[nH]nc(-c3cn(-c4ccc(C(=O)N5CC[C@H]5C(C)(C)O)cc4)nn3)c2cc1F] | 7.5E−09 | 2.4E−07 |

TABLE 2-continued
Inhibition ($IC_{50}$) of c-KIT (V654A) and GIST 430/654 of some representative compounds of the formula I in comparison to the corresponding triazole derivatives
| | isoxazole derivatives presently claimed | | | triazole derivatives | | |
|---|---|---|---|---|---|---|
| Nr. | structure | c-Kit (V654A) $IC_{50}$ [M] | GIST 430/654 $IC_{50}$ [M] | structure | c-Kit (V654A) $IC_{50}$ [M] | GIST 430/654 $IC_{50}$ [M] |
| "A171" | 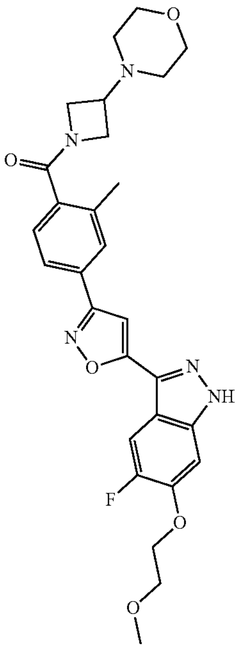 [SMILES: COCCOc1cc2[nH]nc(-c3cc(-c4ccc(C(=O)N5CC(N6CCOCC6)C5)c(C)c4)no3)c2cc1F] | 1.4E−09 | 6.3E−08 | 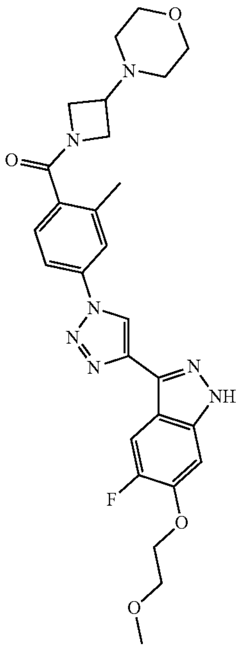 [SMILES: COCCOc1cc2[nH]nc(-c3cn(-c4ccc(C(=O)N5CC(N6CCOCC6)C5)c(C)c4)nn3)c2cc1F] | 1.3E−08 | 8.7E−07 |
| "A168" | 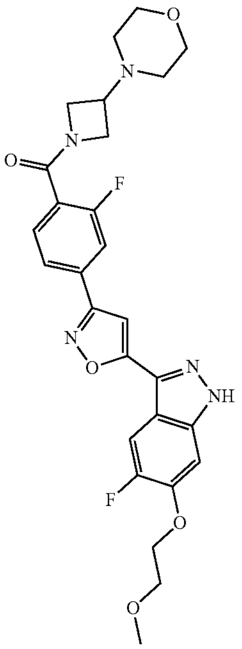 [SMILES: COCCOc1cc2[nH]nc(-c3cc(-c4ccc(C(=O)N5CC(N6CCOCC6)C5)c(F)c4)no3)c2cc1F] | 3.3E−09 | 4.9E−08 | 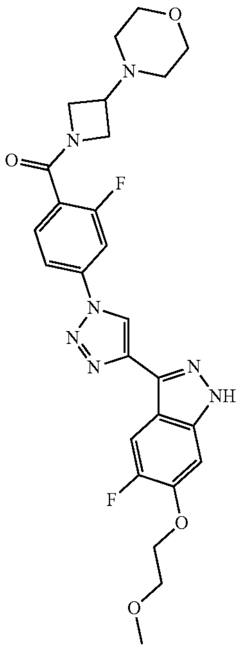 [SMILES: COCCOc1cc2[nH]nc(-c3cn(-c4ccc(C(=O)N5CC(N6CCOCC6)C5)c(F)c4)nn3)c2cc1F] | 2.0E−08 | 7.0E−07 |

TABLE 2-continued
| Inhibition ($IC_{50}$) of c-KIT (V654A) and GIST 430/654 of some representative compounds of the formula I in comparison to the corresponding triazole derivatives | | | | | | |
|---|---|---|---|---|---|---|
| | isoxazole derivatives presently claimed | | | triazole derivatives | | |
| Nr. | structure | c-Kit (V654A) $IC_{50}$ [M] | GIST 430/654 $IC_{50}$ [M] | structure | c-Kit (V654A) $IC_{50}$ [M] | GIST 430/654 $IC_{50}$ [M] |
| "A183" | 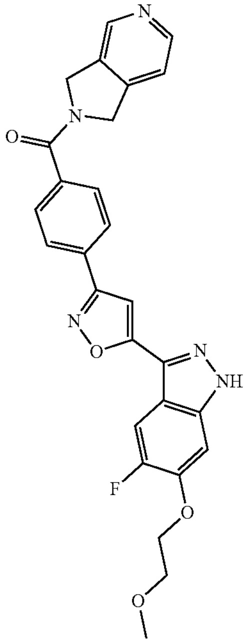 [SMILES: COCCOc1cc2[nH]nc(-c3cc(-c4ccc(C(=O)N5Cc6ccncc6C5)cc4)no3)c2cc1F] | 5.5E−10 | 1.8E−08 | 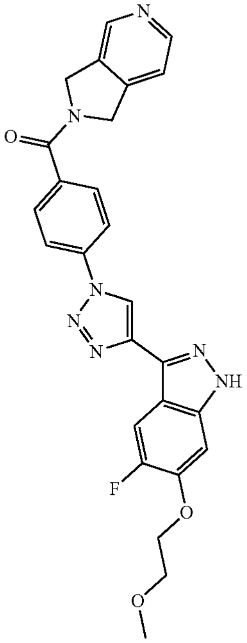 [SMILES: COCCOc1cc2[nH]nc(-c3cn(-c4ccc(C(=O)N5Cc6ccncc6C5)cc4)nn3)c2cc1F] | 2.3E−09 | 1.4E−07 |
| "A202" | 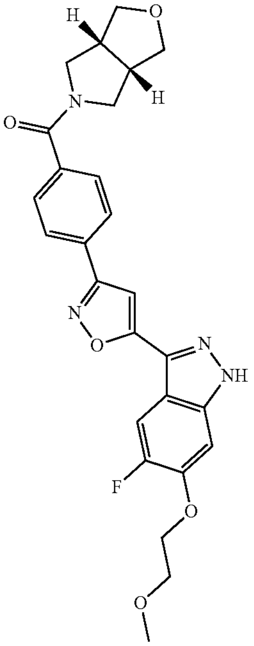 [SMILES: COCCOc1cc2[nH]nc(-c3cc(-c4ccc(C(=O)N5C[C@H]6COC[C@H]6C5)cc4)no3)c2cc1F] | 1.1E−09 | 1.9E−08 | 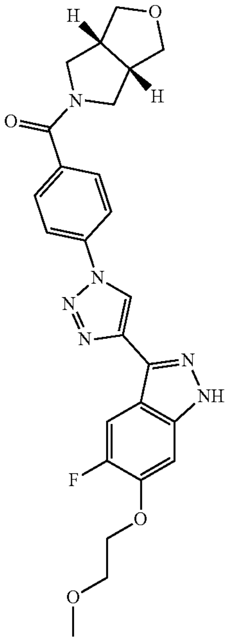 [SMILES: COCCOc1cc2[nH]nc(-c3cn(-c4ccc(C(=O)N5C[C@H]6COC[C@H]6C5)cc4)nn3)c2cc1F] | 5.0E−09 | 4.7E−07 |

TABLE 2-continued
| Inhibition ($IC_{50}$) of c-KIT (V654A) and GIST 430/654 of some representative compounds of the formula I in comparison to the corresponding triazole derivatives | | | | | | |
|---|---|---|---|---|---|---|
| | isoxazole derivatives presently claimed | | | triazole derivatives | | |
| Nr. | structure | c-Kit (V654A) $IC_{50}$ [M] | GIST 430/654 $IC_{50}$ [M] | structure | c-Kit (V654A) $IC_{50}$ [M] | GIST 430/654 $IC_{50}$ [M] |
| "A120" | 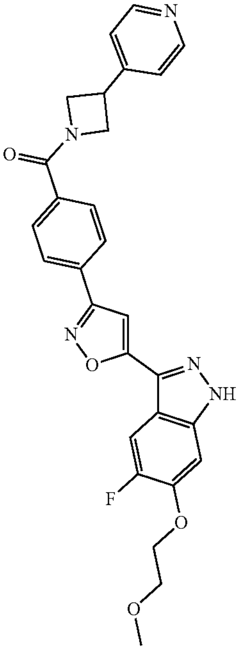 [SMILES: COCCOc1cc2[nH]nc(-c3cc(-c4ccc(C(=O)N5CC(c6ccncc6)C5)cc4)no3)c2cc1F] | 6.4E−10 | 2.4E−08 | 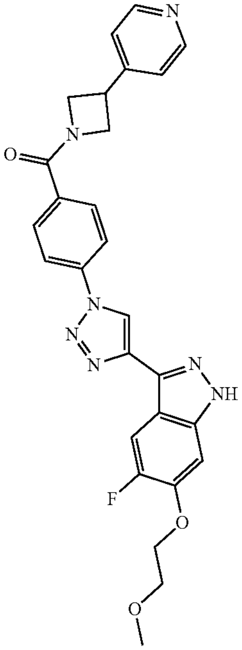 [SMILES: COCCOc1cc2[nH]nc(-c3cn(-c4ccc(C(=O)N5CC(c6ccncc6)C5)cc4)nn3)c2cc1F] | 2.6E−09 | 1.6E−07 |
| "A45" | 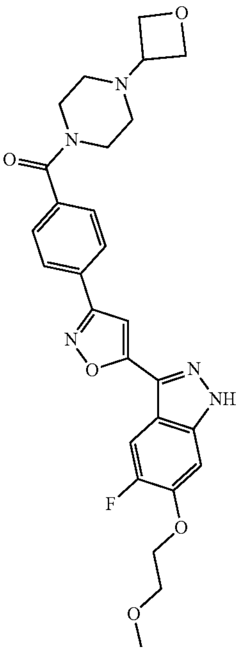 [SMILES: COCCOc1cc2[nH]nc(-c3cc(-c4ccc(C(=O)N5CCN(C6COC6)CC5)cc4)no3)c2cc1F] | 1.2E−09 | 5.9E−08 | 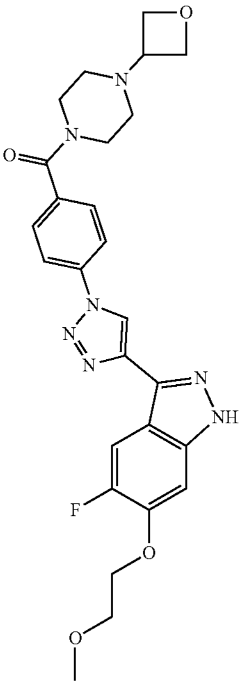 [SMILES: COCCOc1cc2[nH]nc(-c3cn(-c4ccc(C(=O)N5CCN(C6COC6)CC5)cc4)nn3)c2cc1F] | 7.8E−09 | 7.9E−07 |

Synthesis of Intermediates

Indazoles

Synthesis of 6-(2-methoxy-ethoxy)-1H-indazole

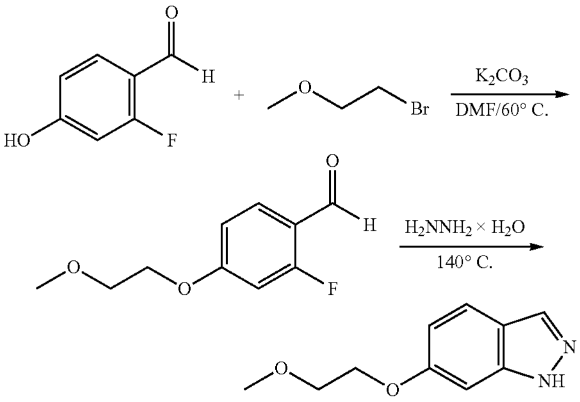

To a solution of 2-fluoro-4-hydroxybenzaldehyde (2.80 g, 20.0 mmol) in DMF (50 ml) is added potassium carbonate (8.29 g, 60 mmol) and the resultant slurry is stirred for 18 hours at 60° C. The reaction mixture is allowed to reach room temperature and is treated with water and dichloromethane. The organic phase is separated and the aqueous phase is extracted twice with dichloromethane. The combined organic phases are dried over sodium sulfate, filtered and evaporated. The residue is dried under high vacuum to afford 2-fluoro-4-(2-methoxy-ethoxy)-benzaldehyde as colorless oil; HPLC/MS 1.36 min (A), $[M+H]^+$ 199.

$^1H$ NMR (400 MHz, DMSO-$d_6$) δ 10.07 (s, 1H), 7.78 (t, J=8.6 Hz, 1H), 7.02 (dd, J=13.0, 2.4 Hz, 1H), 6.96 (dd, J=8.7, 2.4 Hz, 1H), 4.29-4.19 (m, 2H), 3.74-3.63 (m, 2H), 3.31 (s, 3H).

A solution of 2-fluoro-4-(2-methoxy-ethoxy)-benzaldehyde (6.16 g, 31.1 mmol) in hydrazinium hydroxide (30.2 ml, 31.1 g, 621 mmol) is heated to 140° C. under stirring and kept at this temperature for 16 hours. The reaction mixture is allowed to reach room temperature and diluted with water. Then conc. hydrochloric acid and 2 N hydrochloric acid are cautiously added until a pH value of 2 is reached. The mixture is extracted four times with dichloromethane. The combined organic phases are extracted with saturated sodium chloride solution and dried over sodium sulfate. The sodium sulfate is filtered off and the filtrate is evaporated and dried under vacuum to afford 6-(2-methoxy-ethoxy)-1H-indazole as pale-yellow crystalline solid; HPLC/MS 1.21 min (A), $[M+H]^+$ 193.

$^1H$ NMR (400 MHz, DMSO-$d_6$) δ 12.76 (s, 1H), 7.93 (s, 1H), 7.61 (d, J=8.8 Hz, 1H), 6.93 (s, 1H), 6.75 (dd, J=8.8, 2.1 Hz, 1H), 4.20-4.11 (m, 2H), 3.88-3.65 (m, 2H), 3.33 (s, 3H).

Synthesis of 5-fluoro-6-(2-methoxy-ethoxy)-1H-indazole

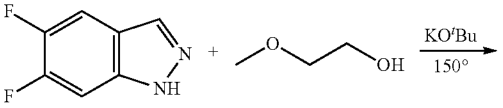

-continued

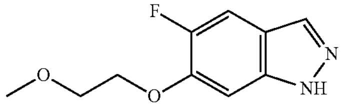

Under nitrogen, potassium tert-butylate (6.43 g, 57.3 mmol) is added in portions to a solution of 5,6-difluoro-1H-indazole (2.94 g, 19.1 mmol) in ethylene glycol monomethyl ether (40 ml). The mixture is heated to 150° C. and stirred at this temperature for five days. The reaction mixture is allowed to reach room temperature and diluted with water (150 ml) and 1 N hydrochloric acid (39 ml) to reach a pH value of about 6. The mixture is extracted twice with dichloromethane. The combined organic phases are washed with water, dried over sodium sulfate and evaporated. The residue is chromatographed on a silica gel column with cyclohexane/ethyl acetate as eluent to afford 5-fluoro-6-(2-methoxy-ethoxy)-1H-indazole as off-white solid; HPLC/MS 1.31 min (B), $[M+H]^+$ 211.

$^1H$ NMR (400 MHz, DMSO-$d_6$) δ 12.92 (s, 1H), 7.93 (t, J=1.3 Hz, 1H), 7.53 (d, J=11.0 Hz, 1H), 7.12 (dd, J=7.1, 1.0 Hz, 1H), 4.54-4.06 (m, 2H), 4.06-3.58 (m, 2H), 3.34 (s, 3H).

Alternative Synthesis of 5-fluoro-6-(2-methoxy-ethoxy)-1H-indazole

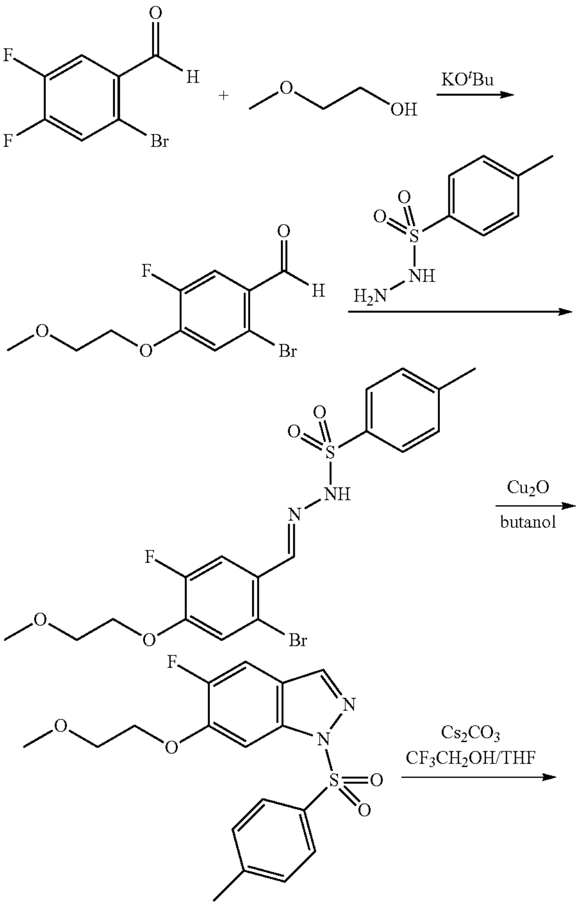

-continued

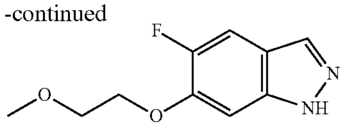

In a nitrogen-flushed 10 l reactor equipped with a cooling and heating jacket, 2-bromo-4,5-difluorobenzaldehyde (500 g, 2.26 mol) is dissolved in 2-methoxyethanol (4.5 l). Potassium tert-butylate (381 g, 3.39 mol) is added in portions over a period of 1 hour at a temperature of 20-25° C. The resultant solution is stirred for 16 hours at a temperature of 18° C. The reaction mixture is quenched with water (2 l) and a saturated solution of citric acid in water (2 l). The mixture is treated with tert-butyl-methyl-ether (5 l) and the organic phase is separated. The organic phase is washed once with water and two times with brine and dried over sodium sulfate. Sodium sulfate is filtered off and the filtrate is evaporated to afford 2-bromo-5-fluoro-4-(2-methoxy-ethoxy)-benzaldehyde as light yellow partially crystalline oil, which is used as such in the next step. By chromatography on a silica gel column with dichloro-methane/ethyl acetate as eluent a pure sample is obtained: white crystalline solid; HPLC/MS 1.60 min (A), $[M+H]^+$ 277/279.

$^1H$ NMR (500 MHz, DMSO-$d_6$) δ 10.05 (d, J=3.0 Hz, 1H), 7.66 (d, J=11.3 Hz, 1H), 7.63 (d, J=7.5 Hz, 1H), 4.40-4.31 (m, 2H), 3.75-3.68 (m, 2H), 3.32 (s, 3H).

4-Toluenesulfonohydrazide (377 g, 2.02 mol) is slurried in methanol (4 l) and the slurry is stirred for 30 min at 60° C. Then, a solution of crude 2-bromo-5-fluoro-4-(2-methoxy-ethoxy)-benzaldehyde (700 g, approx. 2.02 mol) in methanol (1 l) is added over a period of 30 min and the reaction mixture is stirred for 18 hours at 60° C. The reaction mixture is cooled to 0° C. The precipitate is filtered off by suction, washed with methanol and dried under vacuum at 40° C. to afford N-[(E)-[2-bromo-5-fluoro-4-(2-methoxy-ethoxy)-phenyl]methyleneamino]-4-methyl-benzenesulfonamide as white crystals; UPLC/MS 0.85 min, $[M+H]^+$ 445/447.

$^1H$ NMR (400 MHz, DMSO-$d_6$) δ 11.65 (s, 1H), 8.10 (d, J=2.0 Hz, 1H), 7.77 (d, J=8.3 Hz, 2H), 7.49-7.36 (m, 4H), 4.28-4.21 (m, 2H), 3.70-3.57 (m, 2H), 3.30 (s, 3H), 2.38 (s, 3H).

A suspension of N-[(E)-[2-bromo-5-fluoro-4-(2-methoxyethoxy)phenyl]-methyleneamino]-4-methyl-benzenesulfonamide (445 g, 1.00 mol) and copper(I)oxide (100 g, 700 mmol) in 1-butanol (5 l) is flushed with nitrogen. The mixture is heated to 117° C. and stirred at this temperature for 5 h. The reaction mixture is allowed to reach room temperature and evaporated. The residue is taken up in toluene (5 l), the suspension is heated to 80°, treated with activated charcoal (100 g) and stirred for 1 h at 50° C. The suspension is filtered and the filtrate is evaporated. The solid residue is crystallized from heptane (2 l) to afford 5-fluoro-6-(2-methoxy-ethoxy)-1-(toluene-4-sulfonyl)-1H-indazole as yellow crystals; HPLC/MS 1.66 min (B), $[M+H]^+$ 365.

$^1H$ NMR (500 MHz, DMSO-$d_6$) δ 8.38 (s, 1H), 7.84 (d, J=8.4 Hz, 2H), 7.72 (d, J=6.9 Hz, 1H), 7.69 (d, J=10.4 Hz, 1H), 7.39 (d, J=8.1 Hz, 2H), 4.43-4.34 (m, 2H), 3.86-3.71 (m, 2H), 3.36 (s, 3H), 2.34 (s, 3H).

A suspension of 5-fluoro-6-(2-methoxy-ethoxy)-1-(toluene-4-sulfonyl)-1H-indazole (360 g, 988 mmol) and cesium carbonate (644 g, 1.98 mol) in a mixture of THF (2.0 l) and 2,2,2-trifluoroethanol (2.0 l) is stirred for 18 h at 40° C. The reaction mixture is diluted with ethyl acetate and filtered by suction. The residue is washed with ethyl acetate. The filtrate is evaporated and partitioned between water and ethyl acetate. The organic phase is dried over sodium sulfate and evaporated. The residue is recrystallized from ethyl acetate/heptane to afford 5-fluoro-6-(2-methoxy-ethoxy)-1H-indazole as off-white crystalline solid; UPLC/MS 0.57 min, $[M+H]^+$ 211.

The following compounds are prepared analogously

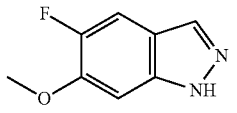

5-Fluoro-6-methoxy-1H-indazole; white crystalline solid; UPLC/MS 0.56 min, $[M+H]^+$ 167.

$^1H$ NMR (700 MHz, DMSO-$d_6$) δ 12.95 (s, 1H), 7.94 (s, 1H), 7.54 (d, J=11.1 Hz, 1H), 7.11 (d, J=7.1 Hz, 1H), 3.91 (s, 3H).

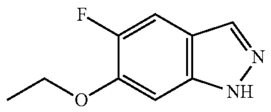

6-Ethoxy-5-fluoro-1H-indazole; white solid; UPLC/MS 0.61 min, $[M+H]^+$ 181.

$^1H$ NMR (500 MHz, DMSO-$d_6$) δ 12.87 (s, 1H), 7.92 (d, J=1.2 Hz, 1H), 7.52 (d, J=11.1 Hz, 1H), 7.08 (d, J=7.1 Hz, 1H), 4.15 (q, J=7.0 Hz, 2H), 1.40 (t, J=6.9 Hz, 3H).

Synthesis of 5-chloro-6-(2-methoxy-ethoxy)-1H-indazole

The compound was synthesized according to the following synthetic scheme

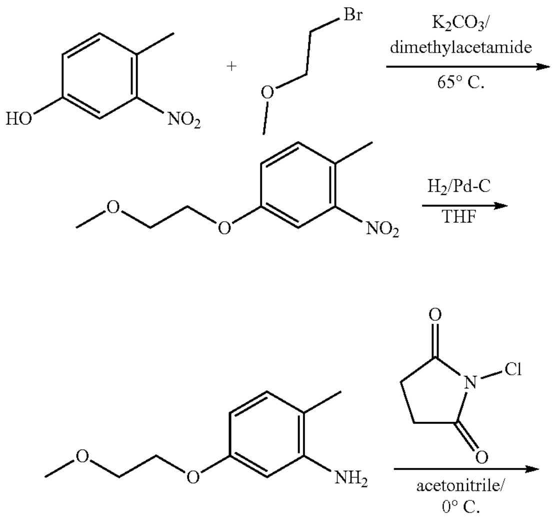

-continued

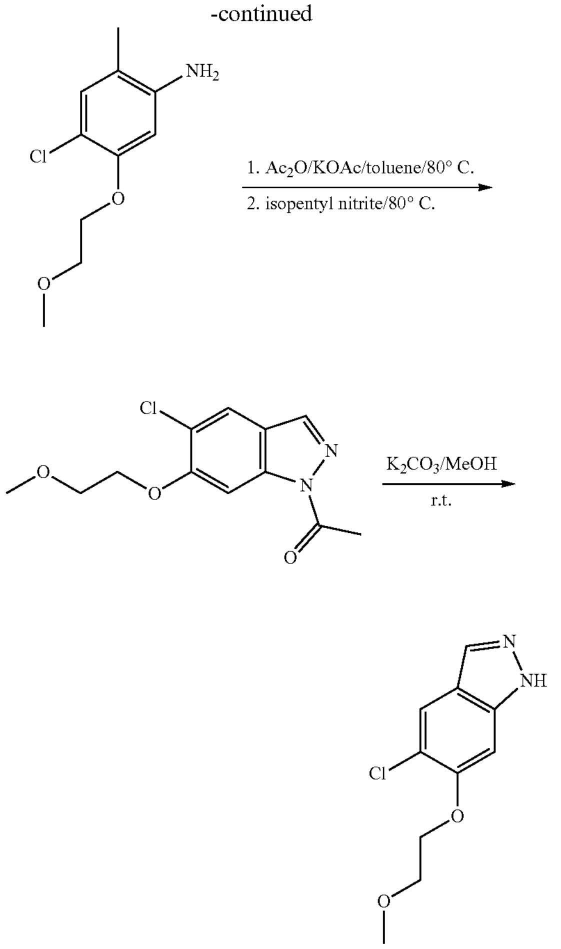

pale yellow crystalline solid; HPLC/MS 1.39 min (A), $[M+H]^+$ 227.

$^1$H NMR (300 MHz, Chloroform-$d_1$) δ 10.19 (s, 1H), 7.96 (d, J=0.9 Hz, 1H), 7.76 (s, 1H), 6.91 (s, 1H), 4.36-4.16 (m, 2H), 3.99-3.66 (m, 2H), 3.53 (s, 3H).

Synthesis of 6-(2-methoxy-ethoxy)-1H-indazole-5-carbonitrile

The compound is synthesized according to the following synthetic scheme

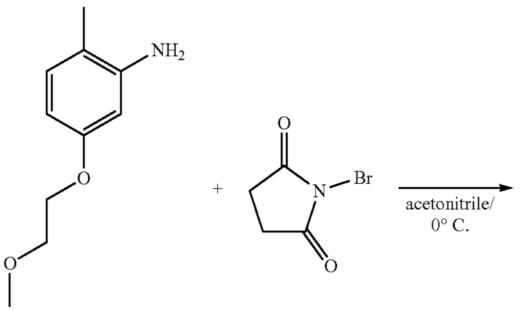

-continued

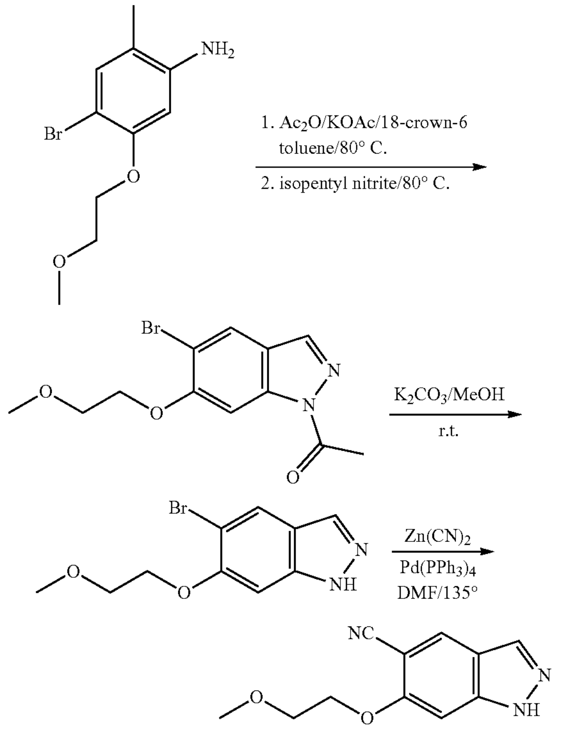

white crystalline solid; HPLC/MS 1.22 min (A), $[M+H]^+$ 281.

$^1$H NMR (400 MHz, Chloroform-$d_1$) δ 8.10 (s, 1H), 8.06 (s, 1H), 7.28 (s, 2H), 7.00 (s, 1H), 4.32-4.26 (m, 2H), 3.95-3.82 (m, 2H).

3-Ethynyl-indazoles

Synthesis of 3-ethynyl-6-trifluoromethyl-1H-indazole

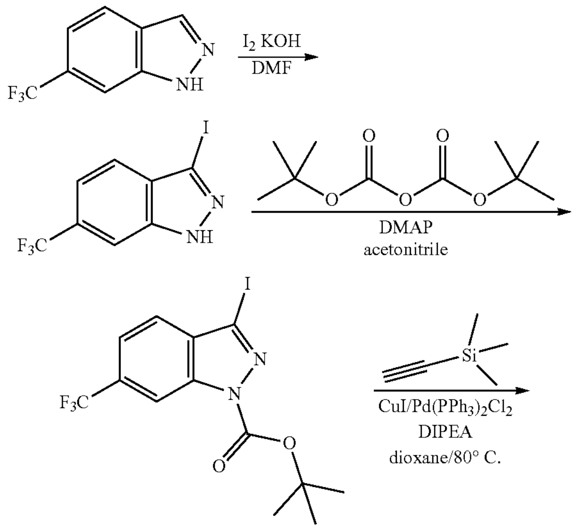

-continued

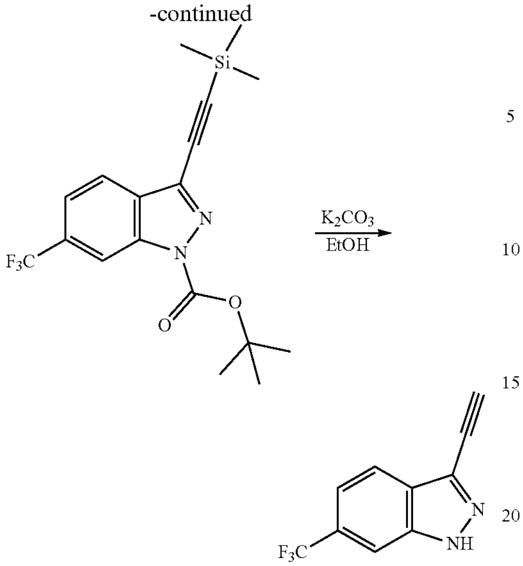

To a solution of 6-trifluoromethylindazole (990 mg, 5.32 mmol) in DMF (200 ml) is added iodine (2.00 g, 7.88 mmol) followed by portionwise addition of potassium hydroxide pellets (1.20 g, 21.4 mmol) and the reaction mixture is stirred at room temperature. After 18 hours, the reaction mixture is poured into a saturated aqueous sodium thiosulfate solution and the resultant mixture is extracted two times with ethyl acetate. The combined organic phases are washed with brine and dried over sodium sulfate. The sodium sulfate is filtered off and the residue is evaporated to afford 3-iodo-6-trifluoromethyl-1H-indazole as beige solid; UPLC/MS 0.80 min, $[M+H]^+$ 313.

$^1$H NMR (400 MHz, DMSO-$d_6$) δ 13.95 (s, 1H), 7.97 (s, 1H), 7.69 (d, J=8.6 Hz, 1H), 7.48 (dd, J=8.5, 1.5 Hz, 1H).

To a suspension of 3-iodo-6-trifluoromethyl-1H-indazole (1.69 g, 5.43 mmol) in acetonitrile (100 ml) is added N,N-dimethylpyridin-4-amine (133 mg, 1.09 mmol) and di-tert-butyl dicarbonate (1.78 g, 8.15 mmol) and the reaction mixture is stirred for 3 days at room temperature. The reaction mixture is concentrated under reduced pressure. The residue is taken up in ethyl acetate and washed twice with saturated aqueous ammonium chloride solution and once with brine. The organic phase is dried over sodium sulfate and evaporated to afford 3-iodo-6-trifluoromethyl-indazole-1-carboxylic acid tert-butyl ester as pale yellow solid; UPLC/MS 1.00 min, $[M-^tBu]^+$ 357.

$^1$H NMR (400 MHz, DMSO-$d_6$) δ 8.40 (s, 1H), 7.83 (d, J=8.5 Hz, 1H), 7.78 (dd, J=8.5, 1.5 Hz, 1H), 1.67 (s, 9H).

A solution of 3-iodo-6-trifluoromethyl-indazole-1-carboxylic acid tert-butyl ester (1.87 g, 4.53 mmol) in 1,4-dioxane (45 ml) is flushed with nitrogen. Then, bis(triphenylphosphine)palladium(II) chloride (470 mg, 0.67 mmol), copper(I)iodide (127 mg, 0.67 mmol), N-ethyldiisopropylamine (1.57 ml, 9.07 mmol) and trimethylsilylacetylene (1.34 g, 13.6 mmol) are added under nitrogen and the reaction mixture is stirred in a closed reaction vial for 1 hour at 80° C. The reaction mixture is allowed to reach room temperature, absorbed on Celite and chromatographed on a silica gel column with cyclohexane/ethyl acetate as eluent to afford 6-trifluoromethyl-3-trimethylsilanylethynyl-indazole-1-carboxylic acid tert-butyl ester as off-white solid; UPLC/MS 1.12 min, $[M-^tBu]^+$ 327.

$^1$H NMR (400 MHz, DMSO-$d_6$) δ 8.19 (s, 1H), 7.80 (d, J=8.5 Hz, 1H), 7.55 (dd, J=8.4, 1.5 Hz, 1H), 1.43 (s, 9H), 0.09 (s, 9H).

To a solution of 6-trifluoromethyl-3-trimethylsilanylethynyl-indazole-1-carboxylic acid tert-butyl ester (1.60 g, 4.18 mmol) in ethanol (5 ml) is added potassium carbonate (120 mg, 0.87 mmol) and the reaction mixture is stirred for 18 hours at room temperature. The reaction mixture is concentrated under reduced pressure. The residue is dissolved in ethyl acetate and washed 3 times with water. The organic phase is dried over sodium sulfate and evaporated to afford 3-ethynyl-6-trifluoromethyl-1H-indazole as pale brown solid; UPLC/MS 0.75 min, $[M+H]^+$ 211.

$^1$H NMR (400 MHz, DMSO-$d_6$) δ 13.87 (s, 1H), 7.98 (s, 1H), 7.94 (d, J=8.5 Hz, 1H), 7.50 (dd, J=8.5, 1.5 Hz, 1H), 4.59 (s, 1H).

The following compounds are prepared analogously:

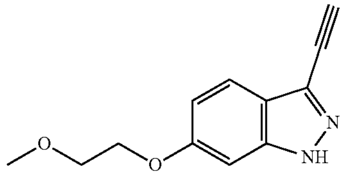 [SMILES: C#Cc1n[nH]c2cc(OCCOC)ccc12]

3-Ethynyl-6-(2-methoxy-ethoxy)-1H-indazole, off-white solid; UPLC/MS 0.63 min, $[M+H]^+$ 217.

$^1$H NMR (500 MHz, DMSO-$d_6$) δ 13.15 (s, 1H), 7.56 (d, J=8.8 Hz, 1H), 6.97 (d, J=2.0 Hz, 1H), 6.86 (dd, J=8.8, 2.1 Hz, 1H), 4.43 (s, 1H), 4.20-4.13 (m, 2H), 3.76-3.66 (m, 2H), 3.33 (s, 3H).

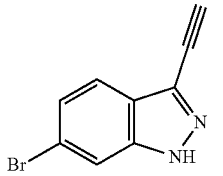

6-Bromo-3-ethynyl-1H-indazole, pale brown powder; UPLC/MS 0.75 min, $[M+H]^+$ 221, 223.

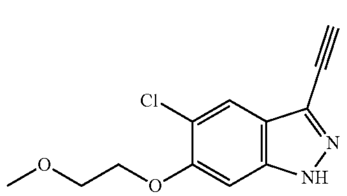 [SMILES: C#Cc1n[nH]c2cc(OCCOC)c(Cl)cc12]

5-Chloro-3-ethynyl-6-(2-methoxy-ethoxy)-1H-indazole, pale brown solid; UPLC/MS 1.05 min, $[M+H]^+$ 251.

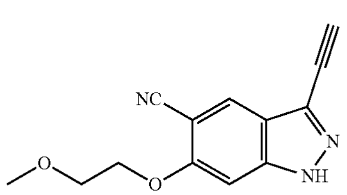 [SMILES: C#Cc1n[nH]c2cc(OCCOC)c(C#N)cc12]

3-Ethynyl-6-(2-methoxy-ethoxy)-1H-indazole-5-carbonitrile, pale brown solid; HPLC/MS 1.85 min (A), $[M+H]^+$ 242.

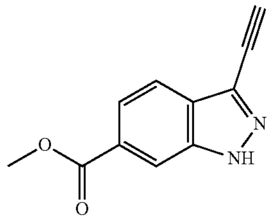

3-Ethynyl-1H-indazole-6-carboxylic acid methyl ester, off-white solid; UPLC/MS 0.95 min, $[M+H]^+$ 201.

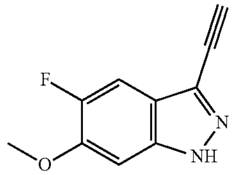

3-Ethynyl-5-fluoro-6-methoxy-1H-indazole, off-white solid; UPLC/MS 0.65 min, $[M+H]^+$ 191.

$^1$H NMR (400 MHz, DMSO-$d_6$) δ 13.34 (s, 1H), 7.47 (d, J=10.6 Hz, 1H), 7.17 (d, J=7.0 Hz, 1H), 4.48 (s, 1H), 3.92 (s, 3H).

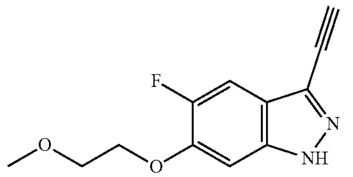 [SMILES: C#Cc1n[nH]c2cc(OCCOC)c(F)cc12]

3-Ethynyl-5-fluoro-6-(2-methoxy-ethoxy)-1H-indazole, pale-brown solid; UPLC/MS 0.66 min. [M+H]+ 235.

$^1$H NMR (400 MHz, DMSO-$d_6$) δ 13.32 (s, 1H), 7.45 (d, J=10.5 Hz, 1H), 7.19 (d, J=6.9 Hz, 1H), 4.45 (s, 1H), 4.41-4.17 (m, 2H), 3.80-3.64 (m, 2H), 3.34 (s, 3H).

Synthesis of 3-ethynyl-5-fluoro-6-(2-methoxy-ethoxy)-indazole-1-carboxylic Acid Tert-Butyl Ester

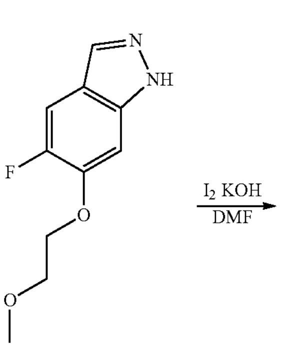

-continued

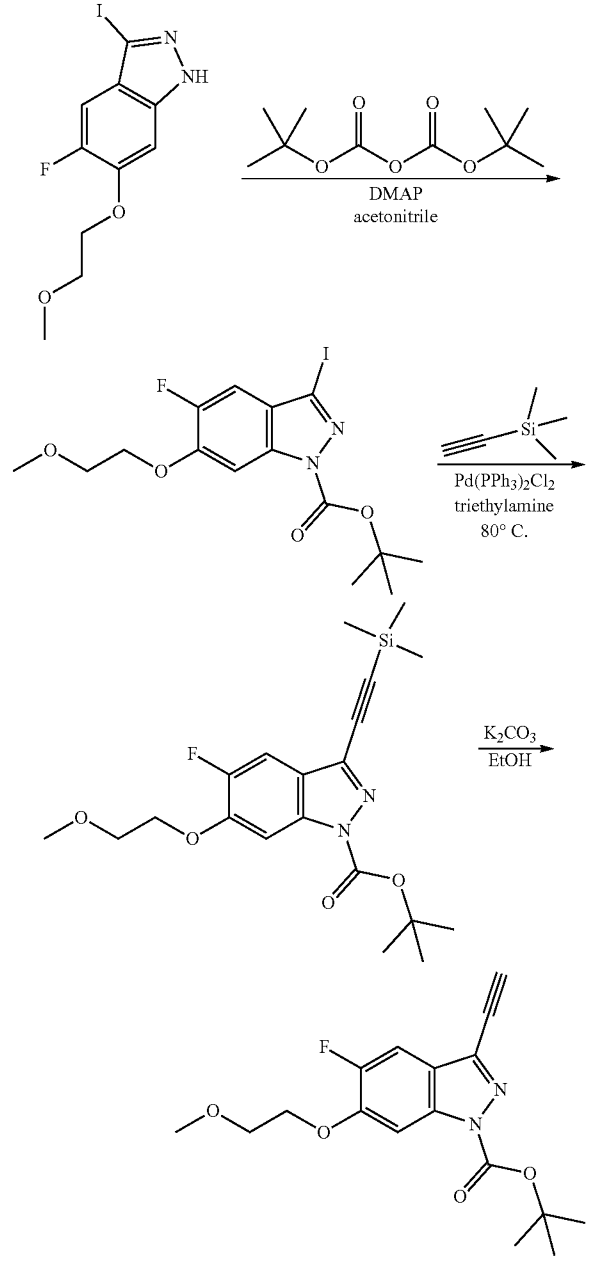

To a solution of 5-fluoro-6-(2-methoxy-ethoxy)-1H-indazole (173 g, 822 mmol) in DMF (2.0 l) is added iodine (228 g, 905 mmol) followed by portionwise addition of potassium hydroxide powder (115 g, 2.57 mol) and the reaction mixture is stirred at room temperature. After 18 hours, the reaction mixture is poured into a mixture of cold water (12 l) and ethyl acetate (6 l). The phases are separated and the water layer is extracted with ethyl acetate (2 l). The combined organic layers are washed with water (3 l), aqueous sodium thiosulfate solution (3 l) and three times with water (2 l). The organic layer is then dried over sodium sulfate, filtered and concentrated. The resultant slurry is treated with heptane (2 l). The solid is filtered off and dried under vacuum to afford 5-fluoro-3-iodo-6-(2-methoxy-ethoxy)-1H-indazole as beige solid; UPLC/MS 0.71 min. $[M+H]^+$ 337.

$^1H$ NMR (400 MHz, DMSO-$d_6$) δ 13.37 (s, 1H), 7.20 (d, J=10.6 Hz, 1H), 7.17 (d, J=7.0 Hz, 1H), 4.32-4.16 (m, 2H), 3.82-3.65 (m, 2H), 3.34 (s, 3H).

To a solution of 5-fluoro-3-iodo-6-(2-methoxy-ethoxy)-1H-indazole (249 g, 0.74 mmol) in acetonitrile (2.5 l) is added 4-(dimethylamino)-pyridine (133 mg, 150 mmol). Then di-tert-butyl dicarbonate (238 ml, 1.11 mol) is added slowly and the mixture is stirred for 18 hours at room temperature. The reaction mixture is concentrated under reduced pressure. The residue is taken up in ethyl acetate (4 l) and washed with water (5 l), 10% aqueous citric acid solution (3 l), water (3 l) and brine (2 l). The organic phase is dried over sodium sulfate and concentrated under reduced pressure. The residue is crystallized from heptane to afford 5-fluoro-3-iodo-6-(2-methoxy-ethoxy)-indazole-1-carboxylic acid tert-butyl ester ester as white crystalline solid; UPLC/MS 0.93 min, $[M-^tBu]^+$ 381.

$^1H$ NMR (400 MHz, DMSO-$d_6$) δ 7.71 (d, J=7.1 Hz, 1H), 7.40 (d, J=10.0 Hz, 1H), 4.35-4.25 (m, 2H), 3.94-3.67 (m, 2H), 3.34 (s, 3H), 1.65 (s, 9H).

Under nitrogen, to a suspension of 5-fluoro-3-iodo-6-(2-methoxy-ethoxy)-indazole-1-carboxylic acid tert-butyl ester (297 g, 680 mmol) and bis(triphenyl-phosphine)palladium (II) chloride (14.2 g, 20.3 mmol) in triethylamine (2 l) is added trimethylsilylacetylene (112 ml, 810 mmol) and the mixture is stirred for 3 hours at 84° C. The reaction mixture is allowed to reach room temperature and diluted with tert-butyl methyl ether. The solution is washed five times with water (5 l each) and brine (4 l). The organic layer is dried over sodium sulfate and evaporated to afford 5-fluoro-6-(2-methoxy-ethoxy)-3-trimethylsilanylethynyl-indazole-1-carboxylic acid tert-butyl ester as pale brown solid; UPLC/MS 1.03 min, $[M-^tBu]^+$ 351.

$^1H$ NMR (400 MHz, DMSO-$d_6$) δ 7.73 (d, J=7.1 Hz, 1H), 7.59 (d, J=9.9 Hz, 1H), 4.31-4.24 (m, 2H), 3.78-3.70 (m, 2H), 3.33 (s, 3H), 1.64 (s, 9H), 0.30 (s, 9H).

To a solution of 5-fluoro-6-(2-methoxy-ethoxy)-3-trimethylsilanylethynyl-indazole-1-carboxylic acid tert-butyl ester (273 g, 671 mmol) in ethanol (1.5 l) is added potassium carbonate (18.6 g, 143 mmol) and the reaction mixture is stirred for 3 hours at 30° C. The reaction mixture is poured into cold water and the solid is filtered off and washed with water. The solid is dissolved in dichloromethane (3 l) and filtered over silica gel (3 kg) with dichloromethane and tert-butyl methyl ether as eluent. The eluate is concentrated under reduced pressure and crystallized from heptane (300 ml) to afford 3-ethynyl-5-fluoro-6-(2-methoxy-ethoxy)-indazole-1-carboxylic acid tert-butyl ester as pale brown solid; HPLC/MS 2.54 min (A), $[M-^tBu]^+$ 279.

$^1H$ NMR (400 MHz, DMSO-$d_6$) δ 7.73 (d, J=7.1 Hz, 1H), 7.62 (d, J=9.9 Hz, 1H), 4.82 (s, 1H), 4.42-4.26 (m, 2H), 3.94-3.72 (m, 2H), 3.35 (s, 3H), 1.66 (s, 9H).

The following compound is prepared analogously:

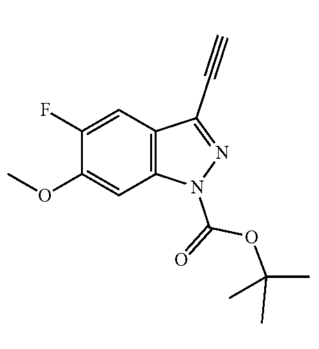 [SMILES: C#Cc1nn(C(=O)OC(C)(C)C)c2cc(OC)c(F)cc12]

tert-butyl 6-ethoxy-3-ethynyl-5-fluoro-1H-indazole-1-carboxylate; off-white solid; UPLC/MS 0.93 min, $[M-^tBu]^+$ 249.

$^1H$ NMR (400 MHz, DMSO-$d_6$) δ 7.71 (d, J=7.1 Hz, 1H), 7.63 (d, J=10.0 Hz, 1H), 4.81 (s, 1H), 4.23 (q, J=7.0 Hz, 2H), 1.65 (s, 8H), 1.43 (t, J=6.9 Hz, 3H).

Alternative Synthesis of 3-ethynyl-5-fluoro-6-(2-methoxy-ethoxy)-indazole-1-carboxylic Acid Tert-Butyl Ester

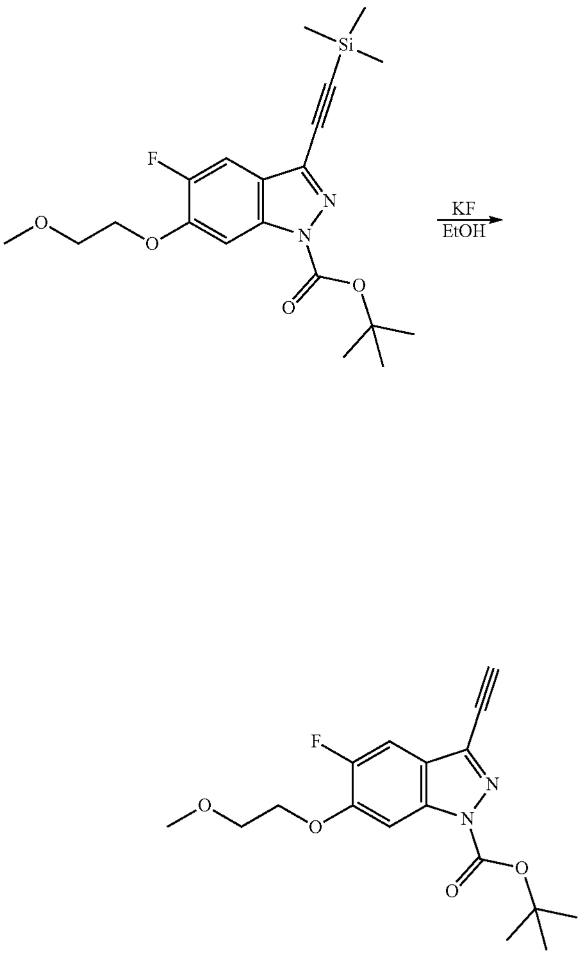

To a solution of 5-fluoro-6-(2-methoxy-ethoxy)-3-trimethylsilanylethynyl-indazole-1-carboxylic acid tert-butyl ester (488 mg, 1.20 mmol) in ethanol (12 ml) is added potassium fluoride (3.5 mg, 0.06 mmol) and the reaction mixture is stirred for 3 hours at room temperature. The reaction mixture is cooled in an ice bath. The solids are filtered off, washed with ice-cold ethanol and dried under vacuum to afford 3-ethynyl-5-fluoro-6-(2-methoxy-ethoxy)-indazole-1-carboxylic acid tert-butyl ester as off-white solid; HPLC/MS 2.54 min (A), $[M-^tBu]^+$ 279.

Carboxylic Acids

Synthesis of 4-[5-(6-trifluoromethyl-1H-indazol-3-yl)-isoxazol-3-yl]-benzoic Acid Methyl Ester

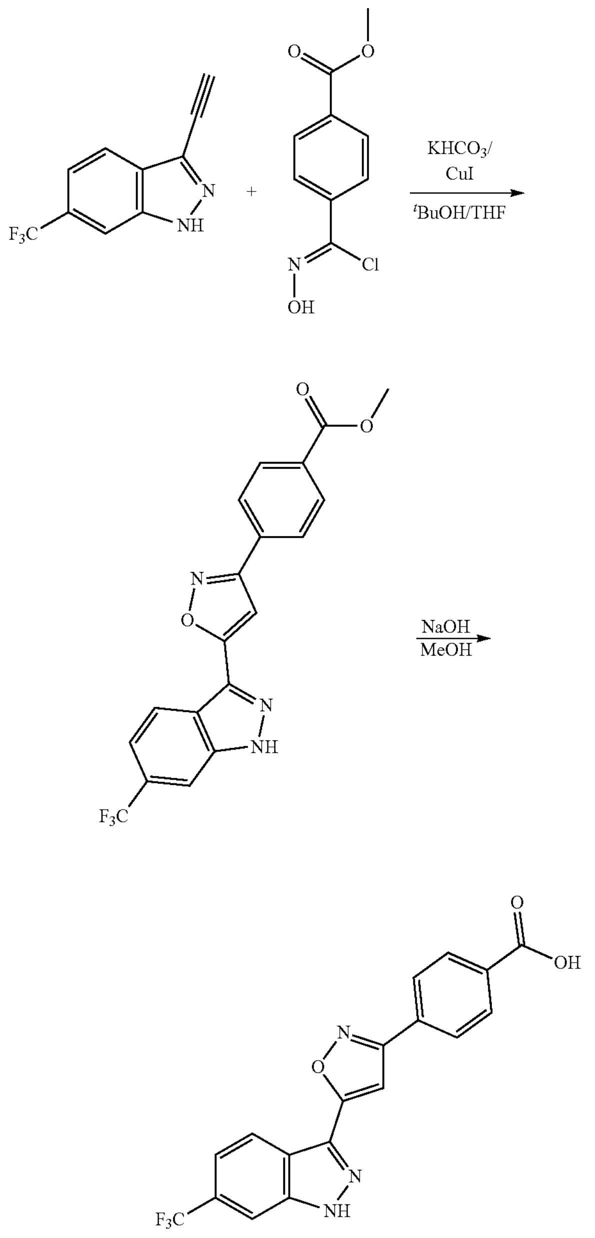

A suspension of 3-ethynyl-6-trifluoromethyl-1H-indazole (166 mg, 0.79 mmol) and methyl 4-[(Z)—C-chloro-N-hydroxy-carbonimidoyl]benzoate (187 mg, 0.88 mmol) in a mixture of tert-butanol (1.2 ml) and THF (0.4 ml) is flushed with nitrogen. Under nitrogen, copper(I) iodide (13 mg, 0.068 mmol) is added and the suspension is stirred for 5 minutes at room temperature. Then, potassium hydrogen carbonate (80 mg, 0.80 mmol) is added and the reaction mixture is stirred for 3 days at room temperature. The reaction mixture is treated with water. The resultant solid is filtered off, washed with water and airdried. The residue is triturated with ethyl acetate and dried under vacuum to afford 4-[5-(6-trifluoromethyl-1H-indazol-3-yl)-isoxazol-3-yl]-benzoic acid methyl ester as off-white solid; UPLC/MS 0.93 min, $[M+H]^+$ 388.

$^1H$ NMR (400 MHz, DMSO-$d_6$) δ 14.30 (s, 1H), 8.48 (d, J=8.6 Hz, 1H), 8.22 (d, J=8.1 Hz, 2H), 8.15 (d, J=8.0 Hz, 2H), 8.10 (d, J=1.9 Hz, 1H), 7.89 (s, 1H), 7.65 (d, J=8.5 Hz, 1H), 3.92 (s, 3H).

To a solution of 4-[5-(6-trifluoromethyl-1H-indazol-3-yl)-isoxazol-3-yl]-benzoic acid methyl ester (124 mg, 0.32 mmol) in methanol is added a 2 M aqueous solution of sodium hydroxide (1.3 ml) and the reaction mixture is stirred for 1 hour at 80° C. and for 16 hours at room temperature. The resultant suspension is acidified with conc. hydrochloric acid. The resultant solid is filtered off, washed with water and dried under vacuum to afford 4-[5-(6-trifluoromethyl-1H-indazol-3-yl)-isoxazol-3-yl]-benzoic acid as off-white solid; UPLC/MS 0.82 min, $[M+H]^+$ 374.

$^1H$ NMR (500 MHz, DMSO-$d_6$) δ 14.48 (s, 1H), 13.20 (s, 1H), 8.48 (d, J=8.7 Hz, 1H), 8.19 (d, J=8.5 Hz, 2H), 8.15-8.08 (m, 3H), 7.88 (s, 1H), 7.65 (dd, J=8.7, 1.5 Hz, 1H).

The following compounds are prepared analogously:

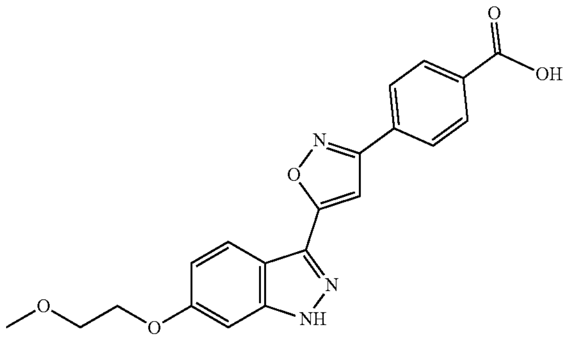 [SMILES: COCCOc1ccc2c(-c3cc(-c4ccc(C(=O)O)cc4)no3)n[nH]c2c1]

4-{5-[6-(2-Methoxy-ethoxy)-1H-indazol-3-yl]-isoxazol-3-yl}-benzoic acid, brown solid; HPLC/MS 1.52 min (A), $[M+H]^+$ 380.

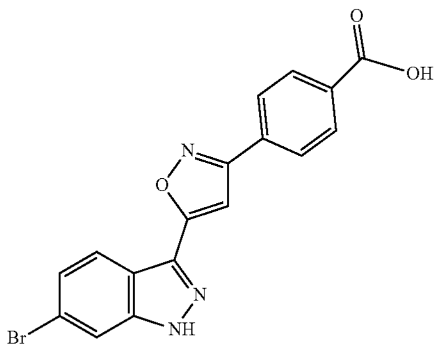 [SMILES: O=C(O)c1ccc(-c2cc(-c3n[nH]c4cc(Br)ccc34)on2)cc1]

4-[5-(6-Bromo-1H-indazol-3-yl)-isoxazol-3-yl]-benzoic acid, brown solid; UPLC/MS 0.82 min, $[M+H]^+$ 384/386.

$^1$H NMR (500 MHz, DMSO-$d_6$) δ 13.99 (s, 1H), 13.1 (s, 1H), 8.20 (d, J=8.7 Hz, 1H), 8.17 (d, J=8.4 Hz, 2H), 8.11 (d, J=8.3 Hz, 2H), 7.95 (d, J=1.5 Hz, 1H), 7.81 (s, 1H), 7.50 (dd, J=8.7, 1.6 Hz, 1H).

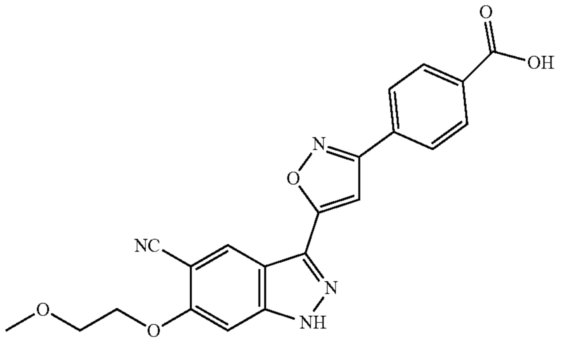 [SMILES: COCCOc1cc2[nH]nc(-c3cc(-c4ccc(C(=O)O)cc4)no3)c2cc1C#N]

4-{5-[5-Cyano-6-(2-methoxy-ethoxy)-1H-indazol-3-yl]-isoxazol-3-yl}-benzoic acid, off-white solid; HPLC/MS 2.04 min (A), $[M+H]^+$ 405.

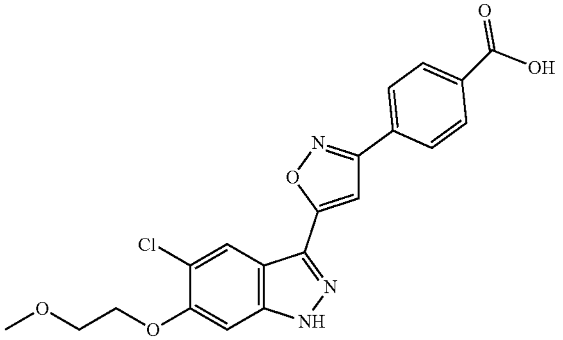 [SMILES: COCCOc1cc2[nH]nc(-c3cc(-c4ccc(C(=O)O)cc4)no3)c2cc1Cl]

4-{5-[5-chloro-6-(2-methoxyethoxy)-1H-indazol-3-yl]-1,2-oxazol-3-yl}benzoic acid, brown solid; HPLC/MS 1.05 min, $[M+H]^+$ 414.

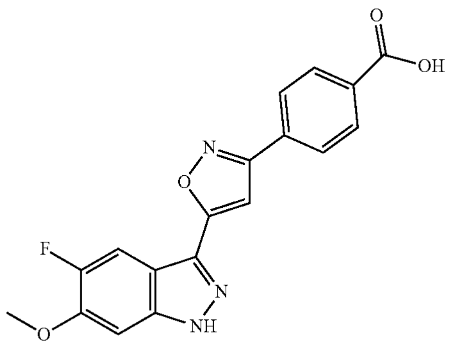 [SMILES: COc1cc2[nH]nc(-c3cc(-c4ccc(C(=O)O)cc4)no3)c2cc1F]

4-[5-(5-Fluoro-6-methoxy-1H-indazol-3-yl)-isoxazol-3-yl]-benzoic acid, brown solid; UPLC/MS 0.75 min, $[M+H]^+$ 354.

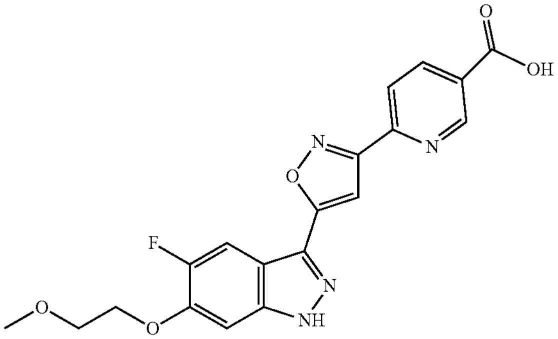 [SMILES: COCCOc1cc2[nH]nc(-c3cc(-c4ccc(C(=O)O)cn4)no3)c2cc1F]

6-{5-[5-Fluoro-6-(2-methoxy-ethoxy)-1H-indazol-3-yl]-isoxazol-3-yl}-nicotinic acid, brown solid; HPLC/MS 2.52 min (A), $[M+H]^+$ 399.

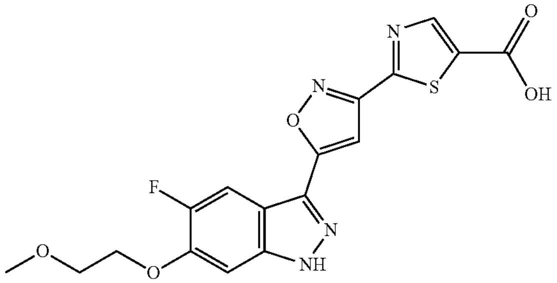 [SMILES: COCCOc1cc2[nH]nc(-c3cc(-c4ncc(C(=O)O)s4)no3)c2cc1F]

2-{5-[5-Fluoro-6-(2-methoxy-ethoxy)-1H-indazol-3-yl]-isoxazol-3-yl}-thiazole-5-carboxylic acid, brown solid; HPLC/MS 2.57 min (A), $[M+H]^+$ 405.

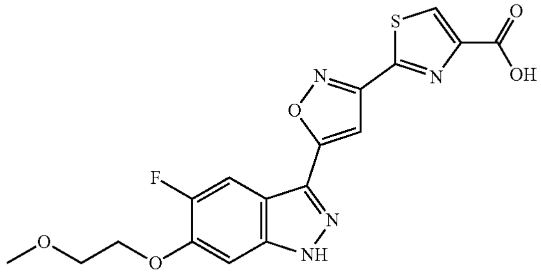 [SMILES: COCCOc1cc2[nH]nc(-c3cc(-c4nc(C(=O)O)cs4)no3)c2cc1F]

2-{5-[5-Fluoro-6-(2-methoxy-ethoxy)-1H-indazol-3-yl]-isoxazol-3-yl}-thiazole-4-carboxylic acid, brown solid; HPLC/MS 2.56 min (A), $[M+H]^+$ 405.

Synthesis of 4-{5-[5-fluoro-6-(2-methoxy-ethoxy)-1H-indazol-3-yl]-isoxazol-3-yl}-benzoic Acid

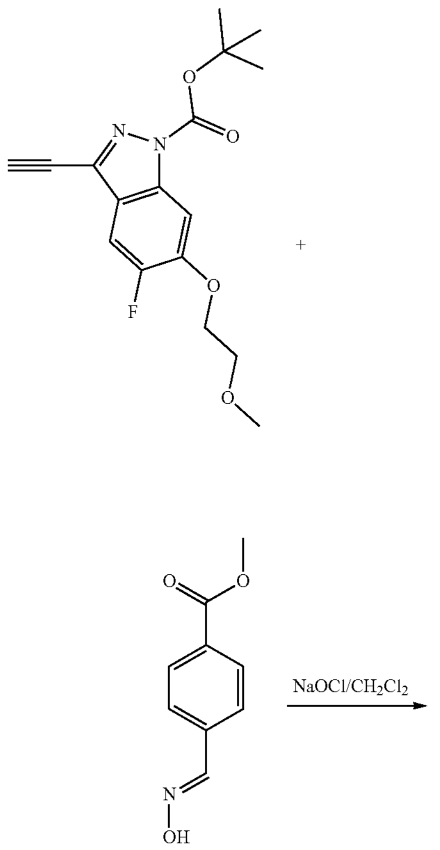

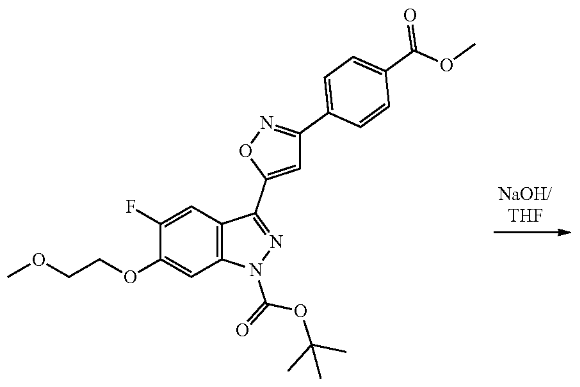

-continued

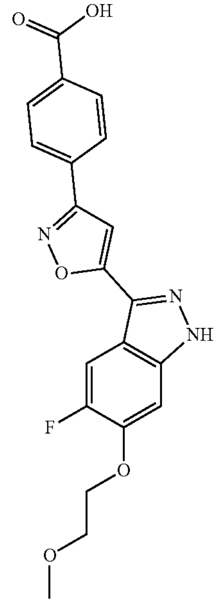

To a solution of 3-ethynyl-5-fluoro-6-(2-methoxy-ethoxy)-indazole-1-carboxylic acid tert-butyl ester (205 g, 614 mmol) and 4-(hydroxyimino-methyl)-benzoic acid methyl ester in dichloromethane (2.6 l) aqueous sodium hypochlorite solution (content approx. 12%, 944 ml, approx. 1.84 mol) is added dropwise. During the addition the temperature of the mixture is adjusted between 22° C. and 26° C. by external cooling. The reaction mixture is stirred for 18 hours at room temperature. The reaction mixture is filtered. The filter cake is washed with water (1 l) and two times with acetonitrile (300 ml) and dried under vacuum to afford 5-fluoro-3-[3-(4-methoxycarbonyl-phenyl)-isoxazol-5-yl]-6-(2-methoxy-ethoxy)-indazole-1-carboxylic acid tert-butyl ester as pale yellow crystals; HPLC/MS 2.16 min (A), $[M\text{-}^tBu]^+$ 456.

$^1$H NMR (500 MHz, DMSO-d$_6$) δ 8.26-8.20 (m, 3H), 8.15 (d, J=8.4 Hz, 2H), 8.12 (s, 1H), 7.84 (d, J=7.2 Hz, 1H), 4.38-4.34 (m, 2H), 3.92 (s, 3H), 3.82-3.76 (m, 2H), 3.30 (s, 9H).

To a suspension of 5-fluoro-3-[3-(4-methoxycarbonyl-phenyl)-isoxazol-5-yl]-6-(2-methoxy-ethoxy)-indazole-1-carboxylic acid tert-butyl ester (339 g, 662 mmol) in THF (3.36 l) is added 2 M aqueous sodium hydroxide solution (1.33 l, 2.65 mol) slowly via a dropping funnel and the reaction mixture is stirred for 5 hours at 60° C. The reaction mixture is cooled to room temperature and the organic solvent is evaporated under vacuum. The resultant suspension was diluted with ice water (3 l). The pH value of the suspension is adjusted with 2.5 N aqueous hydrochloric acid from pH11 to pH2 under continuous stirring. The solids are filtered off and washed with water (3 times 600 ml) and tert-butyl methyl ether (300 ml). The solid is dried for several days under reduced pressure at 45° C. to afford 4-{5-[5-fluoro-6-(2-methoxy-ethoxy)-1H-indazol-3-yl]-isoxazol-3-yl}-benzoic acid, off-white solid; HPLC/MS 1.55 min (A), $[M+H]^+$ 398.

$^1$H NMR (400 MHz, DMSO-d$_6$) δ 13.72 (s, 1H), 13.20 (s, 1H), 8.18 (d, J=8.5 Hz, 2H), 8.11 (d, J=8.5 Hz, 2H), 8.06-8.00 (m, 2H), 7.80 (s, 1H), 7.29 (d, J=7.1 Hz, 1H), 4.34-4.26 (m, 2H), 3.84-3.72 (m, 2H), 3.36 (s, 3H).

The following compound is prepared analogously

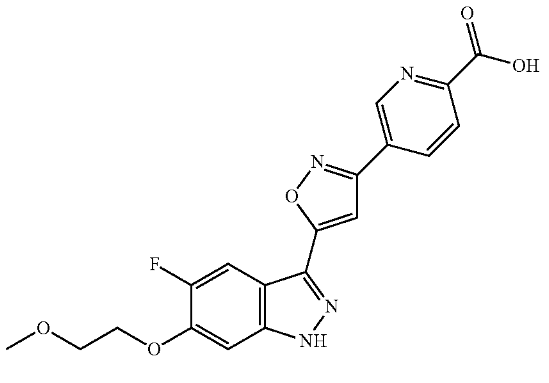 [SMILES: COCCOc1cc2[nH]nc(-c3cc(-c4ccc(C(=O)O)nc4)no3)c2cc1F]

5-{5-[5-fluoro-6-(2-methoxyethoxy)-1H-indazol-3-yl]-1,2-oxazol-3-yl}pyridine-2-carboxylic acid, yellow solid; HPLC/MS 2.51 min (A), $[M+H]^+$ 399.

Synthesis of 4-{5-[5-fluoro-6-(2-hydroxyethoxy)-1H-indazol-3-yl]-1,2-oxazol-3-yl}benzoic Acid

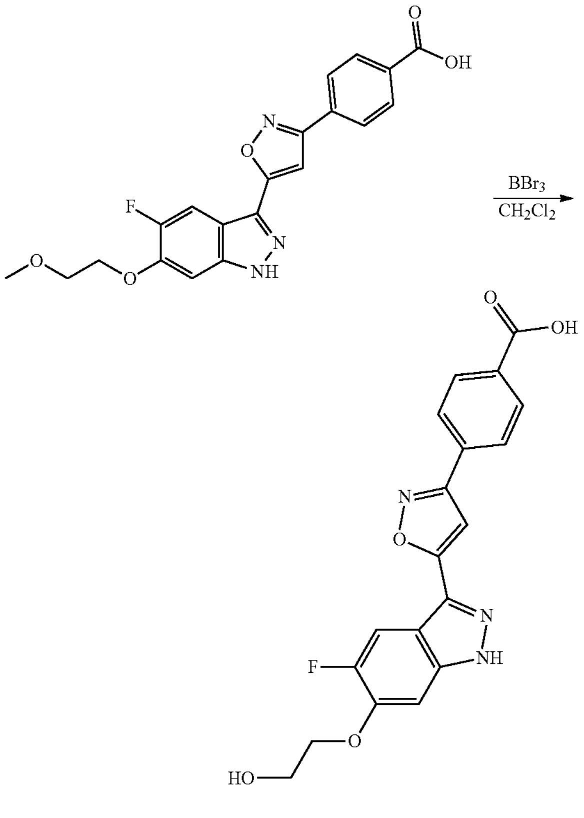

To a solution of 4-{5-[5-fluoro-6-(2-methoxy-ethoxy)-1H-indazol-3-yl]-isoxazol-3-yl}-benzoic acid (234 mg, 0.59 mmol) in dichloromethane (8 ml) a 1 M solution of boron tribromide (1.2 ml) is added dropwise. The reaction mixture is stirred for 16 hours at room temperature. The solids are filtered off and washed with dichloromethane and water. The residue is dried under high vacuum to afford 4-{5-[5-fluoro-6-(2-hydroxyethoxy)-1H-indazol-3-yl]-1,2-oxazol-3-yl}benzoic acid as off-white solid; UPLC/MS 0.63 min, $[M+H]^+$ 384.

$^1$H NMR (400 MHz, DMSO-$d_6$) δ 13.71 (s, 1H), 8.17 (d, J=8.5 Hz, 1H), 8.11 (d, J=8.5 Hz, 2H), 8.02 (d, J=11.0 Hz, 1H), 7.79 (s, 1H), 7.28 (d, J=7.1 Hz, 1H), 4.19 (t, J=4.9 Hz, 1H), 3.82 (t, J=4.8 Hz, 1H).

Example 1

2-[1-(4-{5-[6-(trifluoromethyl)-1H-indazol-3-yl]-1,2-oxazol-3-yl}benzoyl)pyrrolidin-2-yl]propan-2-ol ("A1")

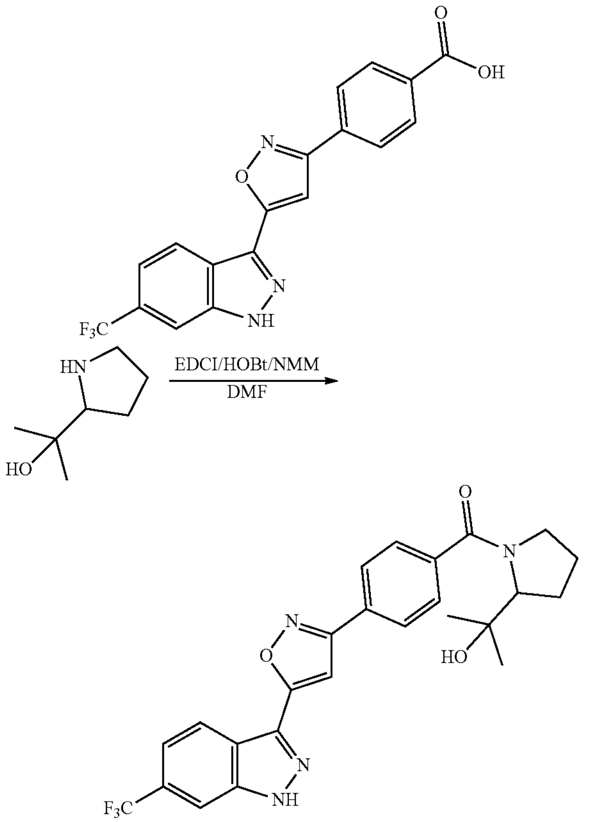

To a suspension of 4-[5-(6-trifluoromethyl-1H-indazol-3-yl)-isoxazol-3-yl]-benzoic acid (52 mg, 0.14 mmol), 2-(pyrrolidin-2-yl)-propan-2-ol (23 mg, 0.18 mmol), N-(3-dimethylaminopropyl)-N'-ethylcarbodiimide hydrochloride (41 mg, 0.21 mmol) and 1-hydroxybenzotriazole hydrate (25 mg, 153 mmol) in DMF (1.4 ml) is added 4-methylmorpholine (63 μl, 0.57 mmol). The reaction mixture is heated to 80° C. and stirred at this temperature for 16 hours. The reaction mixture is allowed to reach room temperature and saturated sodium hydrogen carbonate solution is added. The solid is filtered off, washed with water and dried. The residue is chromatographed on a silica gel column with cyclohexane/ethyl acetate as eluent to afford 2-[1-(4-{5-[6-(trifluoromethyl)-1H-indazol-3-yl]-1,2-oxazol-3-yl}benzoyl)pyrrolidin-2-yl]propan-2-ol as off-white powder; UPLC/MS 0.87 min, $[M+H]^+$ 485.

$^1$H NMR (500 MHz, DMSO-$d_6$) δ 14.28 (s, 1H), 8.47 (d, J=8.6 Hz, 1H), 8.12 (d, J=8.1 Hz, 2H), 8.10 (s, 1H), 7.84 (s, 1H), 7.74 (d, J=8.0 Hz, 2H), 7.64 (dd, J=8.7, 1.6 Hz, 1H), 4.88 (s, 1H), 4.31 (t, J=7.2 Hz, 1H), 3.62-3.47 (m, 1H), 3.44-3.33 (m, 1H), 1.98-1.82 (m, 3H), 1.68-1.55 (m, 1H), 1.17 (s, 3H), 1.14 (s, 3H).

The following compounds are prepared analogously:

2-[(2R)-1-(4-{5-[6-(2-methoxyethoxy)-1H-indazol-3-yl]-1,2-oxazol-3-yl}benzoyl)pyrrolidin-2-yl]propan-2-ol ("A2")

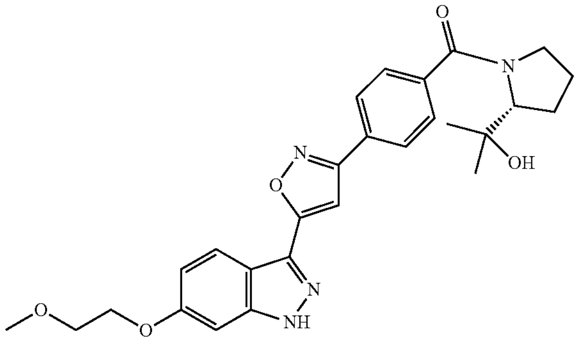 [SMILES: COCCOc1ccc2c(-c3cc(-c4ccc(C(=O)N5CCC[C@@H]5C(C)(C)O)cc4)no3)n[nH]c2c1]

off-white solid; HPLC/MS 1.60 min (A), $[M+H]^+$ 491.

$^1$H NMR (500 MHz, DMSO-$d_6$) δ 13.57 (s, 1H), 8.10 (d, J=8.2 Hz, 2H), 8.08 (d, J=8.9 Hz, 1H), 7.73 (d, J=8.0 Hz, 2H), 7.70 (s, 1H), 7.06 (d, J=2.1 Hz, 1H), 6.99 (dd, J=8.9, 2.1 Hz, 1H), 4.88 (s, 1H), 4.31 (t, J=7.2 Hz, 1H), 4.24-4.19 (m, 2H), 3.76-3.70 (m, 2H), 3.56-3.48 (m, 1H), 3.41-3.33 (m, 4H), 2.00-1.81 (m, 3H), 1.68-1.54 (m, 1H), 1.17 (s, 3H), 1.14 (s, 3H).

3-(3-{4-[(2S)-2,4-dimethylpiperazine-1-carbonyl]phenyl}-1,2-oxazol-5-yl)-5-fluoro-6-(2-methoxyethoxy)-1H-indazole ("A3")

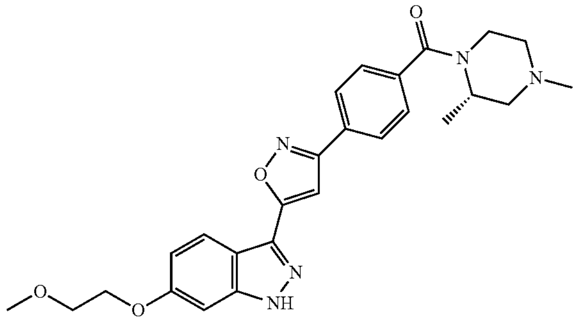

off-white solid; HPLC/MS 1.27 min (A), $[M+H]^+$ 494.

$^1$H NMR (400 MHz, DMSO-$d_6$) δ 13.71 (s, 1H), 8.11 (d, J=8.3 Hz, 2H), 8.03 (d, J=11.0 Hz, 1H), 7.76 (s, 1H), 7.55 (d, J=8.3 Hz, 2H), 7.29 (d, J=7.1 Hz, 1H), 4.34-4.26 (m, 2H), 3.81-3.74 (m, 2H), 3.36 (s, 3H), 3.20 (broad, 1H), 2.75 (broad, 1H), 2.69-2.59 (m, 1H), 2.18 (s, 3H), 2.10-2.03 (m, 1H), 1.93-1.83 (m, 1H), 1.29 (d, J=6.8 Hz, 3H).

{4-[5-(6-bromo-1H-indazol-3-yl)-isoxazol-3-yl]-phenyl}-[(R)-2-(1-hydroxy-1-methyl-ethyl)-pyrrolidin-1-yl]-methanone ("A3a")

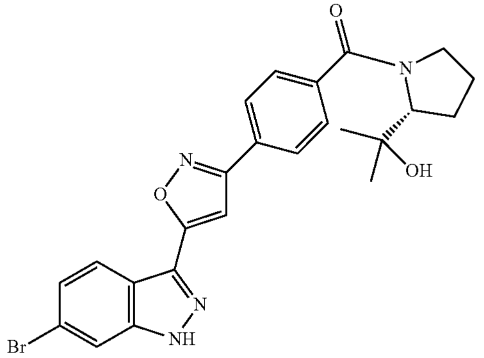 [SMILES: CC(C)(O)[C@H]1CCCN1C(=O)c1ccc(-c2cc(-c3n[nH]c4cc(Br)ccc34)on2)cc1]

off-white solid; UPLC/MS 0.86 min, $[M+H]^+$ 495/497.

{4-[5-(6-bromo-1H-indazol-3-yl)-isoxazol-3-yl]-phenyl}-[(S)-2-(1-hydroxy-1-methyl-ethyl)-pyrrolidin-1-yl]-methanone ("A4")

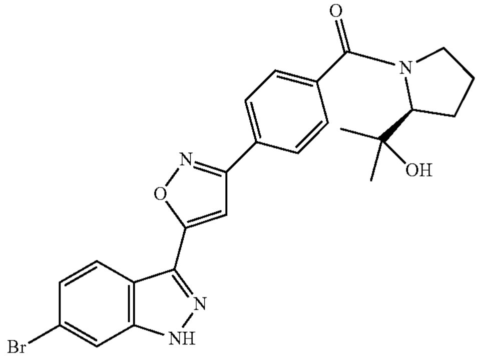 [SMILES: CC(C)(O)[C@@H]1CCCN1C(=O)c1ccc(-c2cc(-c3n[nH]c4cc(Br)ccc34)on2)cc1]

UPLC/MS 0.86 min, $[M+H]^+$ 495/497.

$^1$H NMR (400 MHz, DMSO-$d_6$) δ 13.96 (s, 1H), 8.20 (d, J=8.6 Hz, 1H), 8.12 (d, J=8.0 Hz, 2H), 7.95 (d, J=1.5 Hz, 1H), 7.79 (s, 1H), 7.74 (d, J=7.9 Hz, 2H), 7.50 (dd, J=8.7, 1.7 Hz, 1H), 4.89 (s, 1H), 4.32 (t, J=7.1 Hz, 1H), 3.53 (q, J=9.1, 8.4 Hz, 1H), 3.38 (t, J=9.0 Hz, 1H), 2.04-1.78 (m, 3H), 1.69-1.55 (1H), 1.18 (s, 3H), 1.14 (s, 3H).

2-[(2S)-1-(4-{5-[5-fluoro-6-(2-methoxyethoxy)-1H-indazol-3-yl]-1,2-oxazol-3-yl}benzoyl)pyrrolidin-2-yl]propan-2-ol ("A5")

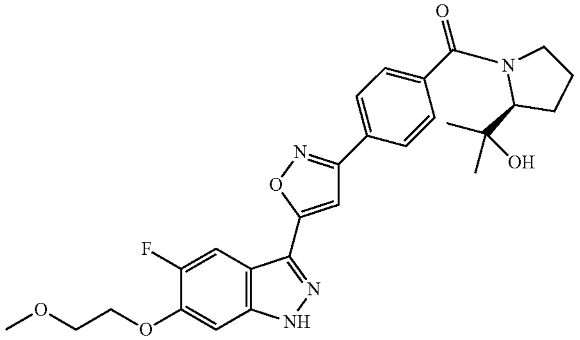 [SMILES: COCCOc1cc2[nH]nc(-c3cc(-c4ccc(C(=O)N5CCC[C@H]5C(C)(C)O)cc4)no3)c2cc1F]

white solid; HPLC/MS 1.27 min (A), $[M+H]^+$ 509.

$^1$H NMR (500 MHz, DMSO-$d_6$) δ 13.70 (s, 1H), 8.11 (d, J=8.0 Hz, 2H), 8.03 (d, J=10.9 Hz, 1H), 7.77 (s, 1H), 7.73 (d, J=7.9 Hz, 2H), 7.28 (d, J=7.0 Hz, 1H), 4.88 (s, 1H), 4.36-4.23 (m, 3H), 3.79-3.73 (m, 2H), 3.58-3.47 (m, 1H), 3.41-3.34 (m, 4H), 2.00-1.80 (m, 3H), 1.67-1.55 (m, 1H), 1.17 (s, 3H), 1.14 (s, 3H).

{4-[5-(6-bromo-1H-indazol-3-yl)-isoxazol-3-yl]-phenyl}-((S)-2,4-dimethyl-piperazin-1-yl)-methanone ("A5a")

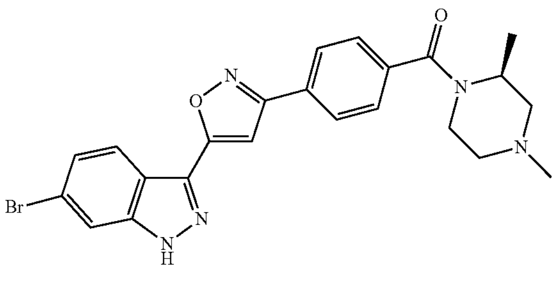 [SMILES: C[C@H]1CN(C)CCN1C(=O)c1ccc(-c2cc(-c3n[nH]c4cc(Br)ccc34)on2)cc1]

off-white solid; UPLC/MS 0.54 min, $[M+H]^+$ 480/482.

$^1$H NMR (400 MHz, DMSO-$d_6$) δ 13.96 (s, 1H), 8.20 (d, J=8.7 Hz, 1H), 8.11 (d, J=8.3 Hz, 2H), 7.95 (d, J=1.5 Hz, 1H), 7.78 (s, 1H), 7.55 (d, J=8.2 Hz, 2H), 7.50 (dd, J=8.6, 1.6 Hz, 1H), 2.80-2.71 (m, 1H), 2.64 (d, J=10.7 Hz, 1H), 2.18 (s, 3H), 2.06 (dd, J=11.3, 3.8 Hz, 1H), 1.91-1.83 (m, 1H), 1.29 (d, J=6.8 Hz, 3H).

4-{5-[5-cyano-6-(2-methoxyethoxy)-1H-indazol-3-yl]-1,2-oxazol-3-yl}-N,N-dimethylbenzamide ("A6")

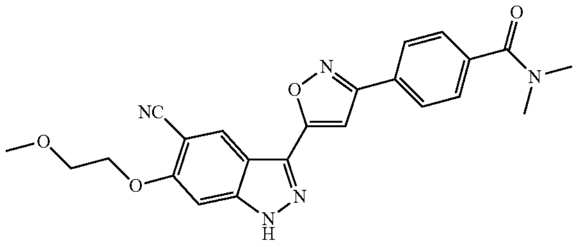

off-white powder; HPLC/MS 2.01 min (A), $[M+H]^+$ 432. $^1$H NMR (700 MHz, DMSO-$d_6$) δ 13.99 (s, 1H), 8.76 (s, 1H), 8.10 (d, J=8.4 Hz, 2H), 7.95 (s, 1H), 7.60 (d, J=8.2 Hz, 2H), 7.29 (s, 1H), 4.43-4.32 (m, 2H), 3.95-3.73 (m, 2H), 3.38 (s, 3H), 3.02 (s, 3H), 2.96 (s, 3H).

5-fluoro-3-(3-{4-[(2S)-2-(methanesulfonylmethyl)pyrrolidine-1-carbonyl]phenyl}-1,2-oxazol-5-yl)-6-(2-methoxyethoxy)-1H-indazole ("A7")

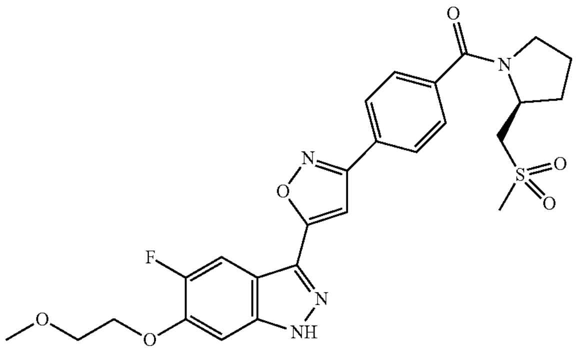 [SMILES: COCCOc1cc2[nH]nc(-c3cc(-c4ccc(C(=O)N5CCC[C@H]5CS(C)(=O)=O)cc4)no3)c2cc1F]

white powder; HPLC/MS 1.55 min (A), $[M+H]^+$ 543. $^1$H NMR (400 MHz, DMSO-$d_6$) δ 13.70 (s, 1H), 8.11 (d, J=8.3 Hz, 2H), 8.03 (d, J=11.0 Hz, 1H), 7.76 (s, 1H), 7.69 (d, J=8.3 Hz, 2H), 7.28 (d, J=7.1 Hz, 1H), 4.56 (broad, 1H), 4.34-4.25 (m, 2H), 3.81-3.67 (m, 3H), 3.52 (q, J=7.9, 7.3 Hz, 1H), 3.42-3.29 (m, 6H), 3.10 (s, 3H), 2.24-2.14 (m, 1H), 2.10-1.90 (m, 2H), 1.85-1.75 (m, 1H).

3-(3-{4-[(2S)-2,4-dimethylpiperazine-1-carbonyl]phenyl}-1,2-oxazol-5-yl)-6-(trifluoromethyl)-1H-indazole ("A50")

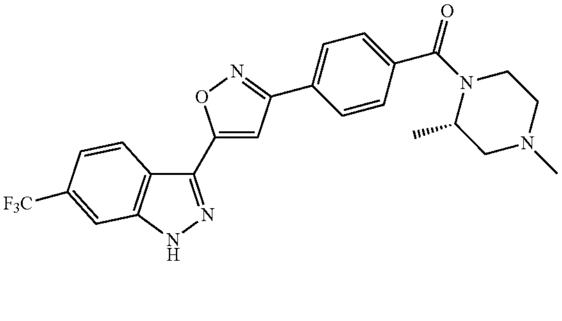 [SMILES: C[C@H]1CN(C)CCN1C(=O)c1ccc(-c2cc(-c3n[nH]c4cc(C(F)(F)F)ccc34)on2)cc1]

[(2S)-1-(4-{5-[5-fluoro-6-(2-methoxyethoxy)-1H-indazol-3-yl]-1,2-oxazol-3-yl}benzoyl)pyrrolidin-2-yl]methanol ("A51")

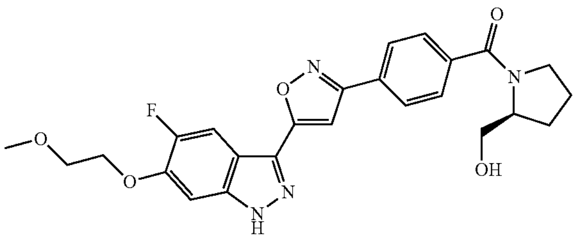 [SMILES: COCCOc1cc2[nH]nc(-c3cc(-c4ccc(C(=O)N5CCC[C@H]5CO)cc4)no3)c2cc1F]

off-white solid; UPLC/MS 0.70 min, $[M+H]^+$ 481.

$^1H$ NMR (400 MHz, DMSO-$d_6$, rotational isomers) δ 13.72 (s, 1H), 8.09 (d, J=8.1 Hz, 2H), 8.03 (d, J=11.0 Hz, 1H), 7.76 (s, 1H), 7.68 (d, J=7.9 Hz, 2H), 7.28 (d, J=7.1 Hz, 1H), 4.80 (broad, 1H), 4.34-4.22 (m, 2H), 4.18 (broad, 1H), 3.80-3.69 (m, 2H), 3.69-3.41 (m, 4H), 3.36 (s, 3H), 2.03-1.66 (m; 6H).

[(2R)-1-(4-{5-[5-fluoro-6-(2-methoxyethoxy)-1H-indazol-3-yl]-1,2-oxazol-3-yl}benzoyl)pyrrolidin-2-yl]methanol ("A52")

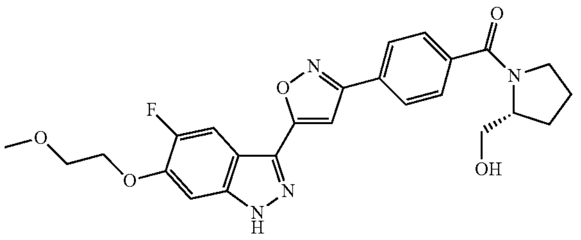 [SMILES: COCCOc1cc2[nH]nc(-c3cc(-c4ccc(C(=O)N5CCC[C@@H]5CO)cc4)no3)c2cc1F]

off-white solid; UPLC/MS 0.70 min, $[M+H]^+$ 481.

$^1H$ NMR (400 MHz, DMSO-$d_6$, rotational isomers) δ 13.72 (s, 1H), 8.09 (d, J=8.1 Hz, 2H), 8.03 (d, J=11.0 Hz, 1H), 7.76 (s, 1H), 7.68 (d, J=7.9 Hz, 2H), 7.28 (d, J=7.1 Hz, 1H), 4.80 (broad, 1H), 4.34-4.22 (m, 2H), 4.18 (broad, 1H), 3.80-3.69 (m, 2H), 3.69-3.41 (m, 4H), 3.36 (s, 3H), 2.03-1.66 (m; 6H).

5-fluoro-6-(2-methoxyethoxy)-3-(3-{4-[3-(morpholin-4-yl)azetidine-1-carbonyl]phenyl}-1,2-oxazol-5-yl)-1H-indazole ("A53")

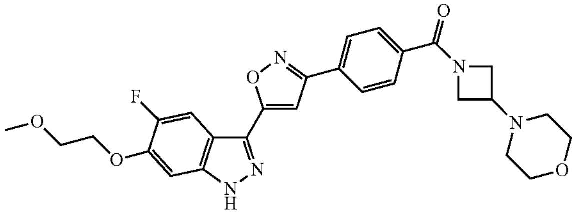 [SMILES: COCCOc1cc2[nH]nc(-c3cc(-c4ccc(C(=O)N5CC(N6CCOCC6)C5)cc4)no3)c2cc1F]

white crystals; HPLC/MS 1.33 min (A), $[M+H]^+$ 522.

$^1H$ NMR (500 MHz, DMSO-$d_6$) δ 13.71 (s, 1H), 8.10 (d, J=8.4 Hz, 1H), 8.02 (d, J=11.0 Hz, 1H), 7.83-7.79 (m, 2H), 7.76 (s, 1H), 7.28 (d, J=7.1 Hz, 1H), 4.36 (t, J=8.1 Hz, 1H), 4.32-4.28 (m, 2H), 4.19 (dd, J=9.2, 4.9 Hz, 1H), 4.14-4.06 (m, 1H), 3.92 (dd, J=10.9, 4.4 Hz, 1H), 3.84-3.73 (m, 2H), 3.60 (t, J=4.7 Hz, 4H), 3.36 (s, 3H), 3.18 (tt, J=7.2, 5.0 Hz, 1H), 2.34 (broad, 4H).

[1-(4-{5-[5-fluoro-6-(2-methoxyethoxy)-1H-indazol-3-yl]-1,2-oxazol-3-yl}benzoyl)-4-methylpiperazin-2-yl]methanol ("A54")

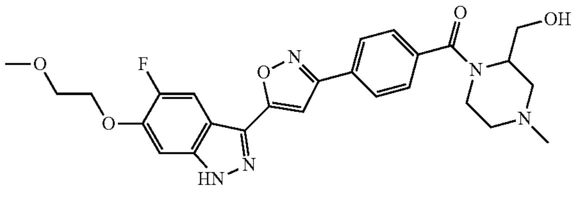 [SMILES: COCCOc1cc2[nH]nc(-c3cc(-c4ccc(C(=O)N5CCN(C)CC5CO)cc4)no3)c2cc1F]

pale brown solid; HPLC/MS 1.22 min (A), $[M+H]^+$ 510.

$^1H$ NMR (500 MHz, DMSO-$d_6$, rotational isomers, selection of signals) δ 13.72 (s, 1H), 8.08 (d, J=7.9 Hz, 2H), 8.03 (d, J=11.0 Hz, 1H), 7.76 (s, 1H), 7.57 (d, J=7.9 Hz, 2H), 7.28 (d, J=7.0 Hz, 1H), 4.83 (s, 1H), 4.31-4.28 (m, 2H), 3.96-3.56 (m, 5H), 3.35 (s, 3H), 2.16 (s, 3H).

5-fluoro-3-(3-{4-[(2R)-2-(methanesulfonylmethyl)pyrrolidine-1-carbonyl]phenyl}-1,2-oxazol-5-yl)-6-(2-methoxyethoxy)-1H-indazole ("A55")

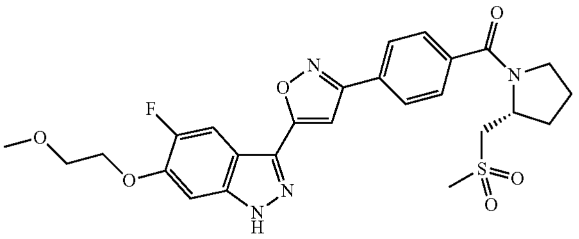 [SMILES: COCCOc1cc2[nH]nc(-c3cc(-c4ccc(C(=O)N5CCC[C@@H]5CS(C)(=O)=O)cc4)no3)c2cc1F]

white solid; UPLC/MS 0.73 min, $[M+H]^+$ 543.

$^1H$ NMR (500 MHz, DMSO-$d_6$) δ 13.73 (s, 1H), 8.12 (d, J=8.4 Hz, 2H), 8.04 (d, J=10.9 Hz, 1H), 7.79 (s, 1H), 7.70 (d, J=8.3 Hz, 2H), 7.29 (d, J=7.1 Hz, 1H), 4.62-4.51 (m, 1H), 4.35-4.24 (m, 2H), 3.83-3.71 (m, 3H), 3.53 (dt, J=10.1, 7.0 Hz, 1H), 3.42-3.29 (m, 5H), 3.11 (s, 3H), 2.20 (dq, J=13.9, 7.1 Hz, 1H), 2.05 (dq, J=12.5, 6.4 Hz, 1H), 1.96 (dp, J=13.1, 6.6 Hz, 1H), 1.86-1.75 (m, 1H).

1-(4-{5-[5-fluoro-6-(2-methoxyethoxy)-1H-indazol-3-yl]-1,2-oxazol-3-yl}benzoyl)-3-methylazetidin-3-amine ("A56")

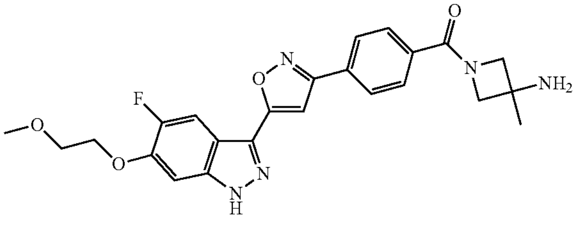 [SMILES: COCCOc1cc2[nH]nc(-c3cc(-c4ccc(C(=O)N5CC(C)(N)C5)cc4)no3)c2cc1F]

trifluoroacetate; white solid; HPLC/MS 2.24 min (A), $[M+H]^+$ 465.

$^1H$ NMR (500 MHz, DMSO-$d_6$) δ 13.74 (s, 1H), 8.28 (s, 3H), 8.15 (d, J=8.3 Hz, 2H), 8.03 (d, J=10.9 Hz, 1H), 7.82 (d, J=8.3 Hz, 2H), 7.80 (s, 1H), 7.29 (d, J=7.1 Hz, 1H), 4.43 (d, J=9.5 Hz, 1H), 4.36-4.26 (m, 3H), 4.17 (d, J=10.8 Hz, 1H), 4.02 (d, J=10.8 Hz, 1H), 3.81-3.73 (m, 2H), 3.35 (s, 3H), 1.58 (s, 3H).

4-[1-(4-{5-[5-fluoro-6-(2-methoxyethoxy)-1H-indazol-3-yl]-1,2-oxazol-3-yl}benzoyl)azetidin-3-yl]-1lambda6-thiomorpholine-1,1-dione ("A57")

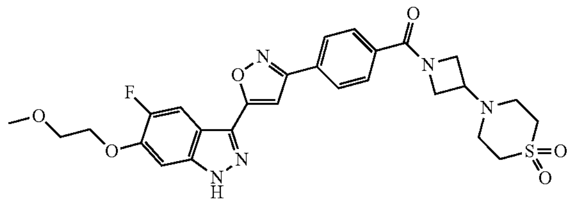 [SMILES: COCCOc1cc2[nH]nc(-c3cc(-c4ccc(C(=O)N5CC(N6CCS(=O)(=O)CC6)C5)cc4)no3)c2cc1F]

white powder; UPLC/MS 0.68 min, $[M+H]^+$ 570.

$^1H$ NMR (500 MHz, DMSO-$d_6$) δ 13.73 (s, 1H), 8.11 (d, J=8.4 Hz, 1H), 8.03 (d, J=11.0 Hz, 1H), 7.81 (d, J=8.4 Hz, 2H), 7.78 (s, 1H), 7.28 (d, J=7.1 Hz, 1H), 4.40 (t, J=8.1 Hz, 1H), 4.32-4.25 (m, 2H), 4.20 (dd, J=9.2, 5.0 Hz, 1H), 4.13 (dd, J=10.3, 7.3 Hz, 1H), 3.92 (dd, J=10.5, 5.0 Hz, 1H), 3.81-3.74 (m, 2H), 3.48 (tt, J=7.2, 5.0 Hz, 1H), 3.35 (s, 3H), 3.13 (t, J=5.2 Hz, 4H), 2.88-2.76 (m, 4H).

2-[(2R)-1-(4-{5-[5-fluoro-6-(2-methoxyethoxy)-1H-indazol-3-yl]-1,2-oxazol-3-yl}benzoyl)azetidin-2-yl]propan-2-ol ("A58")

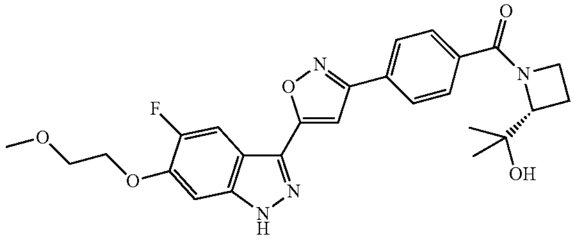 [SMILES: COCCOc1cc2[nH]nc(-c3cc(-c4ccc(C(=O)N5CC[C@@H]5C(C)(C)O)cc4)no3)c2cc1F]

white solid; HPLC/MS 1.59 min (A), $[M+H]^+$ 495.

$^1H$ NMR (500 MHz, DMSO-$d_6$) δ 13.74 (s, 1H), 8.12 (d, J=8.3 Hz, 2H), 8.03 (d, J=10.9 Hz, 1H), 7.82 (d, J=8.2 Hz, 2H), 7.79 (s, 1H), 7.28 (d, J=7.0 Hz, 1H), 5.02 (s, 1H), 4.40 (dd, J=9.2, 5.6 Hz, 1H), 4.35-4.22 (m, 3H), 3.99 (td, J=8.9, 5.5 Hz, 1H), 3.83-3.71 (m, 2H), 3.36 (s, 3H), 2.30 (qd, J=9.8, 6.3 Hz, 1H), 2.13 (ddt, J=11.1, 9.0, 5.6 Hz, 1H), 1.16 (s, 3H), 1.15 (s, 3H).

2-[(2S)-1-(4-{5-[5-fluoro-6-(2-methoxyethoxy)-1H-indazol-3-yl]-1,2-oxazol-3-yl}benzoyl)azetidin-2-yl]propan-2-ol ("A59")

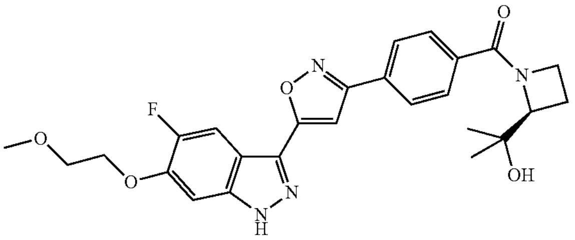 [SMILES: COCCOc1cc2[nH]nc(-c3cc(-c4ccc(C(=O)N5CC[C@H]5C(C)(C)O)cc4)no3)c2cc1F]

pale yellow powder; UPLC/MS 0.76 min, $[M+H]^+$ 495.

$^1H$ NMR (500 MHz, DMSO-$d_6$) δ 13.74 (s, 1H), 8.12 (d, J=8.3 Hz, 2H), 8.03 (d, J=10.9 Hz, 1H), 7.82 (d, J=8.2 Hz, 2H), 7.79 (s, 1H), 7.28 (d, J=7.0 Hz, 1H), 5.02 (s, 1H), 4.40 (dd, J=9.2, 5.6 Hz, 1H), 4.35-4.22 (m, 3H), 3.99 (td, J=8.9, 5.5 Hz, 1H), 3.83-3.71 (m, 2H), 3.36 (s, 3H), 2.30 (qd, J=9.8, 6.3 Hz, 1H), 2.13 (ddt, J=11.1, 9.0, 5.6 Hz, 1H), 1.16 (s, 3H), 1.15 (s, 3H).

7-(4-{5-[5-fluoro-6-(2-methoxyethoxy)-1H-indazol-3-yl]-1,2-oxazol-3-yl}benzoyl)-2-oxa-7-azaspiro[3.5]nonane ("A60")

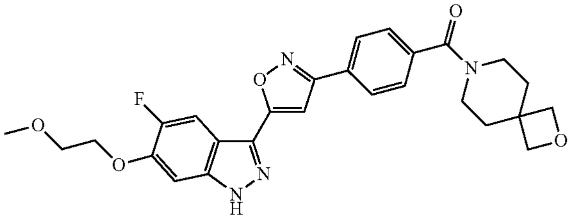 [SMILES: COCCOc1cc2[nH]nc(-c3cc(-c4ccc(C(=O)N5CCC6(CC5)COC6)cc4)no3)c2cc1F]

off-white solid; UPLC/MS 0.72 min, $[M+H]^+$ 507.

$^1H$ NMR (400 MHz, DMSO-$d_6$) δ 13.71 (s, 1H), 8.10 (d, J=8.3 Hz, 2H), 8.03 (d, J=11.0 Hz, 1H), 7.76 (s, 1H), 7.56 (d, J=8.2 Hz, 2H), 7.29 (d, J=7.1 Hz, 1H), 4.36 (s, 4H), 4.33-4.28 (m, 2H), 3.80-3.72 (m, 2H), 3.55 (bs, 2H), 3.37 (s, 3H), 3.30 (bs, 2H), 1.84 (bs, 4H).

5-fluoro-6-methoxy-3-(3-{4-[3-(morpholin-4-yl)azetidine-1-carbonyl]phenyl}-1,2-oxazol-5-yl)-1H-indazole ("A61")

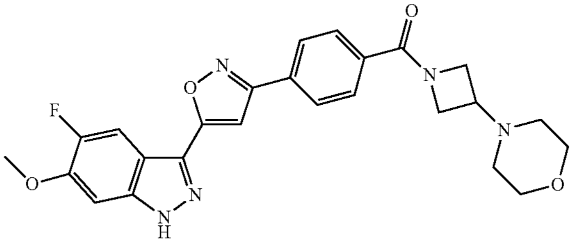 [SMILES: COc1cc2[nH]nc(-c3cc(-c4ccc(C(=O)N5CC(N6CCOCC6)C5)cc4)no3)c2cc1F]

(5-{5-[5-fluoro-6-(2-methoxy-ethoxy)-1H-indazol-3-yl]-isoxazol-3-yl}-pyridin-2-yl)-((R)-2-hydroxymethyl-pyrrolidin-1-yl)-methanone ("A62")

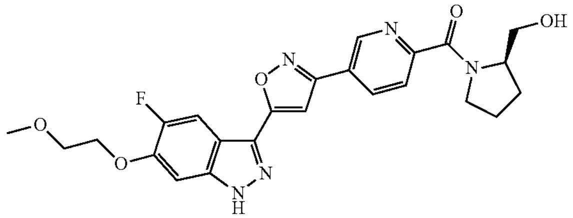 [SMILES: COCCOc1cc2[nH]nc(-c3cc(-c4ccc(C(=O)N5CCC[C@@H]5CO)nc4)no3)c2cc1F]

(5-{5-[5-fluoro-6-(2-methoxy-ethoxy)-1H-indazol-3-yl]-isoxazol-3-yl}-pyridin-2-yl)-((S)-2-hydroxymethyl-pyrrolidin-1-yl)-methanone ("A63")

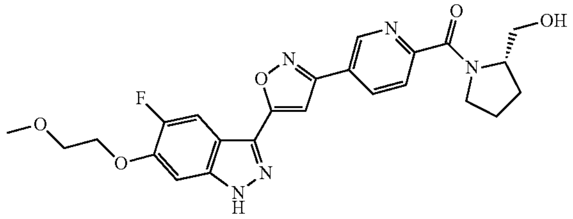 [SMILES: COCCOc1cc2[nH]nc(-c3cc(-c4ccc(C(=O)N5CCC[C@H]5CO)nc4)no3)c2cc1F]

(4-{5-[5-chloro-6-(2-methoxy-ethoxy)-1H-indazol-3-yl]-isoxazol-3-yl}-phenyl)-(3-morpholin-4-yl-azetidin-1-yl)-methanone ("A64")

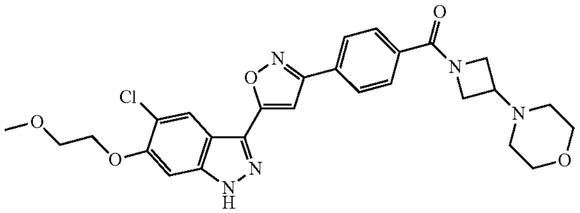 [SMILES: COCCOc1cc2[nH]nc(-c3cc(-c4ccc(C(=O)N5CC(N6CCOCC6)C5)cc4)no3)c2cc1Cl]

white solid; m. p. 200-201° C., $[M+H]^+$ 538.

$^1H$ NMR (400 MHz, DMSO-$d_6$) δ 13.78 (s, 1H), 8.32 (s, 1H), 8.16-8.09 (m, 2H), 7.88-7.79 (m, 3H), 7.26 (s, 1H), 4.41-4.34 (m, 1H), 4.33-4.27 (m, 2H), 4.24-4.16 (m, 1H), 4.15-4.05 (m, 1H), 3.96-3.88 (m, 1H), 3.82-3.70 (m, 2H), 3.66-3.52 (m, 4H), 3.38 (s, 3H), 3.23-3.13 (m, 1H), 2.43-2.25 (m, 4H).

(4-{5-[5-chloro-6-(2-methoxy-ethoxy)-1H-indazol-3-yl]-isoxazol-3-yl}-phenyl)-[3-(4-methyl-piperazin-1-yl)-azetidin-1-yl]-methanone ("A65")

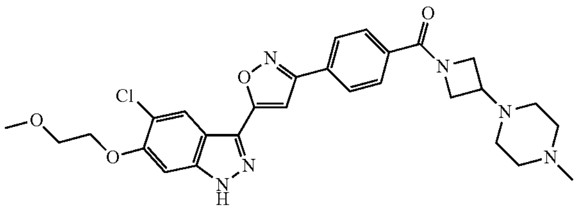

(4-{5-[5-chloro-6-(2-methoxy-ethoxy)-1H-indazol-3-yl]-isoxazol-3-yl}-phenyl)-((S)-3-hydroxymethyl-morpholin-4-yl)-methanone ("A66")

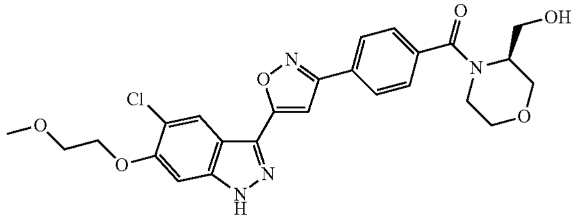 [SMILES: COCCOc1cc2[nH]nc(-c3cc(-c4ccc(C(=O)N5CCOC[C@@H]5CO)cc4)no3)c2cc1Cl]

white solid; m. p. 115-116° C., $[M+H]^+$ 513.

$^1H$ NMR (400 MHz, DMSO-$d_6$+$D_2O$) δ 8.39-8.28 (m, 1H), 8.16-8.01 (m, 2H), 7.95-7.78 (m, 1H), 7.66-7.55 (m, 2H), 7.28 (s, 1H), 4.35-4.25 (m, 2H), 4.22-3.86 (m, 2H), 3.86-3.79 (m, 2H), 3.76-3.45 (m, 6H), 3.39-3.32 (m, 3H), 3.31-2.72 (m, 1H).

(4-{5-[5-chloro-6-(2-methoxy-ethoxy)-1H-indazol-3-yl]-isoxazol-3-yl}-phenyl)-((R)-3-hydroxymethyl-morpholin-4-yl)-methanone ("A67")

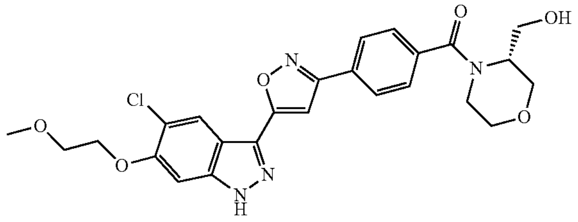 [SMILES: COCCOc1cc2[nH]nc(-c3cc(-c4ccc(C(=O)N5CCOC[C@H]5CO)cc4)no3)c2cc1Cl]

(5-{5-[5-fluoro-6-(2-methoxy-ethoxy)-1H-indazol-3-yl]-isoxazol-3-yl}-pyridin-2-yl)-(4-oxetan-3-yl-piperazin-1-yl)-methanone ("A68")

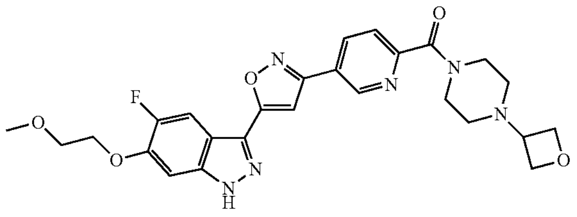 [SMILES: COCCOc1cc2[nH]nc(-c3cc(-c4ccc(C(=O)N5CCN(C6COC6)CC5)nc4)no3)c2cc1F]

(5-{5-[5-fluoro-6-(2-methoxy-ethoxy)-1H-indazol-3-yl]-isoxazol-3-yl}-pyridin-2-yl)-(3-morpholin-4-yl-azetidin-1-yl)-methanone ("A69")

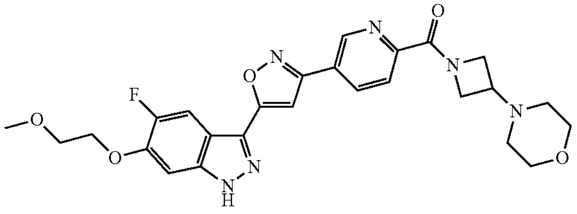 [SMILES: COCCOc1cc2[nH]nc(-c3cc(-c4ccc(C(=O)N5CC(N6CCOCC6)C5)nc4)no3)c2cc1F]

(4-{5-[5-fluoro-6-(2-methoxy-ethoxy)-1H-indazol-3-yl]-isoxazol-3-yl}-2-methyl-phenyl)-(cis)-tetrahydro-furo[3,4-c]pyrrol-5-yl-methanone ("A70")

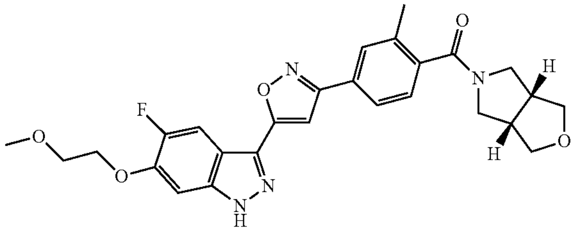 [SMILES: COCCOc1cc2[nH]nc(-c3cc(-c4ccc(C(=O)N5C[C@H]6COC[C@H]6C5)c(C)c4)no3)c2cc1F]

(2-fluoro-4-{5-[5-fluoro-6-(2-methoxy-ethoxy)-1H-indazol-3-yl]-isoxazol-3-yl}-phenyl)-(cis)-tetrahydro-furo[3,4-c]pyrrol-5-yl-methanone ("A71")

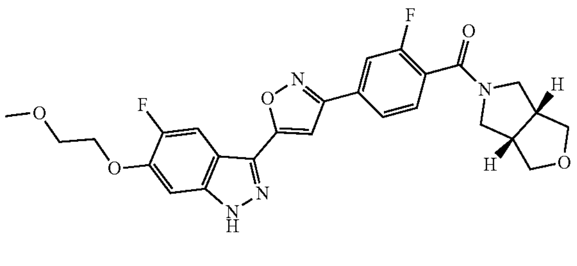 [SMILES: COCCOc1cc2[nH]nc(-c3cc(-c4ccc(C(=O)N5C[C@H]6COC[C@H]6C5)c(F)c4)no3)c2cc1F]

3-{5-[5-fluoro-6-(2-methoxy-ethoxy)-1H-indazol-3-yl]-isoxazol-3-yl}-N,N-dimethyl-benzamide ("A135")

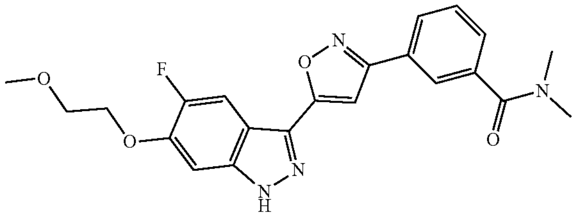

white solid; m.p. 160-165° C., $[M+H]^+$ 424.

$^1H$ NMR (400 MHz, DMSO-$d_6$): δ 13.73 (s, 1H), 8.14-8.05 (m, 3H), 7.83 (s, 1H), 7.64 (t, J=7.7 Hz, 1H), 7.56 (dt, J=7.7, 1.4 Hz, 1H), 7.28 (d, J=7.1 Hz, 1H), 4.30 (dd, J=5.6, 3.3 Hz, 2H), 3.79-3.72 (m, 2H), 3.01 (d, J=31.0 Hz, 6H).

Example 2

2-[(2R)-1-(4-{5-[6-(1-methyl-1H-pyrazol-4-yl)-1H-indazol-3-yl]-1,2-oxazol-3-yl}benzoyl)pyrrolidin-2-yl]propan-2-ol ("A8")

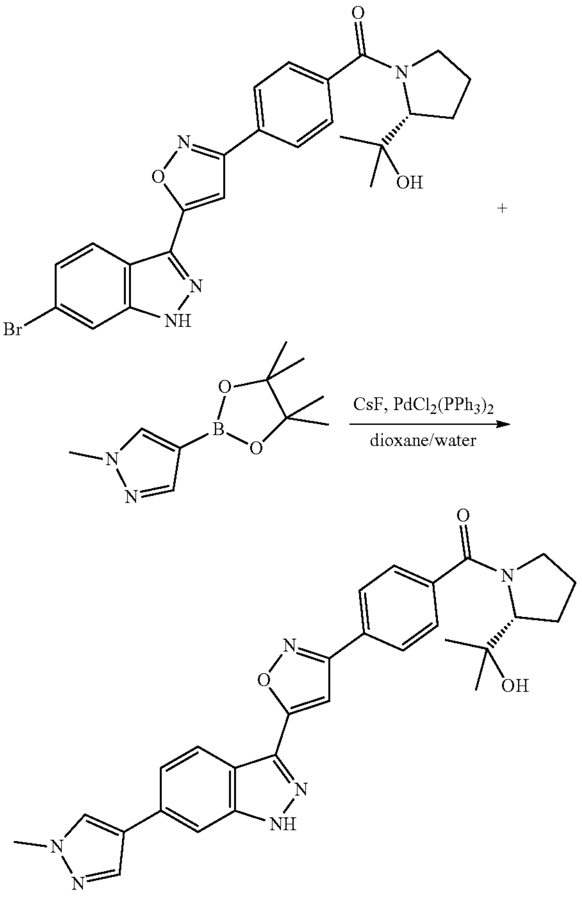

A microwave vial is charged with {4-[5-(6-bromo-1H-indazol-3-yl)-isoxazol-3-yl]-phenyl}-[(R)-2-(1-hydroxy-1-methyl-ethyl)-pyrrolidin-1-yl]-methanone (74 mg, 0.15 mmol), 1-methyl-1H-pyrazole-4-boronic acid pinacol ester (47 mg, 0.23 mmol), cesium fluoride (69 mg, 0.45 mmol), bis(triphenylphosphine)-palladium(II) chloride (11 mg, 0.016 mmol), dioxane (800 μl) and water (400 μl). The vial is flushed with nitrogen and heated to 120° C. in a microwave reactor for 1 hour. Water is added to the reaction mixture. The solid is filtered off and washed with water. The residue is chromatographed on a silica gel column with ethylacetate/methanol to afford 2-[(2R)-1-(4-{5-[6-(1-methyl-1H-pyrazol-4-yl)-1H-indazol-3-yl]-1,2-oxazol-3-yl}benzoyl)pyrrolidin-2-yl]propan-2-ol as white powder; UPLC/MS 0.75 min, $[M+H]^+$ 497.

$^1$H NMR (400 MHz, DMSO-$d_6$) δ 13.76 (s, 1H), 8.31 (s, 1H), 8.20 (dd, J=8.5, 0.8 Hz, 1H), 8.13 (d, J=8.0 Hz, 2H), 8.02 (d, J=0.8 Hz, 1H), 7.78 (t, J=1.1 Hz, 1H), 7.77-7.71 (m, 3H), 7.59 (dd, J=8.5, 1.4 Hz, 1H), 4.89 (s, 1H), 4.32 (t, J=7.2 Hz, 1H), 3.91 (s, 3H), 3.54 (q, J=9.3, 8.7 Hz, 1H), 3.39 (t, J=9.2 Hz, 1H), 2.02-1.81 (m, 3H), 1.69-1.57 (m, 1H), 1.18 (s, 3H), 1.15 (s, 3H).

The following compound is prepared analogously:

3-(3-{4-[(2S)-2,4-dimethylpiperazine-1-carbonyl]phenyl}-1,2-oxazol-5-yl)-6-(1-methyl-1H-pyrazol-4-yl)-1H-indazole ("A9")

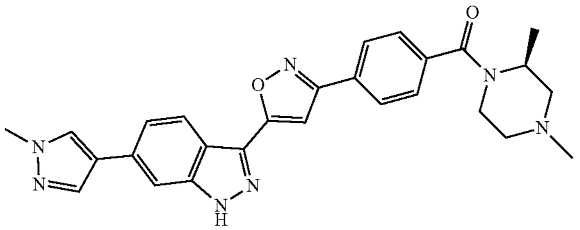

pale yellow solid; UPLC/MS 0.50 min (A), $[M+H]^+$ 482. $^1$H NMR (500 MHz, DMSO-$d_6$) δ 13.76 (s, 1H), 8.31 (s, 1H), 8.19 (dd, J=8.5, 0.8 Hz, 1H), 8.12 (d, J=8.2 Hz, 2H), 8.02 (d, J=0.8 Hz, 1H), 7.78 (s, 1H), 7.73 (s, 1H), 7.59 (dd, J=8.5, 1.4 Hz, 1H), 7.55 (d, J=8.3 Hz, 2H), 3.91 (s, 3H), 3.30 (s, 3H), 3.3-3.1 (broad, 1H), 2.81-2.71 (broad, 1H), 2.68-2.58 (m, OH), 2.18 (s, 1H), 2.07 (dd, J=11.4, 4.0 Hz, 1H), 1.97-1.81 (m, 1H), 1.30 (d, J=6.8 Hz, 3H).

Example 3

5-chloro-3-(5-{4-[(2S)-2,4-dimethylpiperazine-1-carbonyl]phenyl}-1,2-oxazol-3-yl)-6-(2-methoxy-ethoxy)-1H-indazole ("A10")

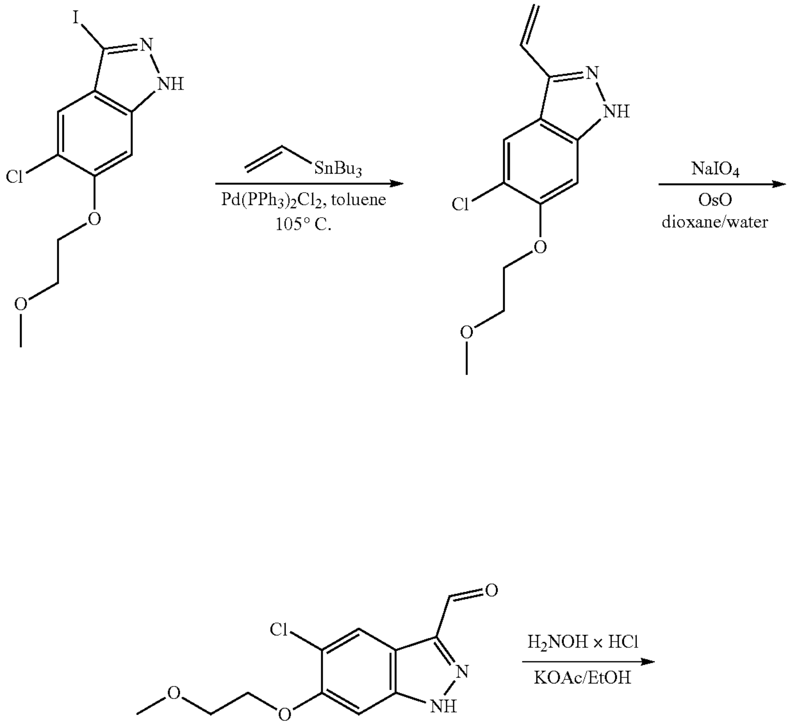

-continued

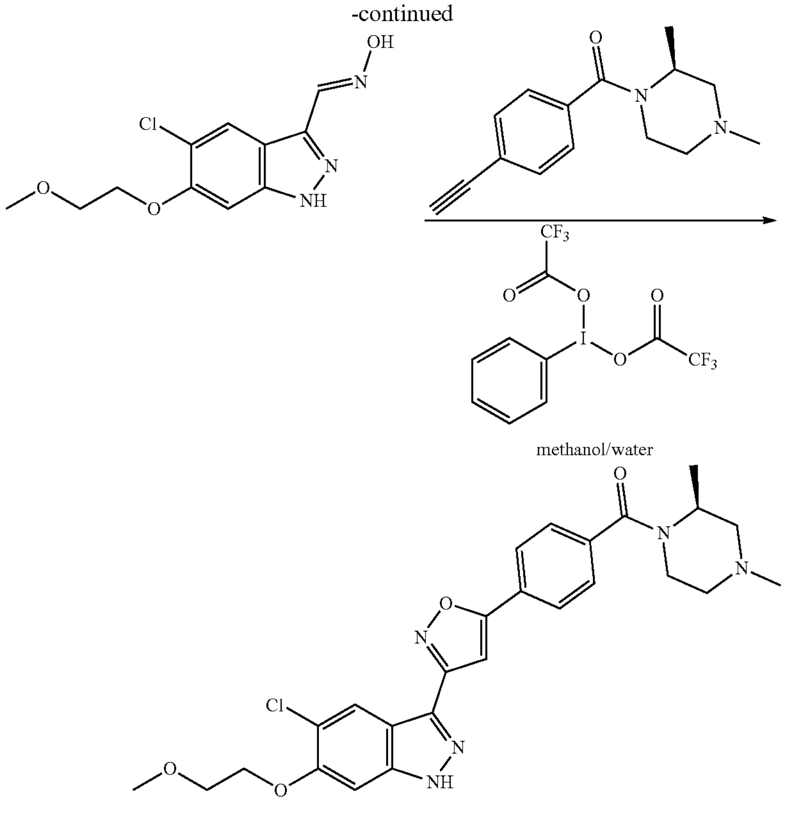

brown solid; UPLC/MS 0.91 min, $[M+H]^+$ 510.

$^1H$ NMR (500 MHz, DMSO-$d_6$) δ 13.62 (s, 1H), 8.17 (s, 1H), 8.08 (d, J=8.3 Hz, 1H), 7.63 (s, 1H), 7.55 (d, J=8.3 Hz, 2H), 7.25 (s, 1H), 4.32-4.26 (m, 2H), 3.81-3.74 (m, 2H), 3.38 (s, 3H), 3.40-3.10 (m, 3H), 2.75 (broad, 1H), 2.64 (broad, 1H), 2.18 (s, 3H), 2.06 (d, J=11.4 Hz, 1H), 1.92-1.82 (m, 1H), 1.28 (d, J=6.8 Hz, 3H).

The following compound is prepared analogously:

3-(5-{4-[(2S)-2,4-dimethylpiperazine-1-carbonyl]phenyl}-1,2-oxazol-3-yl)-6-(2-methoxyethoxy)-1H-indazole-5-carbonitrile ("A11")

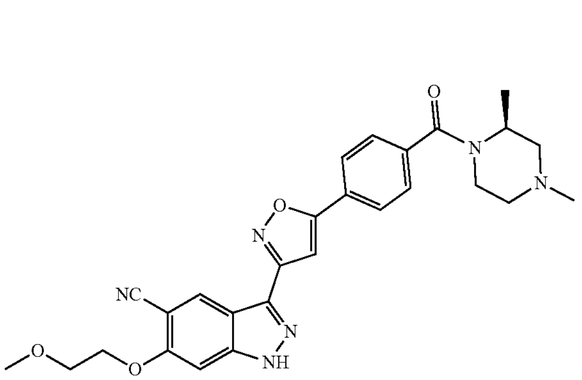

brown solid; HPLC/MS 2.21 min (A), $[M+H]^+$ 501.

$^1H$ NMR (500 MHz, DMSO-$d_6$) δ 13.90 (s, 1H), 8.52 (s, 1H), 8.09 (d, J=8.1 Hz, 2H), 7.70 (s, 1H), 7.57 (d, J=7.9 Hz, 2H), 7.30 (s, 1H), 4.49-4.22 (m, 2H), 3.99-3.57 (m, 2H), 3.39 (s, 3H), 3.32-3.10 (broad, 3H), 2.80-2.70 (broad, 1H), 2.68-2.56 (broad, 1H), 2.18 (s, 3H), 2.06 (d, J=11.1 Hz, 1H), 1.92-1.82 (m, 1H), 1.29 (d, J=6.8 Hz, 3H).

Example 4

4-{5-[5-chloro-6-(2-methoxyethoxy)-1H-indazol-3-yl]-1,2-oxazol-3-yl}-N,N-dimethylbenzamide ("A12")

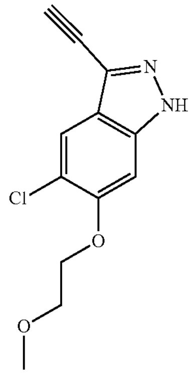

-continued

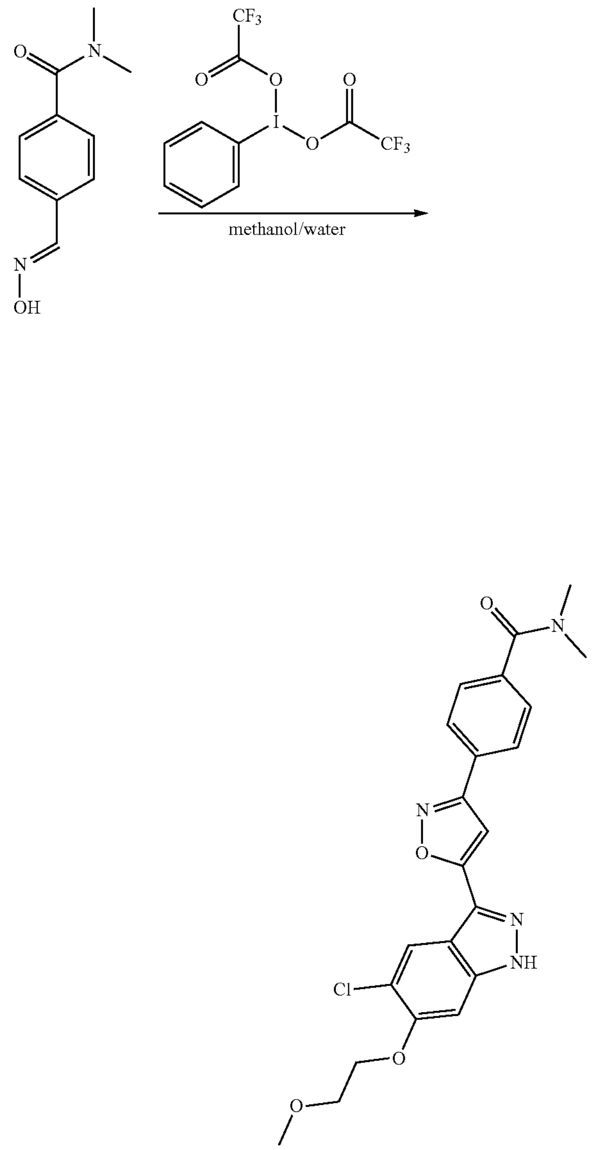

To a stirred solution of 5-chloro-3-ethynyl-6-(2-methoxy-ethoxy)-1H-indazole (97.8 mg, 0.39 mmol) and 4-(hydroxy-imino-methyl)-N,N-dimethyl-benzamide (50.0 mg, 0.26 mmol) in a mixture of methanol (4 ml) and water (800 μl) is added bis(trifluoroacetoxy)-iodobenzene (224 mg, 0.52 mmol) in four portions every two hours and the reaction mixture is stirred for 16 hours at room temperature. The reaction mixture is filtered. The residue is washed with methanol and dried under vacuum to afford 4-{5-[5-chloro-6-(2-methoxy-ethoxy)-1H-indazol-3-yl]-isoxazol-3-yl}-N,N-dimethyl-benzamide as brown solid; HPLC/MS 2.61 min (A), $[M+H]^+$ 441.

$^1$H NMR (500 MHz, DMSO-$d_6$) δ 13.73 (s, 1H), 8.30 (s, 1H), 8.10 (d, J=8.3 Hz, 2H), 7.81 (s, 1H), 7.59 (d, J=8.3 Hz, 2H), 7.26 (s, 1H), 4.37-4.26 (m, 2H), 3.83-3.73 (m, 2H), 3.38 (s, 3H), 3.02 (s, 3H), 2.96 (s, 3H).

The following compounds are prepared analogously 5-chloro-6-(2-methoxyethoxy)-3-[3-(6-methylpyridin-3-yl)-1,2-oxazol-5-yl]-1H-indazole ("A13")

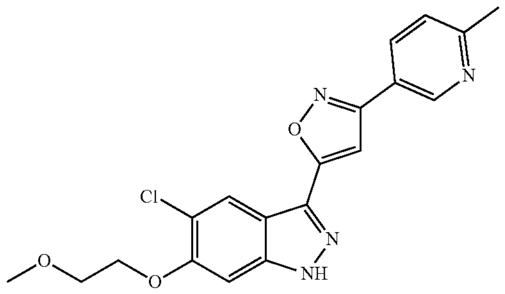

pale brown solid; UPLC/MS 0.99 min, $[M+H]^+$ 385.

$^1$H NMR (700 MHz, DMSO-$d_6$) δ 13.74 (s, 1H), 9.10 (d, J=2.3 Hz, 1H), 8.30-8.27 (m, 2H), 7.82 (s, 1H), 7.46 (d, J=8.1 Hz, 1H), 7.25 (s, 1H), 4.32-4.27 (m, 2H), 3.80-3.76 (m, 2H).

5-chloro-6-(2-methoxyethoxy)-3-{3-[4-(1H-1,2,4-triazol-1-yl)phenyl]-1,2-oxazol-5-yl}-1H-indazole ("A14")

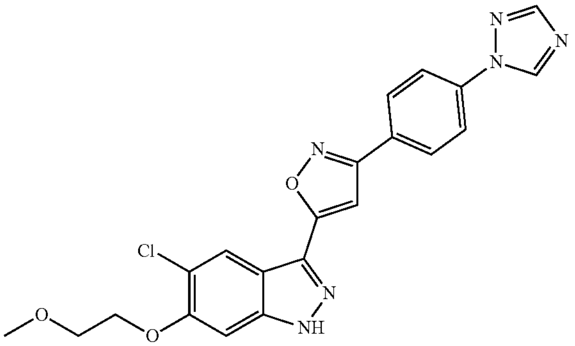 [SMILES: COCCOc1cc2[nH]nc(-c3cc(-c4ccc(-n5cncn5)cc4)no3)c2cc1Cl]

off-white solid; HPLC/MS 2.73 min (A), $[M+H]^+$ 437.

$^1$H NMR (700 MHz, DMSO-$d_6$) δ 13.74 (s, 1H), 9.44 (s, 1H), 8.30 (s, 1H), 8.29 (s, 1H), 8.24 (d, J=8.5 Hz, 2H), 8.08 (d, J=8.6 Hz, 2H), 7.84 (s, 1H), 7.25 (s, 1H), 4.30 (dd, J=5.5, 3.5 Hz, 2H), 3.80-3.74 (m, 2H), 3.38 (s, 3H).

5-chloro-3-[3-(4-methanesulfonylphenyl)-1,2-oxazol-5-yl]-6-(2-methoxyethoxy)-1H-indazole ("A15")

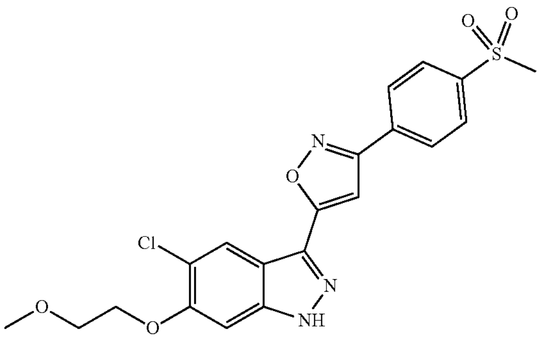

off-white solid; HPLC/MS 2.61 min (A), $[M+H]^+$ 448.

$^{1}$H NMR (500 MHz, DMSO-$d_6$) δ 13.77 (s, 1H), 8.36-8.29 (m, 3H), 8.12 (d, J=8.4 Hz, 2H), 7.91 (s, 1H), 7.26 (s, 1H), 4.34-4.28 (m, 2H), 3.81-3.75 (m, 2H), 3.38 (s, 3H), 3.30 (s, 3H).

5-fluoro-3-[3-(4-methanesulfonylphenyl)-1,2-oxazol-5-yl]-6-(2-methoxyethoxy)-1H-indazole ("A16")

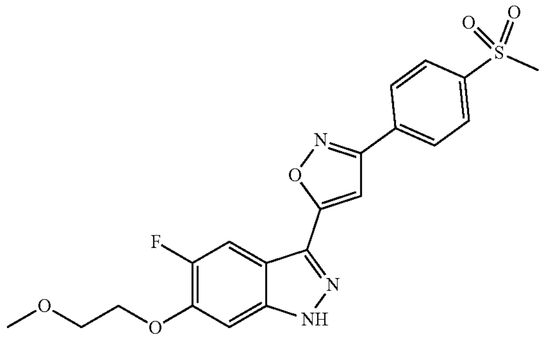

off-white solid; HPLC/MS 2.52 min (A), $[M+H]^+$ 432.

$^{1}$H NMR (500 MHz, DMSO-$d_6$) δ 13.74 (s, 1H), 8.31 (d, J=8.5 Hz, 1H), 8.12 (d, J=8.5 Hz, 2H), 8.03 (d, J=10.9 Hz, 1H), 7.86 (s, 1H), 7.28 (d, J=7.1 Hz, 1H), 4.37-4.17 (m, 2H), 3.89-3.69 (m, 2H), 3.36 (s, 3H), 3.30 (s, 3H).

N-(4-{5-[5-chloro-6-(2-methoxyethoxy)-1H-indazol-3-yl]-1,2-oxazol-3-yl}phenyl)acetamide ("A17")

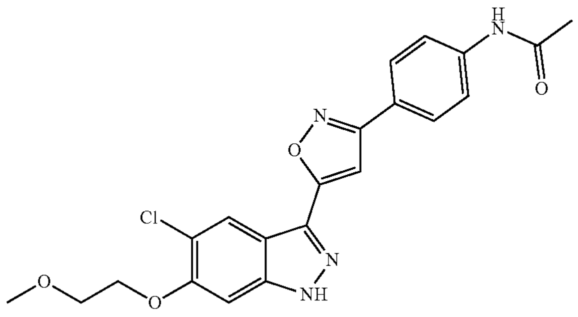 [SMILES: COCCOc1cc2[nH]nc(-c3cc(-c4ccc(NC(C)=O)cc4)no3)c2cc1Cl]

off-white solid; HPLC/MS 2.56 min (A), $[M+H]^+$ 427.

$^{1}$H NMR (500 MHz, DMSO-$d_6$) δ 13.70 (s, 1H), 10.17 (s, 1H), 8.28 (s, 1H), 7.96 (d, J=8.7 Hz, 2H), 7.75 (d, J=8.7 Hz, 2H), 7.68 (s, 1H), 7.24 (s, 1H), 4.32-4.23 (m, 2H), 3.83-3.74 (m, 2H), 3.38 (s, 3H), 2.09 (s, 3H).

N-(4-{5-[5-fluoro-6-(2-methoxyethoxy)-1H-indazol-3-yl]-1,2-oxazol-3-yl}phenyl)acetamide ("A18")

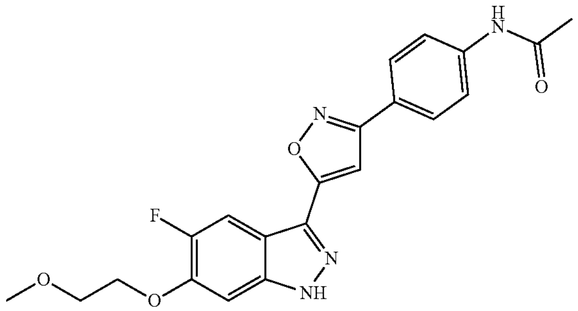 [SMILES: COCCOc1cc2[nH]nc(-c3cc(-c4ccc(NC(C)=O)cc4)no3)c2cc1F]

off-white solid; HPLC/MS 2.43 min (A), $[M+H]^+$ 411.

$^{1}$H NMR (500 MHz, DMSO-$d_6$) δ 13.67 (s, 1H), 10.16 (s, 1H), 8.00 (d, J=11.0 Hz, 1H), 7.95 (d, J=8.7 Hz, 2H), 7.75 (d, J=8.7 Hz, 2H), 7.63 (s, 1H), 7.26 (d, J=7.1 Hz, 1H), 4.33-4.18 (m, 2H), 3.80-3.70 (m, 2H), 3.35 (s, 3H), 2.09 (s, 3H).

methyl 3-{3-[4-(dimethylcarbamoyl)phenyl]-1,2-oxazol-5-yl}-1H-indazole-6-carboxylate ("A19")

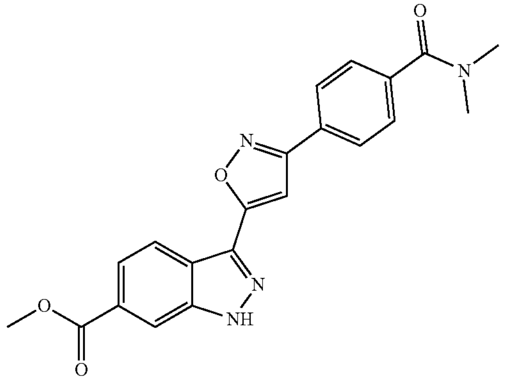

off-white solid; UPLC/MS 1.01 min, $[M-H]^-$ 389.

$^{1}$H NMR (700 MHz, DMSO-$d_6$) δ 14.20 (s, 1H), 8.36 (d, J=8.5 Hz, 1H), 8.29 (s, 1H), 8.10 (d, J=8.3 Hz, 2H), 7.90 (dd, J=8.5, 1.3 Hz, 1H), 7.80 (s, 1H), 7.59 (d, J=8.3 Hz, 2H), 3.94 (s, 3H), 3.02 (s, 3H), 2.96 (s, 3H).

4-{5-[5-fluoro-6-(2-methoxyethoxy)-1H-indazol-3-yl]-1,2-oxazol-3-yl}-N,N-dimethylbenzamide ("A20")

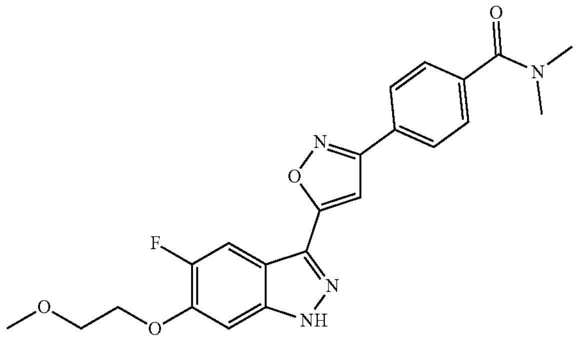

off-white solid; HPLC/MS 2.47 min (A), $[M+H]^+$ 425.

$^1$H NMR (400 MHz, DMSO-$d_6$) δ 13.70 (s, 1H), 8.09 (d, J=8.3 Hz, 2H), 8.02 (d, J=11.0 Hz, 1H), 7.75 (s, 1H), 7.58 (d, J=8.3 Hz, 1H), 7.28 (d, J=7.1 Hz, 1H), 4.40-4.17 (m, 2H), 3.85-3.68 (m, 2H), 3.36 (s, 3H), 3.02 (s, 3H), 2.96 (s, 3H).

5-fluoro-6-(2-methoxyethoxy)-3-{3-[4-(1H-1,2,4-triazol-1-yl)phenyl]-1,2-oxazol-5-yl}-1H-indazole ("A21")

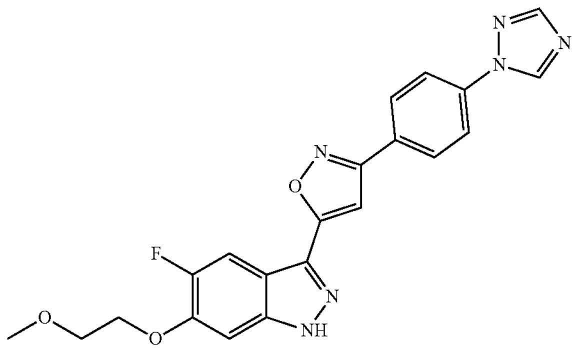 [SMILES: COCCOc1cc2[nH]nc(-c3cc(-c4ccc(-n5cncn5)cc4)no3)c2cc1F]

off-white solid; UPLC/MS 1.04 min, $[M+H]^+$ 421.

$^1$H NMR (500 MHz, DMSO-$d_6$) δ 13.73 (s, 1H), 9.44 (s, 1H), 8.31 (s, 1H), 8.23 (d, J=8.7 Hz, 2H), 8.08 (d, J=8.7 Hz, 2H), 8.04 (d, J=10.9 Hz, 1H), 7.81 (s, 1H), 7.28 (d, J=7.1 Hz, 1H), 4.34-4.24 (m, 2H), 3.79-3.73 (m, 2H), 3.36 (s, 3H).

5-fluoro-6-(2-methoxyethoxy)-3-[3-(6-methylpyridin-3-yl)-1,2-oxazol-5-yl]-1H-indazole ("A22")

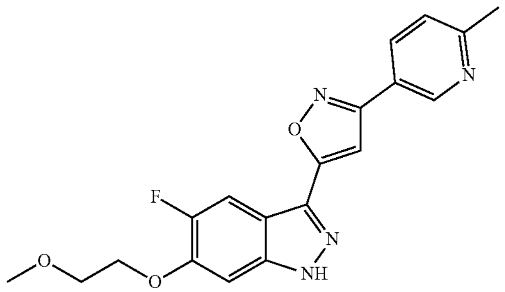

white solid; HPLC/MS 2.08 min (A), $[M+H]^+$ 425.

$^1$H NMR (500 MHz, DMSO-$d_6$) δ 13.73 (s, 1H), 9.10 (d, J=2.2 Hz, 1H), 8.29 (dd, J=8.0, 2.3 Hz, 1H), 8.01 (d, J=10.9 Hz, 1H), 7.78 (s, 1H), 7.47 (d, J=8.1 Hz, 1H), 7.28 (d, J=7.1 Hz, 1H), 4.31-4.25 (m, 2H), 3.80-3.69 (m, 2H), 3.35 (s, 3H).

(4-{5-[5-fluoro-6-(2-methoxyethoxy)-1H-indazol-3-yl]-1,2-oxazol-3-yl}phenyl)(imino)methyl-lambda6-sulfanone ("A226")

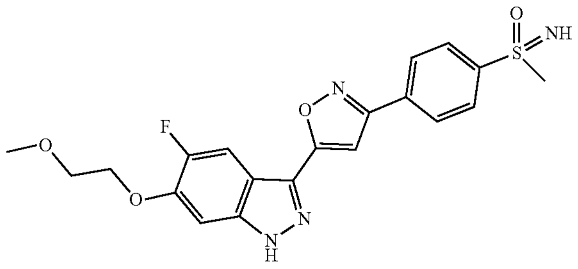 [SMILES: COCCOc1cc2[nH]nc(-c3cc(-c4ccc(S(C)(=N)=O)cc4)no3)c2cc1F]

Example 5

N-(2-methoxyethyl)-3-(3-{4-[(2-methoxyethyl)carbamoyl]phenyl}-1,2-oxazol-5-yl)-1H-indazole-6-carboxamide ("A23")

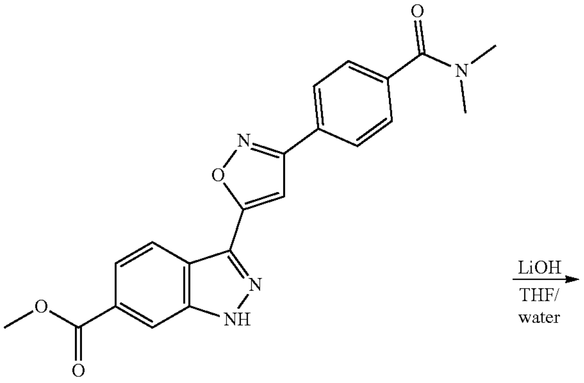

-continued

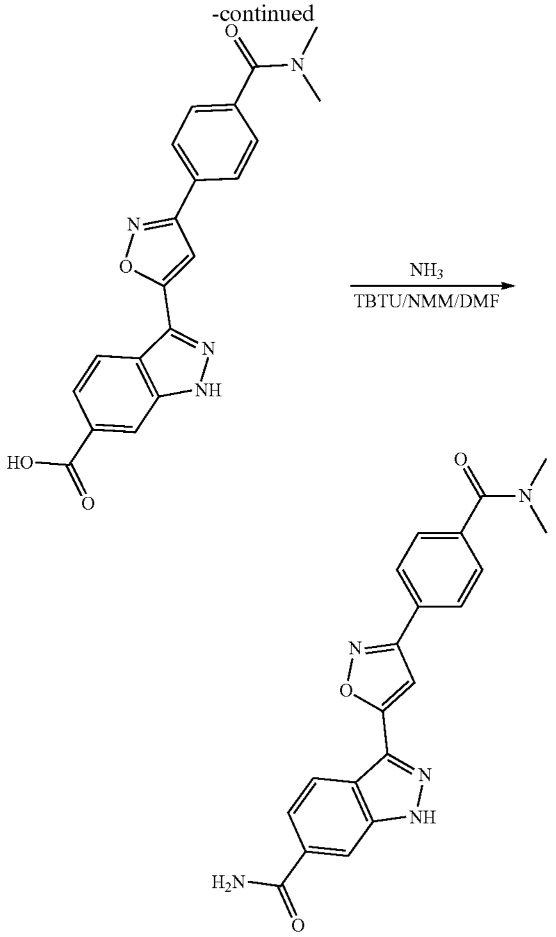

white powder; UPLC/MS 0.85 min, $[M-H]^-$ 374.

$^1H$ NMR (400 MHz, DMSO-$d_6$) δ 14.0 (broad, 1H) 8.27 (d, J=8.6 Hz, 1H), 8.22-8.17 (m, 2H), 8.11 (d, J=8.3 Hz, 2H), 7.84 (dd, J=8.6, 1.3 Hz, 1H), 7.78 (s, 1H), 7.59 (d, J=8.2 Hz, 2H), 7.50 (s, 1H), 3.02 (s, 3H), 2.96 (s, 3H).

The following compounds are prepared analogously:

3-[3-(4-dimethylcarbamoyl-phenyl)-isoxazol-5-yl]-1H-indazole-6-carboxylic acid methylamide ("A24")

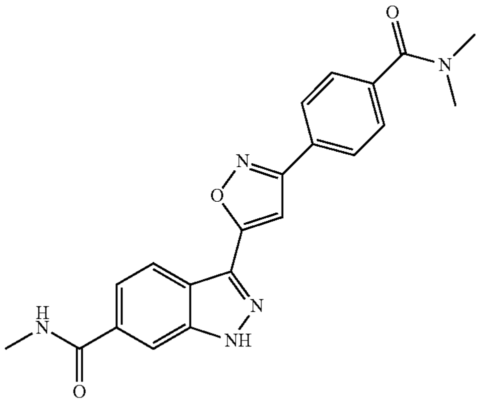

white solid; HPLC/MS 2.16 min (A), $[M+H]^+$ 390.

$^1H$ NMR (400 MHz, DMSO-$d_6$) δ 14.1 (broad, 1H), 8.65 (q, J=4.4 Hz, 1H), 8.28 (d, J=8.6 Hz, 1H), 8.15 (s, 1H), 8.11 (d, J=8.3 Hz, 2H), 7.80 (dd, J=8.6, 1.4 Hz, 1H), 7.78 (s, 1H), 7.59 (d, J=8.3 Hz, 2H), 3.02 (s, 3H), 2.96 (s, 3H), 2.85 (d, J=4.5 Hz, 3H).

3-{3-[4-(dimethylcarbamoyl)phenyl]-1,2-oxazol-5-yl}-N-(2-methoxyethyl)-1H-indazole-6-carboxamide ("A25")

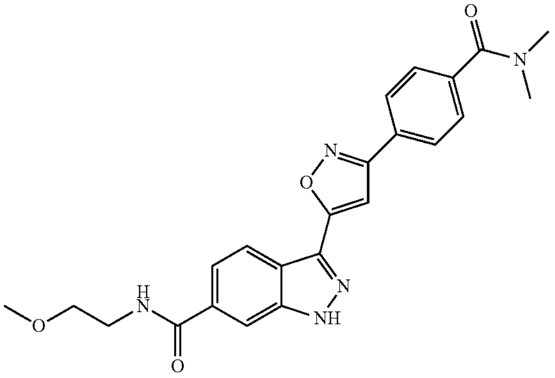

white solid; HPLC/MS 2.21 min (A), $[M+H]^+$ 434.

$^1H$ NMR (400 MHz, DMSO-$d_6$) δ 13.9 (broad, 1H), 8.75 (t, J=5.1 Hz, 1H), 8.29 (dd, J=8.6, 0.9 Hz, 1H), 8.18 (s, 1H), 8.11 (d, J=8.3 Hz, 2H), 7.82 (dd, J=8.6, 1.4 Hz, 1H), 7.79 (s, 1H), 7.59 (d, J=8.3 Hz, 2H), 3.56-3.44 (m, 4H), 3.30 (s, 3H), 3.02 (s, 3H), 2.96 (s, 3H).

Example 6

5-fluoro-3-{3-[4-(3-fluoroazetidine-1-carbonyl)phenyl]-1,2-oxazol-5-yl}-6-(2-methoxyethoxy)-1H-indazole ("A26")

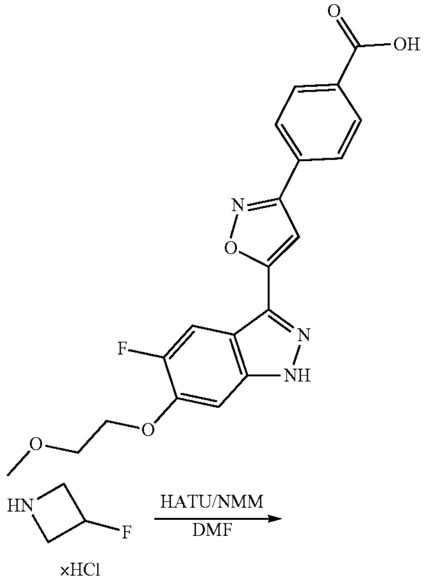

-continued

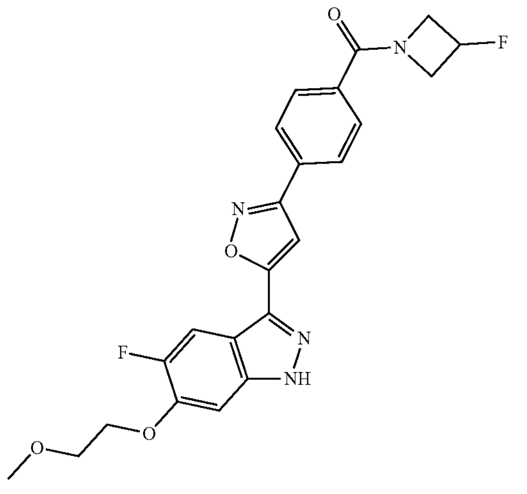

To a solution of 4-{5-[5-fluoro-6-(2-methoxy-ethoxy)-1H-indazol-3-yl]-isoxazol-3-yl}-benzoic acid (52 mg, 0.06 mmol) in DMF (2 ml) is added 3-fluoroazetidine hydrochloride (8.42 mg, 0.08 mmol), followed by 4-methylmorpholine (28 μl, 0.25 mmol) and O-(7-azabenzotriazol-1-yl)-N,N,N',N'-tetramethyl-uronium-hexafluorophosphate (36 mg, 0.09 mmol). The reaction mixture is stirred for 16 hours at room temperature. The reaction mixture is concentrated under vacuum and the residue is chromatographed on a silica gel column with ethyl acetate/methanol as eluent to afford (3-fluoro-azetidin-1-yl)-(4-{5-[5-fluoro-6-(2-methoxy-ethoxy)-1H-indazol-3-yl]-isoxazol-3-yl}-phenyl)-methanone none as white powder; HPLC/MS 2.51 min (A), $[M+H]^+$ 455.

$^1H$ NMR (400 MHz, DMSO-$d_6$) δ 13.8 (broad, 1H), 8.12 (d, J=8.4 Hz, 1H), 8.02 (d, J=11.0 Hz, 1H), 7.83 (d, J=8.4 Hz, 1H), 7.77 (s, 1H), 7.29 (d, J=7.0 Hz, 1H), 5.53 (tt, J=6.1, 3.2 Hz, 0.5H), 5.39 (tt, J=6.2, 3.2 Hz, 0.5H), 4.7-4.0 (m, 4H), 4.33-4.23 (m, 1H), 3.85-3.67 (m, 2H), 3.38 (s, 3H).

The following compounds are prepared analogously:

5-fluoro-3-(3-{4-[(3R)-3-fluoropyrrolidine-1-carbonyl]phenyl}-1,2-oxazol-5-yl)-6-(2-methoxyethoxy)-1H-indazole ("A27")

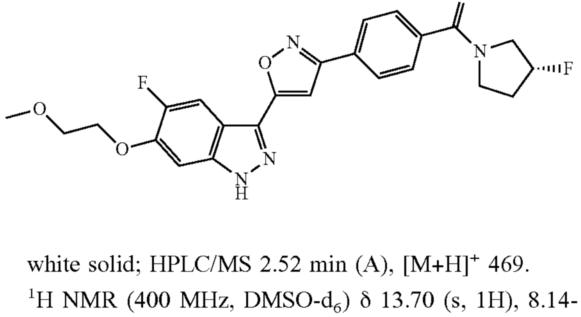

white solid; HPLC/MS 2.52 min (A), $[M+H]^+$ 469.

$^1H$ NMR (400 MHz, DMSO-$d_6$) δ 13.70 (s, 1H), 8.14-8.08 (m, 2H), 8.03 (d, J=11.0 Hz, 1H), 7.77 (s, 1H), 7.78-7.67 (m, 2H), 7.28 (d, J=7.0 Hz, 1H), 5.49-5.24 (m, 1H), 4.33-4.24 (m, 2H), 3.91-3.47 (m, 6H), 3.36 (s, 3H), 2.29-1.96 (m, 2H).

1-(4-{5-[5-fluoro-6-(2-methoxyethoxy)-1H-indazol-3-yl]-1,2-oxazol-3-yl}benzoyl)azetidine-3-carbonitrile ("A28")

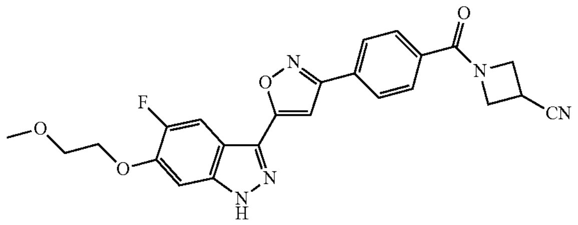 [SMILES: COCCOc1cc2[nH]nc(-c3cc(-c4ccc(C(=O)N5CC(C#N)C5)cc4)no3)c2cc1F]

white solid; HPLC/MS 2.45 min (A), $[M+H]^+$ 462.

$^1H$ NMR (700 MHz, DMSO-$d_6$) δ 13.72 (s, 1H), 8.12 (d, J=8.2 Hz, 2H), 8.03 (d, J=10.9 Hz, 1H), 7.81 (d, J=8.3 Hz, 2H), 7.80 (s, 1H), 7.28 (d, J=6.9 Hz, 1H), 4.64 (broad, 1H), 4.57 (broad, 1H), 4.39 (broad, 1H), 4.33-4.26 (m, 2H), 4.22 (broad, 1H), 3.88 (tt, J=9.3, 6.3 Hz, 1H), 3.78-3.71 (m, 2H), 3.35 (s, 3H).

5-fluoro-3-{3-[4-(3-methanesulfonylazetidine-1-carbonyl)phenyl]-1,2-oxazol-5-yl}-6-(2-methoxy-ethoxy)-1H-indazole ("A29")

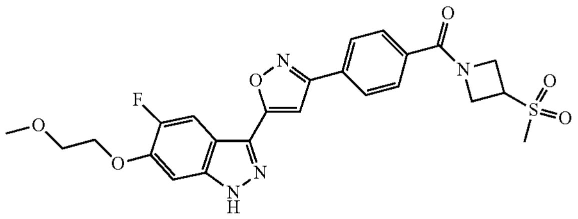 [SMILES: COCCOc1cc2[nH]nc(-c3cc(-c4ccc(C(=O)N5CC(S(C)(=O)=O)C5)cc4)no3)c2cc1F]

off-white solid; HPLC/MS 2.38 min (A), $[M+H]^+$ 515.

$^1H$ NMR (700 MHz, DMSO-$d_6$) δ 13.72 (s, 1H), 8.14 (d, J=8.2 Hz, 2H), 8.04 (d, J=10.9 Hz, 1H), 7.83 (d, J=8.2 Hz, 2H), 7.80 (s, 1H), 7.28 (d, J=7.0 Hz, 1H), 4.75-4.64 (m, 1H), 4.54-4.49 (m, 1H), 4.40-4.35 (m, 2H), 4.32-4.25 (m, 3H), 3.79-3.72 (m, 2H), 3.35 (s, 3H), 3.08 (s, 3H).

4-(4-{5-[5-fluoro-6-(2-methoxyethoxy)-1H-indazol-3-yl]-1,2-oxazol-3-yl}benzoyl)-1lambda6-thiomorpholine-1,1-dione ("A30")

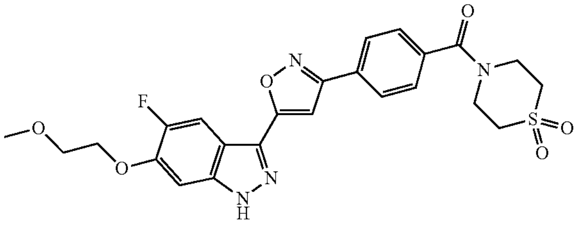 [SMILES: COCCOc1cc2[nH]nc(-c3cc(-c4ccc(C(=O)N5CCS(=O)(=O)CC5)cc4)no3)c2cc1F]

white solid; HPLC/MS 2.55 min (A), $[M+H]^+$ 515.

$^1H$ NMR (500 MHz, DMSO-$d_6$) δ 13.71 (s, 1H), 8.12 (d, J=8.3 Hz, 2H), 8.03 (d, J=10.9 Hz, 1H), 7.78 (s, 1H), 7.69

(d, J=8.3 Hz, 2H), 7.28 (d, J=7.1 Hz, 1H), 4.33-4.24 (m, 2H), 4.04 (broad, 2H), 3.80-3.74 (m, 2H), 3.73 (broad, 2H), 3.36 (s, 3H), 3.29 (broad, 4H).

N-cyclopropyl-4-{5-[5-fluoro-6-(2-methoxyethoxy)-1H-indazol-3-yl]-1,2-oxazol-3-yl}-N-methylbenzamide ("A31")

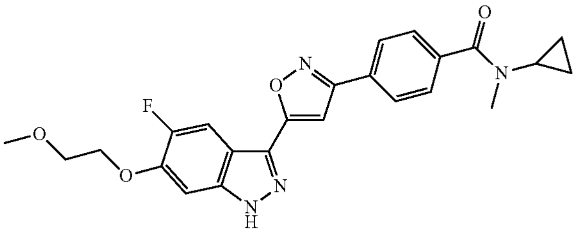 [SMILES: COCCOc1cc2[nH]nc(-c3cc(-c4ccc(C(=O)N(C)C5CC5)cc4)no3)c2cc1F]

white solid; HPLC/MS 2.61 min (A), $[M+H]^+$ 451.

$^1$H NMR (500 MHz, DMSO-$d_6$) δ 13.71 (s, 1H), 8.08 (d, J=8.3 Hz, 2H), 8.04 (d, J=11.0 Hz, 1H), 7.78 (s, 1H), 7.68 (d, J=7.9 Hz, 2H), 7.29 (d, J=7.1 Hz, 1H), 4.35-4.25 (m, 2H), 3.85-3.69 (m, 2H), 3.36 (s, 3H), 3.05-2.93 (m, 4H), 0.63-0.40 (m, 4H).

5-fluoro-3-(3-{4-[(3S)-3-fluoropyrrolidine-1-carbonyl]phenyl}-1,2-oxazol-5-yl)-6-(2-methoxyethoxy)-1H-indazole ("A32")

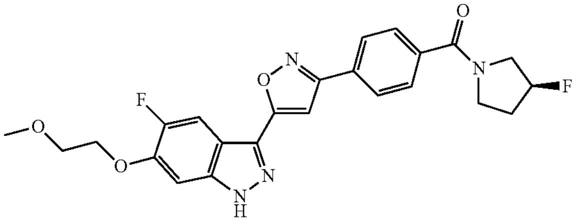 [SMILES: COCCOc1cc2[nH]nc(-c3cc(-c4ccc(C(=O)N5CC[C@H](F)C5)cc4)no3)c2cc1F]

white solid; HPLC/MS 2.53 min (A), $[M+H]^+$ 469.

$^1$H NMR (400 MHz, DMSO-$d_6$) δ 13.70 (s, 1H), 8.14-8.08 (m, 2H), 8.03 (d, J=11.0 Hz, 1H), 7.77 (s, 1H), 7.78-7.67 (m, 2H), 7.28 (d, J=7.0 Hz, 1H), 5.49-5.24 (m, 1H), 4.33-4.24 (m, 2H), 3.91-3.47 (m, 6H), 3.36 (s, 3H), 2.29-1.96 (m, 2H).

5-fluoro-3-{3-[4-(3-methoxyazetidine-1-carbonyl)phenyl]-1,2-oxazol-5-yl}-6-(2-methoxyethoxy)-1H-indazole ("A33")

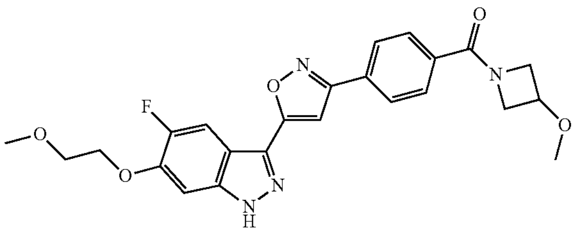 [SMILES: COCCOc1cc2[nH]nc(-c3cc(-c4ccc(C(=O)N5CC(OC)C5)cc4)no3)c2cc1F]

white solid; HPLC/MS 2.51 min (A), $[M+H]^+$ 467.

1H NMR (500 MHz, DMSO-$d_6$) δ 13.73 (s, 1H), 8.12 (d, J=8.4 Hz, 1H), 8.04 (d, J=11.0 Hz, 1H), 7.82 (d, J=8.4 Hz, 2H), 7.79 (s, 1H), 7.29 (d, J=7.1 Hz, 1H), 4.55-4.45 (m, 0.5), 4.41-4.24 (m, 3.5H), 4.23-4.18 (m, 0.5H), 3.92-3.85 (m, 0.5H), 3.83-3.61 (m, 2H), 3.36 (s, 3H), 3.25 (s, 3H).

1-(4-{5-[5-fluoro-6-(2-methoxyethoxy)-1H-indazol-3-yl]-1,2-oxazol-3-yl}benzoyl)-3-methylazetidin-3-ol ("A34")

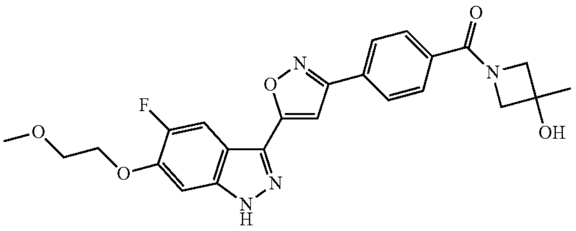

white solid; HPLC/MS 2.38 min (A), $[M+H]^+$ 467.

$^1$H NMR (700 MHz, DMSO-$d_6$) δ 13.73 (s, 1H), 8.12 (d, J=8.0 Hz, 2H), 8.04 (d, J=10.9 Hz, 1H), 7.81 (d, J=8.2 Hz, 2H), 7.79 (s, 1H), 5.71 (s, 1H), 4.30 (dd, J=5.5, 3.4 Hz, 2H), 4.21 (d, J=8.7 Hz, 1H), 4.16 (d, J=8.8 Hz, 1H), 3.95 (d, J=10.0 Hz, 1H), 3.92 (d, J=10.1 Hz, 1H), 3.78-3.74 (m, 2H), 3.36 (s, 3H), 1.42 (s, 3H).

N-[dimethyl(oxo)-lambda6-sulfanylidene]-4-{5-[5-fluoro-6-(2-methoxyethoxy)-1H-indazol-3-yl]-1,2-oxazol-3-yl}benzamide ("A35")

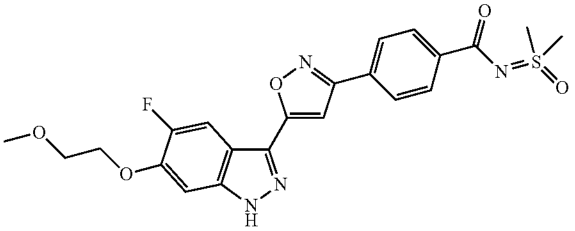

white solid; HPLC/MS 2.49 min (A), $[M+H]^+$ 473.

$^1$H NMR (700 MHz, DMSO-$d_6$) δ 13.73 (s, 1H), 8.15 (d, J=8.5 Hz, 2H), 8.13 (d, J=8.3 Hz, 2H), 8.05 (d, J=10.9 Hz, 1H), 7.80 (s, 1H), 7.29 (d, J=7.0 Hz, 1H), 4.35-4.28 (m, 2H), 3.88-3.72 (m, 2H), 3.51 (s, 6H), 3.36 (s, 3H).

5-fluoro-6-(2-methoxyethoxy)-3-{3-[4-(4-methylpiperazine-1-carbonyl)phenyl]-1,2-oxazol-5-yl}-1H-indazole ("A36") trifluoroacetate

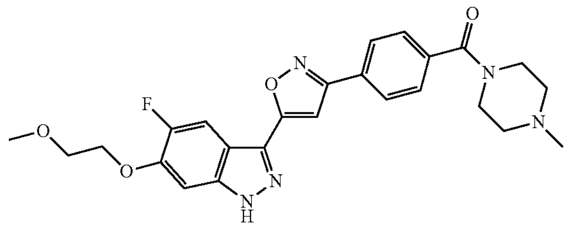

white solid; HPLC/MS 2.19 min (A), $[M+H]^+$ 480.

$^1$H NMR (500 MHz, DMSO-$d_6$) δ 13.74 (s, 1H), 9.76 (s, 1H), 8.15 (d, J=8.3 Hz, 2H), 8.03 (d, J=10.9 Hz, 1H), 7.79 (s, 1H), 7.65 (d, J=8.3 Hz, 2H), 7.30 (s, 1H), 4.58 (broad, 1H), 4.33-4.29 (m, 2H), 3.80 (broad, 1H), 3.81-3.70 (m, 2H), 3.43 (broad, 4H) 3.36 (s, 3H), 3.13 (broad, 2H), 2.85 (s, 3H).

N-[2-(dimethylamino)ethyl]-4-{5-[5-fluoro-6-(2-methoxyethoxy)-1H-indazol-3-yl]-1,2-oxazol-3-yl}benzamide ("A72")

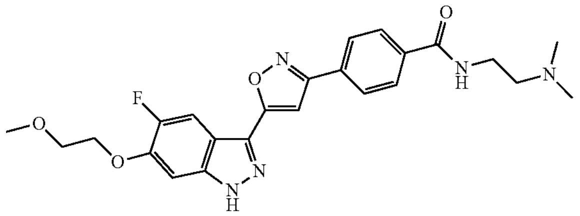

trifluoroacetate; white solid; HPLC/MS 2.24 min (A), $[M+H]^+$ 468.

$^1$H NMR (500 MHz, DMSO-$d_6$) δ 13.75 (s, 1H), 9.30 (s, 1H), 8.84 (t, J=5.7 Hz, 1H), 8.19 (d, J=8.4 Hz, 2H), 8.08-8.00 (m, 3H), 7.81 (s, 1H), 7.29 (d, J=7.1 Hz, 1H), 4.33-4.16 (m, 2H), 3.80-3.74 (m, 2H), 3.65 (q, J=5.9 Hz, 2H), 3.31 (q, J=5.9 Hz, 2H), 2.88 (d, J=4.7 Hz, 6H).

4-{5-[5-fluoro-6-(2-methoxyethoxy)-1H-indazol-3-yl]-1,2-oxazol-3-yl}-N-(1-methylazetidin-3-yl)benzamide ("A73")

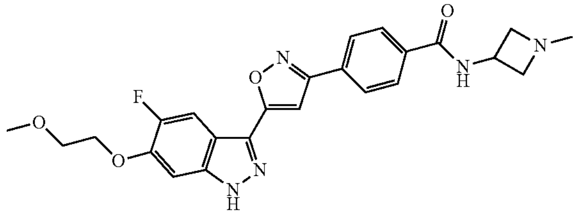

trifluoroacetate; white solid; UPLC/MS 0.86 min; $[M+H]^+$ 466.

$^1$H NMR (400 MHz, DMSO-$d_6$) δ 13.74 (s, 1H), 9.67 (s, 1H), 9.20 (d, J=6.8 Hz, 1H), 8.23-8.13 (m, 2H), 8.11-8.00 (m, 3H), 7.80 (s, 1H), 7.30 (d, J=7.1 Hz, 1H), 4.92-4.72 (m, 1H), 4.59-4.39 (m, 2H), 4.35-4.26 (m, 2H), 4.25-4.04 (m, H), 3.82-3.72 (m, 2H), 3.36 (s, 3H), 2.93 (s, 3H).

5-fluoro-6-(2-methoxyethoxy)-3-[3-(4-{2-oxa-6-azaspiro[3.3]heptane-6-carbonyl}phenyl)-1,2-oxazol-5-yl]-1H-indazole ("A74")

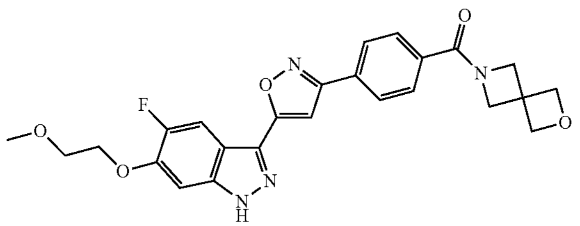 [SMILES: COCCOc1cc2[nH]nc(-c3cc(-c4ccc(C(=O)N5CC6(COC6)C5)cc4)no3)c2cc1F]

white solid; HPLC/MS 2.55 min (A), $[M+H]^+$ 479.

$^1$H NMR (700 MHz, DMSO-$d_6$) δ 13.74 (s, 1H), 8.12 (d, J=8.3 Hz, 2H), 8.04 (d, J=10.8 Hz, 1H), 7.81-7.78 (m, 3H), 7.29 (d, J=7.0 Hz, 1H), 4.73-4.68 (m, 4H), 4.54 (s, 2H), 4.37-4.28 (m, 2H), 4.26 (s, 2H), 3.82-3.69 (m, 2H), 3.36 (s, 3H).

5-fluoro-6-(2-methoxyethoxy)-3-(3-{4-[3-(1H-pyrazol-1-yl)azetidine-1-carbonyl]phenyl}-1,2-oxazol-5-yl)-1H-indazole ("A75")

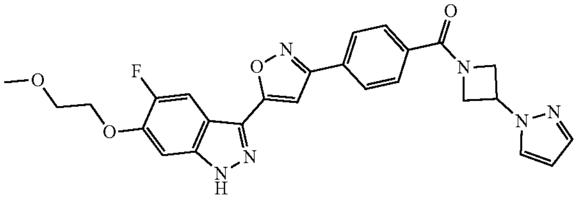 [SMILES: COCCOc1cc2[nH]nc(-c3cc(-c4ccc(C(=O)N5CC(n6cccn6)C5)cc4)no3)c2cc1F]

white solid; HPLC/MS 2.62 min (A), $[M+H]^+$ 503.

$^1$H NMR (400 MHz, DMSO-$d_6$) δ 13.7 (s, 1H), 8.14 (d, J=8.4 Hz, 2H), 8.03 (d, J=11.0 Hz, 1H), 7.95 (d, J=2.3 Hz, 1H), 7.87 (d, J=8.4 Hz, 2H), 7.79 (s, 1H), 7.60 (d, J=1.8 Hz, 0H), 7.29 (d, J=7.1 Hz, 1H), 6.33 (t, J=2.1 Hz, 1H), 5.38 (tt, J=8.2, 5.4 Hz, 1H), 4.82 (t, J=7.9 Hz, 1H), 4.70-4.63 (m, 1H), 4.58 (t, J=9.1 Hz, 1H), 4.40-4.32 (m, 1H), 4.33-4.22 (m, 2H), 3.81-3.69 (m, 2H), 3.37 (s, 3H).

1-(4-{5-[5-fluoro-6-(2-methoxyethoxy)-1H-indazol-3-yl]-1,2-oxazol-3-yl}benzoyl)-N,N-dimethylazetidin-3-amine ("A76")

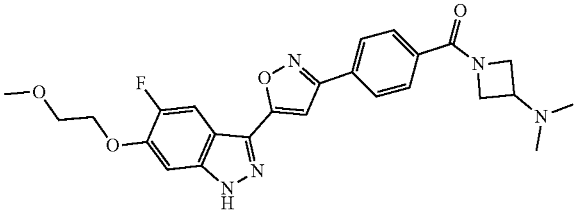

trifluoroacetate; white solid; UPLC/MS 0.84 min, $[M+H]^+$ 480.

$^1$H NMR (700 MHz, DMSO-$d_6$) δ 13.75 (s, 1H), 10.28 (s, 1H), 8.15 (d, J=8.3 Hz, 2H), 8.03 (d, J=10.8 Hz, 1H), 7.82 (d, J=8.3 Hz, 2H), 7.80 (s, 1H), 7.29 (d, J=7.0 Hz, 1H), 4.65 (t, J=9.4 Hz, 1H), 4.51-4.46 (m, 1H), 4.37-4.23 (m, 4H), 4.17-4.05 (m, 1H), 3.79-3.73 (m, 2H), 3.35 (s, 3H), 2.88-2.73 (m, 6H).

5-fluoro-6-(2-methoxyethoxy)-3-[3-(4-{6-oxa-2-azaspiro[3.4]octane-2-carbonyl}phenyl)-1,2-oxazol-5-yl]-1H-indazole ("A77")

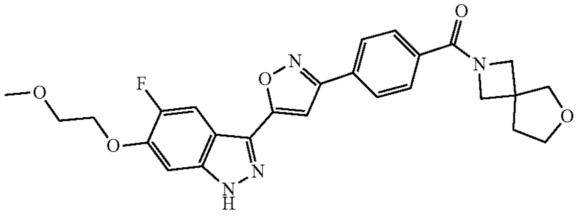 [SMILES: COCCOc1cc2[nH]nc(-c3cc(-c4ccc(C(=O)N5CC6(CCOC6)C5)cc4)no3)c2cc1F]

colorless resin; HPLC/MS 2.63 min (A), $[M+H]^+$ 493.

$^1$H NMR (500 MHz, DMSO-$d_6$) δ 13.71 (s, 1H), 8.11 (d, J=8.3 Hz, 2H), 8.03 (d, J=10.9 Hz, 1H), 7.82 (d, J=8.4 Hz, 2H), 7.78 (s, 1H), 7.28 (d, J=7.0 Hz, 1H), 4.38-4.32 (m, 2H), 4.32-4.27 (m, 2H), 4.09-4.03 (m, 2H), 3.86-3.66 (m, 6H), 3.36 (s, 3H), 2.15 (td, J=7.0, 2.5 Hz, 2H).

4-(4-{5-[5-fluoro-6-(2-methoxyethoxy)-1H-indazol-3-yl]-1,2-oxazol-3-yl}benzoyl)-1lambda4-thiomorpholin-1-one ("A78")

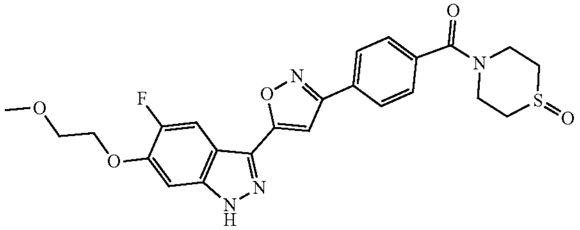 [SMILES: COCCOc1cc2[nH]nc(-c3cc(-c4ccc(C(=O)N5CCS(=O)CC5)cc4)no3)c2cc1F]

colorless resin; HPLC/MS 2.38 min (A), $[M+H]^+$ 499.

$^1$H NMR (500 MHz, DMSO-$d_6$) δ 13.71 (s, 1H), 8.12 (d, J=8.3 Hz, 2H), 8.02 (d, J=11.0 Hz, 1H), 7.77 (s, 1H), 7.64 (d, J=8.3 Hz, 2H), 7.28 (d, J=7.1 Hz, 1H), 4.37 (broad, 1H), 4.33-4.27 (m, 2H), 3.87 (broad, 1H), 3.79-3.73 (m, 3H), 3.58 (broad, 1H), 3.36 (s, 3H), 3.00 (td, J=12.8, 11.6, 3.5 Hz, 2H), 2.94-2.67 (m, 2H).

5-fluoro-6-(2-methoxyethoxy)-3-[3-(4-{1-oxa-6-azaspiro[3.3]heptane-6-carbonyl}phenyl)-1,2-oxazol-5-yl]-1H-indazole ("A79")

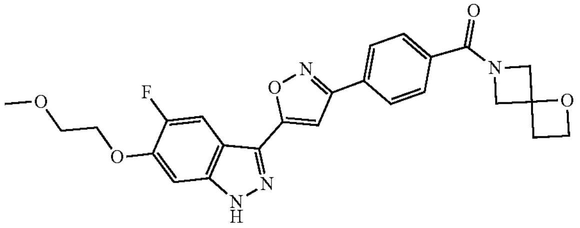 [SMILES: COCCOc1cc2[nH]nc(-c3cc(-c4ccc(C(=O)N5CC6(CCO6)C5)cc4)no3)c2cc1F]

colorless resin; HPLC/MS 2.61 min (A), $[M+H]^+$ 479.

$^1$H NMR (500 MHz, DMSO-$d_6$) δ 13.72 (s, 1H), 8.11 (d, J=8.4 Hz, 2H), 8.03 (d, J=11.0 Hz, 1H), 7.85-7.75 (m, 2H), 7.28 (d, J=7.1 Hz, 1H), 4.62-4.23 (m, 7H), 4.22-4.04 (m, 1H), 3.80-3.73 (m, 2H), 3.36 (s, 3H), 2.86 (t, J=7.5 Hz, 2H).

4-(4-{5-[5-fluoro-6-(2-methoxyethoxy)-1H-indazol-3-yl]-1,2-oxazol-3-yl}benzoyl)-1-imino-1lambda6-thiomorpholin-1-one ("A80")

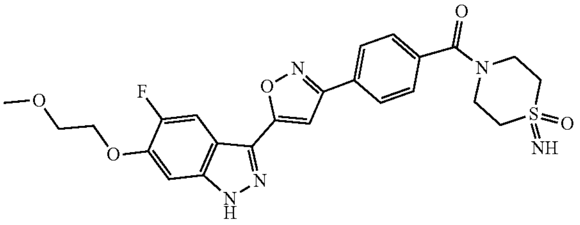 [SMILES: COCCOc1cc2[nH]nc(-c3cc(-c4ccc(C(=O)N5CCS(=N)(=O)CC5)cc4)no3)c2cc1F]

white solid; HPLC/MS 2.32 min (A), $[M+H]^+$ 514.

$^1$H NMR (700 MHz, DMSO-$d_6$) δ 13.72 (s, 1H), 8.13 (d, J=8.3 Hz, 2H), 8.03 (d, J=10.9 Hz, 1H), 7.78 (s, 1H), 7.69 (d, J=8.2 Hz, 2H), 7.28 (d, J=7.0 Hz, 1H), 4.39 (s, 1H), 4.31-4.24 (m, 2H), 4.12-3.12 (broad, 8H), 3.79-3.75 (m, 2H), 3.36 (s, 3H).

5-fluoro-3-{3-[5-(3-fluoroazetidine-1-carbonyl)pyridin-2-yl]-1,2-oxazol-5-yl}-6-(2-methoxyethoxy)-1H-indazole ("A81")

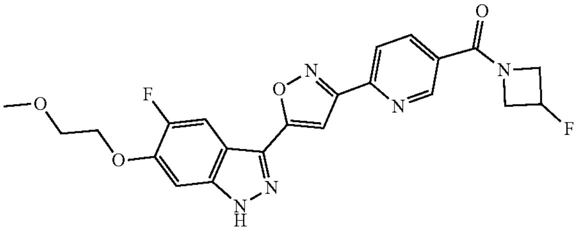 [SMILES: COCCOc1cc2[nH]nc(-c3cc(-c4ccc(C(=O)N5CC(F)C5)cn4)no3)c2cc1F]

white foam; HPLC/MS 2.56 min (A), $[M+H]^+$ 456.

$^1$H NMR (500 MHz, DMSO-$d_6$) δ 13.76 (s, 1H), 9.00 (dd, J=2.2, 0.9 Hz, 1H), 8.26 (dd, J=8.2, 2.2 Hz, 1H), 8.21 (dd, J=8.2, 0.9 Hz, 1H), 7.99 (d, J=10.8 Hz, 1H), 7.61 (s, 1H), 7.29 (d, J=7.0 Hz, 1H), 5.48 (dtt, J=57.5, 6.3, 3.2 Hz, 1H), 4.80-4.38 (m, 3H), 4.33-4.27 (m, 2H), 4.16 (dd, J=24.6, 12.1 Hz, 1H), 3.81-3.73 (m, 2H), 3.36 (s, 3H).

5-fluoro-6-(2-methoxyethoxy)-3-(3-{5-[3-(morpholin-4-yl)azetidine-1-carbonyl]pyridin-2-yl}-1,2-oxazol-5-yl)-1H-indazole ("A82")

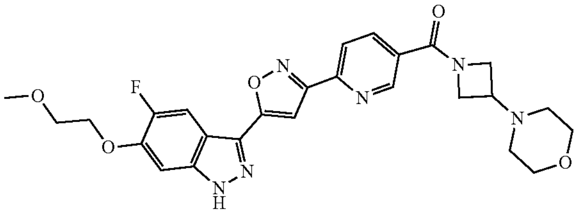 [SMILES: COCCOc1cc2[nH]nc(-c3cc(-c4ccc(C(=O)N5CC(N6CCOCC6)C5)cn4)no3)c2cc1F]

trifluoroacetate, pale yellow foam; HPLC/MS 2.19 min (A), $[M+H]^+$ 523.

$^1$H NMR (700 MHz, DMSO-$d_6$, partially very broad signals, selection of signals) δ 13.78 (s, 1H), 10.57 (s, 1H), 9.01 (s, 1H), 8.30-8.22 (m, 2H), 7.98 (d, J=10.7 Hz, 1H), 7.61 (s, 1H), 7.30 (d, J=7.0 Hz, 1H), 4.72-4.46 (m, 2H), 4.37-4.19 (m, 2H), 3.94-3.69 (m, 2H), 3.36 (s, 3H).

5-fluoro-6-(2-methoxyethoxy)-3-(3-{5-[3-(morpholin-4-yl)azetidine-1-carbonyl]-1,3-thiazol-2-yl}-1,2-oxazol-5-yl)-1H-indazole ("A83")

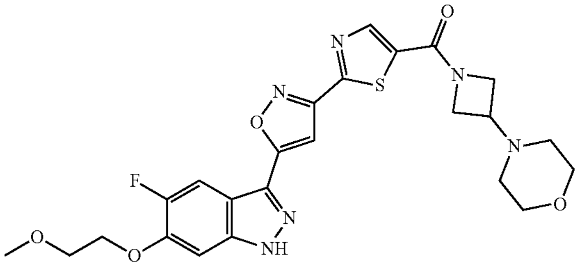 [SMILES: COCCOc1cc2[nH]nc(-c3cc(-c4ncc(C(=O)N5CC(N6CCOCC6)C5)s4)no3)c2cc1F]

trifluoroacetate, white foam; HPLC/MS 2.23 min (A), $[M+H]^+$ 529.

$^1H$ NMR (700 MHz, DMSO-$d_6$, partially very broad signals, selection of signals) δ 13.84 (s, 1H), 10.8 (s, 1H), 8.47 (s, 1H), 8.01 (d, J=10.8 Hz, 1H), 7.65 (s, 1H), 7.29 (d, J=6.9 Hz, 1H), 4.91-4.5 (m, 2H), 4.32-4.28 (m, 2H), 3.88-3.66 (m, 2H).

5-fluoro-6-(2-methoxyethoxy)-3-(3-{4-[3-(morpholin-4-yl)azetidine-1-carbonyl]-1,3-thiazol-2-yl}-1,2-oxazol-5-yl)-1H-indazole ("A84")

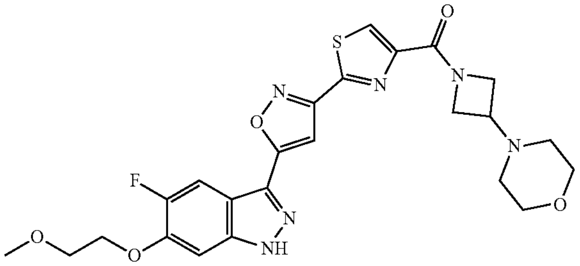 [SMILES: COCCOc1cc2[nH]nc(-c3cc(-c4nc(C(=O)N5CC(N6CCOCC6)C5)cs4)no3)c2cc1F]

trifluoroacetate, white foam; HPLC/MS 2.33 min (A), $[M+H]^+$ 529.

$^1H$ NMR (700 MHz, DMSO-$d_6$, partially very broad signals, selection of signals) δ 13.86 (s, 1H), 10.53 (s, 1H), 8.63 (s, 1H), 7.96 (d, J=10.7 Hz, 1H), 7.66 (s, 1H), 7.30 (d, J=6.9 Hz, 1H), 5.07-4.66 (m, 2H), 4.36-4.23 (m, 2H), 3.85-3.73 (m, 2H).

5-fluoro-3-(3-{4-[3-(1H-imidazol-1-yl)azetidine-1-carbonyl]phenyl}-1,2-oxazol-5-yl)-6-(2-methoxyethoxy)-1H-indazole ("A85")

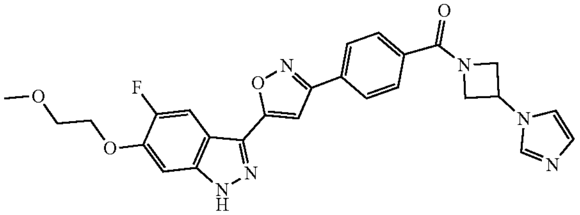 [SMILES: COCCOc1cc2[nH]nc(-c3cc(-c4ccc(C(=O)N5CC(n6ccnc6)C5)cc4)no3)c2cc1F]

trifluoroacetate, white foam; HPLC/MS 2.26 min (A), $[M+H]^+$ 503.

$^1H$ NMR (700 MHz, DMSO-$d_6$) δ 14.53 (s, 1H), 13.75 (s, 1H), 8.16 (d, J=8.3 Hz, 2H), 8.12 (s, 1H), 8.04 (d, J=10.9 Hz, 1H), 7.89 (d, J=8.3 Hz, 2H), 7.81 (s, 1H), 7.77 (s, 1H), 7.29 (d, J=7.0 Hz, 1H), 5.44 (tt, J=8.2, 5.3 Hz, 1H), 4.84 (t, J=8.8 Hz, 1H), 4.76 (dd, J=10.1, 5.3 Hz, 1H), 4.63 (t, J=9.7 Hz, 1H), 4.36 (dd, J=11.3, 5.2 Hz, 1H), 4.32-4.28 (m, 2H), 3.79-3.75 (m, 2H), 3.36 (s, 3H).

5-fluoro-3-{3-[5-(3-fluoroazetidine-1-carbonyl)-1,3-thiazol-2-yl]-1,2-oxazol-5-yl}-6-(2-methoxyethoxy)-1H-indazole ("A86")

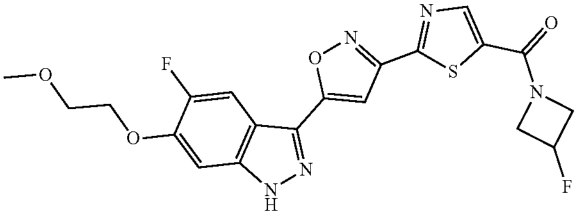 [SMILES: COCCOc1cc2[nH]nc(-c3cc(-c4ncc(C(=O)N5CC(F)C5)s4)no3)c2cc1F]

white foam; HPLC/MS 2.66 min (A), $[M+H]^+$ 462.

$^1H$ NMR (700 MHz, DMSO-$d_6$) δ 13.83 (s, 1H), 8.48 (s, 1H), 8.02 (d, J=10.8 Hz, 1H), 7.65 (s, 1H), 7.30 (d, J=7.0 Hz, 1H), 5.52 (dtt, J=57.5, 6.2, 3.1 Hz, 1H), 4.87 (d, J=20.1 Hz, 1H), 4.78-4.67 (m, 1H), 4.51-4.32 (m, 1H), 4.36-4.27 (m, 2H), 4.16 (dd, J=24.5, 12.5 Hz, 1H), 3.82-3.69 (m, 2H), 3.36 (s, 3H).

5-fluoro-3-{3-[4-(3-fluoroazetidine-1-carbonyl)-1,3-thiazol-2-yl]-1,2-oxazol-5-yl}-6-(2-methoxyethoxy)-1H-indazole ("A87")

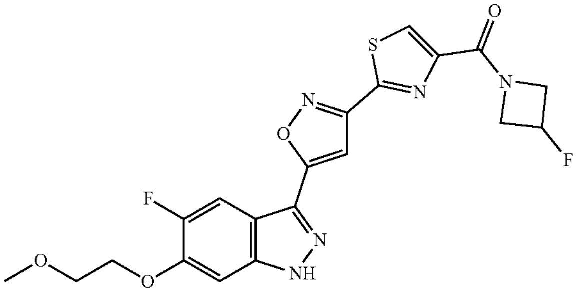 [SMILES: COCCOc1cc2[nH]nc(-c3cc(-c4nc(C(=O)N5CC(F)C5)cs4)no3)c2cc1F]

white foam; HPLC/MS 2.74 min (A), $[M+H]^+$ 462.

$^1H$ NMR (700 MHz, DMSO-$d_6$) δ 13.85 (s, 1H), 8.59 (s, 1H), 8.03 (d, J=10.7 Hz, 1H), 7.68 (s, 1H), 7.30 (d, J=7.0 Hz, 1H), 5.51 (dtt, J=57.8, 6.0, 3.1 Hz, 1H), 5.04 (dddd, J=22.5, 12.0, 5.9, 1.9 Hz, 1H), 4.82 (ddt, J=25.3, 12.4, 2.6 Hz, 1H), 4.45 (dddd, J=21.6, 11.8, 6.0, 1.9 Hz, 1H), 4.34-4.26 (m, 2H), 4.15 (ddt, J=24.8, 11.8, 2.3 Hz, 1H), 3.82-3.72 (m, 2H), 3.36 (s, 3H).

5-fluoro-6-(2-methoxyethoxy)-3-[3-(4-{6-methyl-2,6-diazaspiro[3.3]heptane-2-carbonyl}phenyl)-1,2-oxazol-5-yl]-1H-indazole ("A88")

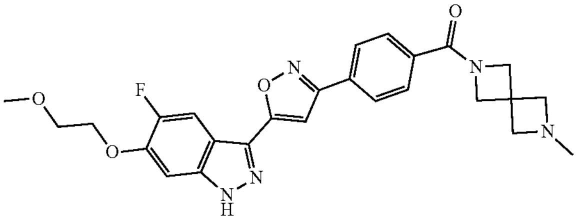

trifluoroacetate, white foam; HPLC/MS 2.24 min (A), $[M+H]^+$ 492.

$^1$H NMR (500 MHz, DMSO-$d_6$) δ 13.74 (s, 1H), 9.56-9.43 (m, 1H), 8.19-8.10 (m, 2H), 8.03 (d, J=11.0 Hz, 1H), 7.81-7.76 (m, 3H), 7.29 (d, J=7.1 Hz, 1H), 4.58 (s, 1H), 4.52 (s, 1H), 4.45-4.35 (m, 2H), 4.34-4.28 (m, 3H), 4.24 (s, 1H), 4.20-4.07 (m, 2H), 3.85-3.71 (m, 2H), 3.36 (s, 3H), 2.84-2.78 (m, 3H).

(cis)-1-(4-{5-[5-fluoro-6-(2-methoxyethoxy)-1H-indazol-3-yl]-1,2-oxazol-3-yl}benzoyl)-octahydro-pyrrolo[3,4-b]pyrrol-6-one ("A89")

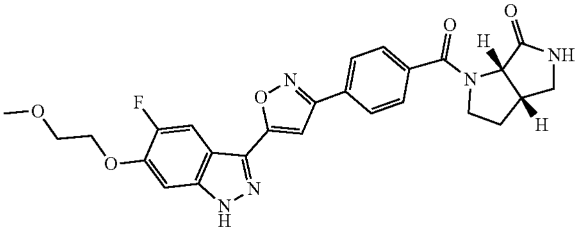 [SMILES: COCCOc1cc2[nH]nc(-c3cc(-c4ccc(C(=O)N5CC[C@H]6CNC(=O)[C@H]65)cc4)no3)c2cc1F]

UPLC/MS 0.65 min, $[M+H]^+$ 506.

N-{[(2S)-1-(4-{5-[5-fluoro-6-(2-methoxyethoxy)-1H-indazol-3-yl]-1,2-oxazol-3-yl}benzoyl)pyrrolidin-2-yl]methyl}methanesulfonamide ("A90")

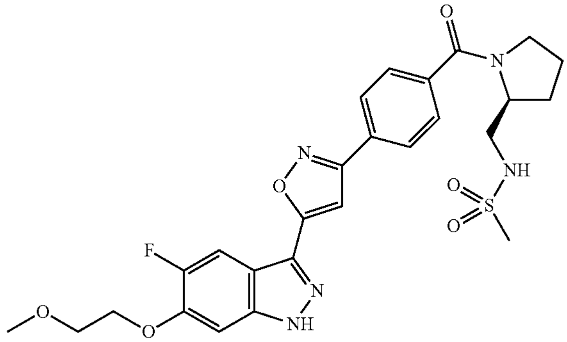 [SMILES: COCCOc1cc2[nH]nc(-c3cc(-c4ccc(C(=O)N5CCC[C@H]5CNS(C)(=O)=O)cc4)no3)c2cc1F]

off-white solid; HPLC/MS 1.53 min (A), $[M+H]^+$ 558.

$^1$H NMR (500 MHz, DMSO-$d_6$) δ 13.73 (s, 1H), 8.14-8.08 (m, 2H), 8.04 (d, J=11.0 Hz, 1H), 7.78 (s, 1H), 7.72 (d, J=8.1 Hz, 2H), 7.29 (d, J=7.1 Hz, 1H), 7.25 (t, J=6.5 Hz,

1H), 4.34-4.28 (m, 2H), 4.27-4.21 (m, 1H), 3.80-3.74 (m, 2H), 3.50 (dt, J=10.2, 6.9 Hz, 1H), 3.39-3.28 (m, 4H), 3.23 (dt, J=12.9, 6.5 Hz, 1H), 2.94 (s, 3H), 2.81-2.69 (m, 3H), 2.07-1.84 (m, 3H), 1.81-1.66 (m, 1H).

6-{5-[5-fluoro-6-(2-methoxyethoxy)-1H-indazol-3-yl]-1,2-oxazol-3-yl}-N,N-dimethylpyridine-3-carboxamide ("A91")

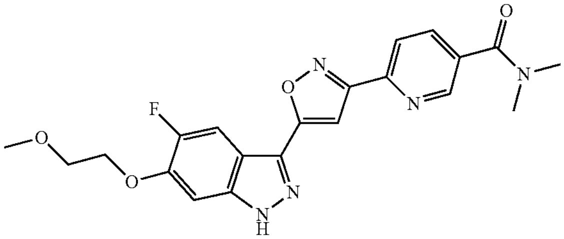

2-{5-[5-fluoro-6-(2-methoxyethoxy)-1H-indazol-3-yl]-1,2-oxazol-3-yl}-N,N-dimethyl-1,3-thiazole-5-carboxamide ("A92")

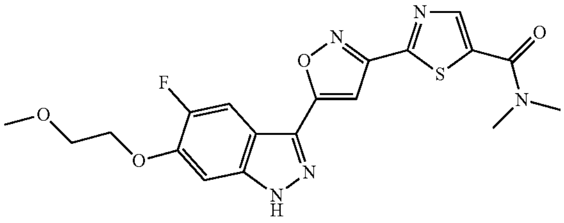

2-{5-[5-fluoro-6-(2-methoxyethoxy)-1H-indazol-3-yl]-1,2-oxazol-3-yl}-N,N-dimethyl-1,3-thiazole-4-carboxamide ("A93")

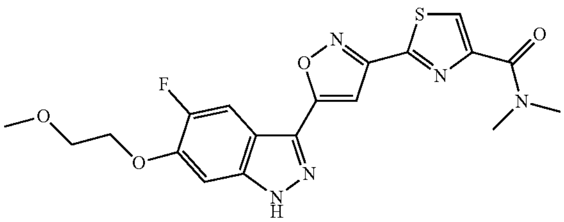

N-{[(2R)-1-(4-{5-[5-fluoro-6-(2-methoxyethoxy)-1H-indazol-3-yl]-1,2-oxazol-3-yl}benzoyl)pyrrolidin-2-yl]methyl}methanesulfonamide ("A94")

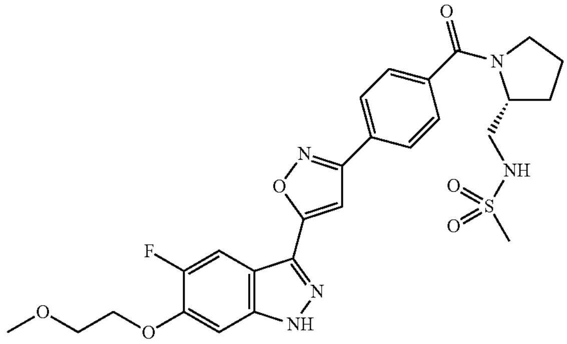 [SMILES: COCCOc1cc2[nH]nc(-c3cc(-c4ccc(C(=O)N5CCC[C@@H]5CNS(C)(=O)=O)cc4)no3)c2cc1F]

[(2S)-1-(4-{5-[5-fluoro-6-(2-methoxyethoxy)-1H-indazol-3-yl]-1,2-oxazol-3-yl}benzoyl)azetidin-2-yl]methanol ("A95")

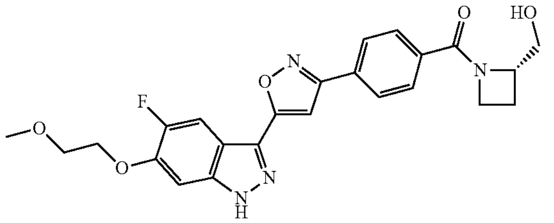 [SMILES: COCCOc1cc2[nH]nc(-c3cc(-c4ccc(C(=O)N5CC[C@H]5CO)cc4)no3)c2cc1F]

off-white solid; HPLC/MS 1.94 min (A), $[M+H]^+$ 467.

$^1$H NMR (700 MHz, DMSO-$d_6$, rotational isomer, selection of signals) δ 13.73 (s, 1H), 8.11 (d, J=7.9 Hz, 2H), 8.03 (d, J=10.9 Hz, 1H), 7.83-7.71 (m, 3H), 7.28 (d, J=7.0 Hz, 1H), 5.02-4.84 (m, 1H), 4.57-4.46 (m, 1H), 4.37-4.25 (m, 3H), 4.10 (q, J=8.1 Hz, 1H), 3.78-3.74 (m, 2H), 3.68-3.58 (m, 1H), 3.36 (s, 3H), 2.45-2.07 (m, 3H).

1-(5-{5-[5-fluoro-6-(2-methoxy-ethoxy)-1H-indazol-3-yl]-isoxazol-3-yl}-pyridine-2-carbonyl)-azetidine-3-carbonitrile ("A96")

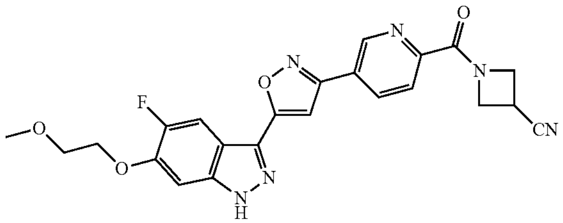 [SMILES: COCCOc1cc2[nH]nc(-c3cc(-c4ccc(C(=O)N5CC(C#N)C5)nc4)no3)c2cc1F]

[(2R)-1-(4-{5-[5-fluoro-6-(2-methoxyethoxy)-1H-indazol-3-yl]-1,2-oxazol-3-yl}benzoyl)azetidin-2-yl]methanol ("A97")

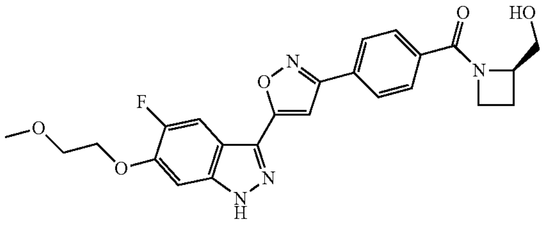 [SMILES: COCCOc1cc2[nH]nc(-c3cc(-c4ccc(C(=O)N5CC[C@@H]5CO)cc4)no3)c2cc1F]

off-white solid; HPLC/MS 1.45 min (A), $[M+H]^+$ 467.

$^1$H NMR (700 MHz, DMSO-$d_6$, rotational isomer, selection of signals) δ 13.73 (s, 1H), 8.11 (d, J=7.9 Hz, 2H), 8.03 (d, J=10.9 Hz, 1H), 7.83-7.71 (m, 3H), 7.28 (d, J=7.0 Hz, 1H), 5.02-4.84 (m, 1H), 4.57-4.46 (m, 1H), 4.37-4.25 (m, 3H), 4.10 (q, J=8.1 Hz, 1H), 3.78-3.74 (m, 2H), 3.68-3.58 (m, 1H), 3.36 (s, 3H), 2.45-2.07 (m, 3H).

(3-fluoro-azetidin-1-yl)-(5-{5-[5-fluoro-6-(2-methoxy-ethoxy)-1H-indazol-3-yl]-isoxazol-3-yl}-pyridin-2-yl)-methanone ("A98")

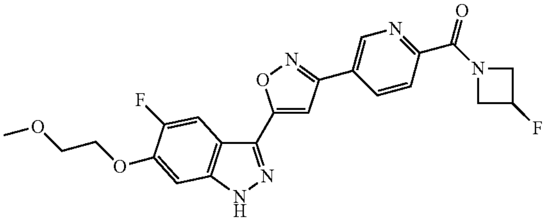 [SMILES: COCCOc1cc2[nH]nc(-c3cc(-c4ccc(C(=O)N5CC(F)C5)nc4)no3)c2cc1F]

5-{5-[5-fluoro-6-(2-methoxy-ethoxy)-1H-indazol-3-yl]-isoxazol-3-yl}-pyridine-2-carboxylic acid dimethylamide ("A99")

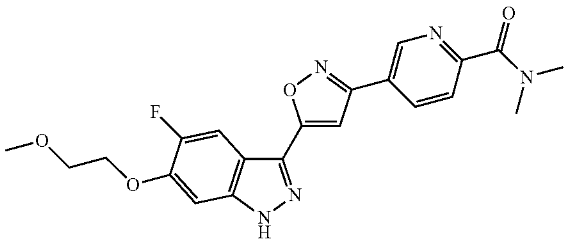

5-fluoro-3-(3-{6-[(3R)-3-fluoropyrrolidine-1'-carbonyl]pyridin-3-yl}-1,2-oxazol-5-yl)-6-(2-methoxyethoxy)-1H-indazole ("A100")

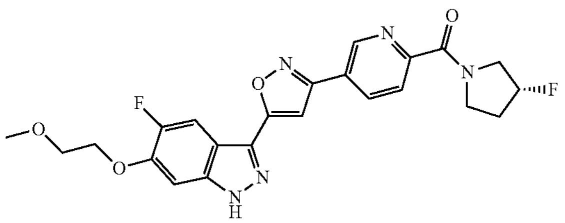 [SMILES: COCCOc1cc2[nH]nc(-c3cc(-c4ccc(C(=O)N5CC[C@@H](F)C5)nc4)no3)c2cc1F]

5-fluoro-3-[3-(4-{3-fluoro-[1,3'-biazetidine]-1-carbonyl}phenyl)-1,2-oxazol-5-yl]-6-(2-methoxyethoxy)-1H-indazole ("A101")

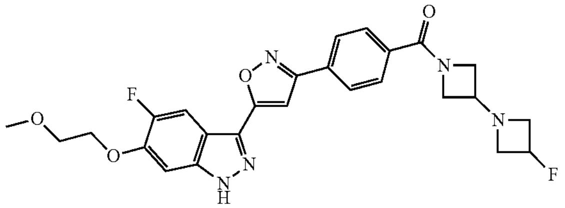 [SMILES: COCCOc1cc2[nH]nc(-c3cc(-c4ccc(C(=O)N5CC(N6CC(F)C6)C5)cc4)no3)c2cc1F]

5-fluoro-6-(2-methoxyethoxy)-3-(3-{4-[3-(4-methylpiperazin-1-yl)azetidine-1-carbonyl]phenyl}-1,2-oxazol-5-yl)-1H-indazole ("A102")

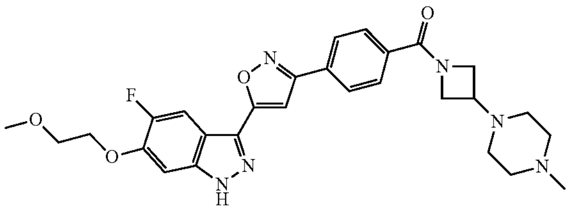

1-[1-(4-{5-[5-fluoro-6-(2-methoxyethoxy)-1H-indazol-3-yl]-1,2-oxazol-3-yl}benzoyl)azetidin-3-yl]piperidin-4-ol ("A103")

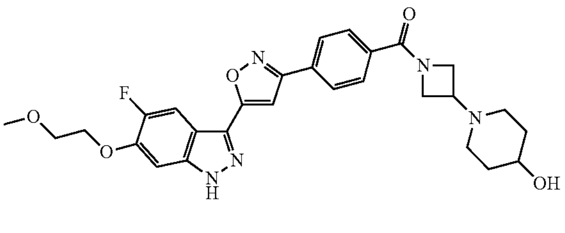 [SMILES: COCCOc1cc2[nH]nc(-c3cc(-c4ccc(C(=O)N5CC(N6CCC(O)CC6)C5)cc4)no3)c2cc1F]

5-fluoro-6-(2-methoxyethoxy)-3-{3-[4-(morpholine-4-carbonyl)phenyl]-1,2-oxazol-5-yl}-1H-indazole ("A104")

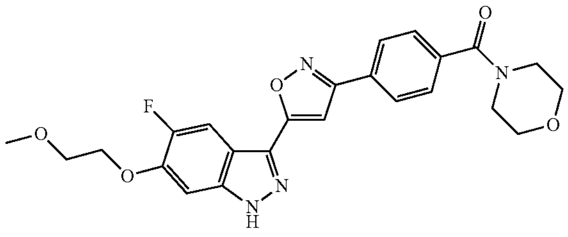 [SMILES: COCCOc1cc2[nH]nc(-c3cc(-c4ccc(C(=O)N5CCOCC5)cc4)no3)c2cc1F]

white solid; UPLC/MS 0.72 min, $[M+H]^+$ 467.

$^1$H NMR (500 MHz, DMSO-$d_6$) δ 13.70 (s, 1H), 8.11 (d, J=8.3 Hz, 2H), 8.02 (d, J=11.0 Hz, 1H), 7.75 (s, 1H), 7.60 (d, J=8.3 Hz, 1H), 7.28 (d, J=7.1 Hz, 1H), 4.35-4.24 (m, 2H), 3.80-3.74 (m, 2H), 3.75-3.30 (broad, 8H), 3.36 (s, 3H).

[(3R)-4-(4-{5-[5-fluoro-6-(2-methoxyethoxy)-1H-indazol-3-yl]-1,2-oxazol-3-yl}benzoyl)morpholin-3-yl]methanol ("A105")

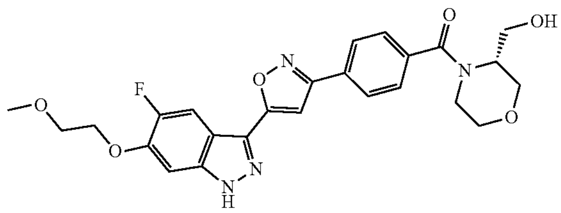 [SMILES: COCCOc1cc2[nH]nc(-c3cc(-c4ccc(C(=O)N5CCOC[C@H]5CO)cc4)no3)c2cc1F]

[(3S)-4-(4-{5-[5-fluoro-6-(2-methoxyethoxy)-1H-indazol-3-yl]-1,2-oxazol-3-yl}benzoyl)morpholin-3-yl]methanol ("A106")

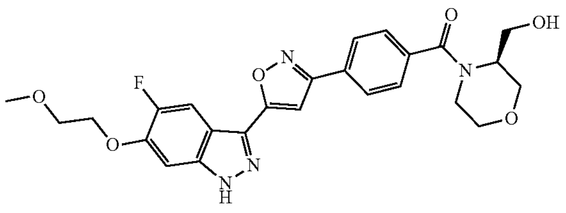 [SMILES: COCCOc1cc2[nH]nc(-c3cc(-c4ccc(C(=O)N5CCOC[C@@H]5CO)cc4)no3)c2cc1F]

off-white solid; HPLC/MS 1.42 min (A), $[M+H]^+$ 497.

$^1$H NMR (500 MHz, DMSO-$d_6$) δ 13.71 (s, 1H), 8.16-8.07 (m, 2H), 8.03 (d, J=11.0 Hz, 1H), 7.76 (s, 1H), 7.61 (d, J=8.0 Hz, 2H), 7.29 (d, J=7.0 Hz, 1H), 4.93 (bs, 1H), 4.37-4.24 (m, 2H), 4.08-3.01 (broad, 11H), 3.36 (s, 3H).

2-[(2S)-1-(5-{5-[5-fluoro-6-(2-methoxyethoxy)-1H-indazol-3-yl]-1,2-oxazol-3-yl}pyridine-2-carbonyl)pyrrolidin-2-yl]propan-2-ol ("A107")

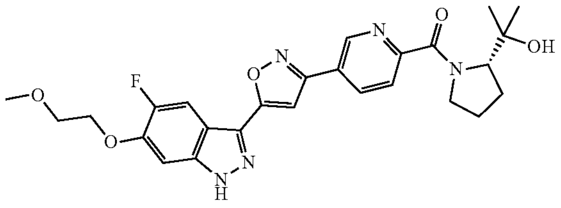 [SMILES: COCCOc1cc2[nH]nc(-c3cc(-c4ccc(C(=O)N5CCC[C@H]5C(C)(C)O)nc4)no3)c2cc1F]

off-white solid; m. p. 119-121° C., $[M+H]^+$ 510.

$^1H$ NMR (400 MHz, DMSO-$d_6$) δ 13.78 (s, 1H), 9.26 (dd, J=2.2, 0.9 Hz, 1H), 8.54 (dd, J=8.2, 2.2 Hz, 1H), 8.03 (d, J=11.0 Hz, 1H), 7.91-7.84 (m, 2H), 7.30 (d, J=7.1 Hz, 1H), 5.05 (s, 1H), 4.34-4.27 (m, 3H), 3.80-3.74 (m, 2H), 3.63-3.48 (m, 2H), 3.36 (s, 3H), 1.98-1.87 (m, 3H), 1.69-1.62 (m, 1H), 1.17 (d, J=5.8 Hz, 6H).

6-(4-{5-[5-fluoro-6-(2-methoxyethoxy)-1H-indazol-3-yl]-1,2-oxazol-3-yl}benzoyl)-3lambda6-thia-6-azabicyclo[3.1.1]heptane-3,3-dione ("A108")

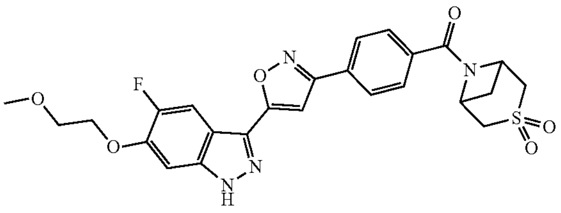 [SMILES: COCCOc1cc2[nH]nc(-c3cc(-c4ccc(C(=O)N5C6CC5CS(=O)(=O)C6)cc4)no3)c2cc1F]

off-white solid; UPLC/MS 0.70 min, $[M+H]^+$ 527.

1H NMR (500 MHz, DMSO-$d_6$) δ 13.72 (s, 1H), 8.16 (d, J=8.4 Hz, 1H), 8.03 (d, J=11.0 Hz, 1H), 7.86 (d, J=8.3 Hz, 2H), 7.79 (s, 1H), 7.29 (d, J=7.0 Hz, 1H), 4.96 (bs, 1H), 4.73 (bs, 1H), 4.34-4.25 (m, 2H), 4.10 (bs, 1H), 3.83-3.71 (m, 3H), 3.36 (s, 3H), 3.02 (dt, J=10.1, 7.0 Hz, 1H), 2.10 (d, J=10.4 Hz, 1H), 1.24 (s, 1H).

(5-{5-[5-fluoro-6-(2-methoxy-ethoxy)-1H-indazol-3-yl]-isoxazol-3-yl}-pyridin-2-yl)-[(R)-2-(1-hydroxy-1-methyl-ethyl)-pyrrolidin-1-yl]-methanone ("A109")

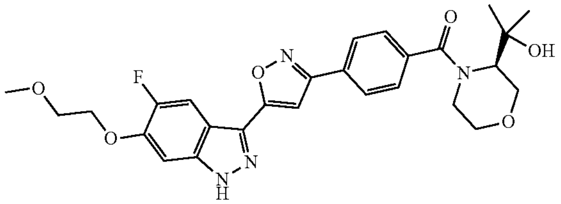 [SMILES: COCCOc1cc2[nH]nc(-c3cc(-c4ccc(C(=O)N5CCOC[C@@H]5C(C)(C)O)cc4)no3)c2cc1F]

5-fluoro-6-(2-methoxyethoxy)-3-(3-{4-[(3S)-3-(methoxymethyl)morpholine-4-carbonyl]phenyl}-1,2-oxazol-5-yl)-1H-indazole ("A110")

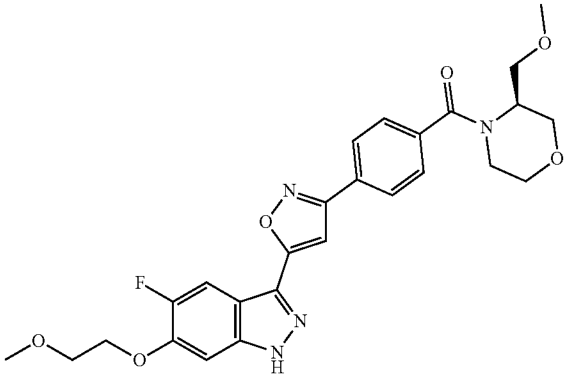 [SMILES: COCCOc1cc2[nH]nc(-c3cc(-c4ccc(C(=O)N5CCOC[C@@H]5COC)cc4)no3)c2cc1F]

off-white solid; HPLC/MS 1.56 min (A), $[M+H]^+$ 511.

$^1H$ NMR (400 MHz, DMSO-$d_6$) δ 13.71 (s, 1H), 8.11 (d, J=8.3 Hz, 2H), 8.03 (d, J=11.0 Hz, 1H), 7.76 (s, 1H), 7.59 (d, J=7.9 Hz, 2H), 7.29 (d, J=7.1 Hz, 1H), 4.35-4.23 (m, 2H), 4.18-3.05 (broad, 12H), 3.80-3.73 (m, 2H), 3.36 (s, 3H).

5-fluoro-6-(2-methoxyethoxy)-3-(3-{4-[(3R)-3-(methoxymethyl)morpholine-4-carbonyl]phenyl}-1,2-oxazol-5-yl)-1H-indazole ("A111")

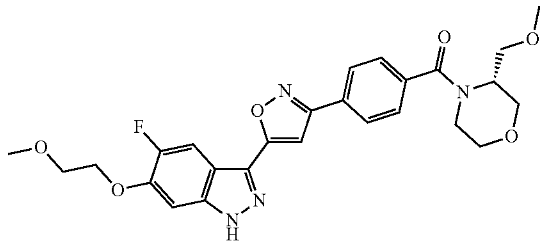

5-fluoro-6-(2-methoxyethoxy)-3-[3-(4-{6-oxa-1-azaspiro[3.3]heptane-1-carbonyl}phenyl)-1,2-oxazol-5-yl]-1H-indazole ("A112")

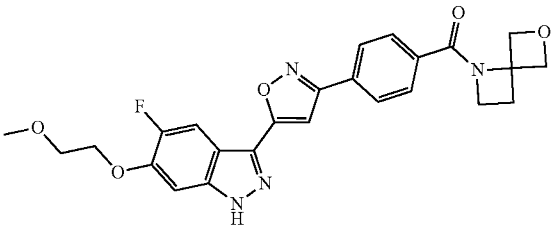 [SMILES: COCCOc1cc2[nH]nc(-c3cc(-c4ccc(C(=O)N5CCC56COC6)cc4)no3)c2cc1F]

white crystals; HPLC/MS 1.54 min (A), $[M+H]^+$ 479.

$^1H$ NMR (700 MHz, DMSO-$d_6$) δ 13.72 (s, 1H), 8.12 (d, J=8.0 Hz, 2H), 8.04 (d, J=10.9 Hz, 1H), 7.81 (d, J=8.2 Hz, 2H), 7.79 (s, 1H), 7.28 (d, J=7.0 Hz, 1H), 5.39 (d, J=6.6 Hz,

2H), 4.59 (d, J=6.6 Hz, 2H), 4.37-4.27 (m, 2H), 4.17 (t, J=7.5 Hz, 2H), 3.76 (dd, J=3.9, 2.3 Hz, 2H), 3.35 (s, 3H), 2.57 (t, J=7.5 Hz, 2H).

5-fluoro-6-(2-methoxyethoxy)-3-(3-{4-[(3R)-3-methylmorpholine-4-carbonyl]phenyl}-1,2-oxazol-5-yl)-1H-indazole ("A114")

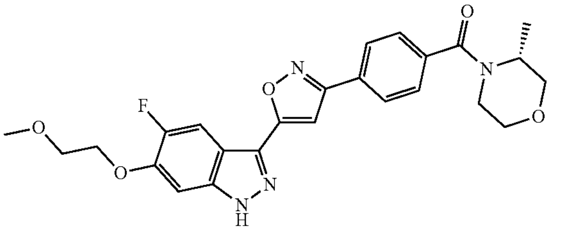 [SMILES: COCCOc1cc2[nH]nc(-c3cc(-c4ccc(C(=O)N5CCOC[C@H]5C)cc4)no3)c2cc1F]

5-fluoro-6-(2-methoxyethoxy)-3-(3-{4-[(3S)-3-methylmorpholine-4-carbonyl]phenyl}-1,2-oxazol-5-yl)-1H-indazole ("A115")

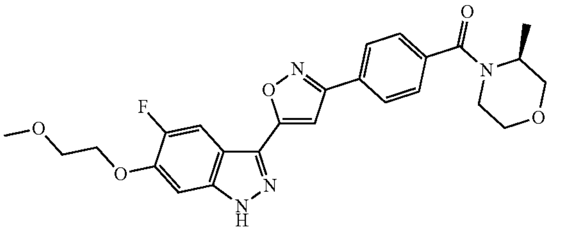 [SMILES: COCCOc1cc2[nH]nc(-c3cc(-c4ccc(C(=O)N5CCOC[C@@H]5C)cc4)no3)c2cc1F]

white solid; UPLC/MS 0.74 min, $[M+H]^+$ 481.

$^1H$ NMR (400 MHz, DMSO-$d_6$) δ 13.71 (s, 1H), 8.12 (d, J=8.2 Hz, 2H), 8.03 (d, J=11.0 Hz, 1H), 7.76 (s, 1H), 7.58 (d, J=8.2 Hz, 2H), 7.29 (d, J=7.1 Hz, 1H), 4.49-4.19 (m, 2H), 3.90-3.74 (m, 3H), 3.69-3.56 (m, 2H), 3.51-3.38 (m, 1H), 3.37 (s, 3H), 1.29 (d, J=6.9 Hz, 3H).

4-(4-{5-[5-fluoro-6-(2-methoxyethoxy)-1H-indazol-3-yl]-1,2-oxazol-3-yl}benzoyl)-1-methylpiperazin-2-one ("A116")

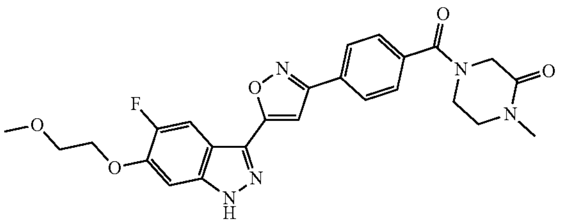 [SMILES: COCCOc1cc2[nH]nc(-c3cc(-c4ccc(C(=O)N5CCN(C)C(=O)C5)cc4)no3)c2cc1F]

5-fluoro-3-(3-{4-[(2S)-2-(methanesulfonylmethyl)pyrrolidine-1-carbonyl]phenyl}-1,2-oxazol-5-yl)-6-methoxy-1H-indazole ("A117")

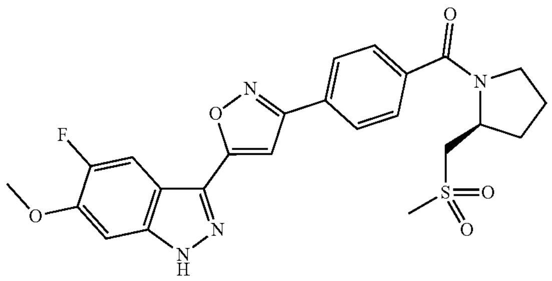 [SMILES: COc1cc2[nH]nc(-c3cc(-c4ccc(C(=O)N5CCC[C@H]5CS(C)(=O)=O)cc4)no3)c2cc1F]

(5-{5-[5-fluoro-6-(2-methoxy-ethoxy)-1H-indazol-3-yl]-isoxazol-3-yl}-pyridin-2-yl)-[(S)-2-(1-hydroxy-1-methyl-ethyl)-azetidin-1-yl]-methanone ("A118")

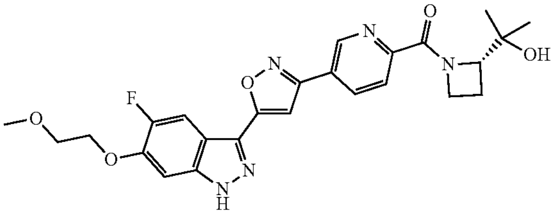 [SMILES: COCCOc1cc2[nH]nc(-c3cc(-c4ccc(C(=O)N5CC[C@H]5C(C)(C)O)nc4)no3)c2cc1F]

(5-{5-[5-fluoro-6-(2-methoxy-ethoxy)-1H-indazol-3-yl]-isoxazol-3-yl}-pyridin-2-yl)-[(R)-2-(1-hydroxy-1-methyl-ethyl)-azetidin-1-yl]-methanone ("A119")

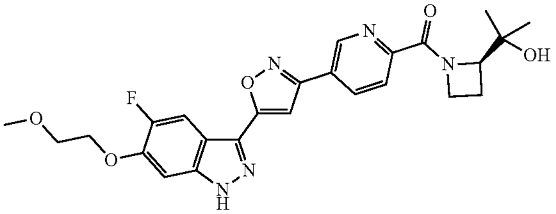 [SMILES: COCCOc1cc2[nH]nc(-c3cc(-c4ccc(C(=O)N5CC[C@@H]5C(C)(C)O)nc4)no3)c2cc1F]

5-fluoro-6-(2-methoxyethoxy)-3-(3-{4-[3-(pyridin-4-yl)azetidine-1-carbonyl]phenyl}-1,2-oxazol-5-yl)-1H-indazole ("A120")

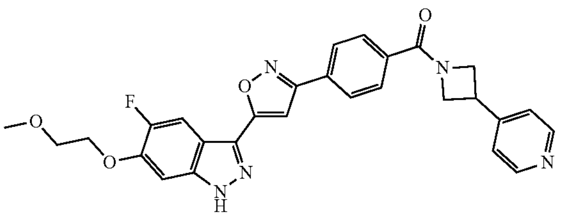 [SMILES: COCCOc1cc2[nH]nc(-c3cc(-c4ccc(C(=O)N5CC(c6ccncc6)C5)cc4)no3)c2cc1F]

white solid; UPLC/MS 0.54 min, $[M+H]^+$ 514.

$^1H$ NMR (400 MHz, DMSO-$d_6$) δ 13.77 (s, 1H), 8.70-8.59 (m, 2H), 8.18 (d, J=8.3 Hz, 2H), 8.08 (d, J=11.0 Hz, 1H), 7.92 (d, J=8.4 Hz, 2H), 7.83 (s, 1H), 7.54-7.46 (m, 2H), 7.34 (d, J=7.0 Hz, 1H), 4.80 (t, J=8.9 Hz, 1H), 4.65-4.48 (m, 2H), 4.41-4.30 (m, 2H), 4.16 (t, J=8.0 Hz, 2H), 4.12-4.01 (m, 1H), 3.84-3.76 (m, 2H), 3.41 (s, 3H).

4-(4-{5-[5-fluoro-6-(2-methoxyethoxy)-1H-indazol-3-yl]-1,2-oxazol-3-yl}benzoyl)-3-methyl-1lambda6-thiomorpholine-1,1-dione ("A121")

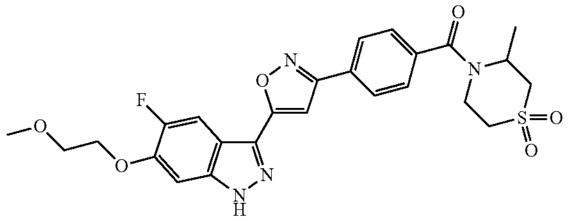 [SMILES: COCCOc1cc2[nH]nc(-c3cc(-c4ccc(C(=O)N5CCS(=O)(=O)CC5C)cc4)no3)c2cc1F]

white solid; UPLC/MS 0.72 min, $[M+H]^+$ 529.

$^1H$ NMR (400 MHz, DMSO-$d_6$) δ 13.72 (s, 1H), 8.12 (d, J=8.3 Hz, 2H), 8.01 (d, J=11.0 Hz, 1H), 7.75 (s, 1H), 7.67 (d, J=8.2 Hz, 2H), 7.28 (d, J=7.1 Hz, 1H), 4.38-4.22 (m, 2H), 3.85-3.71 (m, 2H), 3.65-3.08 (m, 7H), 3.36 (s, 3H), 1.44 (d, J=7.1 Hz, 3H).

Example 7

5-fluoro-6-(2-methoxyethoxy)-3-{3-[4-(4-methylpiperazin-1-yl)phenyl]-1,2-oxazol-5-yl}-1H-indazole ("A37")

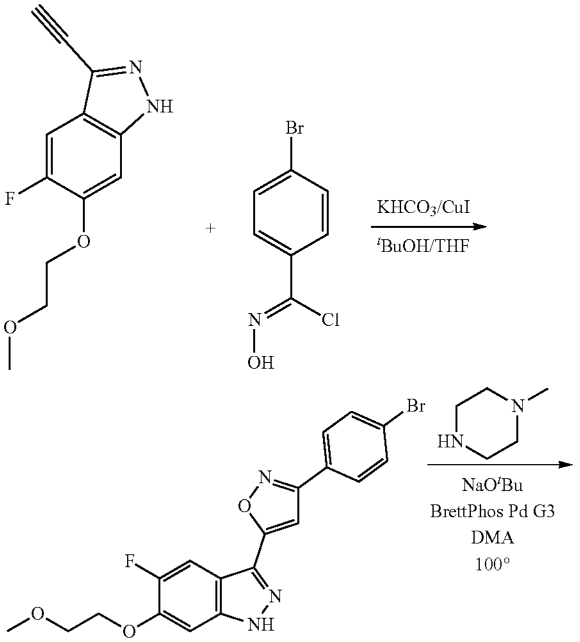

-continued

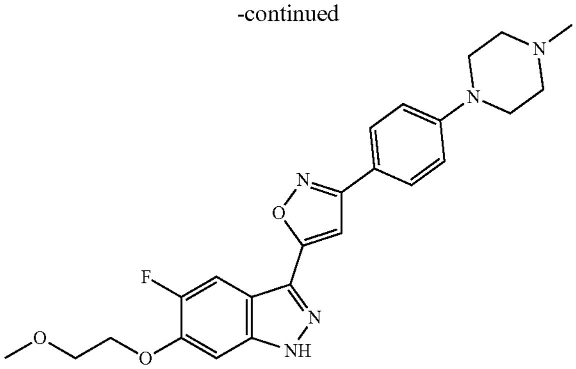

off-white powder; HPLC/MS 1.68 min (A), $[M+H]^+$ 452.

$^1H$ NMR (400 MHz, DMSO-$d_6$) δ 13.64 (s, 1H), 8.00 (d, J=11.0 Hz, 1H), 7.85 (d, J=8.7 Hz, 2H), 7.57 (s, 1H), 7.26 (d, J=7.0 Hz, 1H), 7.07 (d, J=8.8 Hz, 2H), 4.31-4.27 (m, 2H), 4.03-3.60 (m, 2H), 3.35 (s, 3H), 3.32-3.23 (broad, 4H), 2.50-2.44 (broad, 4H) 2.24 (s, 3H).

The following compounds are prepared analogously:

4-(4-{5-[5-fluoro-6-(2-methoxyethoxy)-1H-indazol-3-yl]-1,2-oxazol-3-yl}phenyl)-1lambda6-thiomorpholine-1,1-dione ("A122")

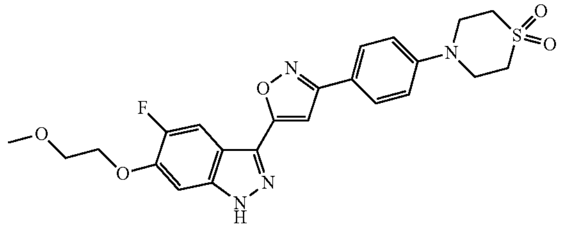 [SMILES: COCCOc1cc2[nH]nc(-c3cc(-c4ccc(N5CCS(=O)(=O)CC5)cc4)no3)c2cc1F]

pale yellow solid; HPLC/MS 2.06 min (A), $[M+H]^+$ 487.

$^1H$ NMR (400 MHz, DMSO-$d_6$) δ 13.65 (s, 1H), 8.01 (d, J=11.0 Hz, 1H), 7.91 (d, J=8.9 Hz, 2H), 7.62 (s, 1H), 7.27 (d, J=7.1 Hz, 1H), 7.19 (d, J=9.0 Hz, 1H), 4.36-4.23 (m, 2H), 3.92 (t, J=5.1 Hz, 4H), 3.82-3.69 (m, 2H), 3.36 (s, 3H), 3.25-3.11 (m, 4H).

5-fluoro-6-(2-methoxyethoxy)-3-{3-[4-(4-methyl-1,4-diazepan-1-yl)phenyl]-1,2-oxazol-5-yl}-1H-indazole ("A123")

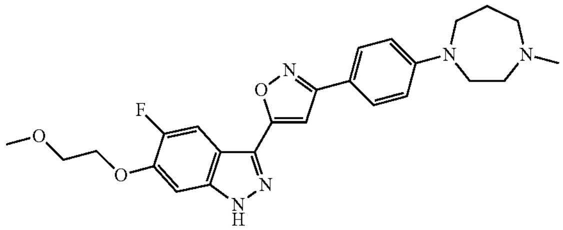

off-white solid; HPLC/MS 1.31 min (A), $[M+H]^+$ 487.

$^1H$ NMR (400 MHz, DMSO-$d_6$) δ 13.63 (s, 1H), 7.99 (d, J=11.0 Hz, 1H), 7.80 (d, J=8.9 Hz, 2H), 7.52 (s, 1H), 7.27 (d, J=7.1 Hz, 1H), 6.83 (d, J=9.0 Hz, 2H), 4.36-4.26 (m, 2H), 3.81-3.73 (m, 2H), 3.64-3.57 (m, 2H), 3.52 (t, J=6.2 Hz, 2H), 3.36 (s, 3H), 2.68-2.62 (m, 2H), 2.50-2.44 (m, 2H), 2.28 (s, 3H), 1.92 (p, J=5.9 Hz, 2H).

3-(3-{4-[(cis)-4-methyl-octahydro-1H-pyrrolo[3,2-b]pyridin-1-yl]phenyl}-1,2-oxazol-5-yl)-5-fluoro-6-(2-methoxyethoxy)-1H-indazole ("A124")

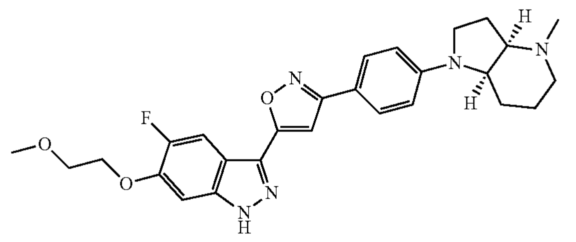

3-(3-{4-[(cis)-4-methyl-octahydropyrrolo[3,2-b]pyrrol-1-yl]phenyl}-1,2-oxazol-5-yl)-5-fluoro-6-(2-methoxyethoxy)-1H-indazole ("A125")

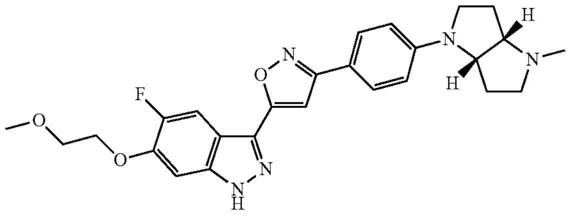

3-(3-{4-[(trans)-4-methyl-octahydropyrrolo[3,2-b]pyrrol-1-yl]phenyl}-1,2-oxazol-5-yl)-5-fluoro-6-(2-methoxyethoxy)-1H-indazole ("A126")

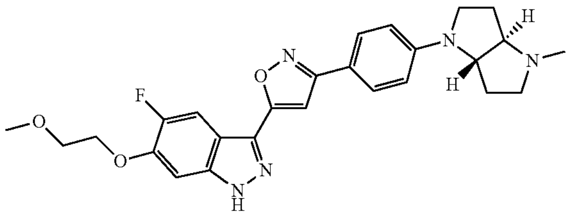

4-(4-{5-[5-fluoro-6-(2-methoxyethoxy)-1H-indazol-3-yl]-1,2-oxazol-3-yl}phenyl)-1lambda4-thiomorpholin-1-one ("A127")

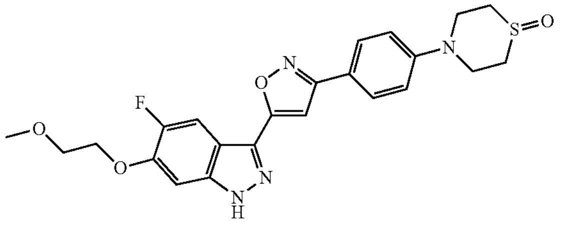 [SMILES: COCCOc1cc2[nH]nc(-c3cc(-c4ccc(N5CCS(=O)CC5)cc4)no3)c2cc1F]

pale yellow solid; HPLC/MS 1.95 min (A), $[M+H]^+$ 471.

$^1H$ NMR (400 MHz, DMSO-$d_6$) δ 13.64 (s, 1H), 8.01 (d, J=11.0 Hz, 1H), 7.90 (d, J=8.9 Hz, 2H), 7.60 (s, 1H), 7.27 (d, J=7.1 Hz, 1H), 7.23-7.03 (m, 2H), 4.36-4.15 (m, 2H), 3.92 (ddd, J=12.9, 11.0, 2.1 Hz, 2H), 3.85-3.71 (m, 4H), 3.36 (s, 3H), 2.96 (ddd, J=13.7, 10.7, 3.2 Hz, 2H), 2.78-2.65 (m, 2H).

1-(4-{5-[5-fluoro-6-(2-methoxyethoxy)-1H-indazol-3-yl]-1,2-oxazol-3-yl}phenyl)piperidin-4-ol ("A128")

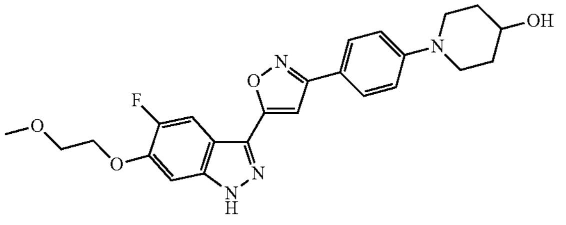 [SMILES: COCCOc1cc2[nH]nc(-c3cc(-c4ccc(N5CCC(O)CC5)cc4)no3)c2cc1F]

1-[(4-{5-[5-fluoro-6-(2-methoxyethoxy)-1H-indazol-3-yl]-1,2-oxazol-3-yl}phenyl)imino]-1lambda6-thiomorpholin-1-one ("A129")

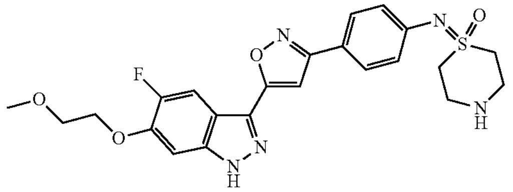 [SMILES: COCCOc1cc2[nH]nc(-c3cc(-c4ccc(N=S5(=O)CCNCC5)cc4)no3)c2cc1F]

hydrochloride, off-white solid; HPLC/MS 1.29 min (A), $[M+H]^+$ 486.

1H NMR (400 MHz, DMSO-$d_6$) δ 13.68 (s, 1H), 9.38 (s, 2H), 8.00 (d, J=11.0 Hz, 1H), 7.91 (d, J=8.5 Hz, 1H), 7.61 (s, 1H), 7.28 (d, J=7.1 Hz, 1H), 7.17 (d, J=8.6 Hz, 1H), 4.40-4.28 (m, 2H), 3.96-3.40 (m, 10H), 3.36 (s, 3H).

Example 8

3-[3-(6-ethoxypyridin-3-yl)-1,2-oxazol-5-yl]-5-fluoro-6-(2-methoxyethoxy)-1H-indazole ("A38")

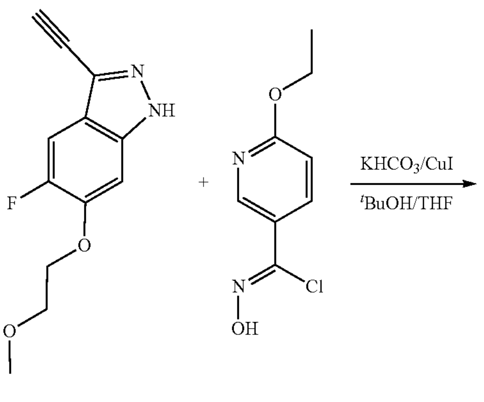

-continued

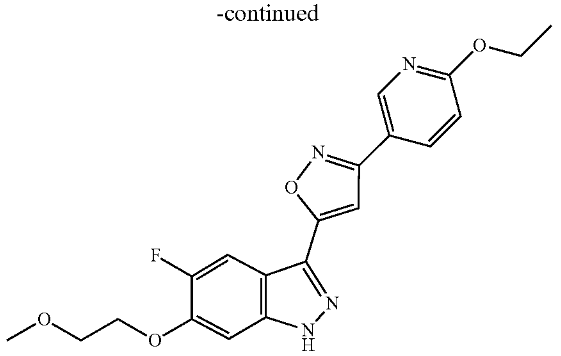

off-white solid; UPLC/MS 0.68 min, $[M+H]^+$ 399.

$^1$H NMR (400 MHz, DMSO-$d_6$) δ 13.70 (s, 1H), 8.83 (d, J=2.4 Hz, 1H), 8.29 (dd, J=8.7, 2.5 Hz, 1H), 7.99 (d, J=11.0 Hz, 1H), 7.71 (s, 1H), 7.28 (d, J=7.0 Hz, 1H), 6.99 (d, J=8.6 Hz, 1H), 4.41 (q, J=7.0 Hz, 2H), 4.36-4.27 (m, 2H), 3.83-3.73 (m, 2H), 3.36 (s, 3H), 1.37 (t, J=7.0 Hz, 3H).

The following compound is prepared analogously:

5-fluoro-6-(2-methoxy-ethoxy)-3-[3-(6-methoxy-pyridin-3-yl)-isoxazol-5-yl]-1H-indazole ("A130")

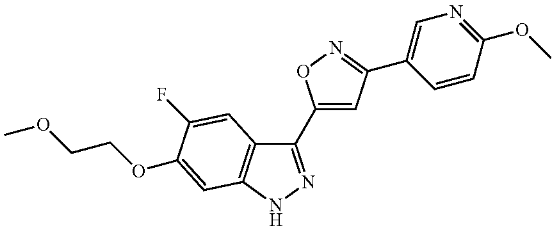

white solid; m.p. 210-213° C.; $[M+H]^+$ 385.

$^1$H NMR (400 MHz, DMSO-$d_6$) 13.73 (s, 1H), 8.85 (d, J=2.4 Hz, 1H), 8.31 (dd, J=8.7, 2.5 Hz, 1H), 8.00 (d, J=11.0 Hz, 1H), 7.73 (s, 1H), 7.28 (d, J=7.1 Hz, 1H), 7.03 (d, J=8.7 Hz, 1H), 4.30 (dd, J=5.6, 3.4 Hz, 2H), 3.95 (s, 3H), 3.80-3.73 (m, 2H), 3.36 (s, 3H).

Example 9

5-fluoro-6-(2-methoxyethoxy)-3-{3-[6-(4-methylpiperazin-1-yl)pyridin-3-yl]-1,2-oxazol-5-yl}-1H-indazole ("A39")

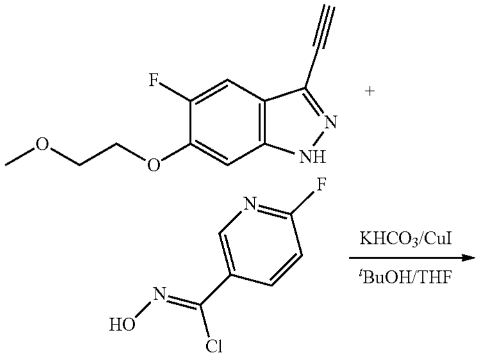

-continued

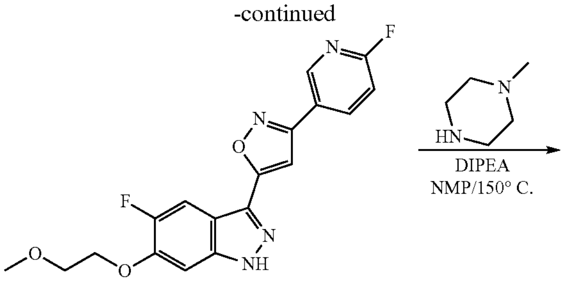

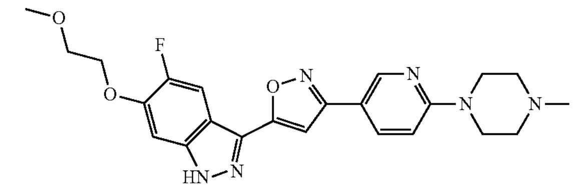

off-white powder; UPLC/MS 0.49 min, $[M+H]^+$ 453.

$^1$H NMR (500 MHz, DMSO-$d_6$) δ 13.68 (s, 1H), 8.75 (dd, J=2.4, 0.7 Hz, 1H), 8.10 (dd, J=9.0, 2.4 Hz, 1H), 7.64 (s, 1H), 7.27 (d, J=7.1 Hz, 1H), 7.00 (d, J=9.0 Hz, 1H), 4.36-4.02 (m, 2H), 3.84-3.69 (m, 2H), 3.71-3.52 (m, 4H), 3.36 (s, 3H), 2.44-2.39 (m, 4H), 2.24 (s, 3H).

The following compound is prepared analogously:

4-(5-{5-[5-fluoro-6-(2-methoxyethoxy)-1H-indazol-3-yl]-1,2-oxazol-3-yl}pyridin-2-yl)-1lambda6-thiomorpholine-1,1-dione ("A131")

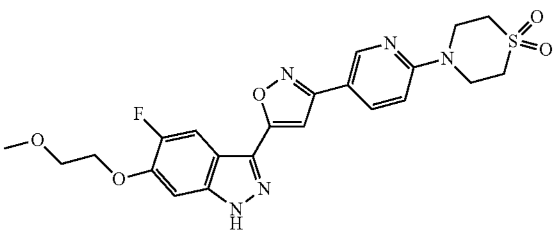 [SMILES: COCCOc1cc2[nH]nc(-c3cc(-c4ccc(N5CCS(=O)(=O)CC5)nc4)no3)c2cc1F]

off-white solid; UPLC/MS 0.73 min, $[M+H]^+$ 488.

$^1$H NMR (700 MHz, DMSO-$d_6$) δ 13.70 (s, 1H), 8.81 (d, J=2.4 Hz, 1H), 8.19 (dd, J=8.9, 2.4 Hz, 1H), 7.99 (d, J=10.9 Hz, 1H), 7.68 (s, 1H), 7.28 (d, J=7.0 Hz, 1H), 7.21 (d, J=8.9 Hz, 1H), 4.39-4.26 (m, 2H), 4.17 (t, J=5.2 Hz, 4H), 3.89-3.65 (m, 2H), 3.36 (s, 3H), 3.18 (t, J=5.2 Hz, 4H).

Example 10

5-fluoro-6-(2-methoxyethoxy)-3-(3-{4-[2-(morpholin-4-yl)ethoxy]phenyl}-1,2-oxazol-5-yl)-1H-indazole ("A40")

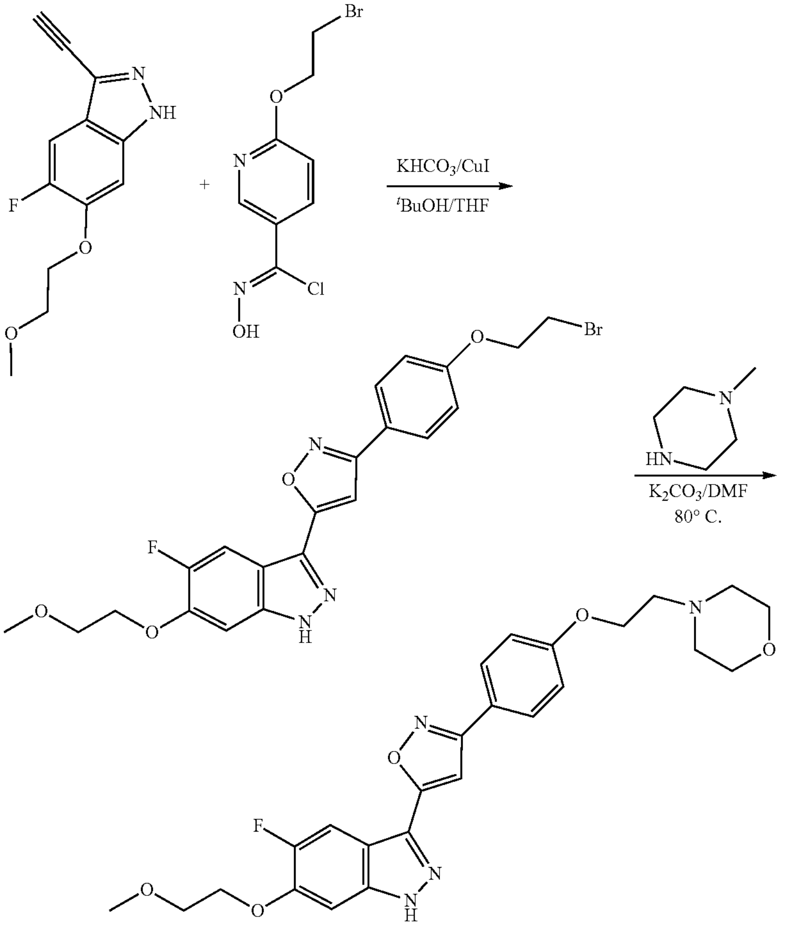

off-white powder; HPLC/MS 1.29 min (A), $[M+H]^+$ 483. $^1$H NMR (500 MHz, DMSO-$d_6$) δ 13.69 (s, 1H), 8.01 (d, J=11.0 Hz, 1H), 7.97 (d, J=8.3 Hz, 2H), 7.65 (s, 1H), 7.27 (d, J=7.1 Hz, 1H), 7.13 (d, J=8.3 Hz, 2H), 4.33-4.27 (m, 2H), 4.21 (broad, 2H), 3.80-3.71 (m, 2H), 3.62 (broad, 4H), 3.35 (s, 3H), 2.74 (broad, 2H).

The following compounds are prepared analogously:

4-[2-(4-{5-[5-fluoro-6-(2-methoxyethoxy)-1H-indazol-3-yl]-1,2-oxazol-3-yl}phenoxy)ethyl]-1lambda6-thiomorpholine-1,1-dione ("A132")

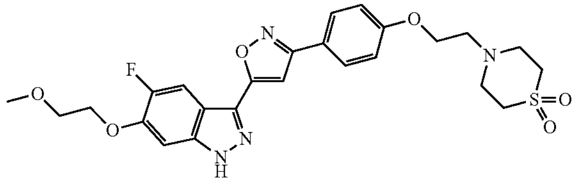 [SMILES: COCCOc1cc2[nH]nc(-c3cc(-c4ccc(OCCN5CCS(=O)(=O)CC5)cc4)no3)c2cc1F]

white powder; HPLC/MS 2.06 min (A), $[M+H]^+$ 531. $^1$H NMR (500 MHz, DMSO-$d_6$) δ 13.66 (s, 1H), 8.00 (d, J=11.0 Hz, 1H), 7.96 (d, J=8.8 Hz, 2H), 7.63 (s, 1H), 7.27 (d, J=7.1 Hz, 1H), 7.12 (d, J=8.8 Hz, 2H), 4.32-4.24 (m, 2H), 4.18 (t, J=5.6 Hz, 2H), 3.85-3.67 (m, 2H), 3.35 (s, 3H), 3.14-3.04 (m, 8H), 2.97 (t, J=5.6 Hz, 2H).

5-fluoro-6-(2-methoxyethoxy)-3-(3-{4-[2-(4-methylpiperazin-1-yl)ethoxy]phenyl}-1,2-oxazol-5-yl)-1H-indazole ("A133")

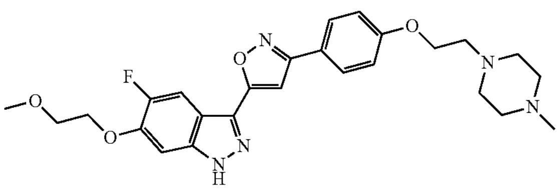

5-fluoro-6-(2-methoxyethoxy)-3-(3-{4-[2-(piperazin-1-yl)ethoxy]phenyl}-1,2-oxazol-5-yl)-1H-indazole ("A134")

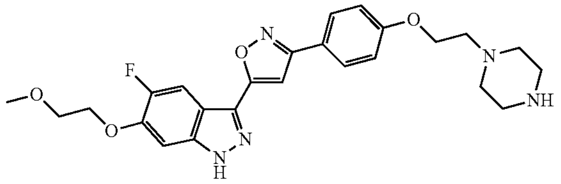 [SMILES: COCCOc1cc2[nH]nc(-c3cc(-c4ccc(OCCN5CCNCC5)cc4)no3)c2cc1F]

Example 11

1-(4-{5-[5-Fluoro-6-(2-methoxy-ethoxy)-1H-indazol-3-yl]-isoxazol-3-yl}-phenyl)-1H-pyridin-2-one ("A41") Hydrochloride

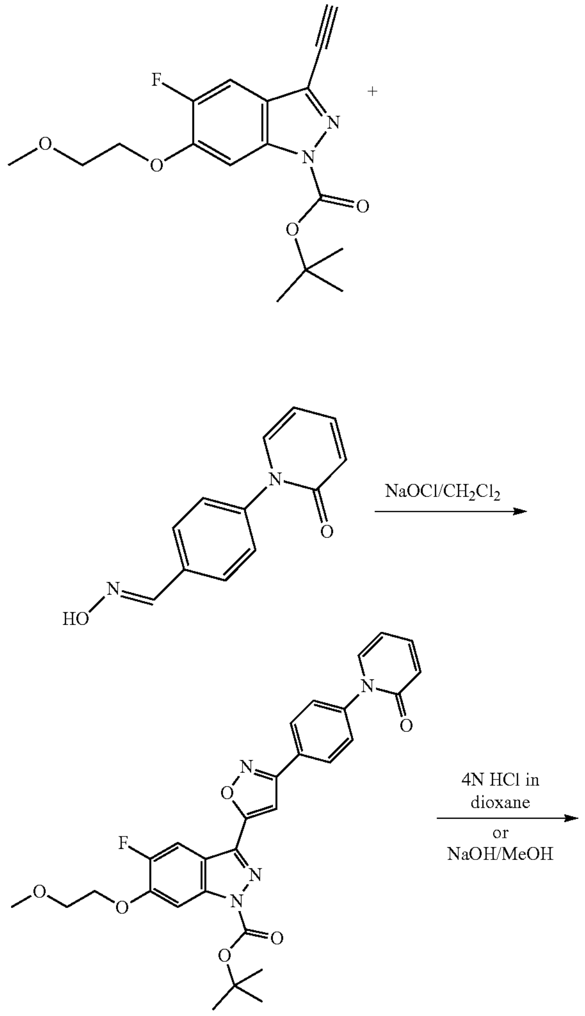

-continued

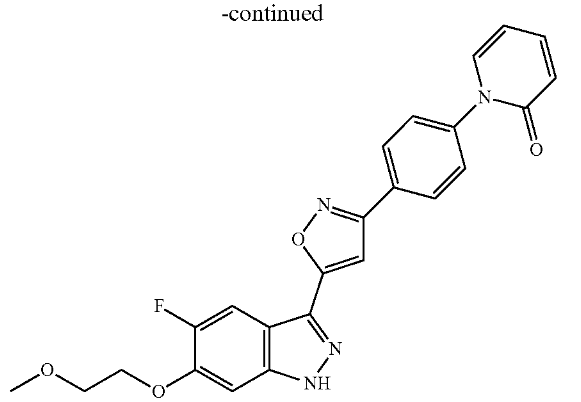

off-white solid; HPLC/MS 1.54 min (A), $[M+H]^+$ 447. $^1H$ NMR (400 MHz, DMSO-$d_6$) δ 13.72 (s, 1H), 8.17 (d, J=8.0 Hz, 2H), 8.03 (d, J=11.0 Hz, 1H), 7.78 (s, 1H), 7.73 (d, J=6.9 Hz, 1H), 7.62 (d, J=8.1 Hz, 2H), 7.54 (t, J=8.0 Hz, 1H), 7.28 (d, J=7.0 Hz, 1H), 6.52 (d, J=9.3 Hz, 1H), 6.36 (t, J=6.8 Hz, 1H), 4.33-4.28 (m, 2H), 3.79-3.74 (m, 2H), 3.36 (s, 3H).

The following compounds are prepared analogously:

2-(4-{5-[5-fluoro-6-(2-methoxy-ethoxy)-1H-indazol-3-yl]-isoxazol-3-yl}-phenyl)-6-methyl-2H-pyridazin-3-one ("A136")

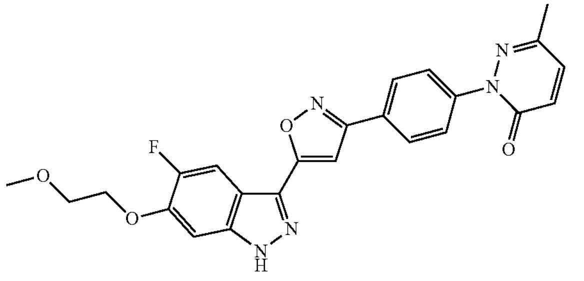 [SMILES: COCCOc1cc2[nH]nc(-c3cc(-c4ccc(-n5nc(C)ccc5=O)cc4)no3)c2cc1F]

5-fluoro-6-(2-methoxy-ethoxy)-3-[3-(1-methyl-1H-pyrazol-4-yl)-isoxazol-5-yl]-1H-indazole ("A137")

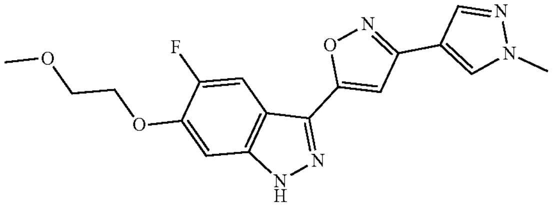

2-(4-{5-[5-fluoro-6-(2-methoxyethoxy)-1H-indazol-3-yl]-1,2-oxazol-3-yl}phenyl)-1lambda6,2-thiazolidine-1,1-dione ("A138")

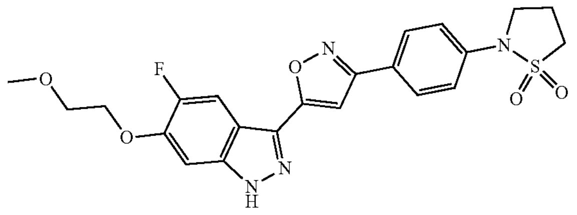 [SMILES: COCCOc1cc2[nH]nc(-c3cc(-c4ccc(N5CCCS5(=O)=O)cc4)no3)c2cc1F]

4-(4-{5-[5-fluoro-6-(2-methoxyethoxy)-1H-indazol-3-yl]-1,2-oxazol-3-yl}phenyl)morpholin-3-one ("A139")

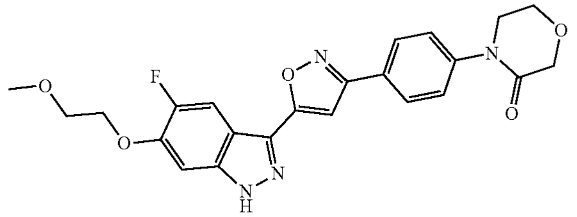 [SMILES: COCCOc1cc2[nH]nc(-c3cc(-c4ccc(N5CCOCC5=O)cc4)no3)c2cc1F]

off-white solid; HPLC/MS 0.71 min, $[M+H]^+$ 453.

$^1$H NMR (500 MHz, DMSO-$d_6$) δ 13.71 (s, 1H), 8.08 (d, J=8.6 Hz, 1H), 8.02 (d, J=11.0 Hz, 1H), 7.72 (s, 1H), 7.63 (d, J=8.6 Hz, 1H), 7.29 (d, J=7.1 Hz, 1H), 4.34-4.28 (m, 2H), 4.26 (s, 2H), 4.07-4.00 (m, 2H), 3.89-3.81 (m, 2H), 3.81-3.73 (m, 2H), 3.36 (s, 3H).

4-(5-{5-[5-fluoro-6-(2-methoxyethoxy)-1H-indazol-3-yl]-1,2-oxazol-3-yl}pyridin-2-yl)-1lambda4-thiomorpholin-1-one ("A140")

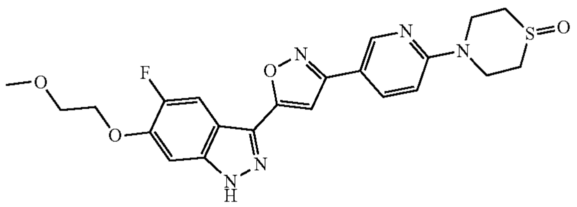 [SMILES: COCCOc1cc2[nH]nc(-c3cc(-c4ccc(N5CCS(=O)CC5)nc4)no3)c2cc1F]

off-white powder; HPLC/MS 1.43 min (A), $[M+H]^+$ 472.

$^1$H NMR (500 MHz, DMSO-$d_6$) δ 13.66 (s, 1H), 8.79 (dd, J=2.4, 0.7 Hz, 1H), 8.15 (dd, J=8.9, 2.4 Hz, 1H), 7.98 (d, J=10.9 Hz, 1H), 7.64 (s, 1H), 7.27 (d, J=7.1 Hz, 1H), 7.14 (d, J=8.8 Hz, 1H), 4.42-4.22 (m, 4H), 3.99 (ddd, J=14.7, 11.1, 2.0 Hz, 2H), 3.82-3.62 (m, 2H), 3.35 (s, 3H), 2.92 (ddd, J=14.1, 11.1, 3.3 Hz, 2H), 2.77-2.66 (m, 2H).

5-fluoro-6-(2-methoxyethoxy)-3-{3-[6-(morpholin-4-yl)pyridin-3-yl]-1,2-oxazol-5-yl}-1H-indazole ("A141")

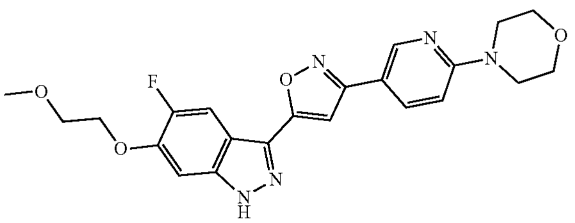 [SMILES: COCCOc1cc2[nH]nc(-c3cc(-c4ccc(N5CCOCC5)nc4)no3)c2cc1F]

2-(4-{5-[5-fluoro-6-(2-methoxyethoxy)-1H-indazol-3-yl]-1,2-oxazol-3-yl}phenyl)-2,3-dihydropyridazin-3-one ("A142")

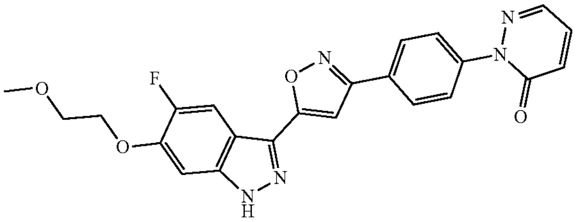 [SMILES: COCCOc1cc2[nH]nc(-c3cc(-c4ccc(-n5ncccc5=O)cc4)no3)c2cc1F]

white solid; HPLC/MS 1.55 min (A), $[M+H]^+$ 448.

$^1$H NMR (400 MHz, DMSO-$d_6$) δ 13.70 (s, 1H), 8.16 (d, J=8.6 Hz, 2H), 8.12 (dd, J=3.8, 1.6 Hz, 1H), 8.03 (d, J=11.0 Hz, 1H), 7.79 (d, J=8.6 Hz, 2H), 7.77 (s, 1H), 7.53 (dd, J=9.5, 3.8 Hz, 1H), 7.28 (d, J=7.0 Hz, 1H), 7.12 (dd, J=9.5, 1.6 Hz, 1H), 4.33-4.20 (m, 2H), 3.79-3.70 (m, 2H), 3.36 (s, 3H).

5-fluoro-6-(2-methoxyethoxy)-3-{3-[4-(pyridin-2-yloxy)phenyl]-1,2-oxazol-5-yl}-1H-indazole ("A143")

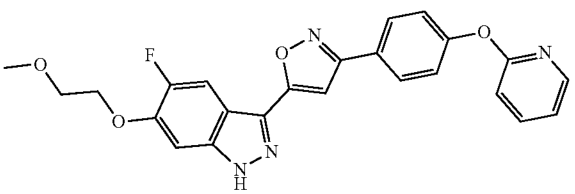 [SMILES: COCCOc1cc2[nH]nc(-c3cc(-c4ccc(Oc5ccccn5)cc4)no3)c2cc1F]

4-{5-[5-fluoro-6-(2-methoxyethoxy)-1H-indazol-3-yl]-1,2-oxazol-3-yl}-N,N-dimethylbenzene-1-sulfonamide ("A144")
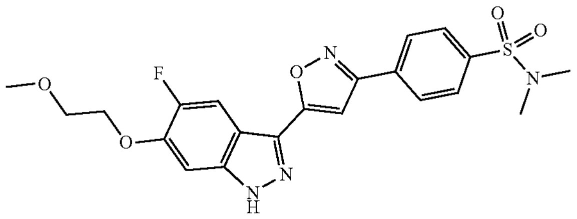
5-fluoro-6-(2-methoxyethoxy)-3-(3-{6-[3-(morpholin-4-yl)azetidin-1-yl]pyridin-3-yl}-1,2-oxazol-5-yl)-1H-indazole ("A145")
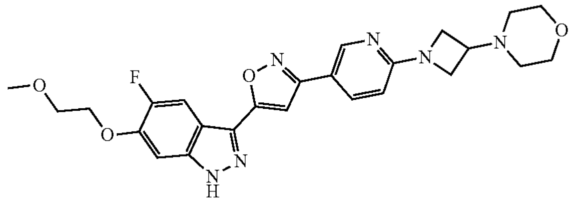 [SMILES: COCCOc1cc2[nH]nc(-c3cc(-c4ccc(N5CC(N6CCOCC6)C5)nc4)no3)c2cc1F]
5-fluoro-6-(2-methoxyethoxy)-3-{3-[4-(morpholine-4-sulfonyl)phenyl]-1,2-oxazol-5-yl}-1H-indazole ("A227")
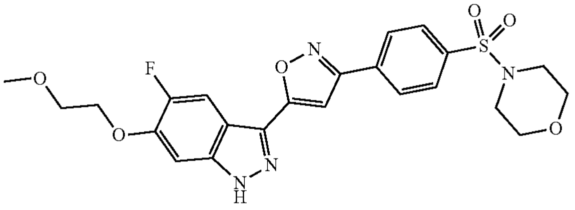 [SMILES: COCCOc1cc2[nH]nc(-c3cc(-c4ccc(S(=O)(=O)N5CCOCC5)cc4)no3)c2cc1F]
Example 12
3-{3-[4-(1,4-diazepan-1-yl)phenyl]-1,2-oxazol-5-yl}-5-fluoro-6-(2-methoxyethoxy)-1H-indazole ("A42") Hydrochloride
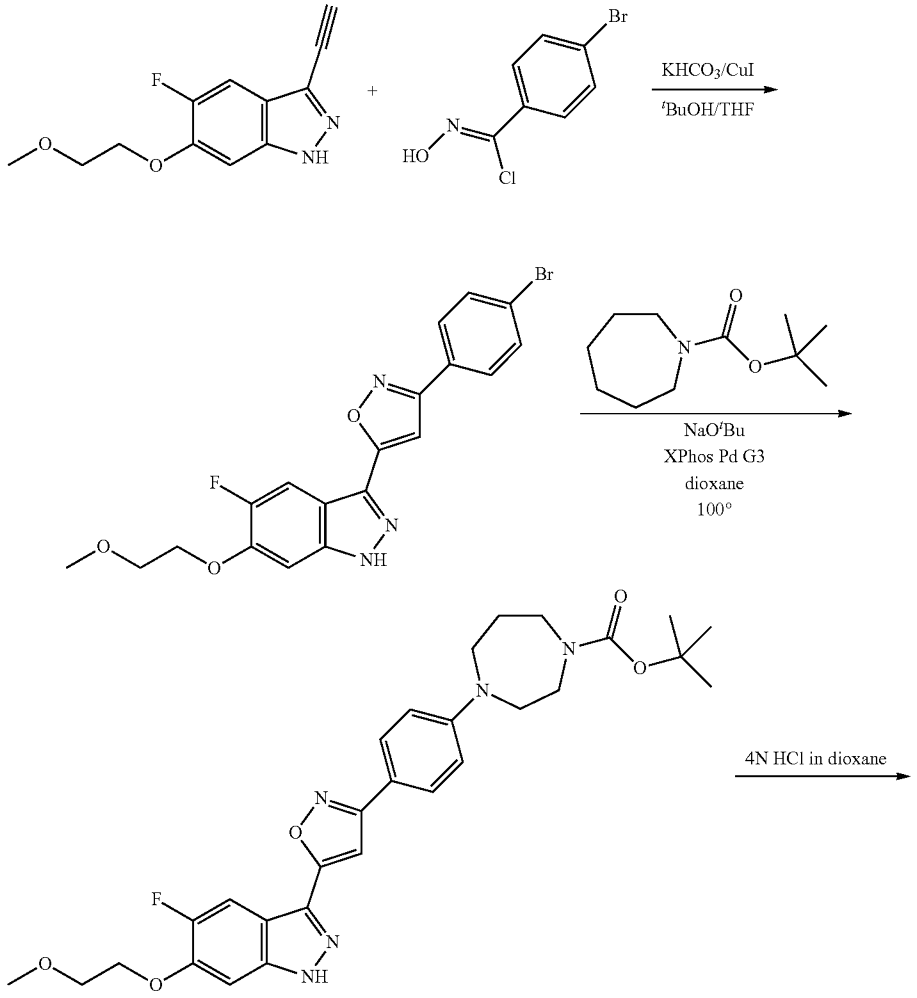

-continued
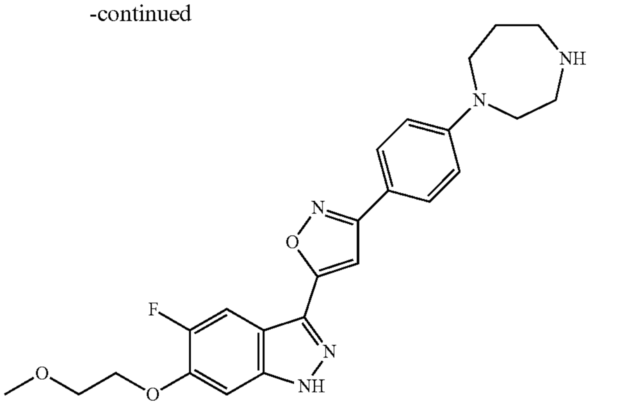
hydrochloide
pale orange solid; HPLC/MS 1.32 min (A), $[M+H]^+$ 452. $^1H$ NMR (500 MHz, DMSO-$d_6$) δ 13.68 (s, 1H), 9.05 (s, 2H), 7.99 (d, J=11.0 Hz, 1H), 7.86 (d, J=8.9 Hz, 2H), 7.56 (s, 1H), 7.27 (d, J=7.1 Hz, 1H), 6.93 (d, J=9.0 Hz, 2H), 4.33-4.18 (m, 2H), 3.81 (t, J=5.1 Hz, 2H), 3.79-3.73 (m, 2H), 3.61 (t, J=6.1 Hz, 2H), 3.36 (s, 3H), 3.27 (p, J=4.8 Hz, 3H), 3.19-3.11 (m, 2H), 2.13 (p, J=5.9 Hz, 2H).
Example 13
(4-{3-[5-fluoro-6-(2-methoxy-ethoxy)-1H-indazol-3-yl]-isoxazol-5-yl}-phenyl)-morpholin-4-yl-methanone ("A43")
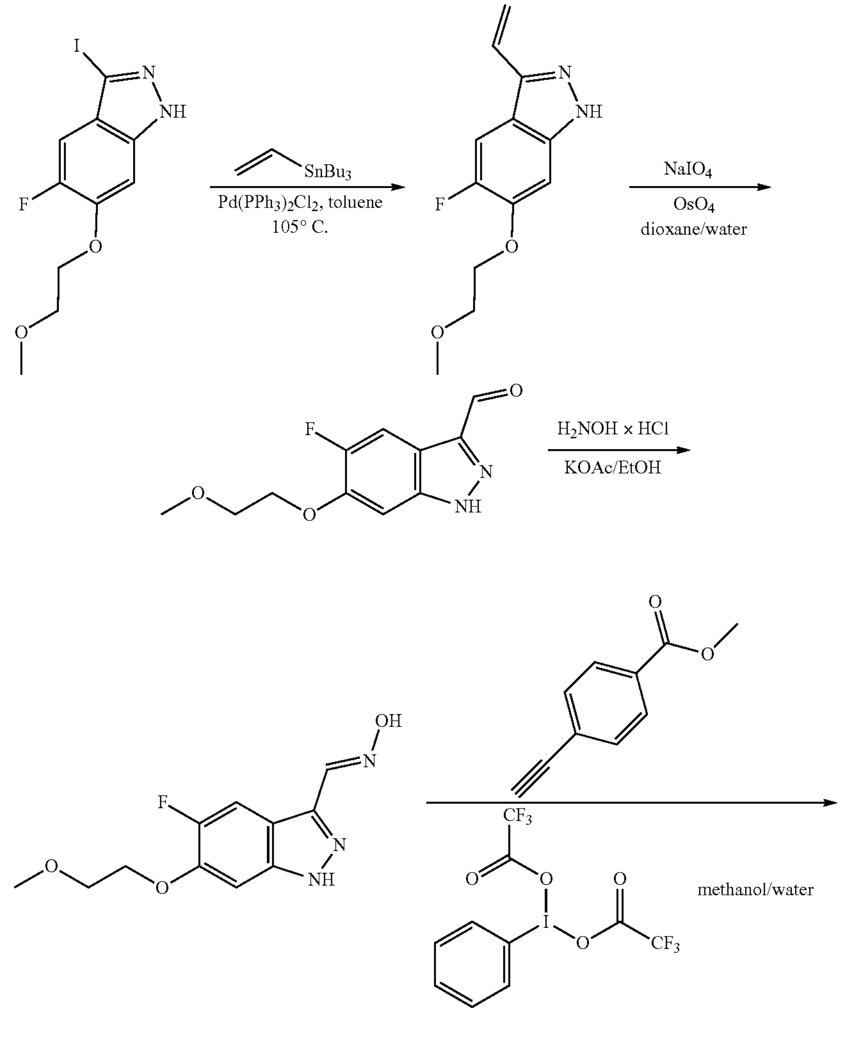

-continued
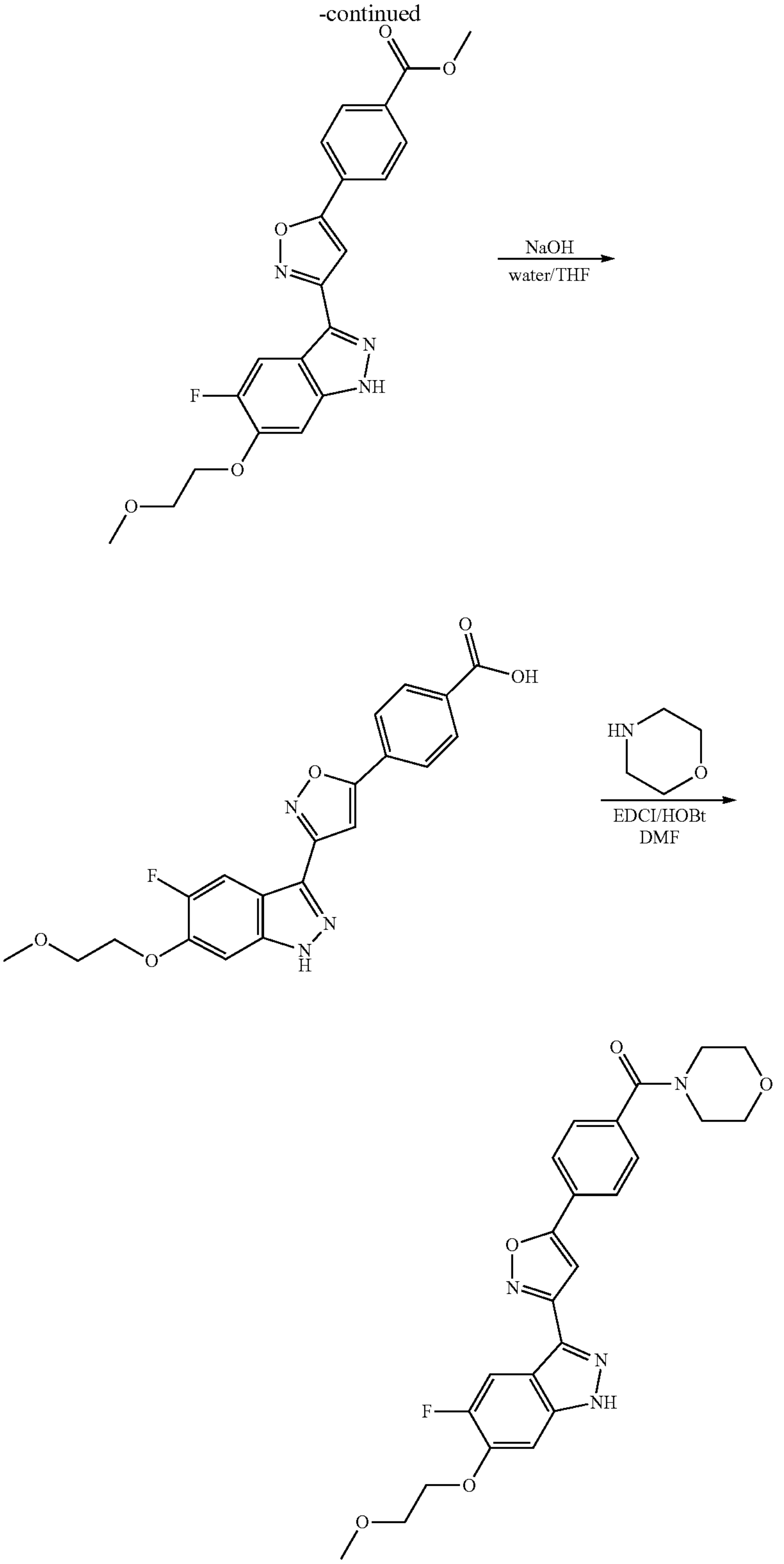
white solid; m.p. 220-221° C., $[M+H]^+$ 467.
1H NMR (400 MHz, DMSO-$d_6$) δ 13.65 (s, 1H), 8.15-8.05 (m, 2H), 7.82 (d, J=10.8 Hz, 1H), 7.67-7.58 (m, 3H), 7.27 (d, J=7.1 Hz, 1H), 4.33-4.26 (m, 2H), 3.80-3.73 (m, 2H), 3.73-3.53 (m, 6H), 3.48-3.43 (m, 5H).

The following compounds are prepared analogously:

(4-{3-[5-fluoro-6-(2-methoxy-ethoxy)-1H-indazol-3-yl]-isoxazol-5-yl}-phenyl)-(4-methyl-piperazin-1-yl)-methanone ("A113")

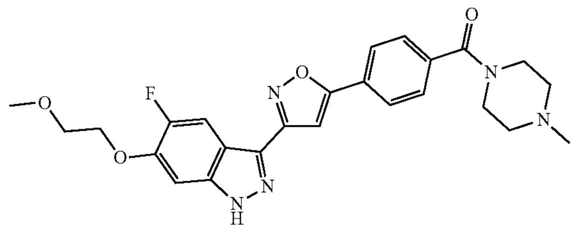

off-white solid; m.p. 210-211° C., $[M+H]^+$ 480.

1H NMR (400 MHz, DMSO-$d_6$) δ 13.63 (s, 1H), 8.12-8.05 (m, 2H), 7.84 (d, J=10.8 Hz, 1H), 7.65 (s, 1H), 7.62-7.55 (m, 2H), 7.27 (d, J=7.0 Hz, 1H), 4.33-4.26 (m, 2H), 3.80-3.74 (m, 2H), 3.65 (s, 2H), 3.36 (s, 5H), 2.34 (d, J=31.8 Hz, 4H), 2.21 (s, 3H).

(4-{3-[5-fluoro-6-(2-methoxy-ethoxy)-1H-indazol-3-yl]-isoxazol-5-yl}-phenyl)-(3-morpholin-4-yl-azetidin-1-yl)-methanone ("A146")

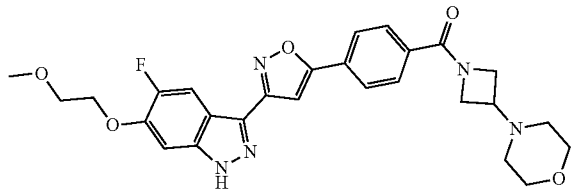 [SMILES: COCCOc1cc2[nH]nc(-c3cc(-c4ccc(C(=O)N5CC(N6CCOCC6)C5)cc4)on3)c2cc1F]

white solid; m.p. 229-230° C., $[M+H]^+$ 522.

1H NMR (400 MHz, DMSO-$d_6$) δ 13.63 (s, 1H), 8.09 (d, J=8.1 Hz, 2H), 7.84 (dd, J=9.6, 4.6 Hz, 3H), 7.69 (s, 1H), 7.27 (d, J=7.0 Hz, 1H), 4.41-4.33 (m, 1H), 4.33-4.26 (m, 2H), 4.24-4.16 (m, 1H), 4.15-4.05 (m, 1H), 3.96-3.88 (m, 1H), 3.80-3.73 (m, 2H), 3.66-3.55 (m, 4H), 3.36 (s, 3H), 3.23-3.12 (m, 1H), 2.44-2.26 (m, 4H).

(4-{3-[5-fluoro-6-(2-methoxy-ethoxy)-1H-indazol-3-yl]-isoxazol-5-yl}-phenyl)-[(R)-2-(1-hydroxy-1-methyl-ethyl)-azetidin-1-yl]-methanone ("A147")

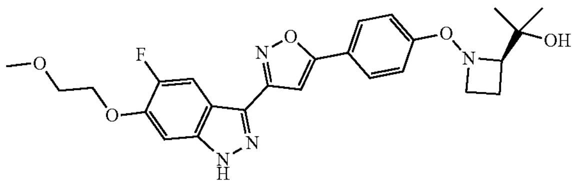 [SMILES: COCCOc1cc2[nH]nc(-c3cc(-c4ccc(ON5CC[C@@H]5C(C)(C)O)cc4)on3)c2cc1F]

off-white solid; m.p. 210-211° C., $[M+H]^+$ 495.

1H NMR (400 MHz, DMSO-$d_6$) δ 13.64 (s, 1H), 8.14-8.07 (m, 2H), 7.88-7.79 (m, 3H), 7.69 (s, 1H), 7.28 (d, J=7.1 Hz, 1H), 5.01 (s, 1H), 4.39 (dd, J=9.0, 5.6 Hz, 1H), 4.34-4.22 (m, 3H), 4.01-3.92 (m, 1H), 3.80-3.73 (m, 2H), 3.36 (s, 3H), 2.34-2.27 (m, 1H), 2.18-2.10 (m, 1H), 1.15 (s, 6H).

(4-{3-[5-fluoro-6-(2-methoxy-ethoxy)-1H-indazol-3-yl]-isoxazol-5-yl}-phenyl)-[(S)-2-(1-hydroxy-1-methyl-ethyl)-azetidin-1-yl]-methanone ("A148")

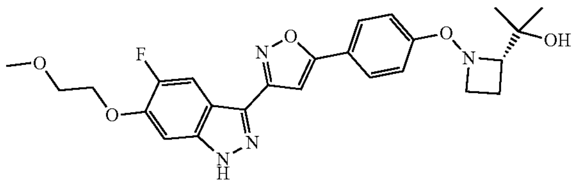 [SMILES: COCCOc1cc2[nH]nc(-c3cc(-c4ccc(ON5CC[C@H]5C(C)(C)O)cc4)on3)c2cc1F]

Example 14

5-fluoro-6-(2-methoxyethoxy)-3-{3-[4-(1,4-oxazepane-4-carbonyl)phenyl]-1,2-oxazol-5-yl}-1H-indazole ("A44")

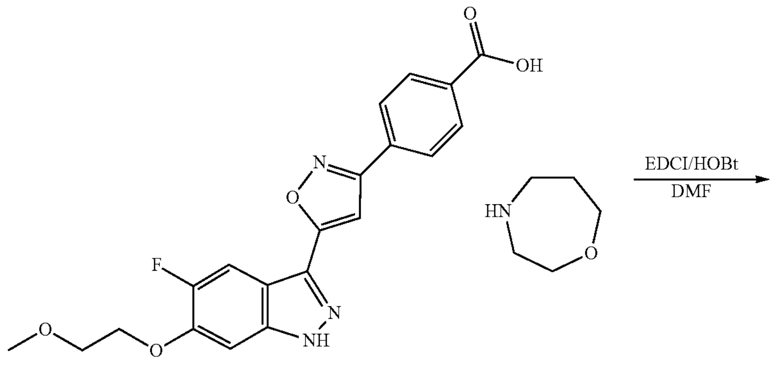

-continued

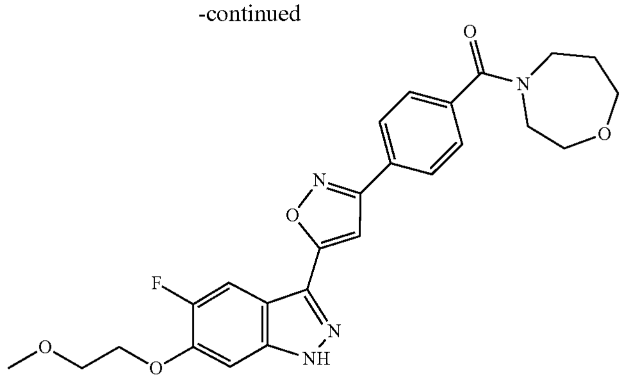

To a suspension of 4-{5-[5-fluoro-6-(2-methoxy-ethoxy)-1H-indazol-3-yl]-isoxazol-3-yl}-benzoic acid (79.5 mg, 0.20 mmol) in DMF (1.0 ml) is added homomorpholine (24.3 mg, 0.24 mmol), followed by 1-hydroxybenzotriazole hydrate (6.1 mg, 0.04 mmol) and N-(3-dimethylaminopropyl)-N'-ethylcarbodiimide hydrochloride (61 mg, 0.32 mmol). The reaction mixture is stirred for 16 hours at room temperature. Water is added to the reaction mixture. The resultant precipitate is filtered off and washed with water. The residue is chromatographed on a silica gel column with methanol/dichloromethane to afford (4-{5-[5-fluoro-6-(2-methoxy-ethoxy)-1H-indazol-3-yl]-isoxazol-3-yl}-phenyl)-[1,4]oxazepan-4-yl-methanone as white solid; UPLC/MS 0.71 min, $[M+H]^+$ 481.

$^1$H NMR (500 MHz, DMSO-$d_6$) δ 13.70 (s, 1H), 8.10 (d, J=6.7 Hz, 3H), 8.02 (d, J=11.0 Hz, 1H), 7.75 (s, 1H), 7.57 (d, J=7.3 Hz, 2H), 7.28 (d, J=7.0 Hz, 1H), 4.33-4.24 (m, 2H), 3.82-3.67 (m, 7H), 3.62 (t, J=5.1 Hz, 1H), 3.49-3.46 (m, 2H), 3.36 (s, 3H), 1.94-1.87 (m, 1H), 1.81-1.69 (m, 1H).

The following compounds are prepared analogously:

5-fluoro-6-(2-methoxyethoxy)-3-(3-{4-[4-(oxetan-3-yl)piperazine-1-carbonyl]phenyl}-1,2-oxazol-5-yl)-1H-indazole ("A45")

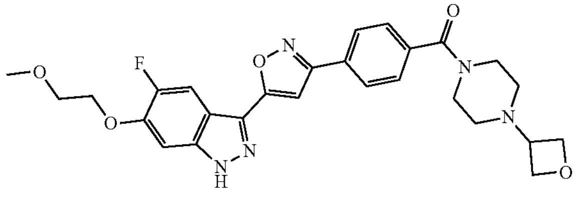 [SMILES: COCCOc1cc2[nH]nc(-c3cc(-c4ccc(C(=O)N5CCN(C6COC6)CC5)cc4)no3)c2cc1F]

white powder; HPLC/MS 1.26 min (A), $[M+H]^+$ 522.

$^1$H NMR (400 MHz, DMSO-$d_6$) δ 13.74 (s, 1H), 8.11 (d, J=8.3 Hz, 2H), 8.04 (d, J=11.0 Hz, 1H), 7.78 (s, 1H), 7.58 (d, J=8.3 Hz, 2H), 7.28 (d, J=7.1 Hz, 1H), 4.55 (t, J=6.5 Hz, 2H), 4.45 (t, J=6.1 Hz, 2H), 4.33-4.26 (m, 2H), 3.82-3.73 (m, 2H), 3.68 (broad, 2H), 3.51-3.37 (m, 3H), 2.35 (broad, 2H), 2.27 (broad, 2H).

5-fluoro-6-(2-methoxyethoxy)-3-(3-{4-[3-(pyridin-2-yl)azetidine-1-carbonyl]phenyl}-1,2-oxazol-5-yl)-1H-indazole ("A149")

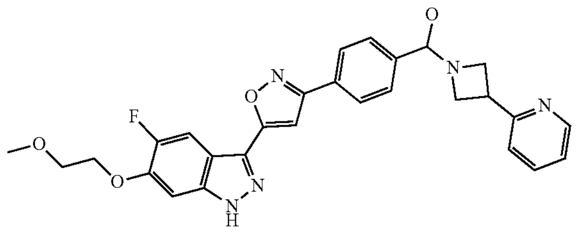 [SMILES: COCCOc1cc2[nH]nc(-c3cc(-c4ccc(C(O)N5CC(c6ccccn6)C5)cc4)no3)c2cc1F]

white solid; UPLC/MS 0.67 min, $[M+H]^+$ 514.

$^1$H NMR (400 MHz, DMSO-$d_6$) δ 13.71 (s, 1H), 8.68-8.56 (m, 1H), 8.13 (d, J=8.4 Hz, 2H), 8.04 (d, J=11.0 Hz, 1H), 7.86 (d, J=8.4 Hz, 2H), 7.84-7.76 (m, 2H), 7.41 (d, J=7.8 Hz, 1H), 7.36-7.24 (m, 2H), 4.75 (t, J=8.6 Hz, 1H), 4.54 (t, J=7.2 Hz, 1H), 4.47 (t, J=9.3 Hz, 1H), 4.35-4.28 (m, 2H), 4.25 (t, J=8.0 Hz, 1H), 4.10 (tt, J=8.9, 6.1 Hz, 1H), 3.80-3.73 (m, 2H), 3.36 (s, 3H).

4-{5-[5-fluoro-6-(2-methoxyethoxy)-1H-indazol-3-yl]-1,2-oxazol-3-yl}-N-(2-methanesulfonylethyl)-N-methylbenzamide ("A150")

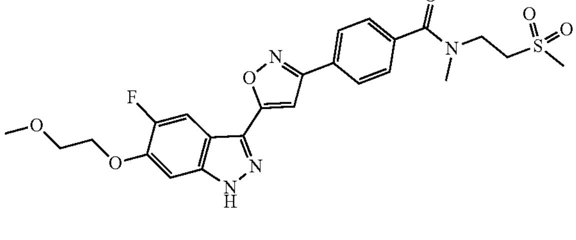

6-(4-{5-[5-fluoro-6-(2-methoxyethoxy)-1H-indazol-3-yl]-1,2-oxazol-3-yl}benzoyl)-2lambda6-thia-6-azaspiro[3.3]heptane-2,2-dione ("A151")

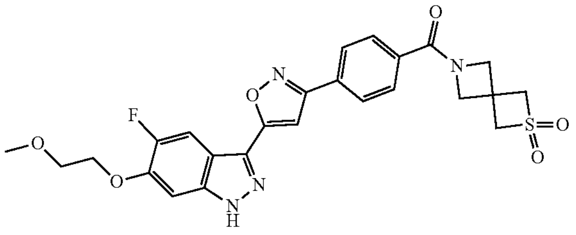 [SMILES: COCCOc1cc2[nH]nc(-c3cc(-c4ccc(C(=O)N5CC6(C5)CS(=O)(=O)C6)cc4)no3)c2cc1F]

5-fluoro-3-(3-{4-[(2S)-2-(methanesulfonylmethyl) azetidine-1-carbonyl]phenyl}-1,2-oxazol-5-yl)-6-(2-methoxyethoxy)-1H-indazole ("A152")

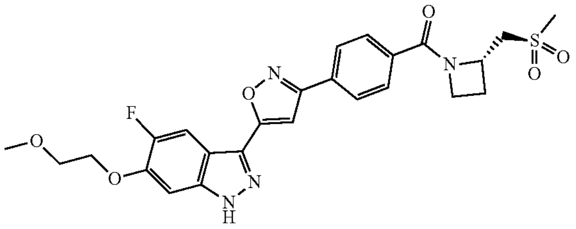

white solid; UPLC/MS 0.71 min, $[M+H]^+$ 529.

$^1$H NMR (400 MHz, DMSO-$d_6$) δ 13.69 (s, 1H), 8.12 (d, J=8.4 Hz, 2H), 8.01 (d, J=11.0 Hz, 1H), 7.80 (d, J=8.4 Hz, 2H), 7.75 (s, 1H), 7.28 (d, J=7.1 Hz, 1H), 4.89 (bs, 1H), 4.46 (bs, 1H), 4.35-4.21 (m, 2H), 4.17 (bs, 1H), 3.85 (bs, 1H), 3.82-3.63 (m, 3H), 3.35 (s, 3H), 3.07 (s, 3H), 2.56 (bs, 1H), 2.44-2.26 (m, 1H).

5-fluoro-6-(2-methoxyethoxy)-3-(3-{4-[3-(morpholin-4-yl)pyrrolidine-1-carbonyl]phenyl}-1,2-oxazol-5-yl)-1H-indazole ("A153")

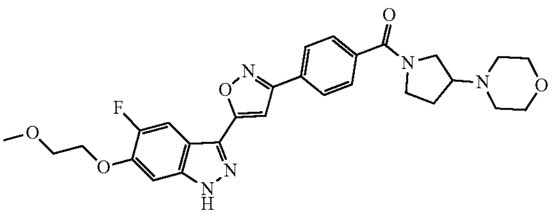 [SMILES: COCCOc1cc2[nH]nc(-c3cc(-c4ccc(C(=O)N5CCC(N6CCOCC6)C5)cc4)no3)c2cc1F]

white powder; HPLC/MS 1.25 min, $[M+H]^+$ 536.

$^1$H NMR (400 MHz, DMSO-$d_6$) δ 13.70 (s, 1H), 8.09 (d, J=7.9 Hz, 1H), 8.02 (d, J=11.0 Hz, OH), 7.76 (s, OH), 7.73-7.66 (m, 2H), 7.28 (d, J=7.1 Hz, 1H), 4.36-4.26 (m, 2H), 3.81-3.71 (m, 2H), 3.72-3.40 (m, 8H), 3.36 (s, 3H), 2.92-2.74 (m, 1H), 2.50-2.36 (m, 3H), 2.34-2.24 (m, 1H), 2.20-2.10 (m, 1H), 1.85-1.65 (m, 1H).

5-fluoro-3-(3-{4-[(2R)-2-(methanesulfonylmethyl) azetidine-1-carbonyl]phenyl}-1,2-oxazol-5-yl)-6-(2-methoxyethoxy)-1H-indazole ("A154")

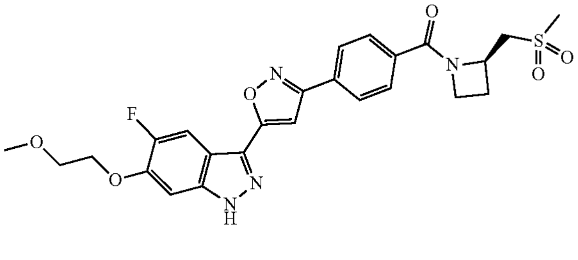 [SMILES: COCCOc1cc2[nH]nc(-c3cc(-c4ccc(C(=O)N5CC[C@@H]5CS(C)(=O)=O)cc4)no3)c2cc1F]

5-(4-{5-[5-fluoro-6-(2-methoxyethoxy)-1H-indazol-3-yl]-1,2-oxazol-3-yl}benzoyl)-2,8-dioxa-5-azaspiro [3.5]nonane ("A155")

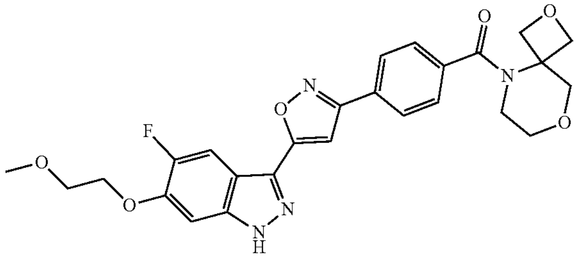 [SMILES: COCCOc1cc2[nH]nc(-c3cc(-c4ccc(C(=O)N5CCOCC56COC6)cc4)no3)c2cc1F]

white solid; UPLC/MS 0.73 min, $[M+H]^+$ 509.

$^1$H NMR (400 MHz, DMSO-$d_6$) δ 13.71 (s, 1H), 8.14 (d, J=8.3 Hz, 2H), 8.02 (d, J=11.0 Hz, 1H), 7.78 (s, 1H), 7.74 (d, J=8.4 Hz, 2H), 7.28 (d, J=7.1 Hz, 1H), 4.78 (d, J=6.8 Hz, 2H), 4.41 (d, J=6.9 Hz, 2H), 4.35-4.20 (m, 2H), 3.99 (s, 2H), 3.81-3.74 (m, 2H), 3.43 (t, J=4.7 Hz, 2H), 3.39-3.34 (m, 5H).

N-[(1H-1,3-benzodiazol-2-yl)methyl]-4-{5-[5-fluoro-6-(2-methoxyethoxy)-1H-indazol-3-yl]-1,2-oxazol-3-yl}benzamide ("A156")

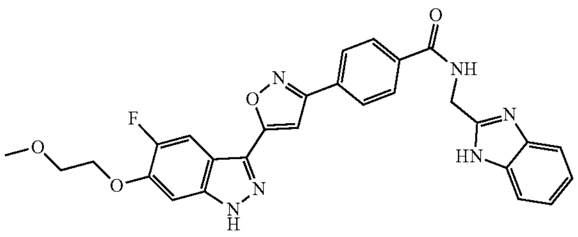 [SMILES: COCCOc1cc2[nH]nc(-c3cc(-c4ccc(C(=O)NCc5nc6ccccc6[nH]5)cc4)no3)c2cc1F]

7-(4-{5-[5-fluoro-6-(2-methoxyethoxy)-1H-indazol-3-yl]-1,2-oxazol-3-yl}benzoyl)-2-oxa-7-azaspiro[4.4]nonane ("A157")

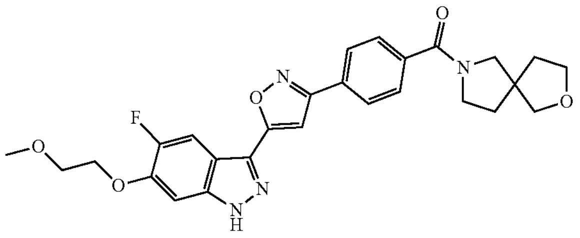 [SMILES: COCCOc1cc2[nH]nc(-c3cc(-c4ccc(C(=O)N5CCC6(CCOC6)C5)cc4)no3)c2cc1F]

white solid; HPLC/MS 1.54 min (A), $[M+H]^+$ 507.

$^1H$ NMR (400 MHz, DMSO-$d_6$; mixture of rotational isomers) δ 13.71 (s, 1H), 8.10 (d, J=8.4 Hz, 2H), 8.06-8.00 (m, 1H), 7.76 (d, J=3.9 Hz, 1H), 7.74-7.66 (m, 2H), 7.28 (d, J=7.1 Hz, 1H), 4.35-4.28 (m, 2H), 3.87-3.46 (m, 9H), 3.41 (s, 1H), 3.36 (s, 3H), 2.04-1.72 (m, 4H).

5-fluoro-6-(2-methoxyethoxy)-3-[3-(4-{2-oxa-6-azaspiro[3.4]octane-6-carbonyl}phenyl)-1,2-oxazol-5-yl]-1H-indazole ("A158")

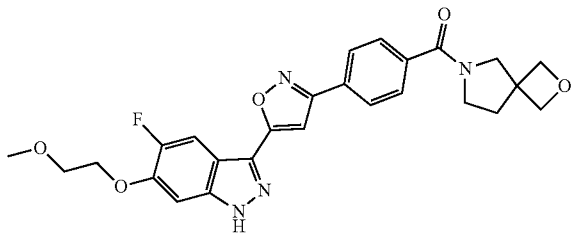 [SMILES: COCCOc1cc2[nH]nc(-c3cc(-c4ccc(C(=O)N5CCC6(COC6)C5)cc4)no3)c2cc1F]

white solid; HPLC/MS 1.48 min (A), $[M+H]^+$ 493.

$^1H$ NMR (700 MHz, DMSO-$d_6$; mixture of rotational isomers) δ 13.72 (d, J=2.6 Hz, 1H), 8.13-8.07 (m, 2H), 8.04 (d, J=10.8 Hz, 1H), 7.79-7.77 (m, 1H), 7.73-7.67 (m, 2H), 7.29-7.26 (m, 1H), 4.64 (d, J=5.9 Hz, 1H), 4.51 (d, J=5.9 Hz, 1H), 4.49 (d, J=6.3 Hz, 1H), 4.45 (d, J=6.3 Hz, 1H), 4.32-4.28 (m, 2H), 3.78-3.65 (m, 2H), 3.74 (s, 1H), 3.69 (s, 1H), 3.52 (t, J=7.2 Hz, 1H), 3.47 (t, J=6.8 Hz, 1H), 3.36 (s, 3H), 2.20 (t, J=7.2 Hz, 1H), 2.16 (t, J=6.8 Hz, 1H).

2-(4-{5-[5-fluoro-6-(2-methoxyethoxy)-1H-indazol-3-yl]-1,2-oxazol-3-yl}benzoyl)-8-oxa-2-azaspiro[4.5]decane ("A159")

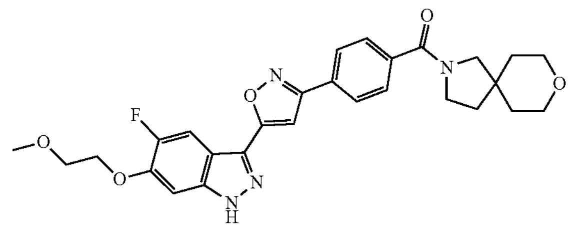 [SMILES: COCCOc1cc2[nH]nc(-c3cc(-c4ccc(C(=O)N5CCC6(CCOCC6)C5)cc4)no3)c2cc1F]

white solid; HPLC/MS 1.50 min (A), $[M+H]^+$ 521.

$^1H$ NMR (700 MHz, DMSO-$d_6$; mixture of rotational isomers) δ 13.72 (s, 1H), 8.12-8.07 (m, 2H), 8.04 (d, J=10.8 Hz, 1H), 7.79-7.77 (m, 1H), 7.76-7.66 (m, 2H), 7.30-7.27 (m, 1H), 4.31-4.28 (m, 2H), 3.84-3.73 (m, 2H), 3.68-3.50 (m, 5H), 3.49-3.44 (m, 1H), 3.43 (s, 1H), 3.36 (s, 3H), 3.33 (s, 1H), 1.86 (t, J=7.3 Hz, 1H), 1.80 (t, J=7.0 Hz, 1H), 1.63-1.53 (m, 2H), 1.50-1.42 (m, 2H).

5-fluoro-6-(2-methoxyethoxy)-3-[3-(4-{2-methyl-2,6-diazaspiro[3.4]octane-6-carbonyl}phenyl)-1,2-oxazol-5-yl]-1H-indazole ("A160")

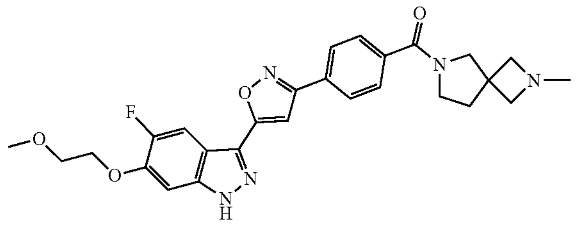

5-fluoro-6-(2-methoxyethoxy)-3-[3-(4-{6-oxa-3-azabicyclo[3.1.1]heptane-3-carbonyl}phenyl)-1,2-oxazol-5-yl]-1H-indazole ("A161")

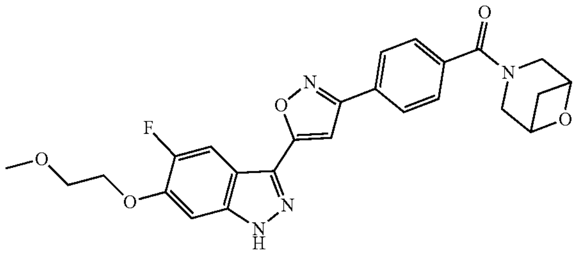 [SMILES: COCCOc1cc2[nH]nc(-c3cc(-c4ccc(C(=O)N5CC6CC(C5)O6)cc4)no3)c2cc1F]

white solid; UPLC/MS 0.69 min, $[M+H]^+$ 479.

$^1H$ NMR (500 MHz, DMSO-$d_6$) δ 13.70 (s, 1H), 8.11 (d, J=8.4 Hz, 1H), 8.03 (d, J=11.0 Hz, 1H), 7.76 (s, 1H), 7.68 (d, J=8.4 Hz, 1H), 7.28 (d, J=7.1 Hz, 1H), 4.67 (s, 1H), 4.50 (s, 1H), 4.38-4.23 (m, 2H), 3.99 (d, J=13.9, 1H), 3.85-3.71 (m, 3H), 3.66-3.56 (m, 1H), 3.55-3.45 (m, 1H), 3.36 (s, 3H), 3.14-3.02 (m, 1H), 1.88 (d, J=8.9 Hz, 1H).

5-fluoro-6-(2-methoxyethoxy)-3-(3-{4-[(1S,4S)-2-oxa-5-azabicyclo[2.2.1]-heptane-5-carbonyl]phenyl}-1,2-oxazol-5-yl)-1H-indazole ("A162")

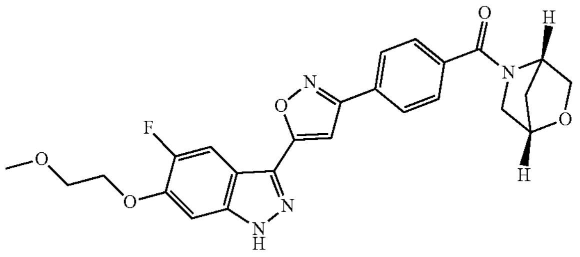 [SMILES: COCCOc1cc2[nH]nc(-c3cc(-c4ccc(C(=O)N5C[C@@H]6C[C@H]5CO6)cc4)no3)c2cc1F]

5-fluoro-6-(2-methoxyethoxy)-3-(3-{4-[(1R,4R)-2-oxa-5-azabicyclo[2.2.1]-heptane-5-carbonyl]phenyl}-1,2-oxazol-5-yl)-1H-indazole ("A163")

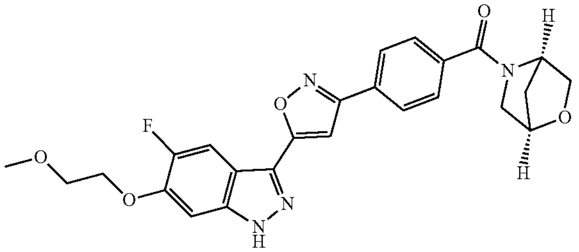 [SMILES: COCCOc1cc2[nH]nc(-c3cc(-c4ccc(C(=O)N5C[C@H]6C[C@@H]5CO6)cc4)no3)c2cc1F]

white solid; UPLC/MS 0.69 min, $[M+H]^+$ 479.

$^1$H NMR (500 MHz, DMSO-$d_6$, mixture of rotational isomers) δ 13.70 (s, 1H), 8.15-8.07 (m, 2H), 8.05-8.00 (m, 1H), 7.76 (d, J=2.2 Hz, 1H), 7.73 (d, J=8.1 Hz, 1H), 7.67 (m, 1H), 7.28 (d, J=7.0 Hz, 1H), 4.87 (s, 0.5H), 4.68 (s, 1H), 4.59 (s, 0.5H), 4.41 (s, 0.5H), 4.34-4.27 (m, 2H), 3.93 (d, J=7.4 Hz, 0.5H), 3.85 (d, J=7.5 Hz, 0.5H), 3.83-3.65 (m, 3H), 3.61-3.51 (m, 1H), 3.36 (s, 3H), 1.98-1.73 (m, 2H).

4-{5-[5-fluoro-6-(2-methoxyethoxy)-1H-indazol-3-yl]-1,2-oxazol-3-yl}-N-[2-methyl-2-(morpholin-4-yl)propyl]benzamide ("A164")

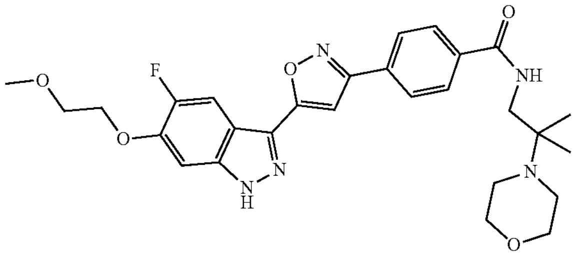 [SMILES: COCCOc1cc2[nH]nc(-c3cc(-c4ccc(C(=O)NCC(C)(C)N5CCOCC5)cc4)no3)c2cc1F]

2-(4-{5-[5-fluoro-6-(2-methoxyethoxy)-1H-indazol-3-yl]-1,2-oxazol-3-yl}benzoyl)-7-oxa-2-azaspiro[3.5]nonane ("A165")

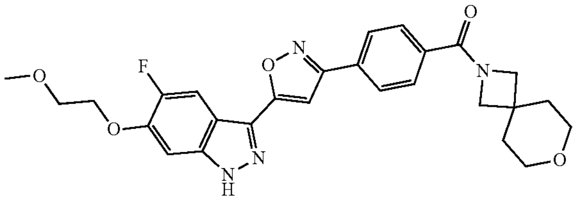 [SMILES: COCCOc1cc2[nH]nc(-c3cc(-c4ccc(C(=O)N5CC6(CCOCC6)C5)cc4)no3)c2cc1F]

white solid; HPLC/MS 1.57 min (A), $[M+H]^+$ 507.

$^1$H NMR (500 MHz, DMSO-$d_6$) δ 13.70 (s, 1H), 8.14-8.09 (m, 2H), 8.02 (d, J=11.0 Hz, 1H), 7.82 (d, J=8.4 Hz, 2H), 7.77 (s, 1H), 7.28 (d, J=7.1 Hz, 1H), 4.34-4.23 (m, 2H), 4.11 (s, 2H), 3.82 (s, 2H), 3.79-3.74 (m, 2H), 3.63-3.43 (m, 4H), 3.36 (s, 3H), 1.79-1.69 (m, 4H).

5-fluoro-6-(2-methoxyethoxy)-3-(3-{4-[3-(3-methyl-1,2,4-oxadiazol-5-yl)azetidine-1-carbonyl]phenyl}-1,2-oxazol-5-yl)-1H-indazole ("A166")

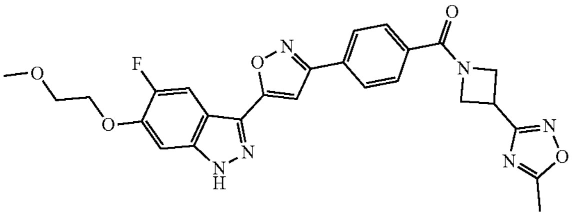 [SMILES: COCCOc1cc2[nH]nc(-c3cc(-c4ccc(C(=O)N5CC(c6noc(C)n6)C5)cc4)no3)c2cc1F]

white solid; HPLC/MS 1.57 min, $[M+H]^+$ 519.

$^1$H NMR (500 MHz, DMSO-$d_6$) δ 13.70 (s, 1H), 8.13 (d, J=8.4 Hz, 2H), 8.03 (d, J=11.0 Hz, 1H), 7.83 (d, J=8.4 Hz, 2H), 7.78 (s, 1H), 7.28 (d, J=7.1 Hz, 1H), 4.78 (t, J=7.7 Hz, 2H), 4.64-4.46 (m, 4H), 4.36-4.22 (m, 5H), 3.83-3.71 (m, 2H), 3.36 (s, 3H), 2.36 (s, 3H).

(4-{5-[5-chloro-6-(2-methoxy-ethoxy)-1H-indazol-3-yl]-isoxazol-3-yl}-phenyl)-(4-methyl-piperazin-1-yl)-methanone ("A167")

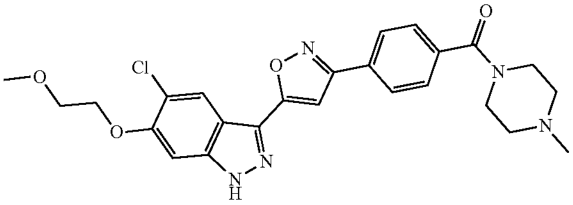

white solid; m. p. 105-106° C., $[M+H]^+$ 496.

$^1$H NMR (400 MHz, DMSO-$d_6$) δ 13.73 (s, 1H), 8.32 (s, 1H), 8.16-8.09 (m, 2H), 7.83 (s, 1H), 7.61-7.53 (m, 2H), 7.27 (s, 1H), 4.34-4.27 (m, 2H), 3.82-3.75 (m, 2H), 3.71-3.59 (m, 2H), 3.41-0.33 (m, 5H), 2.43-2.26 (m, 4H), 2.22 (s, 3H).

(2-fluoro-4-{5-[5-fluoro-6-(2-methoxy-ethoxy)-1H-indazol-3-yl]-isoxazol-3-yl}-phenyl)-(3-morpholin-4-yl-azetidin-1-yl)-methanone ("A168")

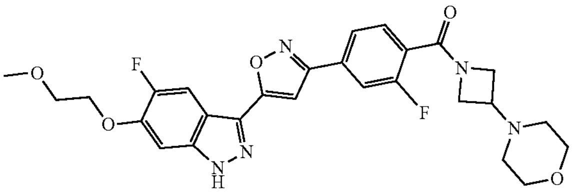 [SMILES: COCCOc1cc2[nH]nc(-c3cc(-c4ccc(C(=O)N5CC(N6CCOCC6)C5)c(F)c4)no3)c2cc1F]

white solid; m. p. 119-120° C., $[M+H]^+$ 540.

$^1$H NMR (400 MHz, DMSO-$d_6$) δ 13.76-13.68 (m, 1H), 8.09-7.91 (m, 3H), 7.82 (s, 1H), 7.72 (t, J=7.5 Hz, 1H), 7.27 (d, J=7.1 Hz, 1H), 4.36-4.25 (m, 2H), 4.15-4.04 (m, 2H), 3.94-3.85 (m, 2H), 3.81-3.73 (m, 2H), 3.68-3.47 (m, 4H), 3.36 (s, 3H), 3.24-3.14 (m, 1H), 2.43-2.19 (m, 4H).

(4-{5-[5-fluoro-6-(2-methoxy-ethoxy)-1H-indazol-3-yl]-isoxazol-3-yl}-2-methyl-phenyl)-(6-oxa-1-aza-spiro[3.3]hept-1-yl)-methanone ("A169")

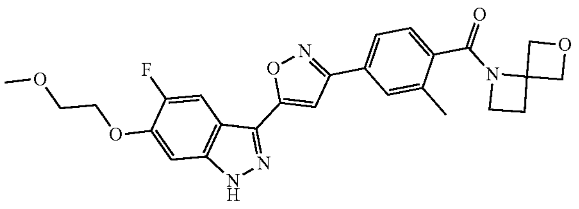

white solid; m. p. 129-130° C., $[M+H]^+$ 493.

$^1$H NMR (400 MHz, DMSO-$d_6$) δ 13.7 (s, 1H), 8.09-7.94 (m, 2H), 7.90 (d, J=7.8 Hz, 1H), 7.74 (s, 1H), 7.47 (d, J=7.9 Hz, 1H), 7.28 (d, J=7.1 Hz, 1H), 5.37 (d, J=6.7 Hz, 2H), 4.64 (d, J=6.7 Hz, 2H), 4.34-4.27 (m, 2H), 3.80-3.69 (m, 4H), 3.37 (s, 3H), 2.55 (m, 2H), 2.42 (s, 3H).

(2-fluoro-4-{5-[5-fluoro-6-(2-methoxy-ethoxy)-1H-indazol-3-yl]-isoxazol-3-yl}-phenyl)-(6-oxa-1-aza-spiro[3.3]hept-1-yl)-methanone ("A170")

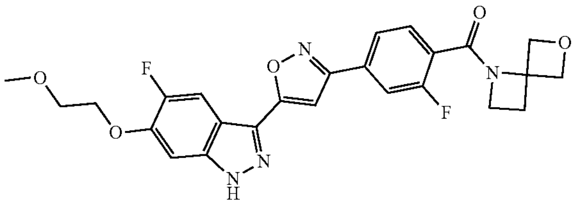 [SMILES: COCCOc1cc2[nH]nc(-c3cc(-c4ccc(C(=O)N5CCC56COC6)c(F)c4)no3)c2cc1F]

(4-{5-[5-fluoro-6-(2-methoxy-ethoxy)-1H-indazol-3-yl]-isoxazol-3-yl}-2-methyl-phenyl)-(3-morpholin-4-yl-azetidin-1-yl)-methanone ("A171")

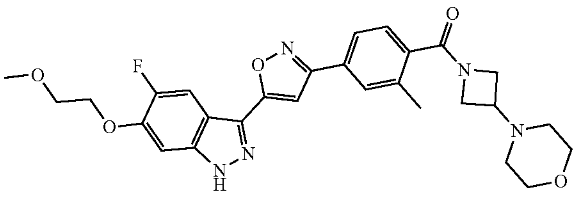

white solid; m. p. 125-126° C., $[M+H]^+$ 536.

$^1$H NMR (400 MHz, DMSO-$d_6$) δ 13.78-13.66 (m, 1H), 8.04 (d, J=11.0 Hz, 1H), 7.99-7.94 (m, 1H), 7.89 (d, J=7.9 Hz, 1H), 7.75 (s, 1H), 7.47 (d, J=7.9 Hz, 1H), 7.28 (d, J=7.1 Hz, 1H), 4.36-4.25 (m, 2H), 4.12-4.05 (m, 1H), 3.98-3.86 (m, 2H), 3.84-3.71 (m, 3H), 3.59 (t, J=4.5 Hz, 4H), 3.41-3.26 (m, 3H), 3.21-3.13 (m, 1H), 2.41 (s, 3H), 2.37-2.21 (m, 4H).

5-fluoro-6-(2-methoxyethoxy)-3-(3-{4-[3-(pyrimidin-4-yl)azetidine-1-carbonyl]phenyl}-1,2-oxazol-5-yl)-1H-indazole ("A172")

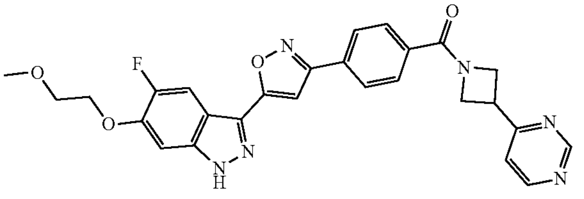 [SMILES: COCCOc1cc2[nH]nc(-c3cc(-c4ccc(C(=O)N5CC(c6ccncn6)C5)cc4)no3)c2cc1F]

white solid; HPLC/MS 1.49 min (A), $[M+H]^+$ 515.

$^1$H NMR (400 MHz, DMSO-$d_6$) δ 13.75 (s, 1H), 9.22 (d, J=1.3 Hz, 1H), 8.77 (d, J=5.2 Hz, 1H), 8.13 (d, J=8.5 Hz, 2H), 8.04 (d, J=11.1 Hz, 1H), 7.85 (d, J=8.4 Hz, 2H), 7.80 (s, 1H), 7.57 (dd, J=5.2, 1.4 Hz, 1H), 7.28 (d, J=7.1 Hz, 1H), 4.75 (t, J=8.7 Hz, 1H), 4.54 (dd, J=8.5, 5.9 Hz, 1H), 4.47 (t, J=9.4 Hz, 1H), 4.35-4.27 (m, 2H), 4.24 (dd, J=9.8, 6.0 Hz, 1H), 4.10 (tt, J=8.8, 5.9 Hz, 1H), 3.85-3.70 (m, 2H), 3.35 (s, 3H).

5-fluoro-6-(2-methoxyethoxy)-3-(3-{4-[3-(2-methylpyrimidin-4-yl)azetidine-1-carbonyl]phenyl}-1,2-oxazol-5-yl)-1H-indazole ("A173")

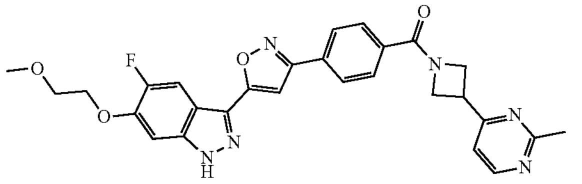

trifluoroacetate, yellow powder; UPLC/MS 0.71 min, $[M+H]^+$ 529.

$^1$H NMR (500 MHz, DMSO-$d_6$) δ 13.71 (s, 1H), 8.65 (d, J=5.2 Hz, 1H), 8.13 (d, J=8.4 Hz, 1H), 8.03 (d, J=11.0 Hz, 1H), 7.85 (d, J=8.4 Hz, 1H), 7.77 (s, 1H), 7.36 (d, J=5.2 Hz, 1H), 7.28 (d, J=7.1 Hz, 1H), 4.72 (t, J=8.7 Hz, 1H), 4.54 (t, J=7.3 Hz, 1H), 4.46 (t, J=9.4 Hz, 1H), 4.33-4.27 (m, 2H), 4.24 (t, J=8.0 Hz, 1H), 4.06 (tt, J=9.0, 6.1 Hz, 1H), 3.80-3.72 (m, 2H), 3.36 (s, 3H), 2.64 (s, 3H).

5-fluoro-6-(2-methoxyethoxy)-3-(3-{4-[2-methyl-4-(oxetan-3-yl)piperazine-1-carbonyl]phenyl}-1,2-oxazol-5-yl)-1H-indazole ("A174")

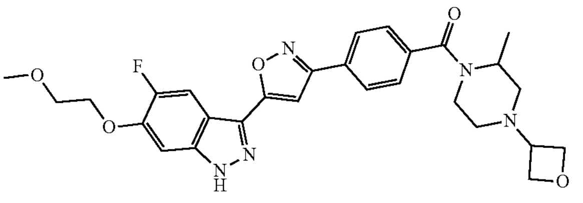 [SMILES: COCCOc1cc2[nH]nc(-c3cc(-c4ccc(C(=O)N5CCN(C6COC6)CC5C)cc4)no3)c2cc1F]

5-fluoro-6-(2-methoxyethoxy)-3-(3-{4-[4-(oxolan-3-yl)piperazine-1-carbonyl]phenyl}-1,2-oxazol-5-yl)-1H-indazole ("A175")

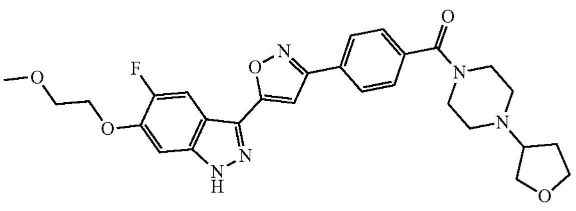 [SMILES: COCCOc1cc2[nH]nc(-c3cc(-c4ccc(C(=O)N5CCN(C6CCOC6)CC5)cc4)no3)c2cc1F]

7-(4-{5-[5-fluoro-6-(2-methoxyethoxy)-1H-indazol-3-yl]-1,2-oxazol-3-yl}benzoyl)-2-methyl-2,7-diazaspiro[3.5]nonane ("A176")

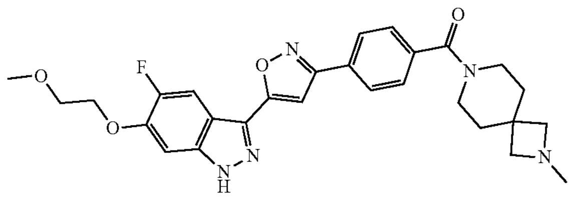

5-fluoro-6-(2-methoxyethoxy)-3-(3-{4-[3-(piperidin-1-yl)azetidine-1-carbonyl]phenyl}-1,2-oxazol-5-yl)-1H-indazole ("A177")

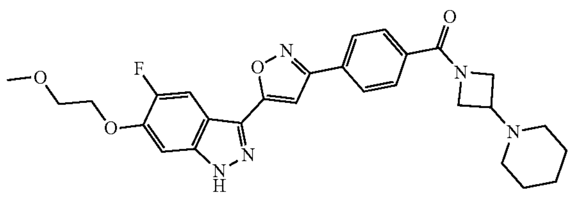 [SMILES: COCCOc1cc2[nH]nc(-c3cc(-c4ccc(C(=O)N5CC(N6CCCCC6)C5)cc4)no3)c2cc1F]

white solid; HPLC/MS 1.28 min (A), $[M+H]^+$ 520.

$^1$H NMR (500 MHz, DMSO-$d_6$) δ 13.71 (s, 1H), 8.15-8.07 (m, 2H), 8.02 (d, J=11.0 Hz, 1H), 7.81 (d, J=8.4 Hz, 2H), 7.77 (s, 1H), 7.28 (d, J=7.1 Hz, 1H), 4.34 (t, J=8.1 Hz, 1H), 4.15 (dd, J=8.7, 5.2 Hz, 1H), 4.12-4.05 (m, 1H), 3.87 (dd, J=10.2, 5.2 Hz, 1H), 3.79-3.74 (m, 2H), 3.36 (s, 3H), 3.12 (tt, J=7.2, 5.3 Hz, 1H), 2.25 (bs, 4H), 1.51 (dq, J=11.0, 5.1 Hz, 4H), 1.45-1.38 (m, 2H).

5-fluoro-6-(2-methoxyethoxy)-3-(3-{4-[3-(pyrrolidin-1-yl)azetidine-1-carbonyl]phenyl}-1,2-oxazol-5-yl)-1H-indazole ("A178")

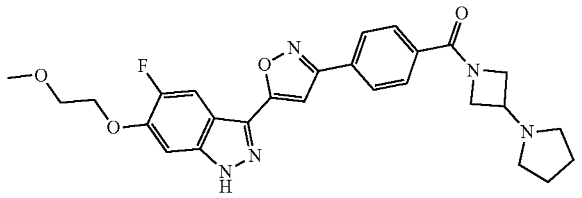 [SMILES: COCCOc1cc2[nH]nc(-c3cc(-c4ccc(C(=O)N5CC(N6CCCC6)C5)cc4)no3)c2cc1F]

white solid; HPLC/MS 1.27 min (A), $[M+H]^+$ 506.

$^1$H NMR (500 MHz, DMSO-$d_6$) δ 13.71 (s, 1H), 8.10 (d, J=8.4 Hz, 2H), 8.02 (d, J=11.0 Hz, 1H), 7.80 (d, J=8.4 Hz, 2H), 7.77 (s, 1H), 7.28 (d, J=7.1 Hz, 1H), 4.39 (t, J=8.0 Hz, 1H), 4.33-4.26 (m, 2H), 4.18 (dd, J=8.8, 4.7 Hz, 1H), 4.16-4.09 (m, 2H), 3.92 (dd, J=10.2, 4.7 Hz, 1H), 3.79-3.74 (m, 2H), 3.36 (s, 3H), 3.34-3.30 (m, 1H), 2.48-2.41 (m, 4H), 1.75-1.67 (m, 4H).

3-(3-{4-[4-(cyclopropylmethyl)piperazine-1-carbonyl]phenyl}-1,2-oxazol-5-yl)-5-fluoro-6-(2-methoxyethoxy)-1H-indazole ("A179")

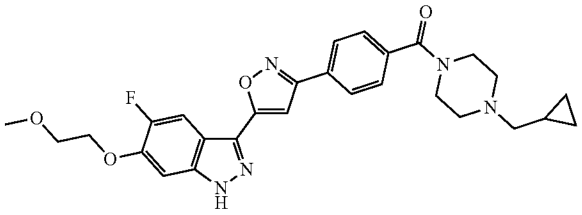 [SMILES: COCCOc1cc2[nH]nc(-c3cc(-c4ccc(C(=O)N5CCN(CC6CC6)CC5)cc4)no3)c2cc1F]

white solid; UPLC/MS 0.51 min, $[M+H]^+$ 520.

$^1$H NMR (500 MHz, DMSO-$d_6$) δ 13.70 (s, 1H), 8.10 (d, J=8.3 Hz, 1H), 8.02 (d, J=11.0 Hz, 1H), 7.75 (s, 1H), 7.56 (d, J=8.3 Hz, 1H), 7.28 (d, J=7.1 Hz, 1H), 4.34-4.22 (m, 2H), 3.81-3.73 (m, 2H), 3.66 (bs, 2H), 3.38 (bs, 2H), 3.36 (s, 3H), 2.44 (bs, 4H), 2.23 (d, J=6.6 Hz, 2H), 0.90-0.78 (m, 1H), 0.52-0.43 (m, 2H), 0.12-0.05 (m, 2H).

5-fluoro-6-(2-methoxyethoxy)-3-(3-{4-[(2R)-2-methylmorpholine-4-carbonyl]phenyl}-1,2-oxazol-5-yl)-1H-indazole ("A180")

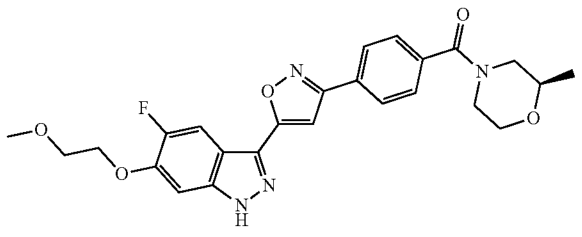

1-(4-{5-[5-fluoro-6-(2-methoxyethoxy)-1H-indazol-3-yl]-1,2-oxazol-3-yl}benzoyl)-N,N,3-trimethylazetidin-3-amine ("A181")

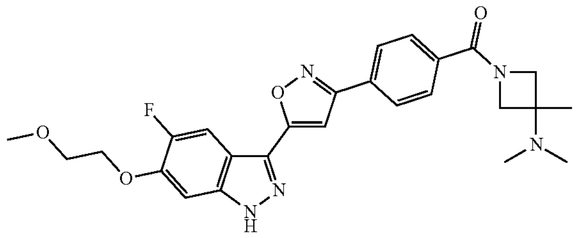

trifluoroacetate, white solid; UPLC/MS 0.79 min, $[M+H]^+$ 494.

$^1$H NMR (500 MHz, DMSO-$d_6$) δ 13.74 (s, 1H), 10.66 (bs, 1H), 8.15 (d, J=8.5 Hz, 2H), 8.02 (d, J=10.9 Hz, 1H), 7.83 (d, J=8.4 Hz, 2H), 7.79 (s, 1H), 7.29 (d, J=7.1 Hz, 1H), 4.51 (d, J=10.0 Hz, 1H), 4.38-4.25 (m, 4H), 3.98 (d, J=11.2 Hz, 1H), 3.81-3.72 (m, 2H), 3.36 (s, 3H), 2.74 (bs, 6H), 1.62 (s, 3H).

5-fluoro-6-(2-methoxyethoxy)-3-[3-(4-{3-oxa-6-azabicyclo[3.1.1]heptane-6-carbonyl}phenyl)-1,2-oxazol-5-yl]-1H-indazole ("A182")

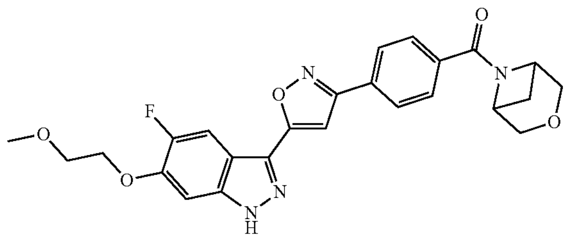 [SMILES: COCCOc1cc2[nH]nc(-c3cc(-c4ccc(C(=O)N5C6COCC5C6)cc4)no3)c2cc1F]

white solid; HPLC/MS 1.54 min (A), $[M+H]^+$ 479.

$^1$H NMR (500 MHz, DMSO-$d_6$) δ 13.71 (s, 1H), 8.12 (d, J=8.3 Hz, 2H), 8.02 (d, J=11.0 Hz, 1H), 7.82 (d, J=8.3 Hz, 2H), 7.76 (s, 1H), 7.28 (d, J=7.1 Hz, 1H), 4.64 (bs, 1H), 4.43 (bs, 1H), 4.35-4.22 (m, 2H), 3.87-3.73 (m, 3H), 3.69 (d, J=10.7 Hz, 1H), 3.36 (s, 3H), 2.77 (q, J=6.9 Hz, 1H), 1.82 (d, J=8.2 Hz, 1H).

5-fluoro-6-(2-methoxyethoxy)-3-[3-(4-{1H,2H,3H-pyrrolo[3,4-c]pyridine-2-carbonyl}phenyl)-1,2-oxazol-5-yl]-1H-indazole ("A183")

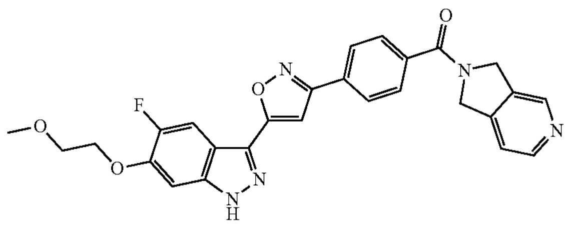 [SMILES: COCCOc1cc2[nH]nc(-c3cc(-c4ccc(C(=O)N5Cc6ccncc6C5)cc4)no3)c2cc1F]

white solid; HPLC/MS 1.34 min (A), $[M+H]^+$ 500.

$^1$H NMR (500 MHz, DMSO-$d_6$, mixture of rotational isomers), δ 13.71 (s, 1H), 8.72 (s, 0.5H), 8.60-8.51 (m, 1.5H), 8.20-8.12 (m, 4H), 8.03 (d, J=10.9 Hz, 2H), 7.81 (d, J=8.1 Hz, 2H), 7.79 (s, 1H), 7.58 (d, J=5.2 Hz, 0.5H), 7.45 (d, J=5.1 Hz, 0.5H), 7.29 (d, J=7.1 Hz, 1H), 5.02-4.95 (m, 2H), 4.91 (s, 2H), 4.36-4.17 (m, 2H), 3.87-3.72 (m, 2H), 3.36 (s, 3H).

(4-{5-[5-fluoro-6-(2-methoxy-ethoxy)-1H-indazol-3-yl]-isoxazol-3-yl}-phenyl)-((R)-3-methanesulfonyl-methyl-morpholin-4-yl)-methanone ("A184")

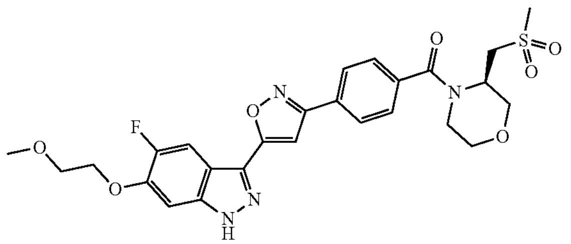 [SMILES: COCCOc1cc2[nH]nc(-c3cc(-c4ccc(C(=O)N5CCOC[C@@H]5CS(C)(=O)=O)cc4)no3)c2cc1F]

5-fluoro-6-(2-methoxyethoxy)-3-[3-(4-{4-[(3R)-oxolan-3-yl]piperazine-1-carbonyl}phenyl)-1,2-oxazol-5-yl]-1H-indazole ("A185")

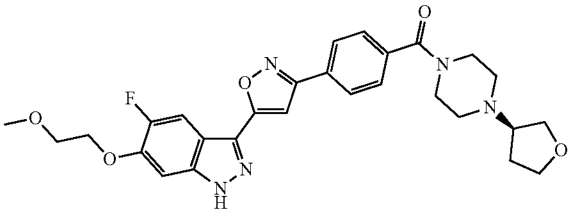 [SMILES: COCCOc1cc2[nH]nc(-c3cc(-c4ccc(C(=O)N5CCN([C@@H]6CCOC6)CC5)cc4)no3)c2cc1F]

5-fluoro-6-(2-methoxyethoxy)-3-[3-(4-{4-[(3S)-oxolan-3-yl]piperazine-1-carbonyl}phenyl)-1,2-oxazol-5-yl]-1H-indazole ("A186")

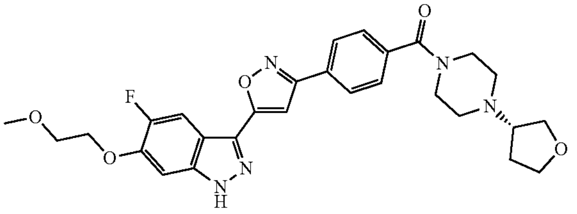 [SMILES: COCCOc1cc2[nH]nc(-c3cc(-c4ccc(C(=O)N5CCN([C@H]6CCOC6)CC5)cc4)no3)c2cc1F]

white solid; HPLC/MS 1.26 min (A), $[M+H]^+$ 536.

1H NMR (400 MHz, DMSO-$d_6$) δ 13.74 (s, 1H), 8.11 (d, J=7.9 Hz, 2H), 8.04 (d, J=11.0 Hz, 1H), 7.78 (s, 1H), 7.58 (d, J=7.9 Hz, 2H), 7.28 (d, J=7.1 Hz, 1H), 4.37-4.26 (m, 2H), 3.86-3.71 (m, 4H), 3.64 (q, J=7.9 Hz, 2H), 3.55-3.48 (m, 1H), 3.35 (s, 3H), 2.96 (t, J=7.1 Hz, 1H), 2.48-2.28 (m, 5H), 2.03-1.93 (m, 1H), 1.81-1.70 (m, 1H).

5-fluoro-6-(2-methoxyethoxy)-3-{3-[4-(3-{2-oxa-6-azaspiro[3.3]heptan-6-yl}azetidine-1-carbonyl)phenyl]-1,2-oxazol-5-yl}-1H-indazole ("A187")

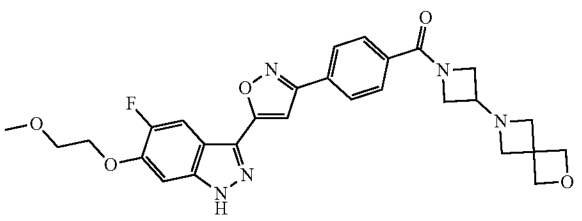 [SMILES: COCCOc1cc2[nH]nc(-c3cc(-c4ccc(C(=O)N5CC(N6CC7(COC7)C6)C5)cc4)no3)c2cc1F]

5-fluoro-6-(2-methoxyethoxy)-3-(3-{4-[4-(oxan-4-yl)piperazine-1-carbonyl]phenyl}-1,2-oxazol-5-yl)-1H-indazole ("A188")

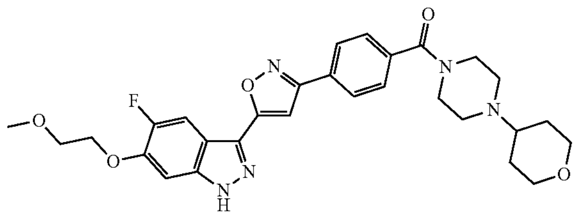 [SMILES: COCCOc1cc2[nH]nc(-c3cc(-c4ccc(C(=O)N5CCN(C6CCOCC6)CC5)cc4)no3)c2cc1F]

off-white solid; HPLC/MS 1.23 min (A), $[M+H]^+$ 550.

$^1$H NMR (500 MHz, DMSO-$d_6$) δ 13.70 (s, 1H), 8.10 (d, J=8.3 Hz, 2H), 8.02 (d, J=10.9 Hz, 1H), 7.75 (s, 1H), 7.57 (d, J=8.2 Hz, 2H), 7.28 (d, J=7.1 Hz, 1H), 4.52-4.20 (m, 2H), 4.03-3.82 (m, 2H), 3.82-3.68 (m, 2H), 3.64 (bs, 2H), 3.37 (bs, 2H), 3.36 (s, 3H), 3.30-3.24 (m, 2H), 2.62-2.40 (m, 5H), 1.74-1.65 (m, 2H), 1.41 (qd, J=12.1, 4.3 Hz, 2H).

5-fluoro-6-(2-methoxyethoxy)-3-(3-{4-[(2S)-2-methylmorpholine-4-carbonyl]phenyl}-1,2-oxazol-5-yl)-1H-indazole ("A189")

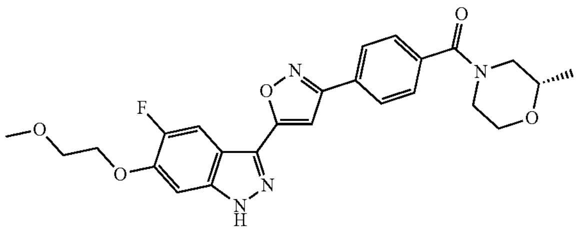

white solid; UPLC/MS 0.73 min, $[M+H]^+$ 481.

$^1$H NMR (500 MHz, DMSO-$d_6$, rotational isomers, selection of peaks) δ 13.70 (s, 1H), 8.11 (d, J=8.3 Hz, 1H), 8.02 (d, J=11.0 Hz, 1H), 7.76 (s, 1H), 7.59 (d, J=8.3 Hz, 1H), 7.28 (d, J=7.1 Hz, 1H), 4.33-4.25 (m, 2H), 3.79-3.73 (m, 2H), 3.58-3.40 (m, 2H), 3.36 (s, 3H), 2.94 (broad, 1H), 1.29-0.94 (m, 3H).

5-fluoro-6-(2-methoxyethoxy)-3-(3-{4-[(2R)-2-methyl-4-(oxetan-3-yl)piperazine-1-carbonyl]phenyl}-1,2-oxazol-5-yl)-1H-indazole ("A190")

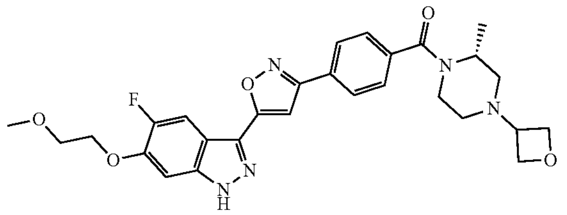 [SMILES: COCCOc1cc2[nH]nc(-c3cc(-c4ccc(C(=O)N5CCN(C6COC6)C[C@H]5C)cc4)no3)c2cc1F]

white solid; HPLC/MS 1.34 min, $[M+H]^+$ 536.

$^1$H NMR (500 MHz, DMSO-$d_6$) δ 13.70 (s, 1H), 8.10 (d, J=8.3 Hz, 2H), 8.02 (d, J=11.0 Hz, 1H), 7.75 (s, 1H), 7.55 (d, J=8.3 Hz, 2H), 7.28 (d, J=7.1 Hz, 1H), 4.54 (td, J=6.5, 4.4 Hz, 2H), 4.46 (t, J=6.1 Hz, 1H), 4.39 (t, J=6.0 Hz, 1H), 4.32-4.27 (m, 2H), 4.2 (broad, 2H), 3.80-3.73 (m, 2H), 3.41 (p, J=6.3 Hz, 1H), 3.36 (s, 3H), 3.28-3.12 (m, 1H), 2.73 (bs, 1H), 2.61-2.53 (m, 1H), 2.03 (dd, J=11.1, 3.8 Hz, 1H), 1.86 (td, J=11.4, 3.4 Hz, 1H), 1.32 (d, J=6.8 Hz, 3H).

5-fluoro-6-(2-methoxyethoxy)-3-(3-{4-[(2S)-2-methyl-4-(oxetan-3-yl)piperazine-1-carbonyl]phenyl}-1,2-oxazol-5-yl)-1H-indazole ("A191")

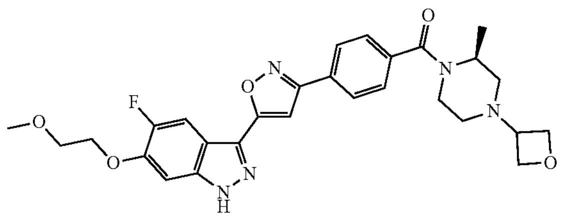 [SMILES: COCCOc1cc2[nH]nc(-c3cc(-c4ccc(C(=O)N5CCN(C6COC6)C[C@@H]5C)cc4)no3)c2cc1F]

5-fluoro-6-(2-methoxyethoxy)-3-(3-{4-[3-(pyridin-3-yl)azetidine-1-carbonyl]phenyl}-1,2-oxazol-5-yl)-1H-indazole ("A192")

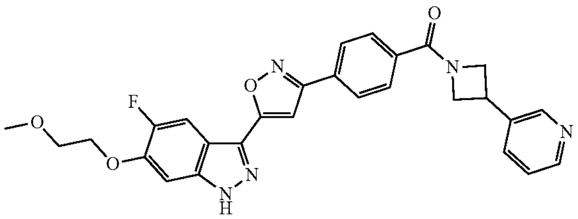 [SMILES: COCCOc1cc2[nH]nc(-c3cc(-c4ccc(C(=O)N5CC(c6cccnc6)C5)cc4)no3)c2cc1F]

white powder; UPLC/MS 0.57 min, $[M+H]^+$ 514.

$^1$H NMR (700 MHz, DMSO-$d_6$) δ 13.71 (s, 1H), 8.61 (d, J=2.4 Hz, 1H), 8.50 (dd, J=4.8, 1.6 Hz, 1H), 8.12 (d, J=8.3 Hz, 2H), 8.02 (d, J=10.9 Hz, 1H), 7.93 (dt, J=7.9, 2.1 Hz, 1H), 7.87 (d, J=8.4 Hz, 2H), 7.77 (s, 1H), 7.45-7.40 (m, 1H), 7.28 (d, J=7.1 Hz, 1H), 4.75 (t, J=8.8 Hz, 1H), 4.51 (dt, J=31.8, 8.7 Hz, 2H), 4.31-4.27 (m, 2H), 4.14-4.08 (m, 1H), 4.03 (tt, J=9.1, 6.3 Hz, 1H), 3.78-3.74 (m, 2H), 3.35 (s, 3H).

(4-{5-[5-fluoro-6-(2-methoxy-ethoxy)-1H-indazol-3-yl]-isoxazol-3-yl}-2-methyl-phenyl)-(4-oxetan-3-yl-piperazin-1-yl)-methanone ("A193")

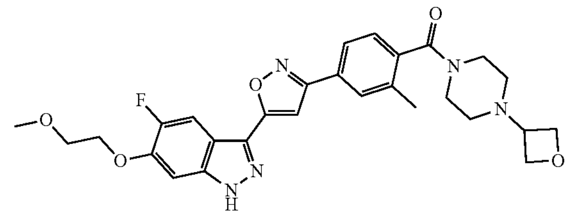 [SMILES: COCCOc1cc2[nH]nc(-c3cc(-c4ccc(C(=O)N5CCN(C6COC6)CC5)c(C)c4)no3)c2cc1F]

white solid; m. p. 138-139° C., $[M+H]^+$ 536.

$^1$H NMR (400 MHz, DMSO-$d_6$) δ 13.74 (s, 1H), 8.04 (d, J=11.0 Hz, 1H), 7.99-7.94 (m, 1H), 7.90 (d, J=7.8, 1.7 Hz, 1H), 7.75 (s, 1H), 7.35 (d, J=7.9 Hz, 1H), 7.28 (d, J=7.1 Hz, 1H), 4.54 (t, J=6.5 Hz, 2H), 4.43 (t, J=6.1 Hz, 2H), 4.33-4.26 (m, 2H), 3.81-3.75 (m, 2H), 3.72-3.60 (m, 2H), 3.49-3.42 (m, 1H), 3.35 (s, 3H), 3.24-3.17 (m, 2H), 2.40-2.30 (m, 5H), 2.26-2.13 (m, 2H).

(4-{5-[5-chloro-6-(2-methoxy-ethoxy)-1H-indazol-3-yl]-isoxazol-3-yl}-phenyl)-(4-oxetan-3-yl-piperazin-1-yl)-methanone ("A194")

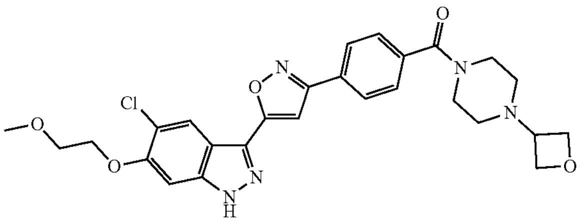 [SMILES: COCCOc1cc2[nH]nc(-c3cc(-c4ccc(C(=O)N5CCN(C6COC6)CC5)cc4)no3)c2cc1Cl]

white solid; m. p. 123-124° C., $[M+H]^+$ 538.

$^1$H NMR (400 MHz, DMSO-$d_6$) δ 13.83-13.66 (m, 1H), 8.30 (s, 1H), 8.15-8.08 (m, 2H), 7.81 (s, 1H), 7.61-7.54 (m, 2H), 7.26 (s, 1H), 4.55 (t, J=6.5 Hz, 2H), 4.45 (t, J=6.1 Hz, 2H), 4.33-4.26 (m, 2H), 3.81-3.74 (m, 2H), 3.73-3.61 (m, 2H), 3.53-3.36 (m, 6H), 2.40-2.22 (m, 4H).

5-fluoro-6-(2-methoxyethoxy)-3-[3-(4-{3-[4-(2-methoxyethyl)-4H-1,2,4-triazol-3-yl]azetidine-1-carbonyl}phenyl)-1,2-oxazol-5-yl]-1H-indazole ("A195")

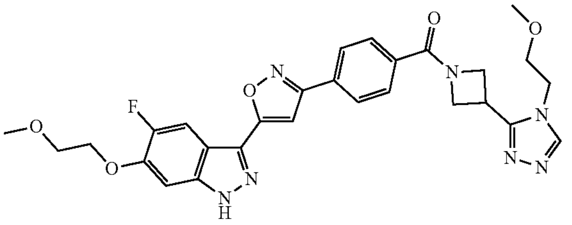 [SMILES: COCCOc1cc2[nH]nc(-c3cc(-c4ccc(C(=O)N5CC(c6nncn6CCOC)C5)cc4)no3)c2cc1F]

(2-fluoro-4-{5-[5-fluoro-6-(2-methoxy-ethoxy)-1H-indazol-3-yl]-isoxazol-3-yl}-phenyl)-(4-oxetan-3-yl-piperazin-1-yl)-methanone ("A196")

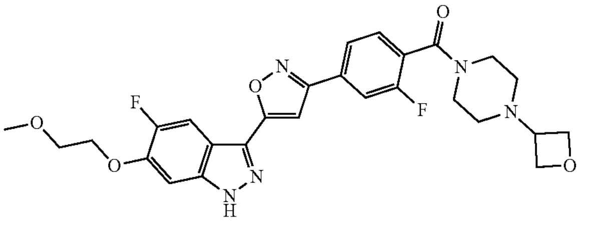 [SMILES: COCCOc1cc2[nH]nc(-c3cc(-c4ccc(C(=O)N5CCN(C6COC6)CC5)c(F)c4)no3)c2cc1F]

yellow solid; m. p. 161-162° C., $[M+H]^+$ 540.

$^1$H NMR (400 MHz, DMSO-$d_6$) δ 13.76 (s, 1H), 8.06-8.01 (m, 1H), 8.01-7.93 (m, 2H), 7.84 (s, 1H), 7.65-7.57 (m, 1H), 7.29 (d, J=7.2 Hz, 1H), 4.55 (t, J=6.5 Hz, 2H), 4.45 (t, J=6.1 Hz, 2H), 4.34-4.27 (m, 2H), 3.80-3.73 (m, 2H), 3.73-3.69 (m, 2H), 3.50-3.43 (m, 1H), 3.36 (s, 3H), 3.33-3.30 (m, 2H), 2.38-2.34 (m, 2H), 2.28-2.24 (m, 2H).

5-fluoro-6-(2-methoxyethoxy)-3-[3-(4-{3-[4-(oxetan-3-yl)piperazin-1-yl]azetidine-1-carbonyl}phenyl)-1,2-oxazol-5-yl]-1H-indazole ("A197")

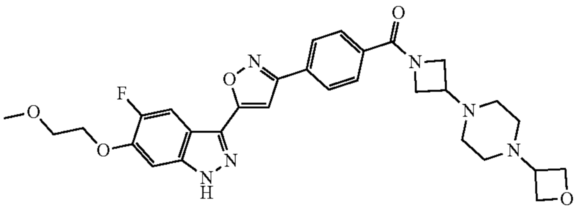 [SMILES: COCCOc1cc2[nH]nc(-c3cc(-c4ccc(C(=O)N5CC(N6CCN(C7COC7)CC6)C5)cc4)no3)c2cc1F]

5-fluoro-6-(2-methoxyethoxy)-3-(3-{4-[4-(oxetan-3-yl)-1,4-diazepane-1-carbonyl]phenyl}-1,2-oxazol-5-yl)-1H-indazole ("A198")

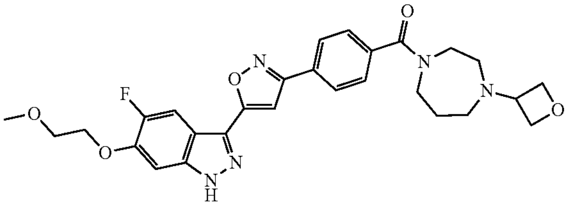 [SMILES: COCCOc1cc2[nH]nc(-c3cc(-c4ccc(C(=O)N5CCCN(C6COC6)CC5)cc4)no3)c2cc1F]

white solid; HPLC/MS 1.24 min (A), $[M+H]^+$ 536.

$^1$H NMR (400 MHz, DMSO-$d_6$) δ 13.70 (s, 1H), 8.09 (d, J=8.3 Hz, 2H), 8.02 (d, J=11.0 Hz, 1H), 7.75 (s, 1H), 7.62-7.52 (m, 2H), 7.28 (d, J=7.1 Hz, 1H), 4.55 (t, J=6.5 Hz, 1H), 4.50 (t, J=6.4 Hz, 1H), 4.40 (t, J=6.1 Hz, 1H), 4.34 (t, J=6.1 Hz, 1H), 4.31-4.28 (m, 2H), 3.79-3.74 (m, 1H), 3.72-3.59 (m, 3H), 3.47-3.38 (m, 3H), 3.35 (s, 2H), 2.60-2.52 (m, 1H), 2.50-2.36 (m, 3H), 1.90-1.81 (m, 1H), 1.79-1.67 (m, 1H).

2-(4-{5-[5-fluoro-6-(2-methoxyethoxy)-1H-indazol-3-yl]-1,2-oxazol-3-yl}benzoyl)-7-(oxetan-3-yl)-2,7-diazaspiro[3.5]nonane ("A199")

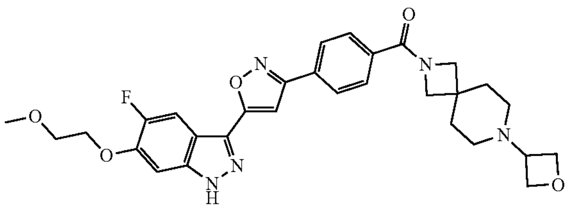 [SMILES: COCCOc1cc2[nH]nc(-c3cc(-c4ccc(C(=O)N5CC6(CCN(C7COC7)CC6)C5)cc4)no3)c2cc1F]

white solid; HPLC/MS 1.23 min (A), $[M+H]^+$ 562.

$^1H$ NMR (500 MHz, DMSO-$d_6$) δ 13.70 (s, 1H), 8.10 (d, J=8.4 Hz, 2H), 8.02 (d, J=11.0 Hz, 1H), 7.81 (d, J=8.4 Hz, 2H), 7.76 (s, 1H), 7.28 (d, J=7.1 Hz, 1H), 4.51 (t, J=6.5 Hz, 2H), 4.41 (t, J=6.1 Hz, 2H), 4.33-4.27 (m, 2H), 4.05 (s, 2H), 3.81-3.73 (m, 4H), 3.36 (s, 3H), 3.36-3.30 (m, 1H), 2.29-1.98 (m, 4H), 1.79-1.71 (m, 4H).

5-fluoro-6-(2-methoxyethoxy)-3-[3-(4-{3-[(3S)-3-methylmorpholin-4-yl]azetidine-1-carbonyl}phenyl)-1,2-oxazol-5-yl]-1H-indazole ("A200")

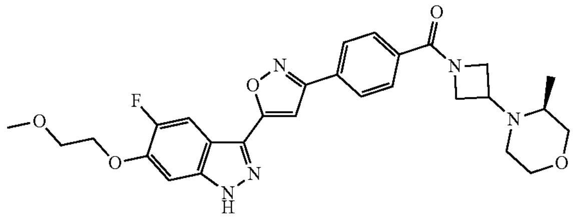 [SMILES: COCCOc1cc2[nH]nc(-c3cc(-c4ccc(C(=O)N5CC(N6CCOC[C@@H]6C)C5)cc4)no3)c2cc1F]

trifluoroacetate, white solid; HPLC/MS 1.27 min (A), $[M+H]^+$ 536.

$^1H$ NMR (500 MHz, DMSO-$d_6$, partially very broad signals, selection of peaks) δ 13.72 (s, 1H), 10.55 (s, 1H), 8.15 (d, J=8.4 Hz, 2H), 8.01 (d, J=10.9 Hz, 1H), 7.83 (d, J=8.4 Hz, 2H), 7.78 (s, 1H), 7.28 (d, J=7.1 Hz, 1H), 4.79-4.4 (m, 2H), 4.35-4.23 (m, 2H), 3.80-3.73 (m, 2H), 3.36 (s, 3H), 1.30-1.30 (bs, 3H).

5-fluoro-6-(2-methoxyethoxy)-3-[3-(4-{3-[(3R)-3-methylmorpholin-4-yl]azetidine-1-carbonyl}phenyl)-1,2-oxazol-5-yl]-1H-indazole ("A201")

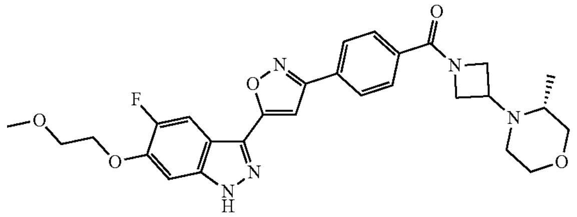 [SMILES: COCCOc1cc2[nH]nc(-c3cc(-c4ccc(C(=O)N5CC(N6CCOC[C@H]6C)C5)cc4)no3)c2cc1F]

3-(3-{4-[(cis)-hexahydro-1H-furo[3,4-c]pyrrole-5-carbonyl]phenyl}-1,2-oxazol-5-yl)-5-fluoro-6-(2-methoxyethoxy)-1H-indazole ("A202")

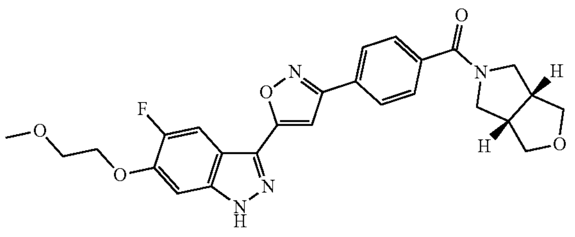 [SMILES: COCCOc1cc2[nH]nc(-c3cc(-c4ccc(C(=O)N5C[C@H]6COC[C@H]6C5)cc4)no3)c2cc1F]

white solid; UPLC/MS 0.69 min, $[M+H]^+$ 493.

$^1H$ NMR (500 MHz, DMSO-$d_6$) δ 13.71 (s, 1H), 8.15-8.07 (m, 2H), 8.02 (d, J=11.0 Hz, 1H), 7.75 (s, 1H), 7.66 (d, J=8.3 Hz, 2H), 7.28 (d, J=7.0 Hz, 1H), 4.35-4.20 (m, 2H), 3.90-3.64 (m, 5H), 3.65-3.44 (m, 3H), 3.36 (s, 3H), 3.34-3.31 (m, 1H), 2.93 (bs, 2H).

(cis)-5-(4-{5-[5-fluoro-6-(2-methoxyethoxy)-1H-indazol-3-yl]-1,2-oxazol-3-yl}benzoyl)-octahydro-pyrrolo[2,3-c]pyrrol-2-one ("A203")

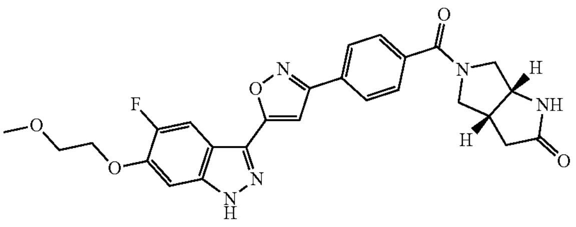 [SMILES: COCCOc1cc2[nH]nc(-c3cc(-c4ccc(C(=O)N5C[C@H]6CC(=O)N[C@H]6C5)cc4)no3)c2cc1F]

4-[1-(4-{5-[5-fluoro-6-(2-methoxyethoxy)-1H-indazol-3-yl]-1,2-oxazol-3-yl}benzoyl)azetidin-3-yl]morpholin-3-one ("A204")

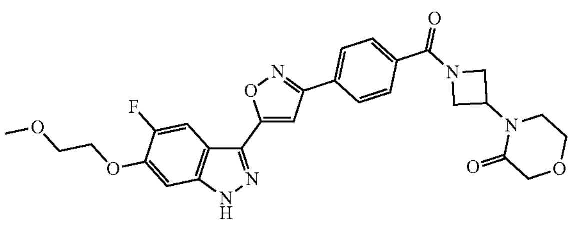 [SMILES: COCCOc1cc2[nH]nc(-c3cc(-c4ccc(C(=O)N5CC(N6CCOCC6=O)C5)cc4)no3)c2cc1F]

white solid; HPLC/MS 1.41 min (A), $[M+H]^+$ 536.

$^1H$ NMR (500 MHz, DMSO-$d_6$) δ 13.70 (s, 1H), 8.15-8.05 (m, 2H), 8.02 (d, J=11.0 Hz, 1H), 7.87-7.80 (m, 2H), 7.77 (s, 1H), 7.28 (d, J=7.1 Hz, 1H), 5.22 (p, J=7.1 Hz, 1H), 4.64-4.45 (m, 2H), 4.35-4.18 (m, 4H), 4.07 (s, 2H), 3.96-3.84 (m, 2H), 3.79-3.73 (m, 2H), 3.71-3.52 (m, 2H), 3.36 (s, 3H).

2-{[5-fluoro-3-(3-{4-[4-(oxetan-3-yl)piperazine-1-carbonyl]phenyl}-1,2-oxazol-5-yl)-1H-indazol-6-yl]oxy}ethan-1-ol ("A205")

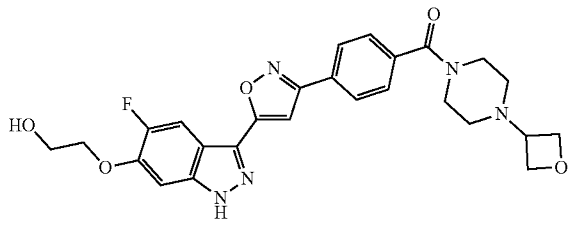 [SMILES: O=C(c1ccc(-c2cc(-c3n[nH]c4cc(OCCO)c(F)cc34)on2)cc1)N1CCN(C2COC2)CC1]

white solid; HPLC/MS 1.13 min (A), $[M+H]^+$ 508.

$^1$H NMR (500 MHz, DMSO-$d_6$) δ 13.67 (s, 1H), 8.10 (d, J=8.2 Hz, 2H), 8.01 (d, J=10.9 Hz, 1H), 7.75 (s, 1H), 7.57 (d, J=8.3 Hz, 2H), 7.27 (d, J=7.1 Hz, 1H), 4.96 (t, J=5.4 Hz, 1H), 4.55 (t, J=6.5 Hz, 2H), 4.45 (t, J=6.1 Hz, 2H), 4.19 (t, J=4.9 Hz, 2H), 3.82 (q, J=5.1 Hz, 2H), 3.68 (bs, 2H), 3.47 (p, J=6.3 Hz, 1H), 3.40 (bs, 2H), 2.41-2.19 (m, 4H).

1-(4-{5-[5-fluoro-6-(2-methoxyethoxy)-1H-indazol-3-yl]-1,2-oxazol-3-yl}benzoyl)-3-(pyridin-4-yl)azetidin-3-ol ("A206")

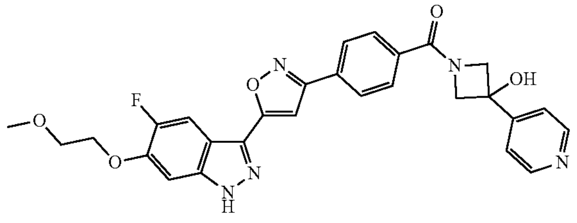 [SMILES: COCCOc1cc2[nH]nc(-c3cc(-c4ccc(C(=O)N5CC(O)(c6ccncc6)C5)cc4)no3)c2cc1F]

off-white solid; HPLC/MS 1.27 min (A), $[M+H]^+$ 530.

$^1$H NMR (400 MHz, DMSO-$d_6$) δ 13.72 (s, 1H), 8.96-8.51 (m, 2H), 8.18-8.11 (m, 2H), 8.02 (d, J=11.0 Hz, 1H), 7.95-7.86 (m, 4H), 7.78 (s, 1H), 7.28 (d, J=7.1 Hz, 1H), 6.96 (bs, 1H), 4.81-4.65 (m, 1H), 4.58-4.44 (m, 1H), 4.39-4.26 (m, 4H), 3.81-3.70 (m, 2H).

5-fluoro-6-(2-methoxyethoxy)-3-[3-(4-{5H,6H,7H-pyrrolo[3,4-d]pyrimidine-6-carbonyl}phenyl)-1,2-oxazol-5-yl]-1H-indazole ("A207")

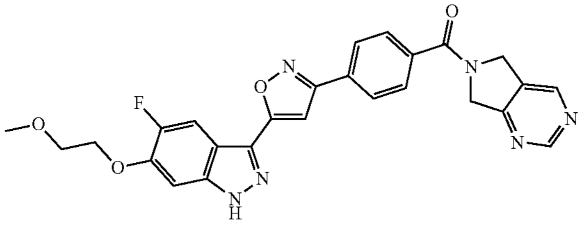 [SMILES: COCCOc1cc2[nH]nc(-c3cc(-c4ccc(C(=O)N5Cc6cncnc6C5)cc4)no3)c2cc1F]

off-white solid; UPLC/MS 0.66 min (A), $[M+H]^+$ 501.

$^1$H NMR (500 MHz, DMSO-$d_6$, mixture of rotational isomers) δ 13.71 (s, 1H), 9.11 (d, J=13.4 Hz, 1H), 8.88 (s, 0.5H), 8.73 (s, 0.5H), 8.19-8.12 (m, 2H), 8.06-8.01 (m, 1H), 7.86-7.73 (m, 2H), 7.28 (d, J=7.1 Hz, 1H), 4.98 (s, 1H), 4.92 (s, 1H), 4.90 (s, 2H), 4.33-4.28 (m, 2H), 3.79-3.72 (m, 2H), 3.36 (s, 3H).

5-fluoro-6-(2-methoxyethoxy)-3-[3-(4-{1H,4H,5H,6H-pyrrolo[3,4-c]pyrazole-5-carbonyl}phenyl)-1,2-oxazol-5-yl]-1H-indazole ("A208")

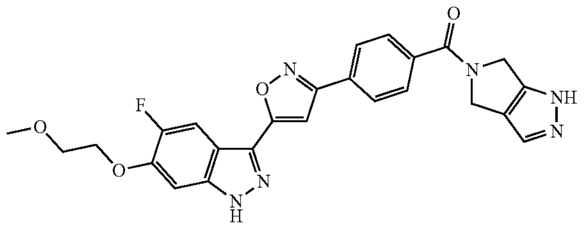 [SMILES: COCCOc1cc2[nH]nc(-c3cc(-c4ccc(C(=O)N5Cc6cn[nH]c6C5)cc4)no3)c2cc1F]

off-white solid; UPLC/MS 0.65 min (A), $[M+H]^+$ 489.

$^1$H NMR (500 MHz, DMSO-$d_6$, mixture of rotational isomers) δ 13.71 (bs, 1H), 12.72 (s, 1H), 8.19-8.10 (m, 2H), 8.06-7.96 (m, 1H), 7.86-7.72 (m, 3H), 7.59 (s, 0.5H), 7.49 (s, 0.5H), 7.28 (d, J=7.1 Hz, 1H), 4.65 (s, 2H), 4.59 (s, 1H), 4.54 (s, 1H), 4.38-4.26 (m, 2H), 3.93-3.72 (m, 2H), 3.36 (s, 3H).

2-{[5-fluoro-3-(3-{4-[3-(morpholin-4-yl)azetidine-1-carbonyl]phenyl}-1,2-oxazol-5-yl)-1H-indazol-6-yl]oxy}ethan-1-ol ("A209")

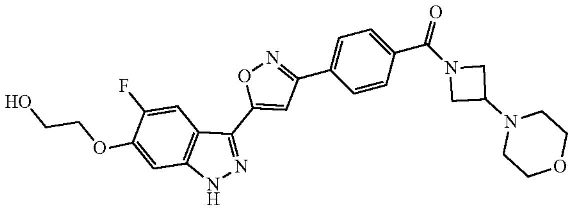 [SMILES: O=C(c1ccc(-c2cc(-c3n[nH]c4cc(OCCO)c(F)cc34)on2)cc1)N1CC(N2CCOCC2)C1]

5-fluoro-6-(2-methoxyethoxy)-3-[3-(4-{3-[(2S)-2-methylmorpholin-4-yl]azetidine-1-carbonyl}phenyl)-1,2-oxazol-5-yl]-1H-indazole ("A210")

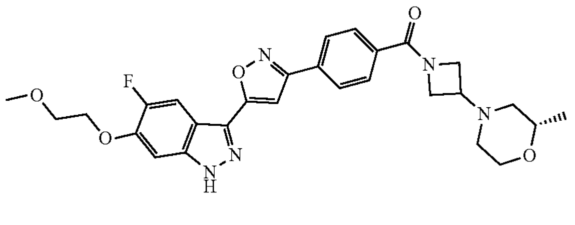

white solid; HPLC/MS 1.30 min (A), $[M+H]^+$ 536.

$^1$H NMR (500 MHz, DMSO-$d_6$, mixture of rotational isomers) δ 13.69 (s, 1H), 8.10 (d, J=8.3 Hz, 2H), 8.02 (d, J=10.9 Hz, 1H), 7.81 (d, J=8.4 Hz, 2H), 7.76 (s, 1H), 7.28 (d, J=7.0 Hz, 1H), 4.35 (t, J=8.1 Hz, 1H), 4.32-4.25 (m, 2H), 4.23-4.16 (m, 1H), 4.09 (t, J=8.8 Hz, 1H), 3.92 (dd, J=10.5, 5.0 Hz, 1H), 3.81-3.71 (m, 3H), 3.56-3.46 (m, 2H), 3.36 (s, 3H), 3.20-3.13 (m, 1H), 2.78 (d, J=11.0 Hz, 0.5H), 2.71 (d, J=11.2 Hz, 1H), 2.67-2.60 (m, 0.5H), 1.92 (t, J=11.4 Hz, 1H), 1.67-1.55 (m, 1H), 1.12-1.00 (m, 3H).

5-fluoro-6-(2-methoxyethoxy)-3-[3-(4-{3-[(2R)-2-methylmorpholin-4-yl]azetidine-1-carbonyl}phenyl)-1,2-oxazol-5-yl]-1H-indazole ("A211")

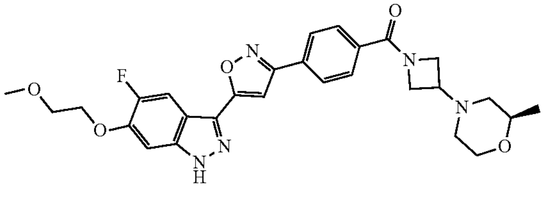

5-fluoro-6-(2-methoxyethoxy)-3-(3-{4-[3-(pyrimidin-5-yl)azetidine-1-carbonyl]phenyl}-1,2-oxazol-5-yl)-1H-indazole ("A212")

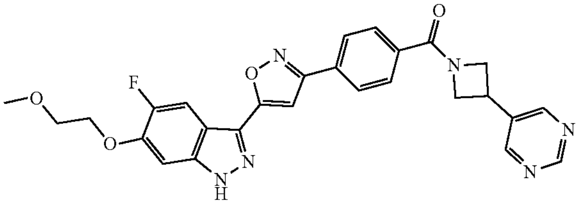 [SMILES: COCCOc1cc2[nH]nc(-c3cc(-c4ccc(C(=O)N5CC(c6cncnc6)C5)cc4)no3)c2cc1F]

white solid; HPLC/MS 1.40 min (A), $[M+H]^+$ 515.

$^1$H NMR (500 MHz, DMSO-$d_6$) δ 13.68 (s, 1H), 9.11 (s, 1H), 8.92 (s, 2H), 8.12 (d, J=8.4 Hz, 2H), 8.01 (d, J=10.9 Hz, 1H), 7.87 (d, J=8.3 Hz, 2H), 7.75 (s, 1H), 7.28 (d, J=7.1 Hz, 1H), 4.72 (d, J=8.9 Hz, 1H), 4.65-4.47 (m, 4H), 4.39-4.26 (m, 2H), 4.19 (s, 1H), 4.05 (tt, J=9.1, 6.3 Hz, 1H), 3.83-3.70 (m, 2H), 3.36 (s, 3H).

5-fluoro-6-(2-methoxyethoxy)-3-[3-(4-{1-methyl-1H,4H,5H,6H-pyrrolo[3,4-c]pyrazole-5-carbonyl}phenyl)-1,2-oxazol-5-yl]-1H-indazole ("A213")

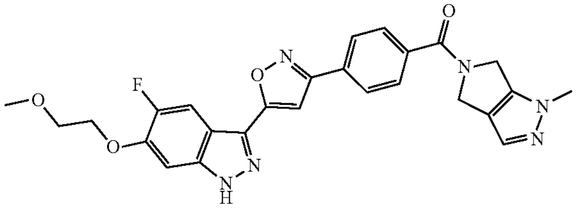

off-white solid; UPLC/MS 0.69 min, $[M+H]^+$ 503.

$^1$H NMR (500 MHz, DMSO-$d_6$, mixture of rotational isomers) δ 13.69 (s, 1H), 8.19-8.09 (m, 2H), 8.08-7.98 (m, 1H), 7.82-7.70 (m, 3H), 7.32-7.26 (m, 1.5H), 7.18 (s, 0.5H), 4.76 (s, 0.5H), 4.68 (m, 0.5H), 4.61 (s, 0.5H), 4.51 (s, 0.5H), 4.35-4.26 (m, 2H), 3.81 (s, 1.5H), 3.80-3.74 (m, 2H), 3.69 (s, 1.5H), 3.36 (s, 3H).

3-(3-{4-[(cis)-octahydropyrano[3,4-c]pyrrole-2-carbonyl]phenyl}-1,2-oxazol-5-yl)-5-fluoro-6-(2-methoxyethoxy)-1H-indazole ("A214")

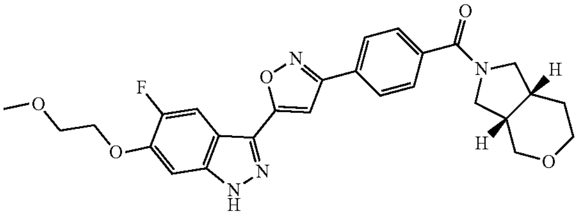 [SMILES: COCCOc1cc2[nH]nc(-c3cc(-c4ccc(C(=O)N5C[C@H]6COCC[C@H]6C5)cc4)no3)c2cc1F]

white solid; HPLC/MS 1.54 min (A), $[M+H]^+$ 507.

$^1$H NMR (500 MHz, DMSO-$d_6$) δ 13.69 (s, 1H), 8.09 (d, J=8.3 Hz, 2H), 8.02 (d, J=10.9 Hz, 1H), 7.75 (s, 1H), 7.71 (d, J=8.3 Hz, 2H), 7.28 (d, J=7.1 Hz, 1H), 4.34-4.17 (m, 2H), 3.82-3.29 (m, 13H), 2.44-2.36 (m, 1H), 2.37-2.30 (m, 2H), 2.31-2.22 (m, 1H).

3-(3-{4-[(cis)-octahydrofuro[3,4-c]pyridine-5-carbonyl]phenyl}-1,2-oxazol-5-yl)-5-fluoro-6-(2-methoxyethoxy)-1H-indazole ("A215")

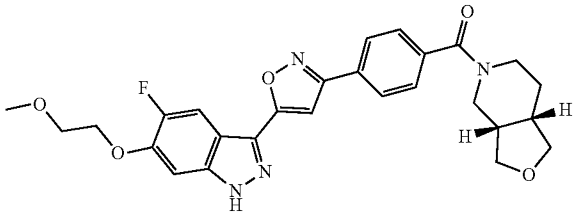 [SMILES: COCCOc1cc2[nH]nc(-c3cc(-c4ccc(C(=O)N5CC[C@@H]6COC[C@@H]6C5)cc4)no3)c2cc1F]

white solid; HPLC/MS 1.53 min (A), $[M+H]^+$ 507.

$^1$H NMR (500 MHz, DMSO-$d_6$) δ 13.69 (s, 1H), 8.10 (d, J=8.3 Hz, 2H), 8.02 (d, J=10.9 Hz, 1H), 7.74 (s, 1H), 7.56 (d, J=8.2 Hz, 2H), 7.28 (d, J=7.0 Hz, 1H), 4.33-4.23 (m, 2H), 3.86-3.32 (m, 12H), 3.26-3.21 (m, 1H), 2.44-2.27 (m, 2H), 2.03-1.33 (m, 2H).

3-(3-{4-[(cis)-5-(oxetan-3-yl)-octahydropyrrolo[3,4-c]pyrrole-2-carbonyl]phenyl}-1,2-oxazol-5-yl)-5-fluoro-6-(2-methoxyethoxy)-1H-indazole ("A216")

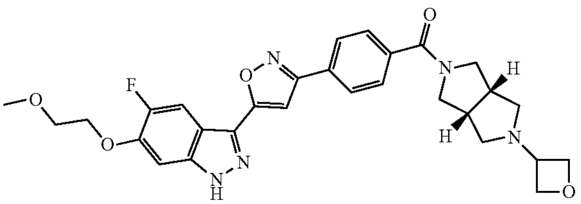 [SMILES: COCCOc1cc2[nH]nc(-c3cc(-c4ccc(C(=O)N5C[C@@H]6CN(C7COC7)C[C@@H]6C5)cc4)no3)c2cc1F]

trifluoroacetate, white solid; UPLC/MS 0.48 min, $[M+H]^+$ 548.

$^1$H NMR (500 MHz, DMSO-$d_6$) δ 13.71 (s, 1H), 11.05 (s, 1H), 8.11 (d, J=8.3 Hz, 2H), 8.01 (d, J=10.9 Hz, 1H), 7.75 (s, 1H), 7.69 (d, J=8.3 Hz, 2H), 7.29 (d, J=7.1 Hz, 1H), 4.77

(t, J=7.3 Hz, 2H), 4.64 (s, 2H), 4.48 (bs, 1H), 4.33-4.27 (m, 2H), 3.9-2.7 (broad signals, 8H), 3.80-3.70 (m, 2H), 3.36 (s, 3H).

(cis)-5-(4-{5-[5-fluoro-6-(2-methoxyethoxy)-1H-indazol-3-yl]-1,2-oxazol-3-yl}benzoyl)-hexahydro-1H-2lambda6-thieno[3,4-c]pyrrole-2,2-dione ("A217")

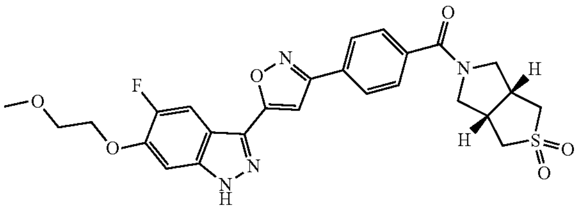 [SMILES: COCCOc1cc2[nH]nc(-c3cc(-c4ccc(C(=O)N5C[C@@H]6CS(=O)(=O)C[C@@H]6C5)cc4)no3)c2cc1F]

white solid; UPLC/MS 0.66 min, $[M+H]^+$ 541.

$^1$H NMR (500 MHz, DMSO-$d_6$) δ 13.69 (s, 1H), 8.10 (d, J=8.3 Hz, 2H), 8.01 (d, J=11.0 Hz, 1H), 7.75 (s, 1H), 7.70 (d, J=8.3 Hz, 2H), 7.28 (d, J=7.1 Hz, 1H), 4.36-4.15 (m, 2H), 3.93 (bs, 1H), 3.80-3.69 (m, 2H), 3.52 (bs, 2H), 3.36 (s, 3H), 3.43-3.19 (broad signals), 3.12 (bs, 3H).

5-fluoro-6-(2-methoxyethoxy)-3-(3-{4-[3-(1-methyl-1H-pyrazol-4-yl)azetidine-1-carbonyl]phenyl}-1,2-oxazol-5-yl)-1H-indazole ("A218")

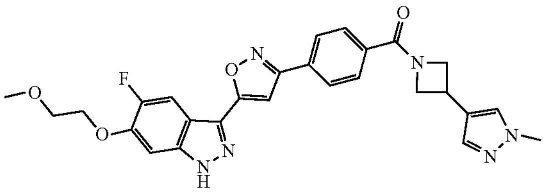

white solid; UPLC/MS 0.70 min, $[M+H]^+$ 517.

$^1$H NMR (400 MHz, DMSO-$d_6$) δ 13.91 (s, 1H), 8.12 (d, J=8.4 Hz, 2H), 8.03 (d, J=11.0 Hz, 1H), 7.84 (d, J=8.4 Hz, 2H), 7.79 (s, 1H), 7.75 (s, 1H), 7.48 (s, 1H), 7.28 (d, J=7.1 Hz, 1H), 4.67 (t, J=8.6 Hz, 1H), 4.44 (t, J=9.3 Hz, 1H), 4.38-4.22 (m, 3H), 4.01-3.91 (m, 1H), 3.89-3.76 (m, 4H), 3.78-3.74 (m, 1H), 3.35 (s, 3H).

{4-[5-(5-Fluoro-6-methoxy-1H-indazol-3-yl)-isoxazol-3-yl]-phenyl}-(4-oxetan-3-yl-piperazin-1-yl)-methanone ("A219")

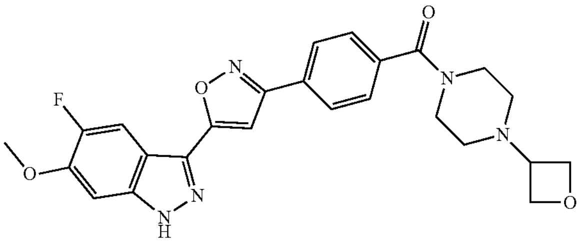 [SMILES: COc1cc2[nH]nc(-c3cc(-c4ccc(C(=O)N5CCN(C6COC6)CC5)cc4)no3)c2cc1F]

{4-[5-(5-Fluoro-6-methoxy-1H-indazol-3-yl)-isoxazol-3-yl]-phenyl}-(cis)-tetrahydro-furo[3,4-c]pyrrol-5-yl-methanone ("A220")

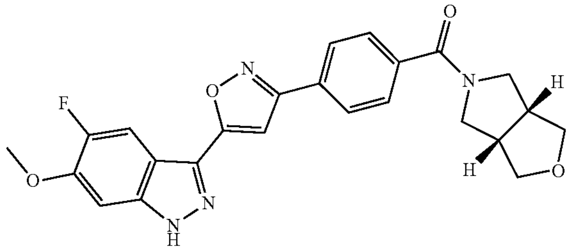 [SMILES: COc1cc2[nH]nc(-c3cc(-c4ccc(C(=O)N5C[C@H]6COC[C@H]6C5)cc4)no3)c2cc1F]

1-(4-{5-[5-fluoro-6-(2-methoxyethoxy)-1H-indazol-3-yl]-1,2-oxazol-3-yl}benzoyl)-3-(pyridin-3-yl)azetidin-3-ol ("A221")

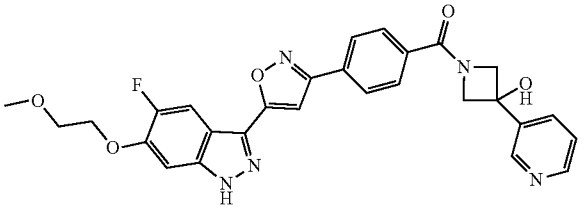 [SMILES: COCCOc1cc2[nH]nc(-c3cc(-c4ccc(C(=O)N5CC(O)(c6cccnc6)C5)cc4)no3)c2cc1F]

5-fluoro-6-(2-methoxyethoxy)-3-(3-{4-[4-(oxetan-3-yl)(2,2,3,3,5,5,6,6-$^2H_8$)piperazine-1-carbonyl]phenyl}-1,2-oxazol-5-yl)-1H-indazole ("A233")

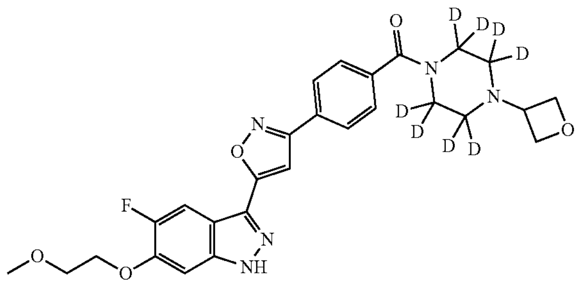 [SMILES: [2H]C1([2H])N(C(=O)c2ccc(-c3cc(-c4n[nH]c5cc(OCCOC)c(F)cc45)on3)cc2)C([2H])([2H])C([2H])([2H])N(C2COC2)C1([2H])[2H]]

2-{[5-fluoro-3-(3-{4-[4-(oxetan-3-yl)(2,2,3,3,5,5,6,6-$^{2}$H8)piperazine-1-carbonyl]phenyl}-1,2-oxazol-5-yl)-1H-indazol-6-yl]oxy}ethan-1-ol ("A234")
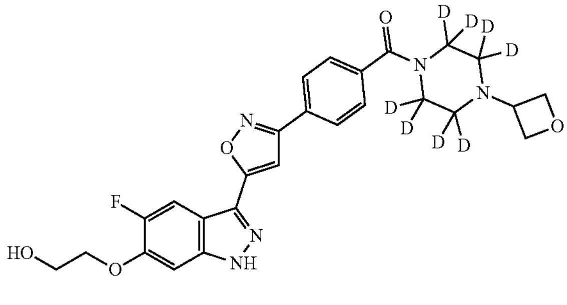 [SMILES: [2H]C1([2H])N(C(=O)c2ccc(-c3cc(-c4n[nH]c5cc(OCCO)c(F)cc45)on3)cc2)C([2H])([2H])C([2H])([2H])N(C2COC2)C1([2H])[2H]]
Example 15
5-fluoro-6-(2-methoxyethoxy)-3-{3-[4-(piperazine-1-carbonyl)phenyl]-1,2-oxazol-5-yl}-1H-indazole ("A46") Hydrochloride
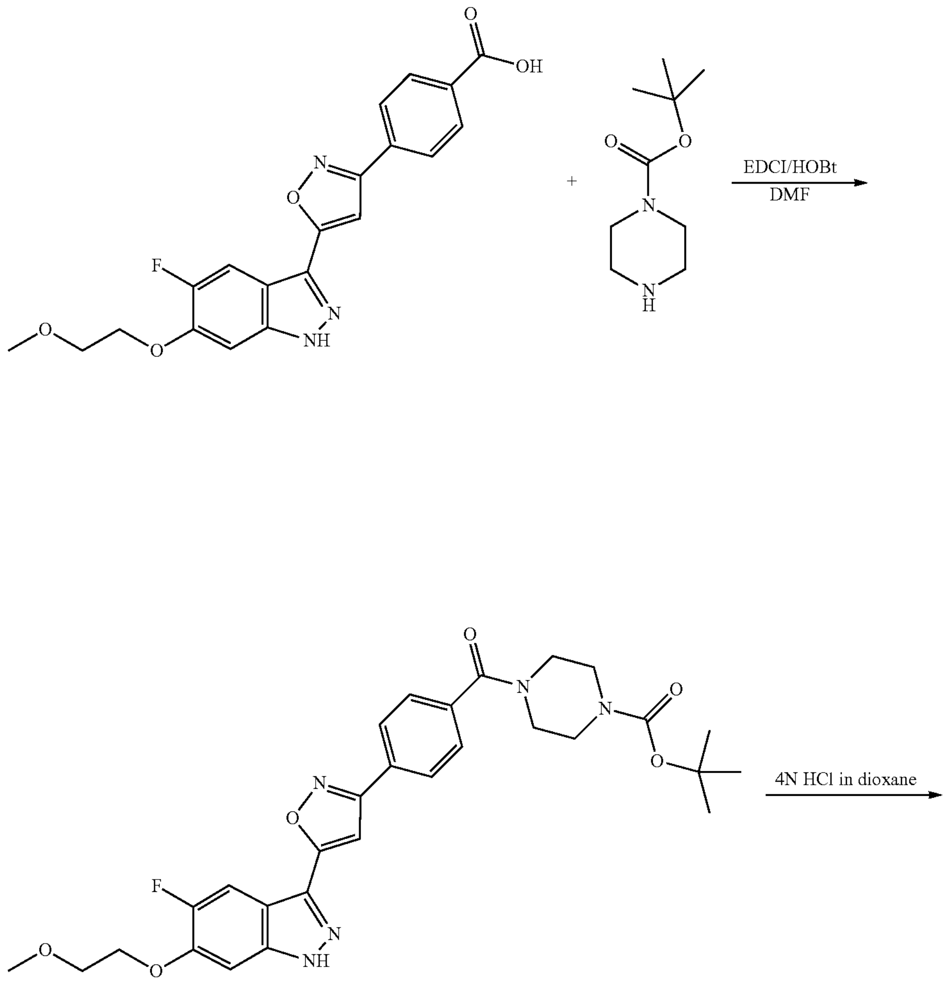

-continued

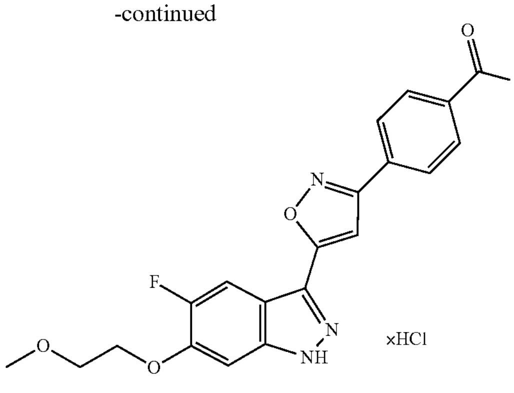

To a suspension of 4-{5-[5-fluoro-6-(2-methoxy-ethoxy)-1H-indazol-3-yl]-isoxazol-3-yl}-benzoic acid (79.5 mg, 0.20 mmol) in DMF (1.0 ml) is added 1-Boc-piperazine (45.2 mg, 0.24 mmol), followed by 1-hydroxybenzotriazole hydrate (6.1 mg, 0.04 mmol) and N-(3-dimethylaminopropyl)-N'-ethylcarbodiimide hydrochloride (61 mg, 0.32 mmol). The reaction mixture is stirred for 16 hours at room temperature. Saturated sodium hydrogen carbonate solution is added to the reaction mixture. The resultant precipitate is filtered off and washed with water. The residue is chromatographed on a silica gel column with cyclohexane/ethyl acetate as eluent to afford tert-butyl 4-(4-{5-[5-fluoro-6-(2-methoxyethoxy)-1H-indazol-3-yl]-1,2-oxazol-3-yl}benzoyl)piperazine-1-carboxylate as white solid; HPLC/MS 1.75 min, $[M+H]^+$ 566.

tert-Butyl 4-(4-{5-[5-fluoro-6-(2-methoxyethoxy)-1H-indazol-3-yl]-1,2-oxazol-3-yl}benzoyl)piperazine-1-carboxylate (90 mg, 0.16 mmol) is dissolved in 4N HCl in dioxane and the reaction mixture is stirred for 2.5 hours at room temperature. The solvent is removed under reduced pressure to afford 5-fluoro-6-(2-methoxyethoxy)-3-{3-[4-(piperazine-1-carbonyl)-phenyl]-1,2-oxazol-5-yl}-1H-indazole hydrochloride as white solid; HPLC/MS 1.21 min (A), $[M+H]^+$ 466.

$^1$H NMR (500 MHz, DMSO-$d_6$) δ 13.75 (s, 1H), 9.22 (s, 2H), 8.13 (d, J=8.3 Hz, 1H), 8.02 (d, J=10.9 Hz, 1H), 7.77 (s, 1H), 7.66 (d, J=8.3 Hz, 1H), 7.28 (d, J=7.0 Hz, 1H), 4.33-4.26 (m, 2H), 3.79-3.74 (m, 2H), 3.72 (broad, 4H), 3.36 (s, 3H), 3.18 (broad, 4H).

The following compounds are prepared analogously:

{[1-(4-{5-[5-fluoro-6-(2-methoxyethoxy)-1H-indazol-3-yl]-1,2-oxazol-3-yl}benzoyl)pyrrolidin-2-yl]methyl}(methyl)amine ("A222")

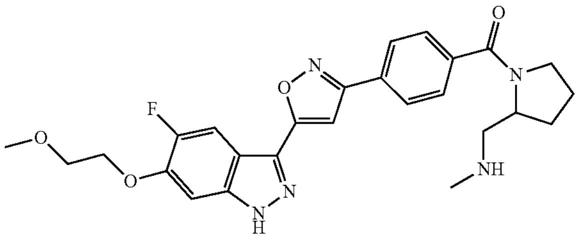 [SMILES: CNCC1CCCN1C(=O)c1ccc(-c2cc(-c3n[nH]c4cc(OCCOC)c(F)cc34)on2)cc1]

pale yellow solid; HPLC/MS 1.31 min (A), $[M+H]^+$ 494.

$^1$H NMR (500 MHz, DMSO-$d_6$, rotational isomers, selection of peaks) δ 8.09 (d, J=8.3 Hz, 1H), 8.04 (d, J=11.0 Hz, 1H), 7.77 (s, 1H), 7.67 (d, J=8.0 Hz, 2H), 7.28 (d, J=7.1 Hz, 1H), 4.35-4.28 (m, 2H), 4.27-4.20 (m, 1H), 3.81-3.72 (m, 2H), 3.52-3.44 (m, 1H), 3.36 (s, 3H), 2.81 (dd, J=11.6, 3.9 Hz, 1H), 2.69-2.56 (m, 1H), 2.34 (s, 3H), 2.05-1.83 (m, 4H), 1.71 (broad, 1H).

3-(3-{4-[(cis)-octahydropyrrolo[3,4-c]pyrrole-2-carbonyl]phenyl}-1,2-oxazol-5-yl)-5-fluoro-6-(2-methoxyethoxy)-1H-indazole ("A223") Hydrochloride

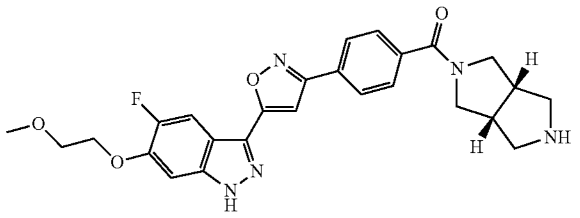 [SMILES: COCCOc1cc2[nH]nc(-c3cc(-c4ccc(C(=O)N5C[C@H]6CNC[C@H]6C5)cc4)no3)c2cc1F]

2-[(5-fluoro-3-{3-[4-(piperazine-1-carbonyl)phenyl]-1,2-oxazol-5-yl}-1H-indazol-6-yl)oxy]ethan-1-ol ("A224")

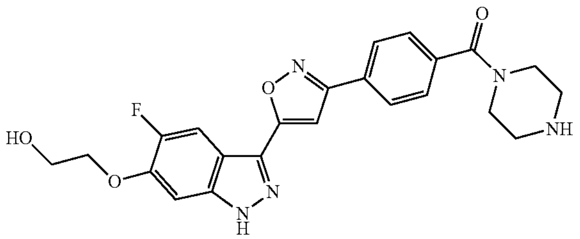 [SMILES: O=C(c1ccc(-c2cc(-c3n[nH]c4cc(OCCO)c(F)cc34)on2)cc1)N1CCNCC1]

{4-[5-(5-fluoro-6-methoxy-1H-indazol-3-yl)-isoxazol-3-yl]-phenyl}-piperazin-1-yl-methanone ("A225")

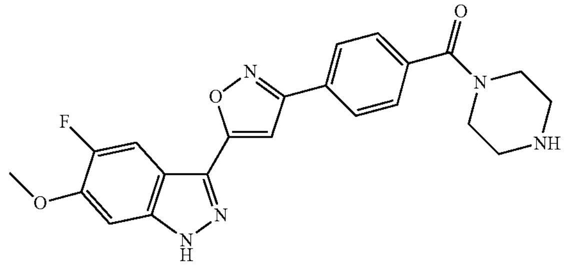 [SMILES: COc1cc2[nH]nc(-c3cc(-c4ccc(C(=O)N5CCNCC5)cc4)no3)c2cc1F]

5-fluoro-6-(2-methoxyethoxy)-3-(3-{4-[(2,2,3,3,5,5,6,6-$^{2}H_{8}$)piperazine-1-carbonyl]phenyl}-1,2-oxazol-5-yl)-1H-indazole hydrochloride ("A232")

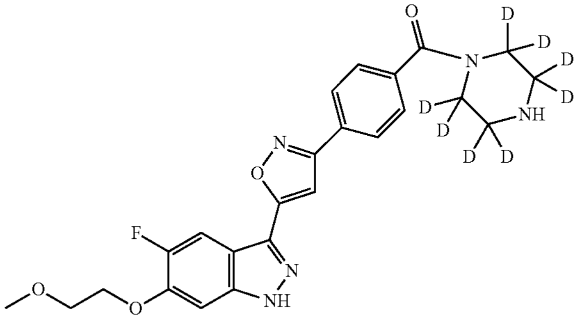 [SMILES: [2H]C1([2H])NC([2H])([2H])C([2H])([2H])N(C(=O)c2ccc(-c3cc(-c4n[nH]c5cc(OCCOC)c(F)cc45)on3)cc2)C1([2H])[2H]]

Example 16

[(4-{5-[5-fluoro-6-(2-methoxyethoxy)-1H-indazol-3-yl]-1,2-oxazol-3-yl}phenyl)imino]dimethyl-lambda6-sulfanone ("A47")

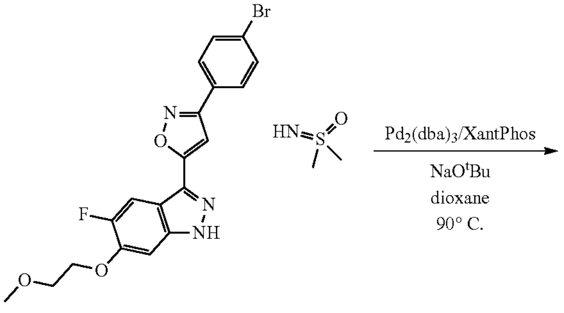

-continued

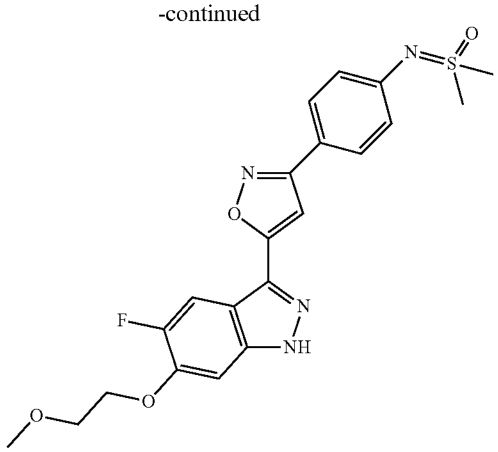

white solid; HPLC/MS 2.52 min (A), $[M+H]^+$ 445.

$^{1}$H NMR (500 MHz, DMSO-$d_6$) δ 13.66 (s, 1H), 8.00 (d, J=11.0 Hz, 1H), 7.84 (d, J=8.6 Hz, 1H), 7.59 (s, 1H), 7.26 (d, J=7.1 Hz, 1H), 7.07 (d, J=8.6 Hz, 2H), 4.32-4.26 (m, 2H), 3.80-3.74 (m, 2H), 3.35 (s, 3H), 3.29 (s, 6H).

Example 17

5-fluoro-6-(2-methoxyethoxy)-3-[3-(1,3-thiazol-5-yl)-1,2-oxazol-5-yl]-1H-indazole ("A48")

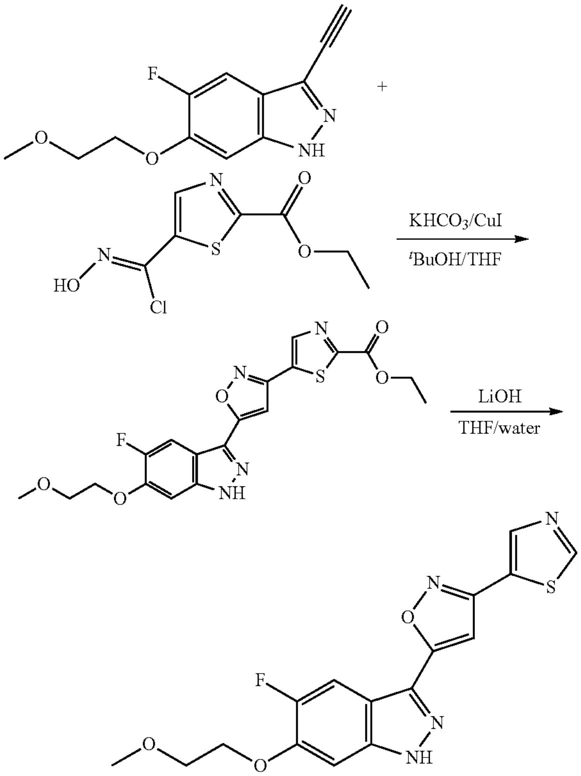

pale brown solid; HPLC/MS 2.61 min (A), $[M+H]^+$ 361.

$^{1}$H NMR (500 MHz, DMSO-$d_6$) δ 13.77 (s, 1H), 9.31 (d, J=0.7 Hz, 1H), 8.68 (d, J=0.7 Hz, 1H), 7.96 (d, J=10.8 Hz,

1H), 7.78 (s, 1H), 7.29 (d, J=7.0 Hz, 1H), 4.38-4.23 (m, 2H), 3.86-3.67 (m, 2H), 3.35 (s, 3H).
Example 18
4-{5-[5-fluoro-6-(3-hydroxy-2-methoxypropoxy)-1H-indazol-3-yl]-1,2-oxazol-3-yl}-N,N-dimethyl-benzamide ("A49")
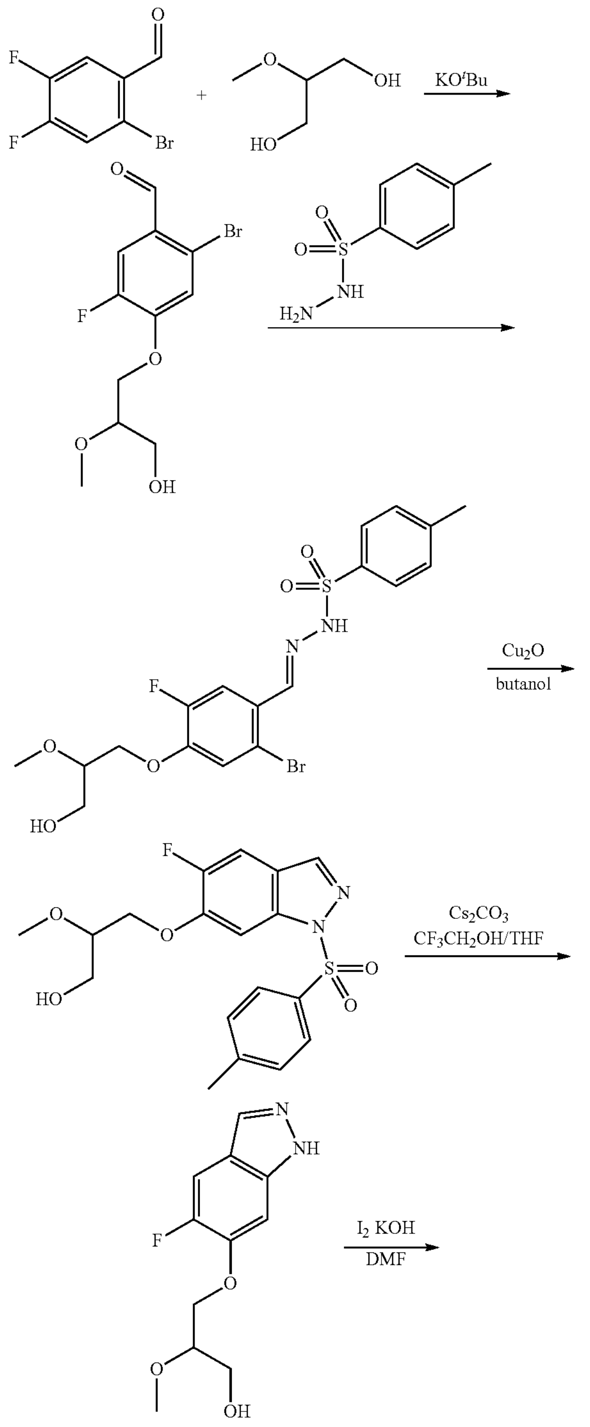
-continued
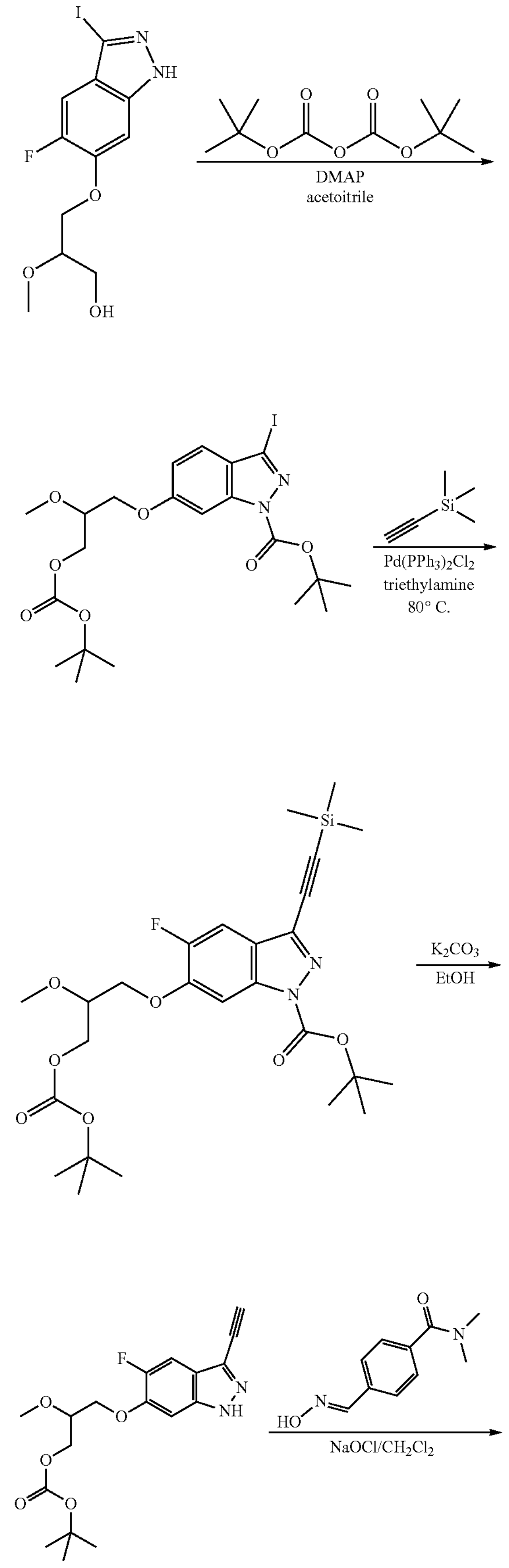

-continued
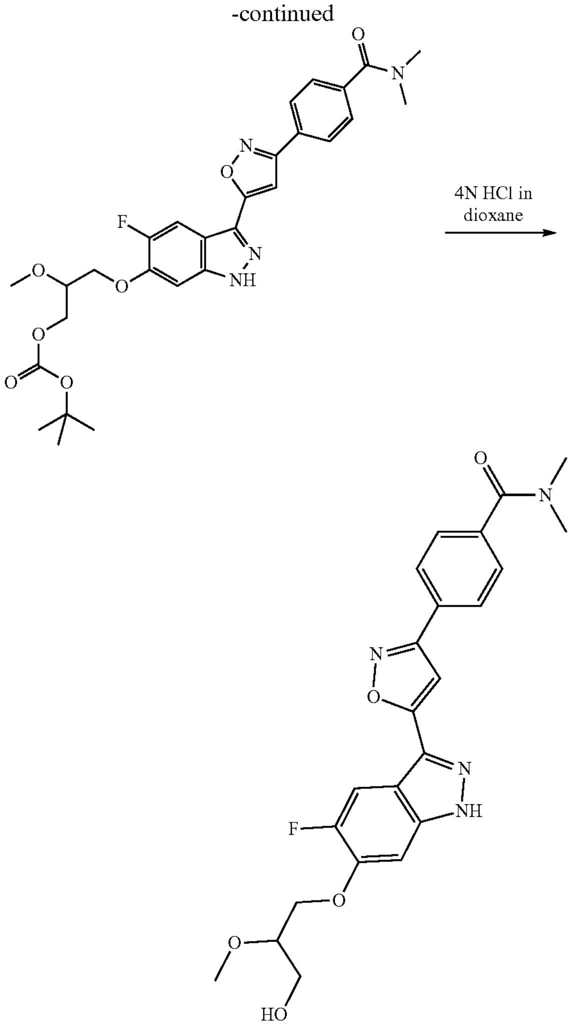
pale yellow solid; UPLC/MS 0.65 min (A), $[M+H]^+$ 455. $^1H$ NMR (400 MHz, DMSO-$d_6$) δ 13.70 (s, 1H), 8.09 (d, J=8.3 Hz, 2H), 8.03 (d, J=10.8 Hz, 1H), 7.76 (s, 1H), 7.59 (d, J=8.3 Hz, 2H), 7.29 (d, J=7.0 Hz, 1H), 4.81 (t, J=5.3 Hz, 1H), 4.30 (dd, J=10.4, 3.2 Hz, 1H), 4.17 (dd, J=10.4, 5.3 Hz, 1H), 3.64-3.56 (p, J=4.0 Hz, 3H), 3.42 (s, 3H), 3.02 (s, 3H), 2.96 (s, 3H).
Example 19
3-{3-[4-(3,3-dimethyl-piperidin-4-yl)-phenyl]-isoxazol-5-yl}-5-fluoro-6-(2-methoxy-ethoxy)-1H-indazole ("A230")
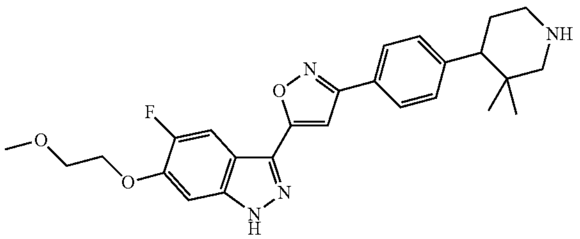 [SMILES: COCCOc1cc2[nH]nc(-c3cc(-c4ccc(C5CCNCC5(C)C)cc4)no3)c2cc1F]
and
5-fluoro-6-(2-methoxy-ethoxy)-3-{3-[4-(1,3,3-trimethyl-piperidin-4-yl)-phenyl]-isoxazol-5-yl}-1H-indazole ("A231")
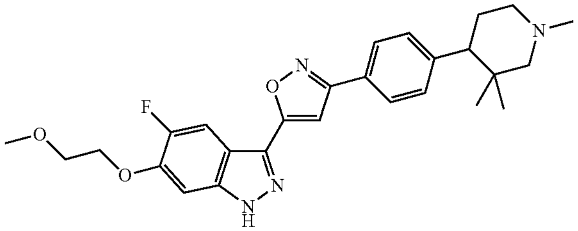
Synthetic Scheme:
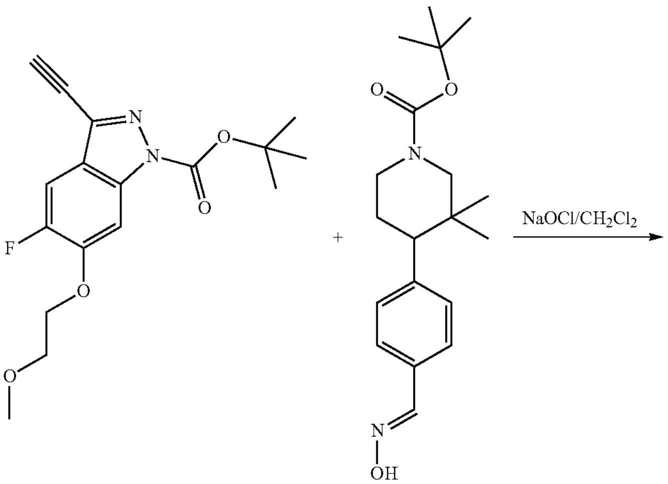

-continued
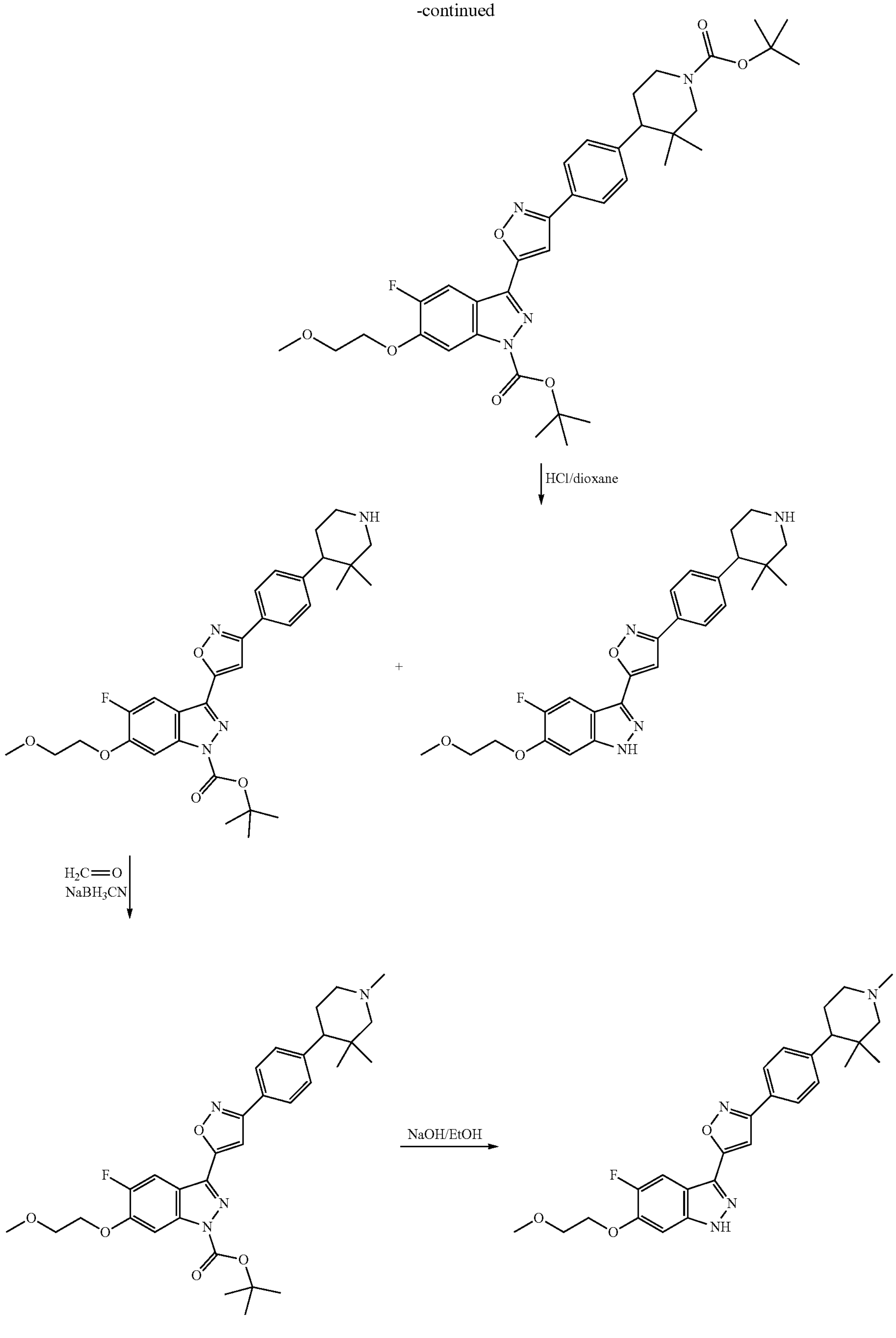

"A230":

yellow solid; $[M+H]^+$ 465; $^1H$ NMR (400 MHz, DMSO-$d_6$) δ 8.02 (d, J=11.0 Hz, 1H), 7.96-7.91 (m, 2H), 7.67 (s, 1H), 7.35-7.31 (m, 2H), 7.27 (d, J=7.1 Hz, 1H), 4.33-4.26 (m, 2H), 3.80-3.73 (m, 2H), 3.35 (s, 3H), 3.13-3.05 (m, 1H), 2.65-2.52 (m, 3H), 2.49-2.41 (m, 1H), 2.12-2.01 (m, 1H), 1.44-1.36 (m, 1H), 0.85 (s, 3H), 0.70 (s, 3H)

"A231":

white solid; $[M+H]^+$ 479; $^1H$ NMR (300 MHz, DMSO-$d_6$) δ 13.70 (s, 1H), 8.00 (d, J=11.0 Hz, 1H), 7.92 (d, J=8.1 Hz, 2H), 7.67 (s, 1H), 7.33 (d, J=8.1 Hz, 2H), 7.26 (d, J=7.1 Hz, 1H), 4.32-4.23 (m, 2H), 3.79-3.69 (m, 2H), 3.33 (s, 3H), 2.97-2.89 (m, 1H), 2.44-2.34 (m, 2H), 2.28-2.13 (m, 4H), 1.92-1.75 (m, 2H), 1.53-1.43 (m, 1H), 0.86 (s, 3H), 0.72 (s, 3H).

Example 20

2-[4-(4-{5-[5-fluoro-6-(2-methoxyethoxy)-1H-indazol-3-yl]-1,2-oxazol-3-yl}benzoyl)piperazin-1-yl]propane-1,3-diol ("A228")

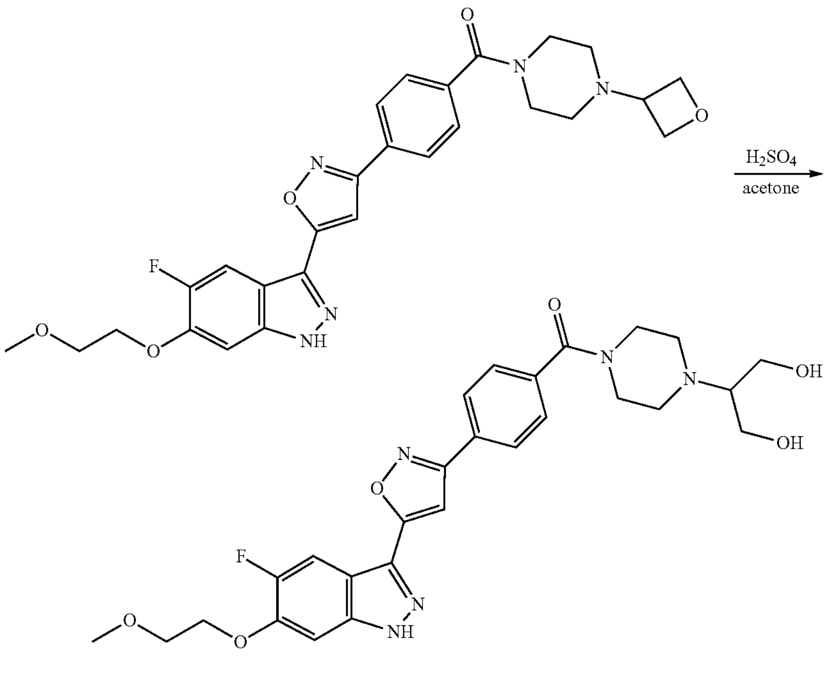

trifluoroacetate; white powder; UPLC/MS 0.47 min, $[M+H]^+$ 540.

$^1H$ NMR (500 MHz, DMSO-$d_6$) δ 13.71 (s, 1H), 9.65 (broad, 1H), 8.13 (d, J=8.3 Hz, 2H), 8.01 (d, J=10.9 Hz, 1H), 7.76 (s, 1H), 7.66 (d, J=8.3 Hz, 2H), 7.29 (d, J=7.1 Hz, 1H), 5.40 (broad, 2H), 4.51 (broad, 1H), 4.38-4.21 (m, 2H), 3.80 (d, J=5.0 Hz, 4H), 3.78-3.75 (m, 2H), 3.54 (broad signal), 3.36 (s, 3H).

Example 21

Alternative Synthesis of "A45":

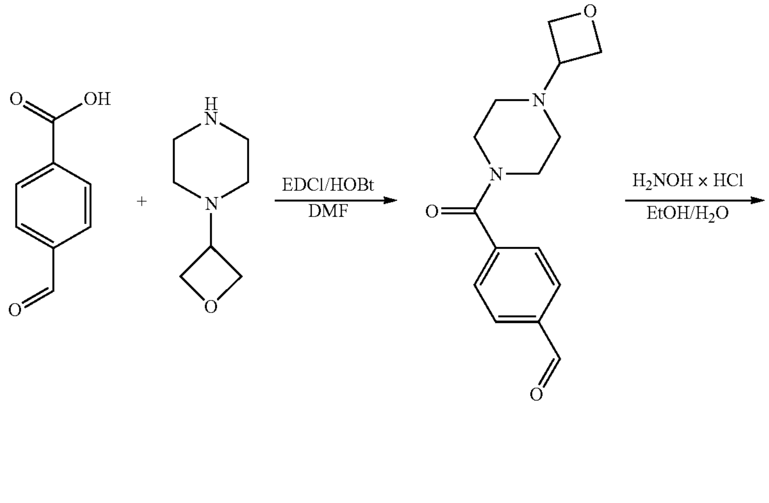

-continued

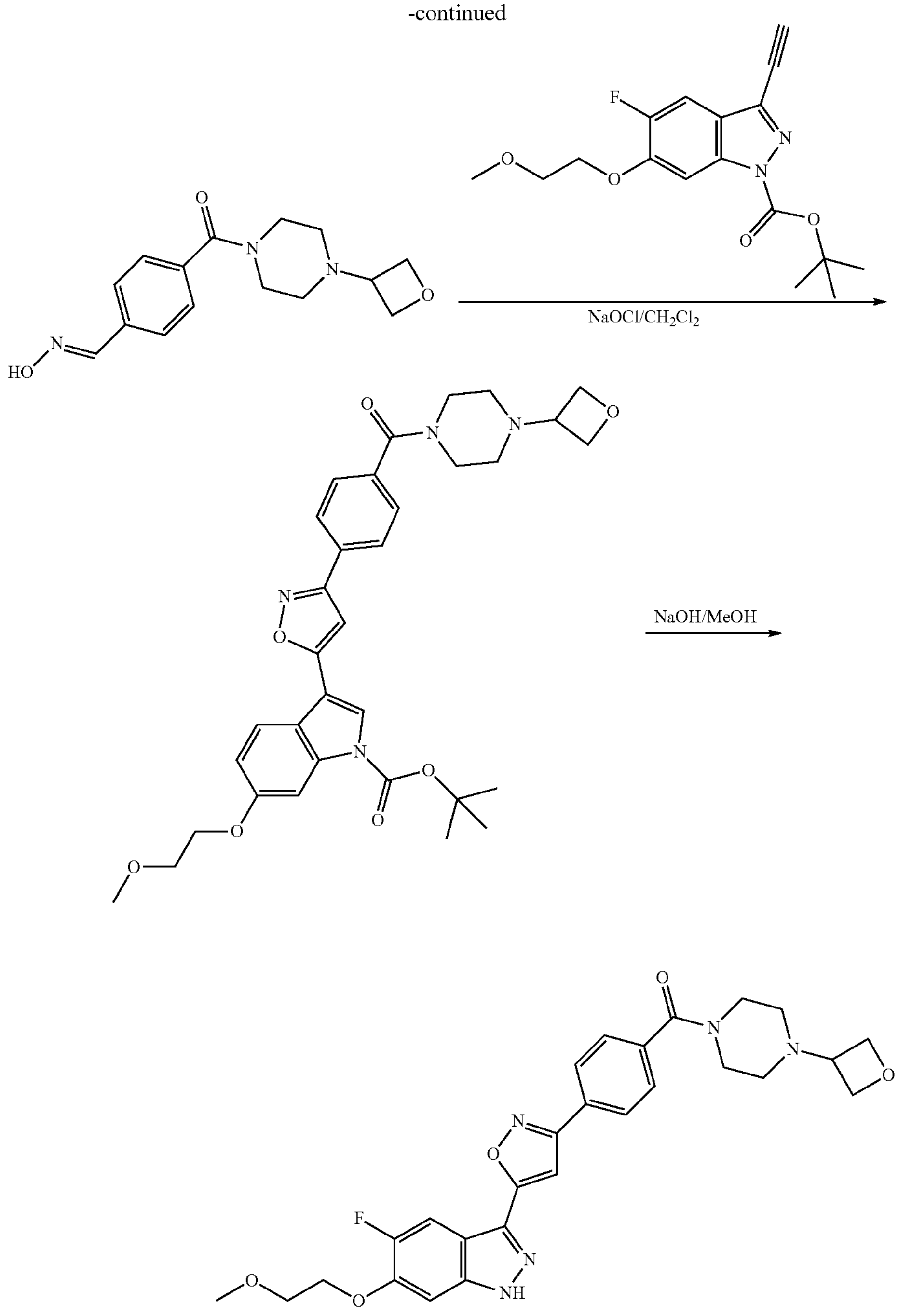

To a solution of terephthalaldehydic acid (300 mg, 2.00 mmol) in DMF (10 ml) is added 1-(oxetan-3-yl)piperazine (313 mg, 2.20 mmol), followed by 1-hydroxybenzotriazole hydrate (15.3 mg, 0.10 mmol) and N-(3-dimethyl-amino-propyl)-N'-ethylcarbodiimide hydrochloride (403 mg, 2.10 mmol). The reaction mixture is stirred for 90 minutes at room temperature. The reaction mixture is evaporated to dryness. The residue is treated with saturated sodium hydrogen carbonate solution and extracted three times with dichloromethane. The combined organic phases are dried over sodium sulfate and evaporated to afford 4-[4-(oxetan-3-yl)piperazine-1-carbonyl]benzaldehyde as yellow oil; HPLC/MS 0.82 min (A), $[M+H]^+$ 275.

$^1H$ NMR (500 MHz, DMSO-$d_6$) δ 10.05 (s, 1H), 7.97 (d, J=8.2 Hz, 2H), 7.60 (d, J=8.1 Hz, 2H), 4.53 (t, J=6.5 Hz, 2H), 4.44 (t, J=6.1 Hz, 2H), 3.67 broad, 2H), 3.49-3.43 (m, 1H), 3.30 (broad, 2H), 2.42-2.19 (m, 4H).

A slurry of 4-[4-(oxetan-3-yl)piperazine-1-carbonyl]benzaldehyde (403 mg, 1.47 mmol) in ethanol (3 ml) is heated to 80° C. The resultant clear solution is allowed to reach room temperature and a solution of hydroxylammonium chloride (204 mg, 2.93 mmol) in water (500 μl) is added and the mixture is stirred for 1 hour at room temperature. The reaction mixture is neutralized with 1 N sodium hydroxide solution (2 ml). The resultant precipitate is filtered off, washed with water and dried under vacuum to afford N-({4-

[4-(oxetan-3-yl)piperazine-1-carbonyl]phenyl}methylidene)hydroxylamine as white powder; UPLC/MS 0.30 min, $[M+H]^+$ 290.

$^1H$ NMR (400 MHz, DMSO-$d_6$) δ 11.37 (s, 1H), 8.18 (s, 1H), 7.65 (d, J=8.2 Hz, 2H), 7.41 (d, J=8.3 Hz, 2H), 4.53 (t, J=6.5 Hz, 3H), 4.44 (t, J=6.1 Hz, 3H), 3.62 (bs, 2H), 3.45 (p, J=6.3 Hz, 1H), 3.37 (bs, 2H), 2.28 (bs, 4H).

To a solution of 3-ethynyl-5-fluoro-6-(2-methoxy-ethoxy)-indazole-1-carboxylic acid tert-butyl ester (41.6 mg, 0.11 mmol) and N-({4-[4-(oxetan-3-yl)piperazine-1-carbonyl]phenyl}methylidene)hydroxylamine in dichloromethane (500 μl) aqueous sodium hypochlorite solution (content approx. 14%, 143 μl, approx. 0.33 mmol) is added dropwise. The reaction mixture is stirred for 18 hours at room temperature. The reaction mixture is treated with water and dichloromethane. The aqueous phase is separated and extracted twice with dichloromethane. The combined organic phases are dried over sodium sulfate and evaporated. The residue is chromatographed on a silica gel column with dichloromethane/methanol as eluent to afford tert-butyl 5-fluoro-6-(2-methoxyethoxy)-3-(3-{4-[4-(oxetan-3-yl)piperazine-1-carbonyl]phenyl}-1,2-oxazol-5-yl)-1H-indazole-1-carboxylate as colorless resin; UPLC/MS 0.69 min, $[M+H]^+$ 622.

To a suspension of tert-butyl 5-fluoro-6-(2-methoxy-ethoxy)-3-(3-{4-[4-(oxetan-3-yl)piperazine-1-carbonyl]phenyl}-1,2-oxazol-5-yl)-1H-indazole-1-carboxylate (62 mg, 0.12 mmol) in methanol (1 ml) is added sodium hydroxide (9.26 mg, 0.23 mmol) and the mixture is stirred for 2 hours at room temperature. The reaction mixture is treated with saturated ammonium chloride solution. The resultant precipitate is filtered off, washed with water and dried under vacuum to afford 5-fluoro-6-(2-methoxy-ethoxy)-3-(3-{4-[4-(oxetan-3-yl)piperazine-1-carbonyl]phenyl}-1,2-oxazol-5-yl)-1H-indazole as off-white solid; UPLC/MS 0.53 min. $[M+H]^+$ 522.

The following compound is prepared analogously:

6-ethoxy-5-fluoro-3-(3-{4-[4-(oxetan-3-yl)piperazine-1-carbonyl]phenyl}-1,2-oxazol-5-yl)-1H-indazole ("A229")

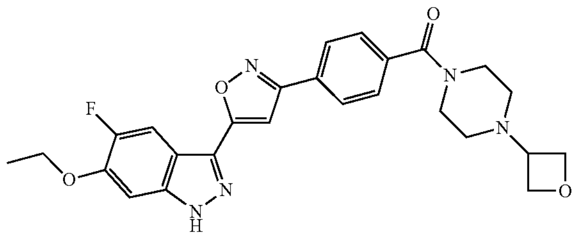 [SMILES: CCOc1cc2[nH]nc(-c3cc(-c4ccc(C(=O)N5CCN(C6COC6)CC5)cc4)no3)c2cc1F]

off-white crystals; HPLC/MS 1.34 min (A), $[M+H]^+$ 492.

$^1H$ NMR (500 MHz, DMSO-$d_6$) δ 13.66 (s, 1H), 8.10 (d, J=8.3 Hz, 2H), 8.00 (d, J=11.0 Hz, 1H), 7.74 (s, 1H), 7.57 (d, J=8.3 Hz, 2H), 7.23 (d, J=7.1 Hz, 1H), 4.54 (t, J=6.5 Hz, 2H), 4.45 (t, J=6.1 Hz, 2H), 4.22 (q, J=7.0 Hz, 2H), 3.67 (broad, 2H), 3.47 (p, J=6.2 Hz, 1H), 3.40 (broad, 2H), 2.31 (broad, 4H), 1.43 (t, J=6.9 Hz, 3H).

Example 22—Salt Formation

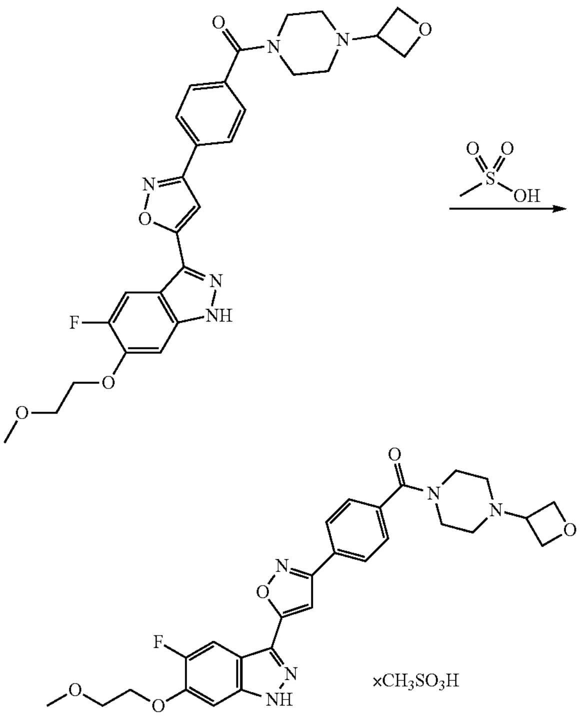

To a suspension of (4-{5-[5-fluoro-6-(2-methoxy-ethoxy)-1H-indazol-3-yl]-isoxazol-3-yl}-phenyl)-(4-oxetan-3-yl-piperazin-1-yl)-methanone ("A45") (104 mg, 0.20 mmol) in 2-propanol (3 ml) is added methanesulfonic acid (18.6 μl, 0.28 mmol) and the suspension is stirred for 1 hour at 75° C. The mixture is allowed to reach room temperature. The solids are filtered off, washed with water and dried under vacuum to afford (4-{5-[5-fluoro-6-(2-methoxy-ethoxy)-1H-indazol-3-yl]-isoxazol-3-yl}-phenyl)-(4-oxetan-3-yl-piperazin-1-yl)-methanone mesylate as white powder.

$^1H$ NMR (500 MHz, DMSO-$d_6$, very broad signals not annotated) δ 13.71 (s, 1H), 10.79 (s, 1H), 8.14 (d, J=8.2 Hz, 2H), 8.01 (d, J=10.9 Hz, 1H), 7.77 (s, 1H), 7.65 (d, J=7.9 Hz, 2H), 7.29 (d, J=7.0 Hz, 1H), 4.74 (s, 4H), 4.41-4.24 (m, 2H), 3.80-3.72 (m, 2H), 3.36 (s, 3H), 3.03 (broad, 4H), 2.31 (s, 3H).

The following salts of (4-{5-[5-fluoro-6-(2-methoxy-ethoxy)-1H-indazol-3-yl]-isoxazol-3-yl}-phenyl)-(4-oxetan-3-yl-piperazin-1-yl)-methanone ("A45") are prepared similarly:

hydrochloride
maleate
hemi-ethanedisulfonate
hemi-phosphate
sulfate
benzenesulfonate
para-toluenesulfonate The following salts of 5-fluoro-6-(2-methoxyethoxy)-3-(3-{4-[3-(morpholin-4-yl)azetidine-1-carbonyl]phenyl}-1,2-oxazol-5-yl)-1H-indazole ("A53") were prepared similarly:

methanesulfonate
trifluoroacetate.

The following examples relate to medicaments:

Example A: Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B: Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C: Solution

A solution is prepared from 1 g of an active ingredient of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D: Ointment 500 mg of an active ingredient of the formula I are mixed with 99.5 g of Vaseline under aseptic conditions.

Example E: Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F: Dragees

Tablets are pressed analogously to Example E and subsequently coated in a conventional manner with a coating of sucrose, potato starch, talc, tragacanth and dye.

Example G: Capsules 2 kg of active ingredient of the formula I are introduced into hard gelatine capsules in a conventional manner in such a way that each capsule contains 20 mg of the active ingredient.

Example H: Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. A compound of the formula Ib

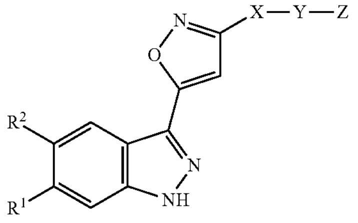

Ib wherein $R^1$ denotes Hal, $CF_3$, $OCH_3$, $OCH_2CH_2OCH_3$, $OCH_2CH_2OH$, 1-methyl-1H-pyrazol-4-yl, $COOCH_3$, $CONH_2$, $CONHCH_3$, or $CONHCH_2CH_2OCH_3$, $R^2$ denotes H, Hal, or CN, $R^3$ denotes H or $CH_3$, X denotes 1,4-phenylen, 1,3-phenylen, 2-fluoro-1,4-phenylen, 2-methyl-1,4-phenylen, pyridine-3,6-diyl, 1,3-thiazol-3,5-diyl, 1,3-thiazol-2,4-diyl, 1,3-thiazol-2,5-diyl, or pyrazol-1,4-diyl, each of which is unsubstituted or mono-, di-, or trisubstituted by Hal and/or A, Y is absent or denotes CO, $SO_2$, NHCO, $NCH_3$, CONH$(CH_2)_n$, $CONHCH_2C(CH_3)_2$, $CON(CH_3)(CH_2)_n$, O, $OCH_2$, $OCH_2CH_2$, S(=O)(=NH), —N=, or $SO_2N(CH_3)$, Z denotes H, A, Hal, OA, $[C(R^3)_2]_n Het^2$ or N=S(=O)$A_2$, A denotes unbranched or branched alkyl with 1-10 C-atoms, wherein one or two non-adjacent CH- and/or $CH_2$-groups may be replaced by O-atoms and wherein 1-7 H-atoms may be replaced by $R^5$,
or denotes $(CH_2)_n Cyc$, Cyc denotes cyclic alkyl having 3-7 C atoms, $R^5$ denotes F, Cl, OH, $SO_2A$, or $N(R^3)_2$, $Het^1$ denotes pyrazolyl which may be mono- or disubstituted by A, $Het^2$ denotes pyrrolidinyl, piperazinyl, piperidinyl, triazolyl, azetidinyl, morpholinyl, thiomorpholinyl, 2-oxa-6-azaspiro[3.3]heptane-6-yl, 6-oxa-2-azaspiro[3.4]octane-2-yl, 1-oxa-6-azaspiro[3.3]heptane-6-yl, 2,6-diazaspiro[3.3]heptane-2-yl, octahydropyrrolo[3,4-b]pyrrolyl, octahydropyrrolo[3,2-b]pyrrolyl, 1,4-diazepanyl, pyridinyl, 1H-pyridinyl, 2H-pyridazinyl, 2,3-dihydropyridazinyl, octahydro-1H-pyrrolo[3.2-b]pyridinyl, 3-thia-6-azabicyclo[3.1.1]heptanyl, 6-oxa-1-azaspiro[3.3]heptane-1-yl, 1H-pyrazolyl, thiazolidinyl, 2-oxa-7-azaspiro[3.5]nonane-7-yl, 1,4-oxazepanyl, 2-thia-6-azaspiro[3.3]heptane-6-yl, 2,8-dioxa-5-azaspiro[3.5]nonane-5-yl, 1H-1,3-benzodiazol-2-yl, 2-oxa-7-azaspiro[4.4]nonane-7-yl, 2-oxa-6-azaspiro[3.4]octane-6-yl, 8-oxa-2-azaspiro[4.5]decane-2-yl, 2,6-diazaspiro[3.4]octane-6-yl, 6-oxa-3-azabicyclo[3.1.1]heptane-3-yl, 2-oxa-5-azabicyclo[2.2.1]heptane-5-yl, 7-oxa-2-azaspiro[3.5]nonane-2-yl, 6-oxa-1-azaspiro[3.3]heptane-1-yl, 2,7-diazaspiro[3.5]nonane-7-yl, 3-oxa-6-azabicyclo[3.1.1]heptane-6-yl, 1H,2H,3H-pyrrolo[3,4-c]pyridine-2-yl, 2,7-diazaspiro[3.5]nonane-2-yl, hexahydro-1H-furo[3,4-c]pyrrole-5-yl, octahydropyrrolo[2,3-c]pyrrole-5-yl, 5H,6H,7H-pyrrolo[3,4-d]pyrimidine-6-yl, 1H, 4H, 5H,6H-pyrrolo[3,4-c]pyrazole-5-yl, octahydropyrano[3,4-c]pyrrole-2-yl, octahydrofuro[3,4-c]pyridine-5-yl, octahydropyrrolo

[3,4-c]pyrrole-2-yl, hexahydro-1H-2lambda6-thieno[3,4-c]pyrrole-5-yl, or tetrahydrofuro[3,4-c]pyrrole-5-yl, each of which may be unsubstituted or mono-, di-, or trisubstituted by A, Hal, CN, $OR^3$, $[C(R^3)_2]_nN(R^3)_2$, $[C(R^3)_2]_nSO_2A$, $[C(R^3)_2]_nNR^3SO_2A$, $Het^3$, $=NR^3$, and/or =O, $Het^3$ denotes morpholinyl, 1H-pyrazolyl, 1lambda6-thiomorpholinyl, imidazolyl, azetidinyl, piperazinyl, piperidinyl, pyridinyl, oxetanyl, 1,2,4-oxadiazolyl, pyrimidinyl, oxolanyl, pyrrolidinyl, 2-oxa-6-azaspiro[3.3]heptane-6-yl, oxan-4-yl, 1,2,3-triazolyl, or 1,2,4-triazolyl, each of which may be unsubstituted or mono- or disubstituted by A, Hal, $OR^3$, oxetanyl, and/or =O, Hal denotes F, Cl, Br, or I, n denotes 0, 1, 2, or 3, or pharmaceutically acceptable salts, tautomers, and stereoisomers thereof, including mixtures thereof in all ratios.

2. The compound according to claim 1, wherein the compound is selected from the group consisting of

| No. | Name |
|---|---|
| "A1" | 2-[1-(4-{5-[6-(trifluoromethyl)-1H-indazol-3-yl]-1,2-oxazol-3-yl}benzoyl)pyrrolidin-2-yl]propan-2-ol |
| "A2" | 2-[(2R)-1-(4-{5-[6-(2-methoxyethoxy)-1H-indazol-3-yl]-1,2-oxazol-3-yl}benzoyl)pyrrolidin-2-yl]propan-2-ol |
| "A3" | 3-(3-{4-[(2S)-2,4-dimethylpiperazine-1-carbonyl]phenyl}-1,2-oxazol-5-yl)-5-fluoro-6-(2-methoxyethoxy)-1H-indazole |
| "A4" | {4-[5-(6-bromo-1H-indazol-3-yl)-isoxazol-3-yl]-phenyl}-[(S)-2-(1-hydroxy-1-methyl-ethyl)-pyrrolidin-1-yl]-methanone |
| "A5" | 2-[(2S)-1-(4-{5-[5-fluoro-6-(2-methoxyethoxy)-1H-indazol-3-yl]-1,2-oxazol-3-yl}benzoyl)pyrrolidin-2-yl]propan-2-ol |
| "A6" | 4-{5-[5-cyano-6-(2-methoxyethoxy)-1H-indazol-3-yl]-1,2-oxazol-3-yl}-N,N-dimethylbenzamide |
| "A7" | 5-fluoro-3-(3-{4-[(2S)-2-(methanesulfonylmethyl)pyrrolidine-1-carbonyl]phenyl}-1,2-oxazol-5-yl)-6-(2-methoxyethoxy)-1H-indazole |
| "A8" | 2-[(2R)-1-(4-{5-[6-(1-methyl-1H-pyrazol-4-yl)-1H-indazol-3-yl]-1,2-oxazol-3-yl}benzoyl)pyrrolidin-2-yl]propan-2-ol |
| "A9" | 3-(3-{4-[(2S)-2,4-dimethylpiperazine-1-carbonyl]phenyl}-1,2-oxazol-5-yl)-6-(1-methyl-1H-pyrazol-4-yl)-1H-indazole |
| "A10" | 5-chloro-3-(5-{4-[(2S)-2,4-dimethylpiperazine-1-carbonyl]phenyl}-1,2-oxazol-3-yl)-6-(2-methoxyethoxy)-1H-indazole |
| "A11" | 3-(5-(4-[(2S)-2,4-dimethylpiperazine-1-carbonyl]phenyl}-1,2-oxazol-3-yl)-6-(2-methoxyethoxy)-1H-indazole-5-carbonitrile |
| "A12" | 4-{5-[5-chloro-6-(2-methoxyethoxy)-1H-indazol-3-yl]-1,2-oxazol-3-yl}-N,N-dimethylbenzamide |
| "A13" | 5-chloro-6-(2-methoxyethoxy)-3-[3-(6-methylpyridin-3-yl)-1,2-oxazol-5-yl]-1H-indazole |
| "A14" | 5-chloro-6-(2-methoxyethoxy)-3-{3-[4-(1H-1,2,4-triazol-1-yl)phenyl]-1,2-oxazol-5-yl}-1H-indazole |
| "A15" | 5-chloro-3-[3-(4-methanesulfonylphenyl)-1,2-oxazol-5-yl]-6-(2-methoxyethoxy)-1H-indazole |
| "A16" | 5-fluoro-3-[3-(4-methanesulfonylphenyl)-1,2-oxazol-5-yl]-6-(2-methoxyethoxy)-1H-indazole |
| "A17" | N-(4-{5-[5-chloro-6-(2-methoxyethoxy)-1H-indazol-3-yl]-1,2-oxazol-3-yl}phenyl)acetamide |
| "A18" | N-(4-{5-[5-fluoro-6-(2-methoxyethoxy)-1H-indazol-3-yl]-1,2-oxazol-3-yl}phenyl)acetamide |
| "A19" | methyl 3-{3-[4-(dimethylcarbamoyl)phenyl]-1,2-oxazol-5-yl}-1H-indazole-6-carboxylate |
| "A20" | 4-{5-[5-fluoro-6-(2-methoxyethoxy)-1H-indazol-3-yl]-1,2-oxazol-3-yl}-N,N-dimethylbenzamide |
| "A21" | 5-fluoro-6-(2-methoxyethoxy)-3-{3-[4-(1H-1,2,4-triazol-1-yl)phenyl]-1,2-oxazol-5-yl}-1H-indazole |
| "A22" | 5-fluoro-6-(2-methoxyethoxy)-3-[3-(6-methylpyridin-3-yl)-1,2-oxazol-5-yl]-1H-indazole |
| "A23" | N-(2-methoxyethyl)-3-(3-{4-[(2-methoxyethyl)carbamoyl]phenyl}-1,2-oxazol-5-yl)-1H-indazole-6-carboxamide |
| "A24" | 3-[3-(4-dimethylcarbamoyl-phenyl)-isoxazol-5-yl]-1H-indazole-6-carboxylic acid methylamide |
| "A25" | 3-{3-[4-(dimethylcarbamoyl)phenyl]-1,2-oxazol-5-yl}-N-(2-methoxyethyl)-1H-indazole-6-carboxamide |

-continued

| No. | Name |
|---|---|
| "A26" | 5-fluoro-3-{3-[4-(3-fluoroazetidine-1-carbonyl)phenyl]-1,2-oxazol-5-yl}-6-(2-methoxyethoxy)-1H-indazole |
| "A27" | 5-fluoro-3-(3-{4-[(3R)-3-fluoropyrrolidine-1-carbonyl]phenyl}-1,2-oxazol-5-yl)-6-(2-methoxyethoxy)-1H-indazole |
| "A28" | 1-(4-{5-[5-fluoro-6-(2-methoxyethoxy)-1H-indazol-3-yl]-1,2-oxazol-3-yl}benzoyl)azetidine-3-carbonitrile |
| "A29" | 5-fluoro-3-{3-[4-(3-methanesulfonylazetidine-1-carbonyl)phenyl]-1,2-oxazol-5-yl}-6-(2-methoxyethoxy)-1H-indazole |
| "A30" | 4-(4-{5-[5-fluoro-6-(2-methoxyethoxy)-1H-indazol-3-yl]-1,2-oxazol-3-yl}benzoyl)-1lambda6-thiomorpholine-1,1-dione |
| "A31" | N-cyclopropyl-4-{5-[5-fluoro-6-(2-methoxyethoxy)-1H-indazol-3-yl]-1,2-oxazol-3-yl}-N-methylbenzamide |
| "A32" | 5-fluoro-3-(3-{4-[(3S)-3-fluoropyrrolidine-1-carbonyl]phenyl}-1,2-oxazol-5-yl)-6-(2-methoxyethoxy)-1H-indazole |
| "A33" | 5-fluoro-3-{3-[4-(3-methoxyazetidine-1-carbonyl)phenyl]-1,2-oxazol-5-yl}-6-(2-methoxyethoxy)-1H-indazole |
| "A34" | 1-(4-{5-[5-fluoro-6-(2-methoxyethoxy)-1H-indazol-3-yl]-1,2-oxazol-3-yl}benzoyl)-3-methylazetidin-3-ol |
| "A35" | N-[dimethyl(oxo)-lambda6-sulfanylidene]-4-{5-[5-fluoro-6-(2-methoxyethoxy)-1H-indazol-3-yl]-1,2-oxazol-3-yl}benzamide |
| "A36" | 5-fluoro-6-(2-methoxyethoxy)-3-{3-[4-(4-methylpiperazine-1-carbonyl)phenyl]-1,2-oxazol-5-yl}-1H-indazole |
| "A37" | 5-fluoro-6-(2-methoxyethoxy)-3-{3-[4-(4-methylpiperazin-1-yl)phenyl]-1,2-oxazol-5-yl}-1H-indazole |
| "A38" | 3-[3-(6-ethoxypyridin-3-yl)-1,2-oxazol-5-yl]-5-fluoro-6-(2-methoxyethoxy)-1H-indazole |
| "A39" | 5-fluoro-6-(2-methoxyethoxy)-3-{3-[6-(4-methylpiperazin-1-yl)pyridin-3-yl]-1,2-oxazol-5-yl}-1H-indazole |
| "A40" | 5-fluoro-6-(2-methoxyethoxy)-3-(3-{4-[2-(morpholin-4-yl)ethoxy]phenyl}-1,2-oxazol-5-yl)-1H-indazole |
| "A41" | 1-(4-{5-[5-Fluoro-6-(2-methoxy-ethoxy)-1H-indazol-3-yl]-isoxazol-3-yl}-phenyl)-1H-pyridin-2-one |
| "A42" | 3-{3-[4-(1,4-diazepan-1-yl)phenyl]-1,2-oxazol-5-yl}-5-fluoro-6-(2-methoxyethoxy)-1H-indazole |
| "A43" | (4-{3-[5-fluoro-6-(2-methoxy-ethoxy)-1H-indazol-3-yl]-isoxazol-5-yl}-phenyl)-morpholin-4-yl-methanone |
| "A44" | 5-fluoro-6-(2-methoxyethoxy)-3-{3-[4-(1,4-oxazepane-4-carbonyl)phenyl]-1,2-oxazol-5-yl}-1H-indazole |
| "A45" | 5-fluoro-6-(2-methoxyethoxy)-3-(3-{4-[4-(oxetan-3-yl)piperazine-1-carbonyl]phenyl}-1,2-oxazol-5-yl)-1H-indazole |
| "A46" | 5-fluoro-6-(2-methoxyethoxy)-3-{3-[4-(piperazine-1-carbonyl)phenyl]-1,2-oxazol-5-yl}-1H-indazole |
| "A47" | [(4-{5-[5-fluoro-6-(2-methoxyethoxy)-1H-indazol-3-yl]-1,2-oxazol-3-yl}phenyl)imino]dimethyl-lambda6-sulfanone |
| "A48" | 5-fluoro-6-(2-methoxyethoxy)-3-[3-(1,3-thiazol-5-yl)-1,2-oxazol-5-yl]-1H-indazole |
| "A49" | 4-{5-[5-fluoro-6-(3-hydroxy-2-methoxypropoxy)-1H-indazol-3-yl]-1,2-oxazol-3-yl}-N,N-dimethylbenzamide |
| "A50" | 3-(3-{4-[(2S)-2,4-dimethylpiperazine-1-carbonyl]phenyl}-1,2-oxazol-5-yl)-6-(trifluoromethyl)-1H-indazole |
| "A51" | [(2S)-1-(4-{5-[5-fluoro-6-(2-methoxyethoxy)-1H-indazol-3-yl]-1,2-oxazol-3-yl}benzoyl)pyrrolidin-2-yl]methanol |
| "A52" | [(2R)-1-(4-{5-[5-fluoro-6-(2-methoxyethoxy)-1H-indazol-3-yl]-1,2-oxazol-3-yl}benzoyl)pyrrolidin-2-yl]methanol |
| "A53" | 5-fluoro-6-(2-methoxyethoxy)-3-(3-{4-[3-(morpholin-4-yl)azetidine-1-carbonyl]phenyl}-1,2-oxazol-5-yl)-1H-indazole |
| "A54" | [1-(4-{5-[5-fluoro-6-(2-methoxyethoxy)-1H-indazol-3-yl]-1,2-oxazol-3-yl}benzoyl)-4-methylpiperazin-2-yl]methanol |
| "A55" | 5-fluoro-3-(3-(4-[(2R)-2-(methanesulfonylmethyl)pyrrolidine-1-carbonyl]phenyl}-1,2-oxazol-5-yl)-6-(2-methoxyethoxy)-1H-indazole |
| "A56" | 1-(4-{5-[5-fluoro-6-(2-methoxyethoxy)-1H-indazol-3-yl]-1,2-oxazol-3-yl}benzoyl)-3-methylazetidin-3-amine |
| "A57" | 4-[1-(4-{5-[5-fluoro-6-(2-methoxyethoxy)-1H-indazol-3-yl]-1,2-oxazol-3-yl}benzoyl)azetidin-3-yl]-1lambda6-thiomorpholine-1,1-dione |
| "A58" | 2-[(2R)-1-(4-{5-[5-fluoro-6-(2-methoxyethoxy)-1H-indazol-3-yl]-1,2-oxazol-3-yl}benzoyl)azetidin-2-yl]propan-2-ol |
| "A59" | 2-[(2S)-1-(4-{5-[5-fluoro-6-(2-methoxyethoxy)-1H-indazol-3-yl]-1,2-oxazol-3-yl}benzoyl)azetidin-2-yl]propan-2-ol |
| "A60" | 7-(4-{5-[5-fluoro-6-(2-methoxyethoxy)-1H-indazol-3-yl]-1,2-oxazol-3-yl}benzoyl)-2-oxa-7-azaspiro[3.5]nonane |

| No. | Name |
|---|---|
| "A61" | 5-fluoro-6-methoxy-3-(3-{4-[3-(morpholin-4-yl)azetidine-1-carbonyl]phenyl}-1,2-oxazol-5-yl)-1H-indazole |
| "A62" | (5-{5-[5-fluoro-6-(2-methoxy-ethoxy)-1H-indazol-3-yl]-isoxazol-3-yl}-pyridin-2-yl)-((R)-2-hydroxymethyl-pyrrolidin-1-yl)-methanone |
| "A63" | (5-{5-[5-fluoro-6-(2-methoxy-ethoxy)-1H-indazol-3-yl]-isoxazol-3-yl}-pyridin-2-yl)-((S)-2-hydroxymethyl-pyrrolidin-1-yl)-methanone |
| "A64" | (4-{5-[5-chloro-6-(2-methoxy-ethoxy)-1H-indazol-3-yl]-isoxazol-3-yl}-phenyl)-(3-morpholin-4-yl-azetidin-1-yl)-methanone |
| "A65" | (4-{5-[5-chloro-6-(2-methoxy-ethoxy)-1H-indazol-3-yl]-isoxazol-3-yl}-phenyl)-[3-(4-methyl-piperazin-1-yl)-azetidin-1-yl]-methanone |
| "A66" | (4-{5-[5-chloro-6-(2-methoxy-ethoxy)-1H-indazol-3-yl]-isoxazol-3-yl}-phenyl)-((S)-3-hydroxymethyl-morpholin-4-yl)-methanone |
| "A67" | (4-{5-[5-chloro-6-(2-methoxy-ethoxy)-1H-indazol-3-yl]-isoxazol-3-yl}-phenyl)-((R)-3-hydroxymethyl-morpholin-4-yl)-methanone |
| "A68" | (5-{5-[5-fluoro-6-(2-methoxy-ethoxy)-1H-indazol-3-yl]-isoxazol-3-yl}-pyridin-2-yl)-(4-oxetan-3-yl-piperazin-1-yl)-methanone |
| "A69" | (5-{5-[5-fluoro-6-(2-methoxy-ethoxy)-1H-indazol-3-yl]-isoxazol-3-yl}-pyridin-2-yl)-(3-morpholin-4-yl-azetidin-1-yl)-methanone |
| "A70" | (4-{5-[5-fluoro-6-(2-methoxy-ethoxy)-1H-indazol-3-yl]-isoxazol-3-yl}-2-methyl-phenyl)-(cis)-tetrahydro-furo[3,4-c] pyrrol-5-yl-methanone |
| "A71" | (2-fluoro-4-{5-[5-fluoro-6-(2-methoxy-ethoxy)-1H-indazol-3-yl]-isoxazol-3-yl}-phenyl)-(cis)-tetrahydro-furo[3,4-c] pyrrol-5-yl-methanone |
| "A72" | N-[2-(dimethylamino)ethyl]-4-{5-[5-fluoro-6-(2-methoxy-ethoxy)-1H-indazol-3-yl]-1,2-oxazol-3-yl}benzamide |
| "A73" | 4-{5-[5-fluoro-6-(2-methoxyethoxy)-1H-indazol-3-yl]-1,2-oxazol-3-yl}-N-(1-methylazetidin-3-yl)benzamide |
| "A74" | 5-fluoro-6-(2-methoxyethoxy)-3-[3-(4-{2-oxa-6-azaspiro [3.3]heptane-6-carbonyl}phenyl)-1,2-oxazol-5-yl]-1H-indazole |
| "A75" | 5-fluoro-6-(2-methoxyethoxy)-3-(3-{4-[3-(1H-pyrazol-1-yl)azetidine-1-carbonyl]phenyl}-1,2-oxazol-5-yl)-1H-indazole |
| "A76" | 1-(4-{5-[5-fluoro-6-(2-methoxyethoxy)-1H-indazol-3-yl]-1,2-oxazol-3-yl}benzoyl)-N,N-dimethylazetidin-3-amine |
| "A77" | 5-fluoro-6-(2-methoxyethoxy)-3-[3-(4-{6-oxa-2-azaspiro [3.4]octane-2-carbonyl}phenyl)-1,2-oxazol-5-yl]-1H-indazole |
| "A78" | 4-(4-{5-[5-fluoro-6-(2-methoxyethoxy)-1H-indazol-3-yl]-1,2-oxazol-3-yl}benzoyl)-1lambda4-thiomorpholin-1-one |
| "A79" | 5-fluoro-6-(2-methoxyethoxy)-3-[3-(4-{1-oxa-6-azaspiro [3.3]heptane-6-carbonyl}phenyl)-1,2-oxazol-5-yl]-1H-indazole |
| "A80" | 4-(4-{5-[5-fluoro-6-(2-methoxyethoxy)-1H-indazol-3-yl]-1,2-oxazol-3-yl}benzoyl)-1-imino-1lambda6-thiomorpholin-1-one |
| "A81" | 5-fluoro-3-{3-[5-(3-fluoroazetidine-1-carbonyl)pyridin-2-yl]-1,2-oxazol-5-yl}-6-(2-methoxyethoxy)-1H-indazole |
| "A82" | 5-fluoro-6-(2-methoxyethoxy)-3-(3-{5-[3-(morpholin-4-yl)azetidine-1-carbonyl]pyridin-2-yl}-1,2-oxazol-5-yl)-1H-indazole |
| "A83" | 5-fluoro-6-(2-methoxyethoxy)-3-(3-{5-[3-(morpholin-4-yl)azetidine-1-carbonyl]-1,3-thiazol-2-yl}-1,2-oxazol-5-yl)-1H-indazole |
| "A84" | 5-fluoro-6-(2-methoxyethoxy)-3-(3-{4-[3-(morpholin-4-yl)azetidine-1-carbonyl]-1,3-thiazol-2-yl}-1,2-oxazol-5-yl)-1H-indazole |
| "A85" | 5-fluoro-3-(3-{4-[3-(1H-imidazol-1-yl)azetidine-1-carbonyl] phenyl}-1,2-oxazol-5-yl)-6-(2-methoxyethoxy)-1H-indazole |
| "A86" | 5-fluoro-3-{3-[5-(3-fluoroazetidine-1-carbonyl)-1,3-thiazol-2-yl]-1,2-oxazol-5-yl}-6-(2-methoxyethoxy)-1H-indazole |
| "A87" | 5-fluoro-3-{3-[4-(3-fluoroazetidine-1-carbonyl)-1,3-thiazol-2-yl]-1,2-oxazol-5-yl}-6-(2-methoxyethoxy)-1H-indazole |
| "A88" | 5-fluoro-6-(2-methoxyethoxy)-3-[3-(4-{6-methyl-2,6-diazaspiro[3.3]heptane-2-carbonyl}phenyl)-1,2-oxazol-5-yl]-1H-indazole |

| No. | Name |
|---|---|
| "A89" | (cis)-1-(4-{5-[5-fluoro-6-(2-methoxyethoxy)-1H-indazol-3-yl]-1,2-oxazol-3-yl}benzoyl)-octahydropyrrolo[3,4-b] pyrrol-6-one |
| "A90" | N-{[(2S)-1-(4-{5-[5-fluoro-6-(2-methoxyethoxy)-1H-indazol-3-yl]-1,2-oxazol-3-yl}benzoyl)pyrrolidin-2-yl] methyl}methanesulfonamide |
| "A91" | 6-{5-[5-fluoro-6-(2-methoxyethoxy)-1H-indazol-3-yl]-1,2-oxazol-3-yl}-N,N-dimethylpyridine-3-carboxamide |
| "A92" | 2-{5-[5-fluoro-6-(2-methoxyethoxy)-1H-indazol-3-yl]-1,2-oxazol-3-yl}-N,N-dimethyl-1,3-thiazole-5-carboxamide |
| "A93" | 2-{5-[5-fluoro-6-(2-methoxyethoxy)-1H-indazol-3-yl]-1,2-oxazol-3-yl}-N,N-dimethyl-1,3-thiazole-4-carboxamide |
| "A94" | N-{[(2R)-1-(4-{5-[5-fluoro-6-(2-methoxyethoxy)-1H-indazol-3-yl]-1,2-oxazol-3-yl}benzoyl)pyrrolidin-2-yl] methyl}methanesulfonamide |
| "A95" | [(2S)-1-(4-{5-[5-fluoro-6-(2-methoxyethoxy)-1H-indazol-3-yl]-1,2-oxazol-3-yl}benzoyl)azetidin-2-yl]methan |
| "A96" | 1-(5-{5-[5-fluoro-6-(2-methoxy-ethoxy)-1H-indazol-3-yl]-isoxazol-3-yl}-pyridine-2-carbonyl)-azetidine-3-carbonitrile |
| "A97" | [(2R)-1-(4-{5-[5-fluoro-6-(2-methoxyethoxy)-1H-indazol-3-yl]-1,2-oxazol-3-yl}benzoyl)azetidin-2-yl]methanol |
| "A98" | (3-fluoro-azetidin-1-yl)-(5-{5-[5-fluoro-6-(2-methoxy-ethoxy)-1H-indazol-3-yl]-isoxazol-3-yl}-pyridin-2-yl)-methanone |
| "A99" | 5-{5-[5-fluoro-6-(2-methoxy-ethoxy)-1H-indazol-3-yl]-isoxazol-3-yl}-pyridine-2-carboxylic acid dimethylamide |
| "A100" | 5-fluoro-3-(3-{6-[(3R)-3-fluoropyrrolidine-1-carbonyl] pyridin-3-yl}-1,2-oxazol-5-yl)-6-(2-methoxyethoxy)-1H-indazole |
| "A101" | 5-fluoro-3-[3-(4-{3-fluoro-[1,3'-biazetidine]-1'-carbonyl} phenyl)-1,2-oxazol-5-yl]-6-(2-methoxyethoxy)-1H-indazole |
| "A102" | 5-fluoro-6-(2-methoxyethoxy)-3-(3-{4-[3-(4-methylpiperazin-1-yl)azetidine-1-carbonyl]phenyl}-1,2-oxazol-5-yl)-1H-indazole |
| "A103" | 1-[1-(4-{5-[5-fluoro-6-(2-methoxyethoxy)-1H-indazol-3-yl]-1,2-oxazol-3-yl}benzoyl)azetidin-3-yl]piperidin-4-ol |
| "A104" | 5-fluoro-6-(2-methoxyethoxy)-3-{3-[4-(morpholine-4-carbonyl)phenyl]-1,2-oxazol-5-yl}-1H-indazole |
| "A105" | [(3R)-4-(4-{5-[5-fluoro-6-(2-methoxyethoxy)-1H-indazol-3-yl]-1,2-oxazol-3-yl}benzoyl)morpholin-3-yl]methanol |
| "A106" | [(3S)-4-(4-{5-[5-fluoro-6-(2-methoxyethoxy)-1H-indazol-3-yl]-1,2-oxazol-3-yl}benzoyl)morpholin-3-yl]methanol |
| "A107" | 2-[(2S)-1-(5-{5-[5-fluoro-6-(2-methoxyethoxy)-1H-indazol-3-yl]-1,2-oxazol-3-yl}pyridine-2-carbonyl)pyrrolidin-2-yl] propan-2-ol |
| "A108" | 6-(4-{5-[5-fluoro-6-(2-methoxyethoxy)-1H-indazol-3-yl]-1,2-oxazol-3-yl}benzoyl)-3lambda6-thia-6-azabicyclo [3.1.1]heptane-3,3-dione |
| "A109" | (5-{5-[5-fluoro-6-(2-methoxy-ethoxy)-1H-indazol-3-yl]-isoxazol-3-yl}-pyridin-2-yl)-[(R)-2-(1-hydroxy-1-methyl-ethyl)-pyrrolidin-1-yl]-methanone |
| "A110" | 5-fluoro-6-(2-methoxyethoxy)-3-(3-{4-[(3S)-3-(methoxy-methyl)morpholine-4-carbonyl]phenyl}-1,2-oxazol-5-yl)-1H-indazole |
| "A111" | 5-fluoro-6-(2-methoxyethoxy)-3-(3-{4-[(3R)-3-(methoxy-methyl)morpholine-4-carbonyl]phenyl}-1,2-oxazol-5-yl)-1H-indazole |
| "A112" | 5-fluoro-6-(2-methoxyethoxy)-3-[3-(4-{6-oxa-1-azaspiro [3.3]heptane-1-carbonyl}phenyl)-1,2-oxazol-5-yl]-1H-indazole |
| "A113" | (4-{3-[5-fluoro-6-(2-methoxy-ethoxy)-1H-indazol-3-yl]-isoxazol-5-yl}-phenyl)-(4-methyl-piperazin-1-yl)-methanone |
| "A114" | 5-fluoro-6-(2-methoxyethoxy)-3-(3-{4-[(3R)-3-methyl-morpholine-4-carbonyl]phenyl}-1,2-oxazol-5-yl)-1H-indazole |
| "A115" | 5-fluoro-6-(2-methoxyethoxy)-3-(3-{4-[(3S)-3-methyl-morpholine-4-carbonyl]phenyl}-1,2-oxazol-5-yl)-1H-indazole |
| "A116" | 4-(4-{5-[5-fluoro-6-(2-methoxyethoxy)-1H-indazol-3-yl]-1,2-oxazol-3-yl}benzoyl)-1-methylpiperazin-2-one |
| "A117" | 5-fluoro-3-(3-{4-[(2S)-2-(methanesulfonylmethyl) pyrrolidine-1-carbonyl]phenyl}-1,2-oxazol-5-yl)-6-methoxy-1H-indazole |
| "A118" | (5-{5-[5-fluoro-6-(2-methoxy-ethoxy)-1H-indazol-3-yl]-isoxazol-3-yl}-pyridin-2-yl)-[(S)-2-(1-hydroxy-1-methyl-ethyl)-azetidin-1-yl]-methanone |

-continued

| No. | Name |
|---|---|
| "A119" | (5-{5-[5-fluoro-6-(2-methoxy-ethoxy)-1H-indazol-3-yl]-isoxazol-3-yl}-pyridin-2-yl)-[(R)-2-(1-hydroxy-1-methyl-ethyl)-azetidin-1-yl]-methanone |
| "A120" | 5-fluoro-6-(2-methoxyethoxy)-3-(3-{4-[3-(pyridin-4-yl) azetidine-1-carbonyl]phenyl}-1,2-oxazol-5-yl)-1H-indazole |
| "A121" | 4-(4-{5-[5-fluoro-6-(2-methoxyethoxy)-1H-indazol-3-yl]-1,2-oxazol-3-yl}benzoyl)-3-methyl-1lambda6-thiomorpholine-1,1-dione |
| "A122" | 4-(4-{5-[5-fluoro-6-(2-methoxyethoxy)-1H-indazol-3-yl]-1,2-oxazol-3-yl}phenyl)-1lambda6-thiomorpholine-1,1-dione |
| "A123" | 5-fluoro-6-(2-methoxyethoxy)-3-{3-[4-(4-methyl-1,4-diazepan-1-yl)phenyl]-1,2-oxazol-5-yl}-1H-indazole |
| "A124" | 3-(3-{4-[(cis)-4-methyl-octahydro-1H-pyrrolo[3,2-b] pyridin-1-yl]phenyl}-1,2-oxazol-5-yl)-5-fluoro-6-(2-methoxyethoxy)-1H-indazole |
| "A125" | 3-(3-{4-[(cis)-4-methyl-octahydropyrrolo[3,2-b]pyrrol-1-yl]phenyl}-1,2-oxazol-5-yl)-5-fluoro-6-(2-methoxyethoxy)-1H-indazole |
| "A126" | 3-(3-{4-[(trans)-4-methyl-octahydropyrrolo[3,2-b]pyrrol-1-yl]phenyl}-1,2-oxazol-5-yl)-5-fluoro-6-(2-methoxyethoxy)-1H-indazole |
| "A127" | 4-(4-{5-[5-fluoro-6-(2-methoxyethoxy)-1H-indazol-3-yl]-1,2-oxazol-3-yl}phenyl)-1lambda4-thiomorpholin-1-one |
| "A128" | 1-(4-{5-[5-fluoro-6-(2-methoxyethoxy)-1H-indazol-3-yl]-1,2-oxazol-3-yl}phenyl)piperidin-4-ol |
| "A129" | 1-[(4-{5-[5-fluoro-6-(2-methoxyethoxy)-1H-indazol-3-yl]-1,2-oxazol-3-yl}phenyl)imino]-1lambda6-thiomorpholin-1-one |
| "A130" | 5-fluoro-6-(2-methoxy-ethoxy)-3-[3-(6-methoxy-pyridin-3-yl)-isoxazol-5-yl]-1H-indazole |
| "A131" | 4-(5-{5-[5-fluoro-6-(2-methoxyethoxy)-1H-indazol-3-yl]-1,2-oxazol-3-yl}pyridin-2-yl)-1lambda6-thiomorpholine-1,1-dione |
| "A132" | 4-[2-(4-{5-[5-fluoro-6-(2-methoxyethoxy)-1H-indazol-3-yl]-1,2-oxazol-3-yl}phenoxy)ethyl]-1lambda6-thiomorpholine-1,1-dione |
| "A133" | 5-fluoro-6-(2-methoxyethoxy)-3-(3-{4-[2-(4-methyl-piperazin-1-yl)ethoxy]phenyl}-1,2-oxazol-5-yl)-1H-indazole |
| "A134" | 5-fluoro-6-(2-methoxyethoxy)-3-(3-{4-[2-(piperazin-1-yl)ethoxy]phenyl}-1,2-oxazol-5-yl)-1H-indazole |
| "A135" | 3-{5-[5-fluoro-6-(2-methoxy-ethoxy)-1H-indazol-3-yl]-isoxazol-3-yl}-N,N-dimethyl-benzamide |
| "A136" | 2-(4-{5-[5-fluoro-6-(2-methoxy-ethoxy)-1H-indazol-3-yl]-isoxazol-3-yl}-phenyl)-6-methyl-2H-pyridazin-3-one |
| "A137" | 5-fluoro-6-(2-methoxy-ethoxy)-3-[3-(1-methyl-1H-pyrazol-4-yl)-isoxazol-5-yl]-1H-indazole |
| "A138" | 2-(4-{5-[5-fluoro-6-(2-methoxyethoxy)-1H-indazol-3-yl]-1,2-oxazol-3-yl}phenyl)-1lambda6,2-thiazolidine-1,1-dione |
| "A139" | 4-(4-{5-[5-fluoro-6-(2-methoxyethoxy)-1H-indazol-3-yl]-1,2-oxazol-3-yl}phenyl)morpholin-3-one |
| "A140" | 4-(5-{5-[5-fluoro-6-(2-methoxyethoxy)-1H-indazol-3-yl]-1,2-oxazol-3-yl}pyridin-2-yl)-1lambda4-thiomorpholin-1-one |
| "A141" | 5-fluoro-6-(2-methoxyethoxy)-3-{3-[6-(morpholin-4-yl) pyridin-3-yl]-1,2-oxazol-5-yl}-1H-indazole |
| "A142" | 2-(4-{5-[5-fluoro-6-(2-methoxyethoxy)-1H-indazol-3-yl]-1,2-oxazol-3-yl}phenyl)-2,3-dihydropyridazin-3-one |
| "A143" | 5-fluoro-6-(2-methoxyethoxy)-3-{3-[4-(pyridin-2-yloxy) phenyl]-1,2-oxazol-5-yl}-1H-indazole |
| "A144" | 4-{5-[5-fluoro-6-(2-methoxyethoxy)-1H-indazol-3-yl]-1,2-oxazol-3-yl}-N,N-dimethylbenzene-1-sulfonamide |
| "A145" | 5-fluoro-6-(2-methoxyethoxy)-3-(3-{6-[3-(morpholin-4-yl)azetidin-1-yl]pyridin-3-yl}-1,2-oxazol-5-yl)-1H-indazole |
| "A146" | (4-{3-[5-fluoro-6-(2-methoxy-ethoxy)-1H-indazol-3-yl]-isoxazol-5-yl}-phenyl)-(3-morpholin-4-yl-azetidin-1-yl)-methanone |
| "A147" | (4-{3-[5-fluoro-6-(2-methoxy-ethoxy)-1H-indazol-3-yl]-isoxazol-5-yl}-phenyl)-[(R)-2-(1-hydroxy-1-methyl-ethyl)-azetidin-1-yl]-methanone |
| "A148" | (4-{3-[5-fluoro-6-(2-methoxy-ethoxy)-1H-indazol-3-yl]-isoxazol-5-yl}-phenyl)-[(S)-2-(1-hydroxy-1-methyl-ethyl)-azetidin-1-yl]-methanone |
| "A149" | 5-fluoro-6-(2-methoxyethoxy)-3-(3-{4-[3-(pyridin-2-yl) azetidine-1-carbonyl]phenyl}-1,2-oxazol-5-yl)-1H-indazole |

-continued

| No. | Name |
|---|---|
| "A150" | 4-{5-[5-fluoro-6-(2-methoxyethoxy)-1H-indazol-3-yl]-1,2-oxazol-3-yl}-N-(2-methanesulfonylethyl)-N-methyl-benzamide |
| "A151" | 6-(4-{5-[5-fluoro-6-(2-methoxyethoxy)-1H-indazol-3-yl]-1,2-oxazol-3-yl}benzoyl)-2lambda6-thia-6-azaspiro[3.3]heptane-2,2-dione |
| "A152" | 5-fluoro-3-(3-{4-[(2S)-2-(methanesulfonylmethyl)azetidine-1-carbonyl]phenyl}-1,2-oxazol-5-yl)-6-(2-methoxyethoxy)-1H-indazole |
| "A153" | 5-fluoro-6-(2-methoxyethoxy)-3-(3-{4-[3-(morpholin-4-yl) pyrrolidine-1-carbonyl]phenyl}-1,2-oxazol-5-yl)-1H-indazole |
| "A154" | 5-fluoro-3-(3-{4-[(2R)-2-(methanesulfonylmethyl)azetidine-1-carbonyl]phenyl}-1,2-oxazol-5-yl)-6-(2-methoxyethoxy)-1H-indazole |
| "A155" | 5-(4-{5-[5-fluoro-6-(2-methoxyethoxy)-1H-indazol-3-yl]-1,2-oxazol-3-yl}benzoyl)-2,8-dioxa-5-azaspiro[3.5]nonane |
| "A156" | N-[(1H-1,3-benzodiazol-2-yl)methyl]-4-{5-[5-fluoro-6-(2-methoxyethoxy)-1H-indazol-3-yl]-1,2-oxazol-3-yl} benzamide |
| "A157" | 7-(4-{5-[5-fluoro-6-(2-methoxyethoxy)-1H-indazol-3-yl]-1,2-oxazol-3-yl}benzoyl)-2-oxa-7-azaspiro[4.4]nonane |
| "A158" | 5-fluoro-6-(2-methoxyethoxy)-3-[3-(4-{2-oxa-6-azaspiro [3.4]octane-6-carbonyl}phenyl)-1,2-oxazol-5-yl]-1H-indazole |
| "A159" | 2-(4-{5-[5-fluoro-6-(2-methoxyethoxy)-1H-indazol-3-yl]-1,2-oxazol-3-yl}benzoyl)-8-oxa-2-azaspiro[4.5]decane |
| "A160" | 5-fluoro-6-(2-methoxyethoxy)-3-[3-(4-{2-methyl-2,6-diazaspiro[3.4]octane-6-carbonyl}phenyl)-1,2-oxazol-5-yl]-1H-indazole |
| "A161" | 5-fluoro-6-(2-methoxyethoxy)-3-[3-(4-{6-oxa-3-azabicyclo [3.1.1]heptane-3-carbonyl}phenyl)-1,2-oxazol-5-yl]-1H-indazole |
| "A162" | 5-fluoro-6-(2-methoxyethoxy)-3-(3-{4-[(1S,4S)-2-oxa-5-azabicyclo[2.2.1]heptane-5-carbonyl]phenyl}-1,2-oxazol-5-yl)-1H-indazole |
| "A163" | 5-fluoro-6-(2-methoxyethoxy)-3-(3-{4-[(1R,4R)-2-oxa-5-azabicyclo[2.2.1]heptane-5-carbonyl]phenyl}-1,2-oxazol-5-yl)-1H-indazole |
| "A164" | 4-{5-[5-fluoro-6-(2-methoxyethoxy)-1H-indazol-3-yl]-1,2-oxazol-3-yl}-N-[2-methyl-2-(morpholin-4-yl)propyl] benzamide |
| "A165" | 2-(4-{5-[5-fluoro-6-(2-methoxyethoxy)-1H-indazol-3-yl]-1,2-oxazol-3-yl}benzoyl)-7-oxa-2-azaspiro[3.5]nonane |
| "A166" | 5-fluoro-6-(2-methoxyethoxy)-3-(3-{4-[3-(3-methyl-1,2,4-oxadiazol-5-yl)azetidine-1-carbonyl]phenyl}-1,2-oxazol-5-yl)-1H-indazole |
| "A167" | (4-{5-[5-chloro-6-(2-methoxy-ethoxy)-1H-indazol-3-yl]-isoxazol-3-yl}-phenyl)-(4-methyl-piperazin-1-yl)-methanone |
| "A168" | (2-fluoro-4-{5-[5-fluoro-6-(2-methoxy-ethoxy)-1H-indazol-3-yl]-isoxazol-3-yl}-phenyl)-(3-morpholin-4-yl-azetidin-1-yl)-methanone |
| "A169" | (4-{5-[5-fluoro-6-(2-methoxy-ethoxy)-1H-indazol-3-yl]-isoxazol-3-yl}-2-methyl-phenyl)-(6-oxa-1-aza-spiro [3.3]hept-1-yl)-methanone |
| "A170" | (2-fluoro-4-{5-[5-fluoro-6-(2-methoxy-ethoxy)-1H-indazol-3-yl]-isoxazol-3-yl}-phenyl)-(6-oxa-1-aza-spiro[3.3]hept-1-yl)-methanone |
| "A171" | (4-{5-[5-fluoro-6-(2-methoxy-ethoxy)-1H-indazol-3-yl]-isoxazol-3-yl}-2-methyl-phenyl)-(3-morpholin-4-yl-azetidin-1-yl)-methanone |
| "A172" | 5-fluoro-6-(2-methoxyethoxy)-3-(3-{4-[3-(pyrimidin-4-yl)azetidine-1-carbonyl]phenyl}-1,2-oxazol-5-yl)-1H-indazole |
| "A173" | 5-fluoro-6-(2-methoxyethoxy)-3-(3-{4-[3-(2-methyl-pyrimidin-4-yl)azetidine-1-carbonyl]phenyl}-1,2-oxazol-5-yl)-1H-indazole |
| "A174" | 5-fluoro-6-(2-methoxyethoxy)-3-(3-{4-[2-methyl-4-(oxetan-3-yl)piperazine-1-carbonyl]phenyl}-1,2-oxazol-5-yl)-1H-indazole |
| "A175" | 5-fluoro-6-(2-methoxyethoxy)-3-(3-{4-[4-(oxolan-3-yl) piperazine-1-carbonyl]phenyl}-1,2-oxazol-5-yl)-1H-indazole |
| "A176" | 7-(4-{5-[5-fluoro-6-(2-methoxyethoxy)-1H-indazol-3-yl]-1,2-oxazol-3-yl}benzoyl)-2-methyl-2,7-diazaspiro[3.5]nonane |

| No. | Name |
|---|---|
| "A177" | 5-fluoro-6-(2-methoxyethoxy)-3-(3-{4-[3-(pyrrolidin-1-yl)azetidine-1-carbonyl]phenyl}-1,2-oxazol-5-yl)-1H-indazole |
| "A178" | 5-fluoro-6-(2-methoxyethoxy)-3-(3-{4-[3-(pyrrolidin-1-yl)azetidine-1-carbonyl]phenyl}-1,2-oxazol-5-yl)-1H-indazole |
| "A179" | 3-(3-{4-[4-(cyclopropylmethyl)piperazine-1-carbonyl]phenyl}-1,2-oxazol-5-yl)-5-fluoro-6-(2-methoxyethoxy)-1H-indazole |
| "A180" | 5-fluoro-6-(2-methoxyethoxy)-3-(3-{4-[(2R)-2-methyl-morpholine-4-carbonyl]phenyl}-1,2-oxazol-5-yl)-1H-indazole |
| "A181" | 1-(4-{5-[5-fluoro-6-(2-methoxyethoxy)-1H-indazol-3-yl]-1,2-oxazol-3-yl}benzoyl)-N,N,3-trimethylazetidin-3-amine |
| "A182" | 5-fluoro-6-(2-methoxyethoxy)-3-[3-(4-{3-oxa-6-azabicyclo[3.1.1]heptane-6-carbonyl}phenyl)-1,2-oxazol-5-yl]-1H-indazole |
| "A183" | 5-fluoro-6-(2-methoxyethoxy)-3-[3-(4-{1H,2H,3H-pyrrolo[3,4-c]pyridine-2-carbonyl}phenyl)-1,2-oxazol-5-yl]-1H-indazole |
| "A184" | (4-{5-[5-fluoro-6-(2-methoxy-ethoxy)-1H-indazol-3-yl]-isoxazol-3-yl}-phenyl)-((R)-3-methanesulfonylmethyl-morpholin-4-yl)-methanone |
| "A185" | 5-fluoro-6-(2-methoxyethoxy)-3-[3-(4-{4-[(3R)-oxolan-3-yl]piperazine-1-carbonyl}phenyl)-1,2-oxazol-5-yl]-1H-indazole |
| "A186" | 5-fluoro-6-(2-methoxyethoxy)-3-[3-(4-{4-[(3S)-oxolan-3-yl]piperazine-1-carbonyl}phenyl)-1,2-oxazol-5-yl]-1H-indazole |
| "A187" | 5-fluoro-6-(2-methoxyethoxy)-3-{3-[4-(3-{2-oxa-6-azaspiro[3.3]heptan-6-yl}azetidine-1-carbonyl)phenyl]-1,2-oxazol-5-yl}-1H-indazole |
| "A188" | 5-fluoro-6-(2-methoxyethoxy)-3-(3-{4-[4-(oxan-4-yl)piperazine-1-carbonyl]phenyl}-1,2-oxazol-5-yl)-1H-indazole |
| "A189" | 5-fluoro-6-(2-methoxyethoxy)-3-(3-{4-[(2S)-2-methyl-morpholine-4-carbonyl]phenyl}-1,2-oxazol-5-yl)-1H-indazole |
| "A190" | 5-fluoro-6-(2-methoxyethoxy)-3-(3-{4-[(2R)-2-methyl-4-(oxetan-3-yl)piperazine-1-carbonyl]phenyl}-1,2-oxazol-5-yl)-1H-indazole |
| "A191" | 5-fluoro-6-(2-methoxyethoxy)-3-(3-{4-[(2S)-2-methyl-4-(oxetan-3-yl)piperazine-1-carbonyl]phenyl}-1,2-oxazol-5-yl)-1H-indazo |
| "A192" | 5-fluoro-6-(2-methoxyethoxy)-3-(3-{4-[3-(pyridin-3-yl)azetidine-1-carbonyl]phenyl}-1,2-oxazol-5-yl)-1H-indazole |
| "A193" | (4-{5-[5-fluoro-6-(2-methoxy-ethoxy)-1H-indazol-3-yl]-isoxazol-3-yl}-2-methyl-phenyl)-(4-oxetan-3-yl-piperazin-1-yl)-methanone |
| "A194" | (4-{5-[5-chloro-6-(2-methoxy-ethoxy)-1H-indazol-3-yl]-isoxazol-3-yl}-phenyl)-(4-oxetan-3-yl-piperazin-1-yl)-methanone |
| "A195" | 5-fluoro-6-(2-methoxyethoxy)-3-[3-(4-{3-[4-(2-methoxy-ethyl)-4H-1,2,4-triazol-3-yl]azetidine-1-carbonyl}phenyl)-1,2-oxazol-5-yl]-1H-indazole |
| "A196" | (2-fluoro-4-{5-[5-fluoro-6-(2-methoxy-ethoxy)-1H-indazol-3-yl]-isoxazol-3-yl}-phenyl)-(4-oxetan-3-yl-piperazin-1-yl)-methanone |
| "A197" | 5-fluoro-6-(2-methoxyethoxy)-3-[3-(4-{3-[4-(oxetan-3-yl)piperazin-1-yl]azetidine-1-carbonyl}phenyl)-1,2-oxazol-5-yl]-1H-indazole |
| "A198" | 5-fluoro-6-(2-methoxyethoxy)-3-(3-{4-[4-(oxetan-3-yl)-1,4-diazepane-1-carbonyl]phenyl}-1,2-oxazol-5-yl)-1H-indazole |
| "A199" | 2-(4-{5-[5-fluoro-6-(2-methoxyethoxy)-1H-indazol-3-yl]-1,2-oxazol-3-yl}benzoyl)-7-(oxetan-3-yl)-2,7-diazaspiro[3.5]nonane |
| "A200" | 5-fluoro-6-(2-methoxyethoxy)-3-[3-(4-{3-[(3S)-3-methyl-morpholin-4-yl]azetidine-1-carbonyl}phenyl)-1,2-oxazol-5-yl]-1H-indazole |
| "A201" | 5-fluoro-6-(2-methoxyethoxy)-3-[3-(4-{3-[(3R)-3-methyl-morpholin-4-yl]azetidine-1-carbonyl}phenyl)-1,2-oxazol-5-yl]-1H-indazole |
| "A202" | 3-(3-{4-[(cis)-hexahydro-1H-furo[3,4-c]pyrrole-5-carbonyl]phenyl}-1,2-oxazol-5-yl)-5-fluoro-6-(2-methoxyethoxy)-1H-indazole |

| No. | Name |
|---|---|
| "A203" | (cis)-5-(4-{5-[5-fluoro-6-(2-methoxyethoxy)-1H-indazol-3-yl]-1,2-oxazol-3-yl}benzoyl)-octahydropyrrolo[2,3-c]pyrrol-2-one |
| "A204" | 4-[1-(4-{5-[5-fluoro-6-(2-methoxyethoxy)-1H-indazol-3-yl]-1,2-oxazol-3-yl}benzoyl)azetidin-3-yl]morpholin-3-one |
| "A205" | 2-{[5-fluoro-3-(3-{4-[4-(oxetan-3-yl)piperazine-1-carbonyl]phenyl}-1,2-oxazol-5-yl)-1H-indazol-6-yl]oxy}ethan-1-ol |
| "A206" | 1-(4-{5-[5-fluoro-6-(2-methoxyethoxy)-1H-indazol-3-yl]-1,2-oxazol-3-yl}benzoyl)-3-(pyridin-4-yl)azetidin-3-ol |
| "A207" | 5-fluoro-6-(2-methoxyethoxy)-3-[3-(4-{5H,6H,7H-pyrrolo[3,4-d]pyrimidine-6-carbonyl}phenyl)-1,2-oxazol-5-yl]-1H-indazole |
| "A208" | 5-fluoro-6-(2-methoxyethoxy)-3-[3-(4-{1H,4H,5H,6H-pyrrolo[3,4-c]pyrazole-5-carbonyl}phenyl)-1,2-oxazol-5-yl]-1H-indazole |
| "A209" | 2-{[5-fluoro-3-(3-{4-[3-(morpholin-4-yl)azetidine-1-carbonyl]phenyl}-1,2-oxazol-5-yl)-1H-indazol-6-yl]oxy}ethan-1-ol |
| "A210" | 5-fluoro-6-(2-methoxyethoxy)-3-[3-(4-{3-[(2S)-2-methylmorpholin-4-yl]azetidine-1-carbonyl}phenyl)-1,2-oxazol-5-yl]-1H-indazole |
| "A211" | 5-fluoro-6-(2-methoxyethoxy)-3-[3-(4-{3-[(2R)-2-methylmorpholin-4-yl]azetidine-1-carbonyl}phenyl)-1,2-oxazol-5-yl]-1H-indazole |
| "A212" | 5-fluoro-6-(2-methoxyethoxy)-3-(3-{4-[3-(pyrimidin-5-yl)azetidine-1-carbonyl]phenyl}-1,2-oxazol-5-yl)-1H-indazole |
| "A213" | 5-fluoro-6-(2-methoxyethoxy)-3-[3-(4-{1-methyl-1H,4H,5H,6H-pyrrolo[3,4-c]pyrazole-5-carbonyl}phenyl)-1,2-oxazol-5-yl]-1H-indazole |
| "A214" | 3-(3-{4-[(cis)-octahydropyrano[3,4-c]pyrrole-2-carbonyl]phenyl}-1,2-oxazol-5-yl)-5-fluoro-6-(2-methoxyethoxy)-1H-indazole |
| "A215" | 3-(3-{4-[(cis)-octahydrofuro[3,4-c]pyridine-5-carbonyl]phenyl}-1,2-oxazol-5-yl)-5-fluoro-6-(2-methoxyethoxy)-1H-indazole |
| "A216" | 3-(3-{4-[(cis)-5-(oxetan-3-yl)-octahydropyrrolo[3,4-c]pyrrole-2-carbonyl]phenyl}-1,2-oxazol-5-yl)-5-fluoro-6-(2-methoxyethoxy)-1H-indazole |
| "A217" | (cis)-5-(4-{5-[5-fluoro-6-(2-methoxyethoxy)-1H-indazol-3-yl]-1,2-oxazol-3-yl}benzoyl)-hexahydro-1H-2lambda6-thieno[3,4-c]pyrrole-2,2-dione |
| "A218" | 5-fluoro-6-(2-methoxyethoxy)-3-(3-{4-[3-(1-methyl-1H-pyrazol-4-yl)azetidine-1-carbonyl]phenyl}-1,2-oxazol-5-yl)-1H-indazole |
| "A219" | {4-[5-(5-Fluoro-6-methoxy-1H-indazol-3-yl)-isoxazol-3-yl]-phenyl}-(4-oxetan-3-yl-piperazin-1-yl)-methanone |
| "A220" | {4-[5-(5-Fluoro-6-methoxy-1H-indazol-3-yl)-isoxazol-3-yl]-phenyl}-(cis)-tetrahydro-furo[3,4-c]pyrrol-5-yl-methanone |
| "A221" | 1-(4-{5-[5-fluoro-6-(2-methoxyethoxy)-1H-indazol-3-yl]-1,2-oxazol-3-yl}benzoyl)-3-(pyridin-3-yl)azetidin-3-ol |
| "A222" | {[1-(4-{5-[5-fluoro-6-(2-methoxyethoxy)-1H-indazol-3-yl]-1,2-oxazol-3-yl}benzoyl)pyrrolidin-2-yl]methyl}(methyl)amine |
| "A223" | 3-(3-{4-[(cis)-octahydropyrrolo[3,4-c]pyrrole-2-carbonyl]phenyl}-1,2-oxazol-5-yl)-5-fluoro-6-(2-methoxyethoxy)-1H-indazole |
| "A224" | 2-[(5-fluoro-3-{3-[4-(piperazine-1-carbonyl)phenyl]-1,2-oxazol-5-yl}-1H-indazol-6-yl)oxy]ethan-1-ol |
| "A225" | {4-[5-(5-fluoro-6-methoxy-1H-indazol-3-yl)-isoxazol-3-yl]-phenyl}-piperazin-1-yl-methanone |
| "A226" | (4-{5-[5-fluoro-6-(2-methoxyethoxy)-1H-indazol-3-yl]-1,2-oxazol-3-yl}phenyl)(imino)methyl-lambda6-sulfanone |
| "A227" | 5-fluoro-6-(2-methoxyethoxy)-3-{3-[4-(morpholine-4-sulfonyl)phenyl]-1,2-oxazol-5-yl}-1H-indazole |
| "A228" | 2-[4-(4-{5-[5-fluoro-6-(2-methoxyethoxy)-1H-indazol-3-yl]-1,2-oxazol-3-yl}benzoyl)piperazin-1-yl]propane-1,3-diol |
| "A229" | 6-ethoxy-5-fluoro-3-(3-{4-[4-(oxetan-3-yl)piperazine-1-carbonyl]phenyl}-1,2-oxazol-5-yl)-1H-indazole |
| "A230" | 3-{3-[4-(3,3-dimethyl-piperidin-4-yl)-phenyl]-isoxazol-5-yl}-5-fluoro-6-(2-methoxy-ethoxy)-1H-indazole |
| "A231" | 5-fluoro-6-(2-methoxy-ethoxy)-3-{3-[4-(1,3,3-trimethyl-piperidin-4-yl)-phenyl]-isoxazol-5-yl}-1H-indazole |
| "A232" | 5-fluoro-6-(2-methoxyethoxy)-3-(3-{4-[(2,2,3,3,5,5,6,6-$^{2}H_{8}$)piperazine-1-carbonyl]phenyl}-1,2-oxazol-5-yl)-1H-indazole |

-continued

| No. | Name |
|---|---|
| "A233" | 5-fluoro-6-(2-methoxyethoxy)-3-(3-{4-[4-(oxetan-3-yl)(2,2,3,3,5,5,6,6-$^2H_8$)piperazine-1-carbonyl]phenyl}-1,2-oxazol-5-yl)-1H-indazole, and |
| "A234" | 2-{[5-fluoro-3-(3-{4-[4-(oxetan-3-yl)(2,2,3,3,5,5,6,6-$^2$H8)piperazine-1-carbonyl]phenyl}-1,2-oxazol-5-yl)-1H-indazol-6-yl]oxy}ethan-1-ol |

or pharmaceutically acceptable solvates, salts, tautomers, and stereoisomers thereof including mixtures thereof in all ratios.

3. A medicament, comprising:

at least one compound of the formula Ib according to claim 1 and/or pharmaceutically acceptable salts, solvates, tautomers, and stereoisomers thereof, including mixtures thereof in all ratios, and optionally a pharmaceutically acceptable carrier, excipient, or vehicle.

4. A method, comprising:

administering, to a patient in need thereof, a compound of the formula Ib according to claim 1 pharmaceutically acceptable salts, solvates, tautomers, and stereoisomers thereof, including mixtures thereof in all ratios, for the treatment of cancer.

5. The method according to claim 4, wherein the cancer is a gastrointestinal stromal tumor.

6. The medicament of claim 3, further comprising at least one medicament active ingredient.

7. A kit, consisting of:

separate packs of (a) an effective amount of a compound of the formula Ib according to claim 5 and/or pharmaceutically acceptable salts, solvates, salts, and stereoisomers thereof, including mixtures thereof in all ratios, and (b) an effective amount of a further medicament active ingredient.

8. The compound according to claim 2, which is compound A45 which is 5-fluoro-6-(2-methoxyethoxy)-3-(3-{4-[4-(oxetan-3-yl)piperazine-1-carbonyl]phenyl}-1,2-oxazol-5-yl)-1H-indazole or pharmaceutically acceptable solvates, salts, stereoisomers thereof, including mixtures thereof in all ratios.

9. A medicament, comprising:

the compound according to claim 8 and/or pharmaceutically acceptable salts, solvates, tautomers, and stereoisomers thereof, including mixtures thereof in all ratios, and optionally a pharmaceutically acceptable carrier, excipient, or vehicle.

10. The medicament of claim 9, further comprising at least one medicament active ingredient.

11. A kit, consisting of:

separate packs of (a) an effective amount of the compound according to claim 8 and/or pharmaceutically acceptable salts, solvates, salts, and stereoisomers thereof, including mixtures thereof in all ratios, and (b) an effective amount of a further medicament active ingredient.

* * * * *